US012662666B2

(12) United States Patent
Choudhary et al.

(10) Patent No.: US 12,662,666 B2
(45) Date of Patent: Jun. 23, 2026

(54) RECOMBINANT OLIVETOLIC ACID CYCLASE POLYPEPTIDES ENGINEERED FOR ENHANCED BIOSYNTHESIS OF CANNABINOIDS

(71) Applicants: WILLOW BIOSCIENCES, INC., Calgary (CA); EPIMERON USA, INC., Sunnyvale, CA (US)

(72) Inventors: Trish Choudhary, Belmont, CA (US); Xueyang Feng, Fremont, CA (US); Thanh Nguyen, Fremont, CA (US); Matthew Workentine, Calgary (CA)

(73) Assignee: Epimeron USA, Inc., Sunnyvale, CA (US)

( * ) Notice: Subject to any disclaimer, the term of this patent is extended or adjusted under 35 U.S.C. 154(b) by 11 days.

(21) Appl. No.: 18/660,840

(22) Filed: May 10, 2024

(65) Prior Publication Data

US 2024/0401019 A1 Dec. 5, 2024

Related U.S. Application Data

(63) Continuation of application No. 18/338,242, filed on Jun. 20, 2023, now Pat. No. 12,018,301, which is a continuation of application No. PCT/US2022/075170, filed on Aug. 18, 2022.

(60) Provisional application No. 63/341,996, filed on May 13, 2022, provisional application No. 63/320,421, filed on Mar. 16, 2022, provisional application No. 63/235,087, filed on Aug. 19, 2021.

(51) Int. Cl.
*C12N 9/88* (2006.01)
*C12N 15/63* (2006.01)
*C12P 17/18* (2006.01)

(52) U.S. Cl.
CPC ............... *C12N 9/88* (2013.01); *C12N 15/63* (2013.01); *C12P 17/182* (2013.01); *C12Y 404/01026* (2015.07)

(58) Field of Classification Search
CPC .......... C12N 9/88; C12N 15/63; C12N 15/52; C12P 17/182; C12Y 404/01026
See application file for complete search history.

(56) References Cited

U.S. PATENT DOCUMENTS 12,018,301 B2 * 6/2024 Choudhary ............ C12N 15/52

* cited by examiner

*Primary Examiner* — Ganapathirama Raghu
(74) *Attorney, Agent, or Firm* — FisherBroyles, LLP; Adam K. Whiting

(57) ABSTRACT

The present disclosure relates to recombinant polypeptides that have olivetolic acid cyclase activity, nucleic acids encoding these recombinant polypeptides, recombinant host cells that produce these recombinant polypeptides, and compositions comprising the recombinant polypeptides, nucleic acids, and/or recombinant host cells. The present disclosure also relates to uses of these recombinant polypeptides, nucleic acids encoding them, and recombinant host cells comprising them, in methods for the preparation of cannabinoids and cannabinoid precursors.

18 Claims, 4 Drawing Sheets

Specification includes a Sequence Listing.

Cannabigerolic acid (CBGA)

Cannabichromenic acid (CBCA)

Cannabichromene (CBC)

Cannabidiolic acid (CBDA)

Cannabidiol (CBD)

$\Delta^9$-Tetrahydrocannibinolic acid (THCA)

$\Delta^9$-Tetrahydrocannibinol (THC)

Butyric acid (BA)

Butanoyl-CoA

Malonyl-CoA 3,5,7-trioxodecanoyl-CoA

Divarinic acid (DA)

Geranyldiphosphate

Cannabigerovarinic acid (CBGVA)

Cannabigerovarinic acid (CBGVA)

Cannabichromevarinic acid (CBCVA)

Cannabichromevarin (CBCV)

Cannabidivarinic acid (CBDVA)

Cannabidivarin (CBDV)

$\Delta^9$-Tetrahydrocannabivarinic acid (THCVA)

$\Delta^9$-Tetrahydrocannibivarin (THCV)

RECOMBINANT OLIVETOLIC ACID CYCLASE POLYPEPTIDES ENGINEERED FOR ENHANCED BIOSYNTHESIS OF CANNABINOIDS

CROSS REFERENCE TO RELATED APPLICATIONS

This application is continuation of U.S. application Ser. No. 18/338,242, filed Jun. 20, 2023, which is a continuation of International Application Number PCT/US2022/075710, filed Aug. 18, 2022, which claims priority of U.S. Provisional Patent Application No. 63/341,996, filed May 13, 2022, U.S. Provisional Patent Application No. 63/320,421, filed Mar. 16, 2022, and U.S. Provisional Patent Application No. 63/235,087, filed Aug. 19, 2021, the entirety of each of which is hereby incorporated by reference herein.

FIELD

The present disclosure relates to engineered genes encoding recombinant polypeptides having olivetolic acid cyclase (OAC) activity and the use of these genes and polypeptides in recombinant host cell and in vitro systems for the production of cannabinoid compounds.

REFERENCE TO SEQUENCE LISTING

The official copy of the Sequence Listing is submitted concurrently with the specification via USPTO Patent Center as an WIPO Standard ST.26 formatted XML file with file name "13421-015WO1.xml", a creation date of Aug. 15, 2022, and a size of 1,289,937 bytes. This Sequence Listing filed via USPTO Patent Center is part of the specification and is incorporated in its entirety by reference herein.

BACKGROUND

Cannabinoids are a class of compounds that act on endocannabinoid receptors and include the phytocannabinoids naturally produced by *Cannabis sativa*. Cannabinoids include the more prevalent and well-known compounds, $\Delta^9$-tetrahydrocannabinol (THC), cannabidiol (CBD), as well as 80 or more less prevalent cannabinoids, cannabinoid precursors, related metabolites, and synthetically produced derivative compounds. Cannabinoids are increasingly used to treat a range of diseases and conditions such as multiple sclerosis and chronic pain. Current large-scale production of cannabinoids for pharmaceutical or other use is through extraction from plants. These plant-based production processes, however, have several challenges including susceptibility of the plants to inconsistent production caused by variance in biotic and abiotic factors, difficulty reproducing identical cannabinoid accumulation profiles, and difficulty in producing a single cannabinoid compound with purity high enough for pharmaceutical applications. While some cannabinoids can be produced as a single pure product via chemical synthesis, these processes have proven very costly and too costly for large-scale production.

More economical biosynthetic approaches to cannabinoid production are being developed using microbial hosts. These processes have the potential to be robust, scalable, and capable of producing single cannabinoid compound with higher purity compared to other current processes. Several biosynthetic systems for cannabinoid compound have been reported (see e.g., WO2019071000, WO2018200888, WO2018148849, WO2019014490, US20180073043, US20180334692, and WO2019046941). These biosynthetic systems typically incorporate a four enzyme pathway derived from *Cannabis sativa* including: (1) an acyl activating enzyme (AAE) of class E.C. 6.2.1.1; (2) an olivetol synthase (OLS) of class E.C. 2.3.1.206; (3) an olivetolic acid cyclase (OAC) of class E.C. 4.4.1.26, and (4) a prenyltransferase (PT) of class E.C. 2.5.1.102. In *C. sativa* this four enzymes cannabinoid pathway is capable of carrying out the conversion of a hexanoic acid (HA) starting compound to the cannabinoid precursor compound, olivetolic acid (OA), followed by the prenylation of OA with geranyl pyrophosphate (GPP) to provide the cannabinoid, cannabigerolic acid (CBGA). A recombinant version of this pathway in microbial hosts has been shown to be capable of producing OA and CBGA to some extent, but are not efficient in the production of these compounds, or the downstream cannabinoid compounds, cannabidiolic acid (CBDA), or $\Delta^9$-tetrahydrocannabinolic acid (THCA).

There exists a need for improved recombinant genes encoding cannabinoid pathway enzymes (such as OAC) that when integrated in recombinant host cell systems enhance the biosynthetic production of cannabinoid precursors, and cannabinoids, such as OA, CBGA, CBDA, and THCA, and the rare precursors and rare cannabinoids such as DA, CBGVA, CBDVA, and THCVA.

SUMMARY

The present disclosure relates generally to engineered genes encoding recombinant polypeptides with olivetolic acid cyclase (OAC) activity, and the use of these engineered genes in recombinant host cell systems for the enhanced biosynthetic production of cannabinoids and cannabinoid precursor compounds. This summary is intended to introduce the subject matter of the present disclosure, but does not cover each and every embodiment, combination, or variation that is contemplated and described within the present disclosure. Further embodiments are contemplated and described by the disclosure of the detailed description, drawings, and claims.

In at least one embodiment, the present disclosure provides a recombinant polypeptide having olivetolic acid cyclase (OAC) activity, wherein the polypeptide comprises an amino acid sequence of at least 80% identity to SEQ ID NO: 6 or 20, and an amino acid residue difference as compared to SEQ ID NO: 6 or 20 at one or more positions selected from: A2, L6, V8, L9, K10, F11, K12, E14, T16, E17, A18, E21, E22, F23, K25, T26, Y27, V28, N29, V31, I33, A36, V40, Y41, K44, D45, V46, T47, Q48, K49, N50, E52, E53, Y55, T56, H57, 158, T62, T62, E64, V66, T68, Q70, D71, I74, P76, A77, H78, G80, G82, D83, V84, Y85, R86, S87, F88, E90, K91, I94, Y97, T98, and R100.

In at least one embodiment, the polypeptide comprises an amino acid sequence of at least 80% identity to SEQ ID NO: 6, and an amino acid residue difference as compared to SEQ ID NO: 6 at each of a combination of six positions, wherein the combination of six positions are selected from the combinations listed in Table 4.

In at least one embodiment, the polypeptide comprises amino acid residue differences are selected from: A2G, A2S, A2P, A2V, L6F, V8I, L9A, L9F, L9G, L9I, L9M, L9S, L9V, K10A, F11L, K12L, K12N, K12Q, K12V, E14G, T16P, T16Q, E17G, A18E, A18S, E21L, E21V, E22L, F23I, K25D, K25G, K25E, K25N, K25R, K25S, T26A, T26N, Y27F, V28C, N29D, N29G, V31A, V31E, V31M, V31S, I33D, I33E, I33V, A36E, A36F, A36L, A36Q, A36S, V40A, V40G, Y41E, Y41Q, Y41S, Y41T, K44P, D45V, V46I, V46L, T47A, T47G, T47S, T47S, Q48C, Q48H, Q48M, Q48P, K49A, K49C, K49G, K49H, K49L, K49N, K49P, K49R, K49S, K49T, K49V, N50Y, E52Q, E52R, E52S, E53A, E53F, E53H, E53L, E53R, E53S, E53V, Y55W, T56S, H57G, I58C, I58V, T62C, T62G, E64D, E64K, V66I, V66L, E67S, T68A, T68C, T68E, T68G, T68H, T68M, T68Q, T68S, Q70A, Q70K, D71G, I74G, I74H, I74K, I74L, I74M, I74N, I74Q, I74R, I74S, I74T, I74V, P76V, A77E, H78P, G80K, G82A, G82R, D83K, D83R, V84I, V84M, Y85F, R86S, S87H, S87K, S87P, F88W, F88Y, E90D, K91E, I94K, Y97F, T98V, R100A, and R100G.

In at least one embodiment, the polypeptide comprises a combination of amino acid differences selected from any of the combinations listed in Table 5, and/or any combination present in a polypeptide listed in Tables 5, 7, 8, 9, 10, 13, 14, and/or 15, as disclosed herein.

In at least one embodiment, the polypeptide comprises an amino acid sequence of at least 80%, at least 85%, at least 90%, at least 95%, at least 97%, at least 98%, or at least 99% identity to a sequence selected from the group consisting of even-numbered SEQ ID NOs: 22 to 890.

In at least one embodiment, the olivetolic acid cyclase activity of the polypeptide as compared to the CsOAC polypeptide consisting of SEQ ID NO: 6 or 20 at least 0.2-fold, at least 0.4-fold, at least 0.6-fold, at least 0.8-fold, at least 1.0-fold, at least 1.2-fold, at least 1.4-fold, at least 1.8-fold, at least 1.6-fold, at least 2-fold, at least 4-fold, or more. In at least one embodiment, the olivetolic acid cyclase activity of the polypeptide is measured as the rate of conversion of the substrate 3,5,7-trioxododecanoyl-CoA (compound (2)) to olivetolic acid (compound (1)); optionally, under reaction conditions of pH 7 and 30 C.

In at least one embodiment, the olivetolic acid cyclase activity of the polypeptide when expressed in a recombinant host cell comprising a pathway capable of producing 3,5,7-trioxododecanoyl-CoA (compound (2)) results in a titer of olivetolic acid (compound (1)) produced by the cell that is relative to a control cell expressing the CsOAC polypeptide of SEQ ID NO: 6 or 20 at least 0.2-fold, at least 0.4-fold, at least 0.6-fold, at least 0.8-fold, at least 1.0-fold, at least 1.2-fold, at least 1.4-fold, at least 1.8-fold, at least 1.6-fold, at least 2-fold, at least 4-fold, or more.

In at least one embodiment, the present disclosure also provides a polynucleotide encoding a recombinant polypeptide having olivetolic acid cyclase activity of the present disclosure. In at least one embodiment, the polynucleotide comprises: (a) a sequence of at least 80%, at least 85%, at least 90%, at least 95%, at least 97%, at least 98%, or at least 99% identity to a sequence selected from the group consisting of odd-numbered SEQ ID NOs: 21 to 889; or (b) a codon degenerate sequence of a sequence selected from the group consisting of odd-numbered SEQ ID NOs: 21 to 889.

In at least one embodiment, the present disclosure also provides an expression vector comprising a polynucleotide encoding a recombinant polypeptide having olivetolic acid cyclase activity of the present disclosure, optionally wherein, the expression vector comprises a control sequence.

In at least one embodiment, the present disclosure also provides a recombinant host cell comprising: (a) a polynucleotide encoding a recombinant polypeptide having olivetolic acid cyclase activity of the present disclosure, or (b) an expression vector comprising a polynucleotide encoding a recombinant polypeptide having olivetolic acid cyclase activity of the present disclosure.

In at least one embodiment, the present disclosure provides a method for preparing a recombinant polypeptide having olivetolic acid cyclase activity of the present disclosure wherein the method comprises culturing a recombinant host cell of the present disclosure and isolating the polypeptide from the cell.

In at least one embodiment, the present disclosure provides a method for preparing a recombinant polypeptide having olivetolic acid cyclase activity comprising:

(a) transforming a host cell with an expression vector comprising a polynucleotide encoding a recombinant polypeptide having olivetolic acid cyclase activity of the present disclosure;

(b) culturing said transformed host cell under conditions whereby said recombinant polypeptide is produced by said host cell; and (c) recovering said recombinant polypeptide from said host cells.

In at least one embodiment, the present disclosure also provides a recombinant host cell comprising a nucleic acid encoding a recombinant polypeptide having olivetolic acid cyclase activity of the present disclosure.

In at least one embodiment of the recombinant host cell, the host cell further comprises a pathway of enzymes capable of producing a cannabinoid precursor; optionally, wherein the cannabinoid precursor is divarinic acid (DA) or olivetolic acid (OA).

In at least one embodiment of the recombinant host cell, the host cell further comprises a pathway of enzymes capable of producing a tetraketide cannabinoid precursor; optionally, wherein the tetraketide cannabinoid precursor is 3,5,7-trioxododecanoyl-CoA. In at least one embodiment, the pathway comprises enzymes capable of converting hexanoic acid (HA) to 3,5,7-trioxododecanoyl-CoA.

In at least one embodiment of the recombinant host cell, the pathway comprises enzymes capable of catalyzing reactions (i)-(ii):

(i)

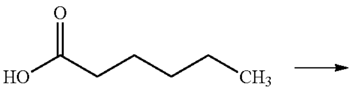

Hexanoic acid

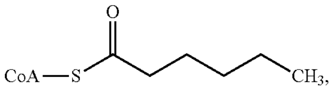

and

Hexanoyl-CoA (ii)

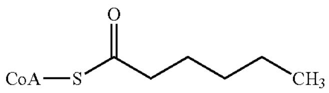

Hexanoyl-CoA

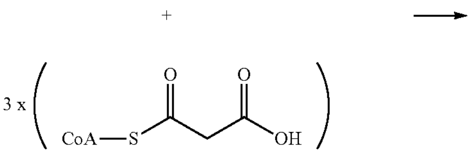

Malonyl-CoA

-continued

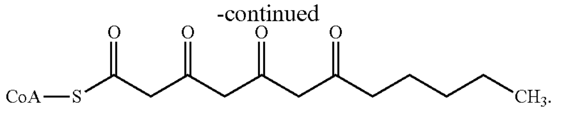

3,5,7-trioxododecanoyl-CoA

In at least one embodiment, the pathway comprises at least the enzymes AAE, and OLS; optionally, wherein the enzymes AAE, and OLS, have an amino acid sequence of at least 90% identity to SEQ ID NO: 2 (AAE), and SEQ ID NO: 4 (OLS), respectively.

In at least one embodiment of the recombinant host cell, the host cell further comprises a nucleic acid encoding an enzyme capable of catalyzing the conversion of OA to CBGA. In at least one embodiment, the pathway comprises an enzyme capable of catalyzing reaction (iv):

(iv)

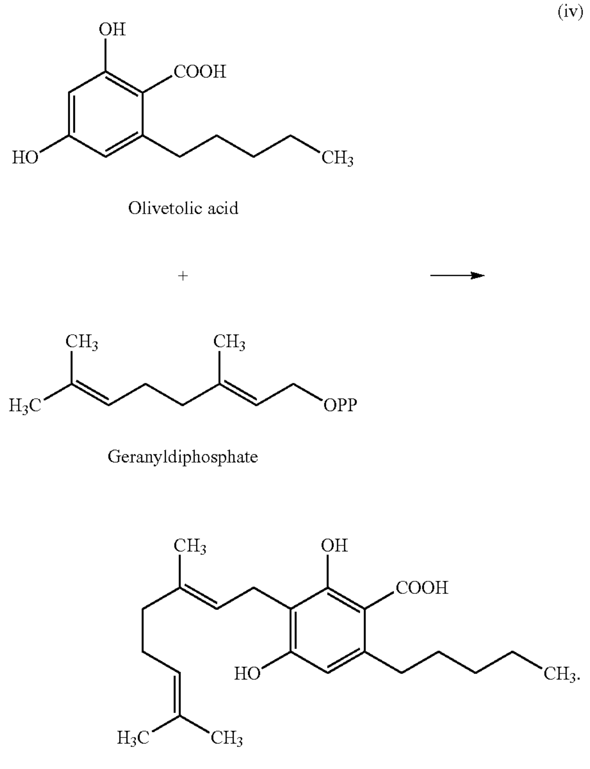

Olivetolic acid

+

Geranyldiphosphate

Cannabigerolic acid (CBGA)

In at least one embodiment, the host cell further comprises a nucleic acid encoding a prenyltransferase; optionally, wherein the prenyltransferase has an amino acid sequence of at least 90% identity to SEQ ID NO: 8 or 10.

In at least one embodiment of the recombinant host cell, the host cell further comprises a nucleic acid encoding an enzyme capable of catalyzing the conversion of CBGA to $\Delta^9$-THCA. CBDA, and/or CBCA; optionally, wherein the host cell further comprises a nucleic acid encoding an enzyme capable of catalyzing a reaction (v), (vi), and/or (vii):

(v)

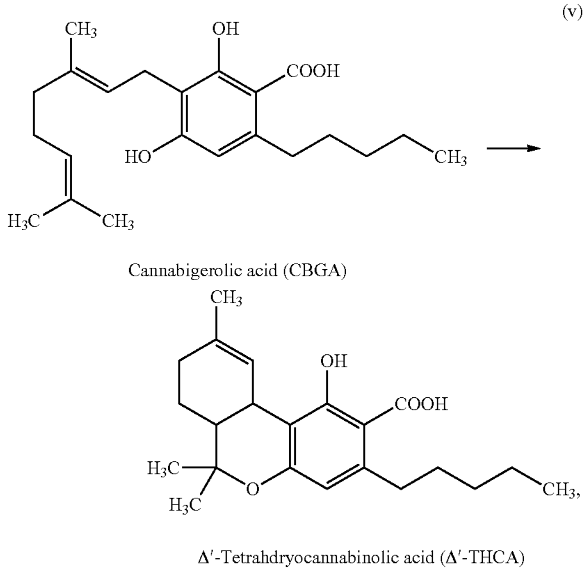

Cannabigerolic acid (CBGA)

Δ'-Tetrahdryocannabinolic acid (Δ'-THCA)

(vi)

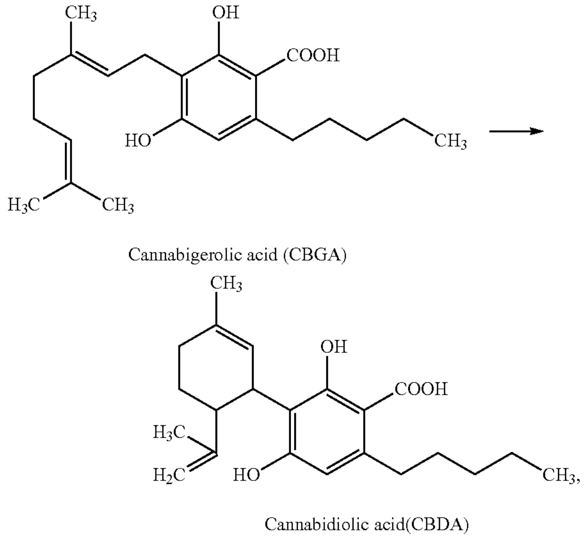

Cannabigerolic acid (CBGA)

Cannabidiolic acid(CBDA)

(vii)

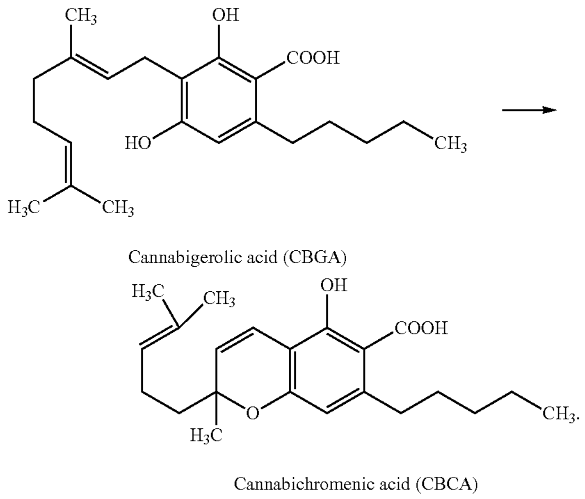

Cannabigerolic acid (CBGA)

Cannabichromenic acid (CBCA)

In at least one embodiment of the recombinant host cell, the host cell further comprises a nucleic acid encoding THCA synthase, CBDA synthase, and/or CBCA synthase; optionally, wherein the CBDA synthase has an amino acid sequence of at least 90% identity to SEQ ID NO: 12 or 14; and the THCA synthase having an amino acid sequence of at least 90% identity to SEQ ID NO: 16 or 18.

In at least one embodiment of the recombinant host cell, the host cell is capable of producing a cannabinoid selected from cannabigerolic acid (CBGA), cannabigerol (CBG), cannabidiolic acid (CBDA), cannabidiol (CBD), $\Delta^9$-tetrahydrocannabinolic acid ($\Delta^9$-THCA), $\Delta^9$-tetrahydrocannabinol ($\Delta^9$-THC). $\Delta^8$-tetrahydrocannabinolic acid ($\Delta^8$-THCA), $\Delta^8$-tetrahydrocannabinol ($\Delta^8$-THC), cannabichromenic acid (CBCA), cannabichromene (CBC), cannabinolic acid (CBNA), cannabinol (CBN), cannabidivarinic acid (CBDVA), cannabidivarin (CBDV), $\Delta^9$-tetrahydrocannabivarinic acid ($\Delta^9$-THCVA), $\Delta^9$-tetrahydrocannabivarin ($\Delta^9$-THCV), cannabidibutolic acid (CBDBA), cannabidibutol (CBDB), $\Delta^9$-tetrahydrocannabutolic acid ($\Delta^9$-THCBA), $\Delta^9$-tetrahydrocannabutol ($\Delta^9$-THCB), cannabidiphorolic acid (CBDPA), cannabidiphorol (CBDP), $\Delta^9$-tetrahydrocannabiphorolic acid ($\Delta^9$-THCPA), $\Delta^9$-tetrahydrocannabiphorol ($\Delta^9$-THCP), cannabichromevarinic acid (CBCVA), cannabichromevarin (CBCV), cannabigerovarinic acid (CBGVA), cannabigerovarin (CBGV), cannabicyclolic acid (CBLA), cannabicyclol (CBL), cannabielsoinic acid (CBEA), cannabielsoin (CBE), cannabicitranic acid (CBTA), cannabicitran (CBT), and any combination thereof.

In at least one embodiment of the recombinant host cell, the host cell comprises a pathway capable of producing CBGA, and the production of CBGA is at least 0.2-fold, at least 0.4-fold, at least 0.6-fold, at least 0.8-fold, at least 1.0-fold, at least 1.2-fold, at least 1.4-fold, at least 1.8-fold, at least 1.6-fold, at least 2-fold, at least 4-fold, or more, relative to a control recombinant host cell comprising a pathway with the recombinant polypeptide having olivetolic acid cyclase activity replaced by a polypeptide of SEQ ID NO: 6 or 20.

In at least one embodiment of the recombinant host cell, the source of the host cell is selected from *Saccharomyces cerevisiae*, *Yarrowia lipolytica*, *Pichia pastoris*, and *Escherichia coli*.

In at least one embodiment, the present disclosure also provides a method for producing a cannabinoid or a cannabinoid precursor comprising: (a) culturing in a suitable medium a recombinant host cell of the present disclosure; and (b) recovering the produced cannabinoid or cannabinoid precursor. In at least one embodiment, the method further comprises contacting a cell-free extract of the culture with a biocatalytic reagent or chemical reagent.

In at least one embodiment, the present disclosure also provides a method for preparing a compound of structural formula (I)

(I)

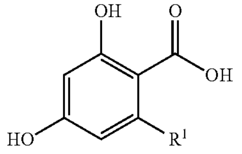

wherein, $R^1$ is C1-C7 alkyl, the method comprising contacting under suitable reactions conditions a compound of structural formula (II)

(II)

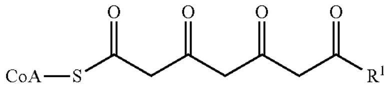

wherein, $R^1$ is C1-C7 alkyl, and a recombinant polypeptide have olivetolic acid cyclase activity of the present disclosure. In at least one embodiment: (a) the compound of structure formula (I) is olivetolic acid (OA) and the compound of structural formula (II) is 3,5,7-trioxododecanoyl-CoA; or (b) the compound of structure formula (I) is divarinic acid (DA) and the compound of structural formula (II) is 3,5,7-trioxodecanoyl-CoA acid.

BRIEF DESCRIPTION OF THE DRAWINGS

A better understanding of the novel features and advantages of the present disclosure will be obtained by reference to the following detailed description that sets forth illustrative embodiments, in which the principles of the disclosure are utilized, and the accompanying drawings (also "Figure" and "FIG." herein), of which.

DETAILED DESCRIPTION

Figure 1:
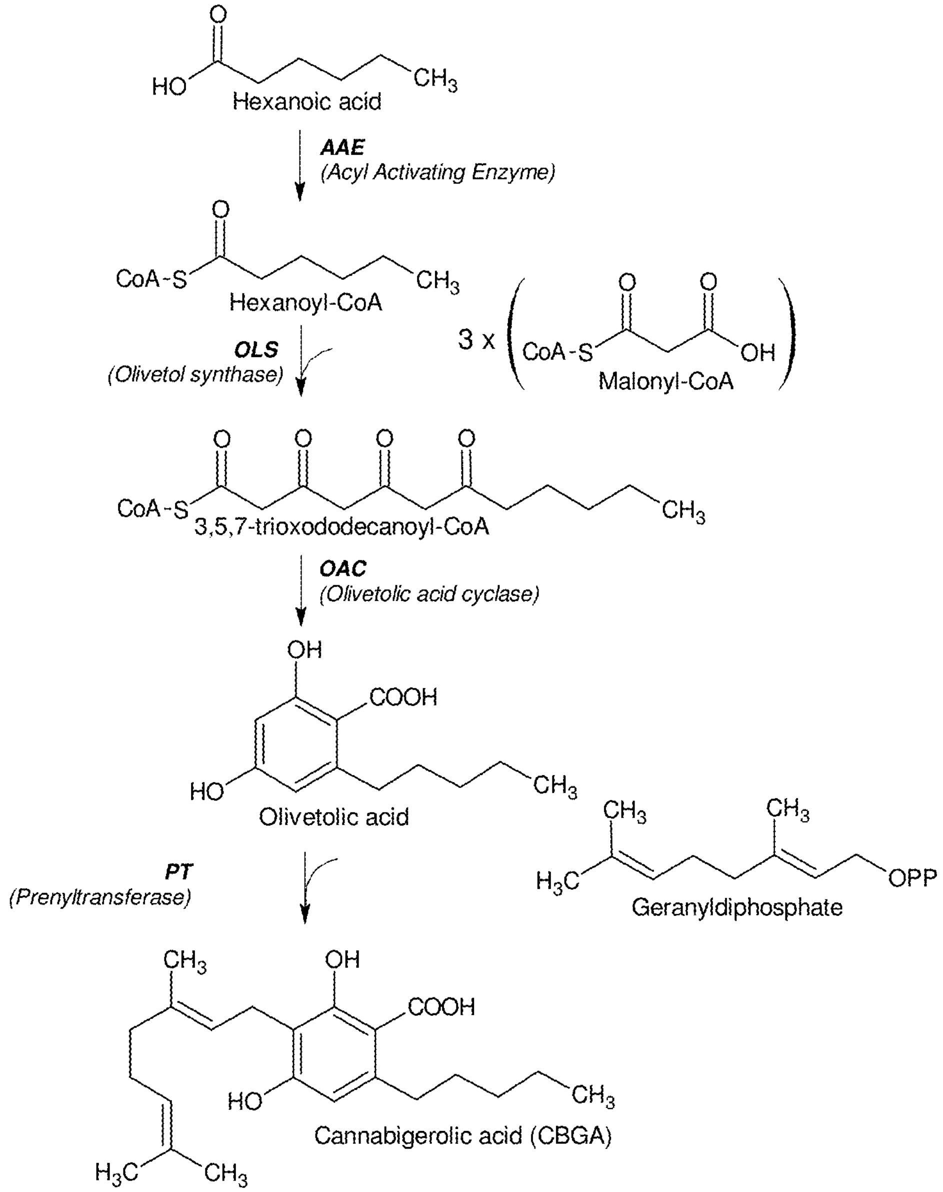
FIG. 1 depicts an exemplary four enzyme pathway capable of converting hexanoic acid (HA) to the cannabinoid precursor, olivetolic acid (OA), and then further converting OA to the cannabinoid, cannabigerolic acid (CBGA). The four enzymes catalyzing the steps in the biosynthetic pathway are AAE, OLS, OAC, and PT.

For the descriptions herein and the appended claims, the singular forms "a", and "an" include plural referents unless the context clearly indicates otherwise. Thus, for example, reference to "a protein" includes more than one protein, and reference to "a compound" refers to more than one compound. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. The use of "comprise," "comprises," "comprising" "include," "includes," and "including" are interchangeable and not intended to be limiting. It is to be further understood that where descriptions of various embodiments use the term "comprising," those skilled in the art would understand that in some specific instances, an embodiment can be alternatively described using language "consisting essentially of" or "consisting of."

Where a range of values is provided, unless the context clearly dictates otherwise, it is understood that each intervening integer of the value, and each tenth of each intervening integer of the value, unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of these limits, ranges excluding (i) either or (ii) both of those included limits are also included in the invention. For example, "1 to 50," includes "2 to 25," "5 to 20," "25 to 50," "1 to 10," etc.

Generally, the nomenclature used herein and the techniques and procedures described herein include those that are well understood and commonly employed by those of ordinary skill in the art, such as the common techniques and methodologies described in e.g., Green and Sambrook, *Molecular Cloning: A Laboratory Manual* (Fourth Edition), Vols. 1-3, Cold Spring Harbor Laboratory, Cold Spring Harbor, N.Y., 2012 (hereinafter "Sambrook"); and *Current Protocols in Molecular Biology*, F. M. Ausubel et al., eds., originally published in 1987 in book form by Greene Publishing Associates, Inc. and John Wiley & Sons, Inc., and regularly supplemented through 2011, and now available in journal format online as *Current Protocols in Molecular Biology, Vols.* 00-130, (1987-2020), published by Wiley & Sons, Inc. in the Wiley Online Library (hereinafter "Ausubel").

All publications, patents, patent applications, and other documents referenced in this disclosure are hereby incorporated by reference in their entireties for all purposes to the same extent as if each individual publication, patent, patent application or other document were individually indicated to be incorporated by reference herein for all purposes.

Unless defined otherwise, all technical and scientific terms used herein have the same meaning as commonly understood by one of ordinary skill in the art to which the present invention pertains. It is to be understood that the terminology used herein is for describing particular embodiments only and is not intended to be limiting. For purposes of interpreting this disclosure, the following description of terms will apply and, where appropriate, a term used in the singular form will also include the plural form and vice versa.

Definitions

"Cannabinoid" refers to a compound that acts on cannabinoid receptor, and is intended to include the endocannabinoid compounds that are produced naturally in animals, the phytocannabinoid compounds produced naturally in cannabis plants, and the synthetic cannabinoids compounds. Cannabinoids as referenced in the present disclosure include, but are not limited to, the exemplary naturally occurring and synthetic cannabinoid product compounds shown below in Table 1 (below).

TABLE 1

Exemplary cannabinoid product compounds

| Compound Name | Abbrev. Name | Chemical Structure |
|---|---|---|
| cannabigerolic acid | CBGA | 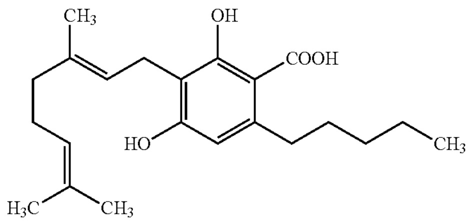 [SMILES: CCCCCc1cc(O)c(C/C=C(\C)CCC=C(C)C)c(O)c1C(=O)O] |
| cannabigerol | CBG | 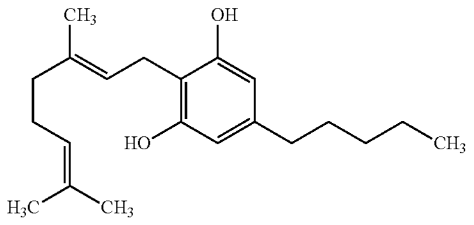 [SMILES: CCCCCc1cc(O)c(C/C=C(\C)CCC=C(C)C)c(O)c1] |

TABLE 1-continued

| Exemplary cannabinoid product compounds | | |
|---|---|---|
| Compound Name | Abbrev. Name | Chemical Structure |
| $\Delta^9$-tetrahydrocannabinolic acid | $\Delta^9$-THCA | 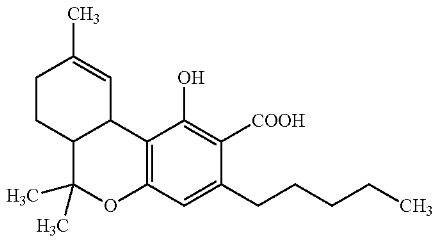 [SMILES: CCCCCc1cc2c(c(O)c1C(=O)O)C1C=C(C)CCC1C(C)(C)O2] |
| $\Delta^9$-tetrahydrocannabinol | $\Delta^9$-THC | 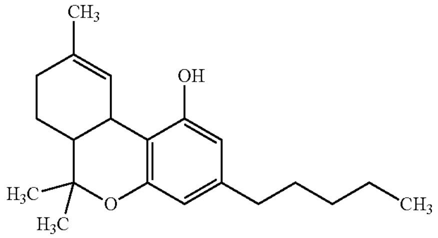 [SMILES: CCCCCc1cc(O)c2c(c1)OC(C)(C)C1CCC(C)=CC21] |
| $\Delta^8$-tetrahydrocannabinolic acid | $\Delta^8$-THCA | 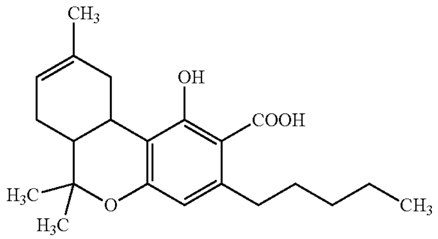 [SMILES: CCCCCc1cc2c(c(O)c1C(=O)O)C1CC(C)=CCC1C(C)(C)O2] |
| $\Delta^8$-tetrahydrocannabinol | $\Delta^8$-THC | 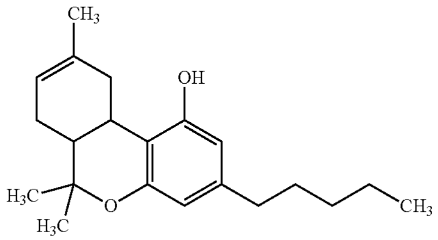 [SMILES: CCCCCc1cc(O)c2c(c1)OC(C)(C)C1CC=C(C)CC21] |
| cannabidiolic acid | CBDA | 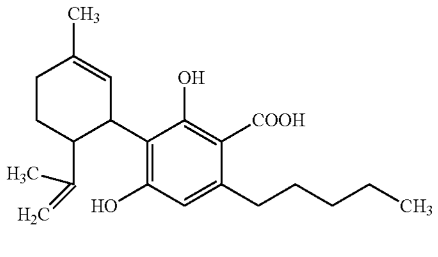 [SMILES: C=C(C)C1CCC(C)=CC1c1c(O)cc(CCCCC)c(C(=O)O)c1O] |
| cannabidiol | CBD | 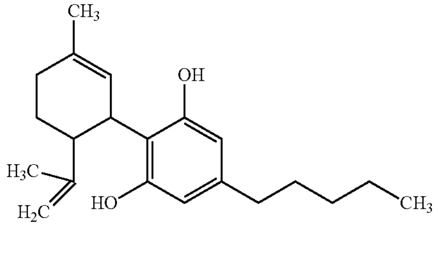 [SMILES: C=C(C)C1CCC(C)=CC1c1c(O)cc(CCCCC)cc1O] |

TABLE 1-continued
| Exemplary cannabinoid product compounds | | |
|---|---|---|
| Compound Name | Abbrev. Name | Chemical Structure |
| cannabichromenic acid | CBCA | 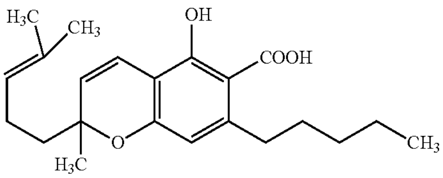 [SMILES: CCCCCc1cc2c(c(O)c1C(=O)O)C=CC(C)(CCC=C(C)C)O2] |
| cannabichromene | CBC | 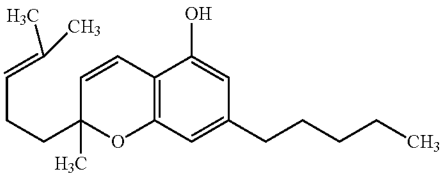 [SMILES: CCCCCc1cc(O)c2c(c1)OC(C)(CCC=C(C)C)C=C2] |
| cannabinolic acid | CBNA | 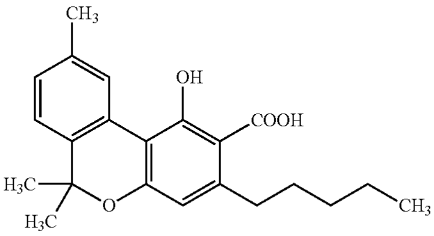 [SMILES: CCCCCc1cc2c(c(O)c1C(=O)O)-c1cc(C)ccc1C(C)(C)O2] |
| cannabinol | CBN | 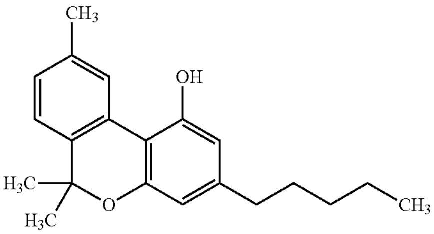 [SMILES: CCCCCc1cc(O)c2c(c1)OC(C)(C)c1ccc(C)cc1-2] |
| cannabidivarinic acid | CBDVA | 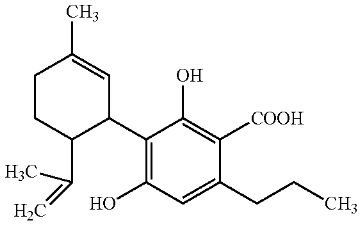 [SMILES: C=C(C)C1CCC(C)=CC1c1c(O)cc(CCC)c(C(=O)O)c1O] |
| cannabidivarin | CBDV | 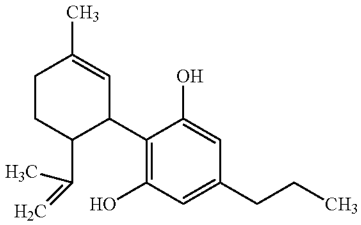 [SMILES: C=C(C)C1CCC(C)=CC1c1c(O)cc(CCC)cc1O] |

TABLE 1-continued

| Exemplary cannabinoid product compounds | | |
|---|---|---|
| Compound Name | Abbrev. Name | Chemical Structure |
| $\Delta^9$-tetrahydrocannabivarinic acid | $\Delta^9$-THCVA | 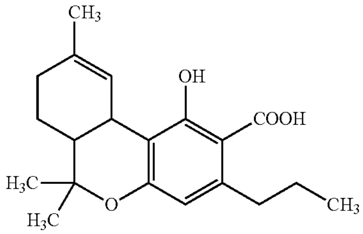 [SMILES: CCCc1cc2c(c(O)c1C(=O)O)C1C=C(C)CCC1C(C)(C)O2] |
| $\Delta^9$-tetrahydrocannabivarin | $\Delta^9$-THCV | 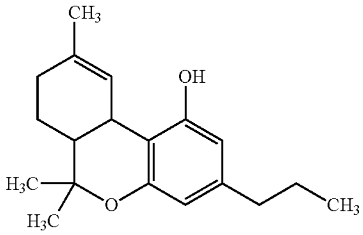 [SMILES: CCCc1cc(O)c2c(c1)OC(C)(C)C1CCC(C)=CC21] |
| cannabidibutolic acid | CBDBA | 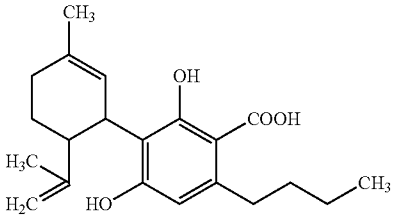 [SMILES: C=C(C)C1CCC(C)=CC1c1c(O)cc(CCCC)c(C(=O)O)c1O] |
| cannabidibutol | CBDB | 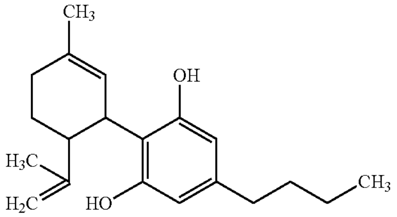 [SMILES: C=C(C)C1CCC(C)=CC1c1c(O)cc(CCCC)cc1O] |
| $\Delta^9$- tetrahydrocannabutolic acid | $\Delta^9$-THCBA | 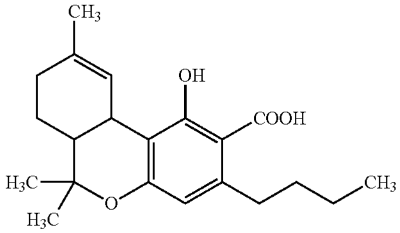 [SMILES: CCCCc1cc2c(c(O)c1C(=O)O)C1C=C(C)CCC1C(C)(C)O2] |
| $\Delta^9$-tetrahydrocannabutol | $\Delta^9$-THCB | 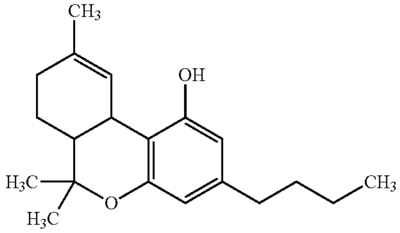 |

TABLE 1-continued
| Exemplary cannabinoid product compounds | | |
|---|---|---|
| Compound Name | Abbrev. Name | Chemical Structure |
| cannabigerophorolic acid | CBGPA | 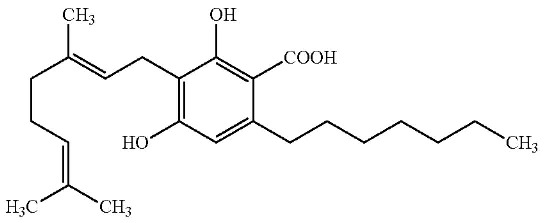 [SMILES: CCCCCCCc1cc(O)c(C/C=C(\C)CCC=C(C)C)c(O)c1C(=O)O] |
| cannabigerophorol | CBGP | 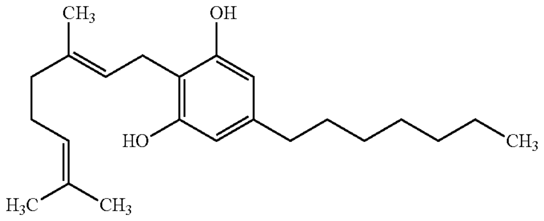 [SMILES: CCCCCCCc1cc(O)c(C/C=C(\C)CCC=C(C)C)c(O)c1] |
| cannabidiphorolic acid | CBDPA | 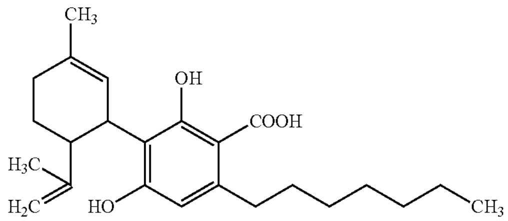 [SMILES: C=C(C)C1CCC(C)=CC1c1c(O)cc(CCCCCCC)c(C(=O)O)c1O] |
| cannabidiphorol | CBDP | 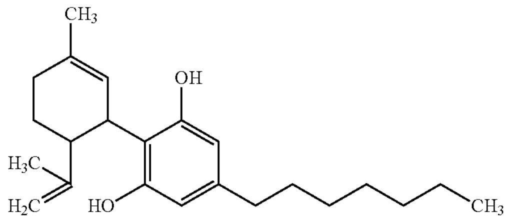 [SMILES: C=C(C)C1CCC(C)=CC1c1c(O)cc(CCCCCCC)cc1O] |
| $\Delta^9$-tetrahydrocannabiphorolic acid | $\Delta^9$-THCPA | 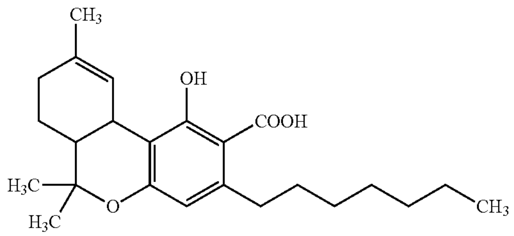 [SMILES: CCCCCCCc1cc2c(c(O)c1C(=O)O)C1C=C(C)CCC1C(C)(C)O2] |
| $\Delta^9$-tetrahydrocannabiphorol | $\Delta^9$-THCP | 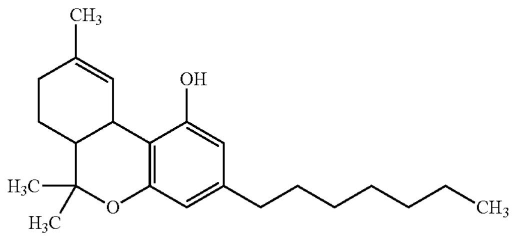 [SMILES: CCCCCCCc1cc(O)c2c(c1)OC(C)(C)C1CCC(C)=CC21] |

TABLE 1-continued
| Exemplary cannabinoid product compounds | | |
|---|---|---|
| Compound Name | Abbrev. Name | Chemical Structure |
| cannabichromevarinic acid | CBCVA | 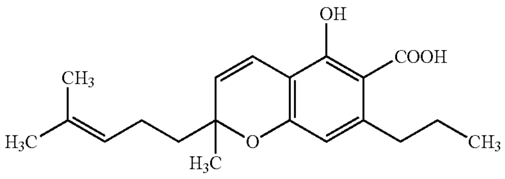 [SMILES: CCCc1cc2c(c(O)c1C(=O)O)C=CC(C)(CCC=C(C)C)O2] |
| cannabichromevarin | CBCV | 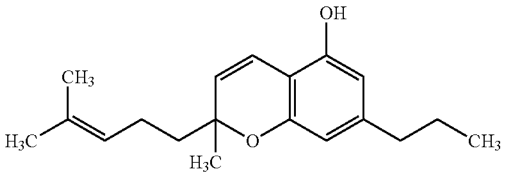 [SMILES: CCCc1cc(O)c2c(c1)OC(C)(CCC=C(C)C)C=C2] |
| cannabigerovarinic acid | CBGVA | 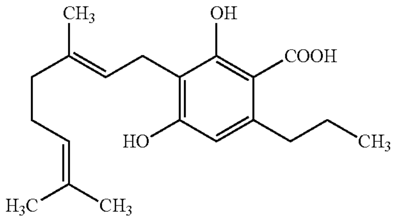 [SMILES: CCCc1cc(O)c(C/C=C(\C)CCC=C(C)C)c(O)c1C(=O)O] |
| cannabigerovarin | CBGV | 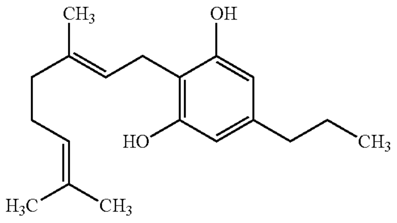 [SMILES: CCCc1cc(O)c(C/C=C(\C)CCC=C(C)C)c(O)c1] |
| cannabicyclolic acid | CBLA | 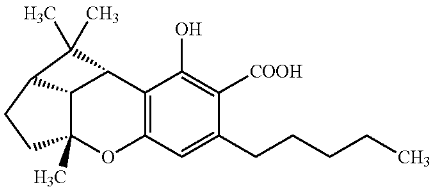 |
| cannabicyclol | CBL | 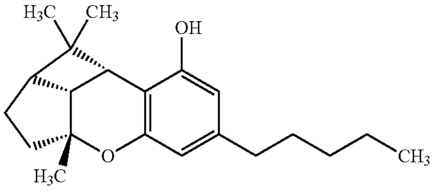 |
| cannabielsoinic acid | CBEA | 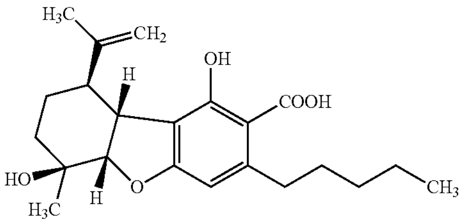 [SMILES: C=C(C)[C@@H]1CC[C@](C)(O)[C@H]2Oc3cc(CCCCC)c(C(=O)O)c(O)c3[C@@H]12] |

TABLE 1-continued

| Exemplary cannabinoid product compounds | | |
|---|---|---|
| Compound Name | Abbrev. Name | Chemical Structure |
| cannabielsoin | CBE | 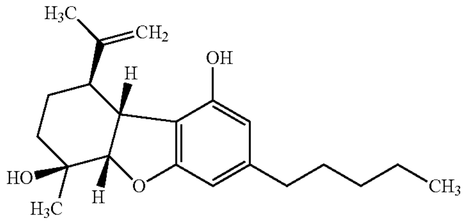 [SMILES: C=C(C)[C@@H]1CC[C@](C)(O)[C@H]2Oc3cc(CCCCC)cc(O)c3[C@@H]12] |
| cannabicitranic acid | CBTA | 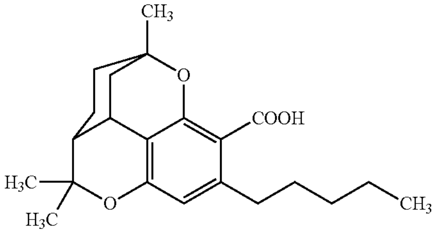 [SMILES: CCCCCc1cc2c3c(c1C(=O)O)OC1(C)CCC(C3C1)C(C)(C)O2] |
| cannabicitran | CBT | 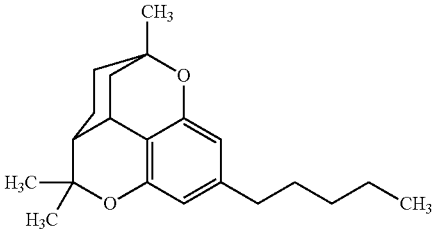 [SMILES: CCCCCc1cc2c3c(c1)OC(C)(C)C1CCC(C)(CC31)O2] |

"Pathway" refers an ordered sequence of enzymes that act in a linked series to convert an initial substrate molecule into final product molecule. As used herein, "pathway" is intended to encompass naturally-occurring pathways and non-naturally occurring, recombinant pathways. Accordingly, a pathway of the present disclosure can include a series of enzymes that are naturally-occurring and/or non-naturally occurring, and can include a series of enzymes that act in vivo or in vitro.

"Pathway capable of producing a cannabinoid" refers to a pathway that can convert a cannabinoid precursor molecule, such as hexanoic acid, into a cannabinoid molecule, such as cannabigerolic acid (CBGA). For example, the four enzymes AAE, OLS, OAC, and PT which convert hexanoic acid to CBGA, form a pathway capable of producing a cannabinoid.

"Cannabinoid precursor" as used herein refers to a compound capable of being converted into a cannabinoid by a pathway capable producing a cannabinoid. Cannabinoid precursors as referenced in the present disclosure include, but are not limited to, the exemplary naturally occurring and synthetic cannabinoid precursors with varying alkyl carbon chain lengths summarized in Table 2 (below).

TABLE 2

| Exemplary cannabinoid precursor compounds | | |
|---|---|---|
| Compound Name | Abbrev. Name | Chemical Structure |
| Orcinolic acid (2,4-dihydroxy-6-methylbenzoic acid) | OrcA | 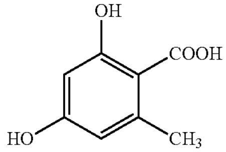 |
| Divarinic acid (2,4-dihydroxy-6-propylbenzoic acid) | DA | 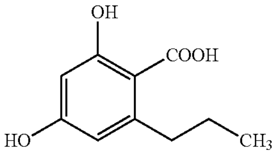 |

TABLE 2-continued

| Exemplary cannabinoid precursor compounds | | |
|---|---|---|
| Compound Name | Abbrev. Name | Chemical Structure |
| Butolic acid (2-butyl-4,6-dihydroxybenzoic acid) | BA | 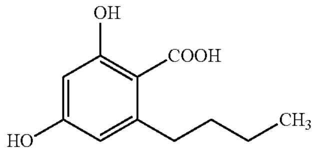 |
| Olivetolic acid (2,4-dihydroxy-6-pentylbenzoic acid) | OA | 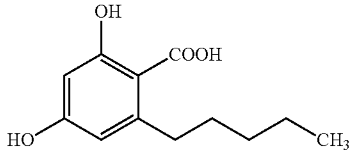 [SMILES: CCCCCc1cc(O)cc(O)c1C(=O)O] |
| 2-hexyl-4,6-dihydroxybenzoic acid | DHBA | 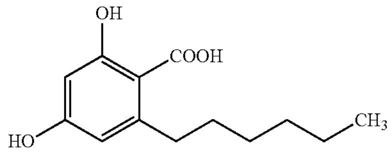 [SMILES: CCCCCCc1cc(O)cc(O)c1C(=O)O] |
| Sphaerophorolic acid (2-heptyl-4,6-dihydroxybenzoic acid) | PA | 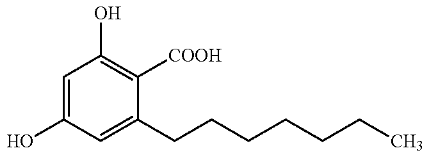 [SMILES: CCCCCCCc1cc(O)cc(O)c1C(=O)O] |

"Conversion" as used herein refers to the enzymatic conversion of a substrate(s) to a corresponding product(s). "Percent conversion" refers to the percent of the substrate that is converted to the product within a period of time under specified conditions. Thus, the "enzymatic activity" or "activity" of an enzymatic conversion can be expressed as "percent conversion" of the substrate to the product.

"Substrate" as used herein in the context of an enzyme mediated process refers to the compound or molecule acted on by the enzyme.

"Product" as used herein in the context of an enzyme mediated process refers to the compound or molecule resulting from the activity of the enzyme.

"Host cell" as used herein refers to a cell capable of being functionally modified with recombinant nucleic acids and functioning to express recombinant products, including polypeptides and compounds produced by activity of the polypeptides.

"Nucleic acid," or "polynucleotide" as used herein interchangeably to refer to two or more nucleosides that are covalently linked together. The nucleic acid may be wholly comprised ribonucleosides (e.g., RNA), wholly comprised of 2'-deoxyribonucleotides (e.g., DNA) or mixtures of ribo- and 2'-deoxyribonucleosides. The nucleoside units of the nucleic acid can be linked together via phosphodiester linkages (e.g., as in naturally occurring nucleic acids), or the nucleic acid can include one or more non-natural linkages (e.g., phosphorothioester linkage). Nucleic acid or polynucleotide is intended to include single-stranded or double-stranded molecules, or molecules having both single-stranded regions and double-stranded regions. Nucleic acid or polynucleotide is intended to include molecules composed of the naturally occurring nucleobases (i.e., adenine, guanine, uracil, thymine, and cytosine), or molecules comprising that include one or more modified and/or synthetic nucleobases, such as, for example, inosine, xanthine, hypoxanthine, etc.

"Protein," "polypeptide," and "peptide" are used herein interchangeably to denote a polymer of at least two amino acids covalently linked by an amide bond, regardless of length or post-translational modification (e.g., glycosylation, phosphorylation, lipidation, myristilation, ubiquitination, etc.). As used herein "protein" or "polypeptide" or "peptide" polymer can include D- and L-amino acids, and mixtures of D- and L-amino acids.

"Naturally-occurring" or "wild-type" as used herein refers to the form as found in nature. For example, a naturally occurring nucleic acid sequence is the sequence present in an organism that can be isolated from a source in nature and which has not been intentionally modified by human manipulation.

"Recombinant," "engineered," or "non-naturally occurring" when used herein with reference to, e.g., a cell, nucleic acid, or polypeptide, refers to a material, or a material corresponding to the natural or native form of the material, that has been modified in a manner that would not otherwise exist in nature, or is identical thereto but is produced or derived from synthetic materials and/or by manipulation using recombinant techniques. Non-limiting examples include, among others, recombinant cells expressing genes that are not found within the native (non-recombinant) form of the cell or express native genes that are otherwise expressed at a different level.

"Nucleic acid derived from" as used herein refers to a nucleic acid having a sequence at least substantially identical to a sequence of found in naturally in an organism. For example, cDNA molecules prepared by reverse transcription of mRNA isolated from an organism, or nucleic acid molecules prepared synthetically to have a sequence at least substantially identical to, or which hybridizes to a sequence at least substantially identical to a nucleic sequence found in an organism.

"Coding sequence" refers to that portion of a nucleic acid (e.g., a gene) that encodes an amino acid sequence of a protein.

"Heterologous nucleic acid" as used herein refers to any polynucleotide that is introduced into a host cell by laboratory techniques, and includes polynucleotides that are removed from a host cell, subjected to laboratory manipulation, and then reintroduced into a host cell.

"Codon degenerate" describes a nucleotide sequence that has one or more different codons relative to the reference nucleotide sequence but which encodes a polypeptide that is identical to the polypeptide encoded by a reference nucleotide sequence. The different codons between the nucleotide sequence and the reference nucleotide sequence are called "synonyms" or "synonymous" codons in that they use different triplets of nucleotides to encode the same amino acid in a polypeptide.

"Codon optimized" refers to changes in the codons of the polynucleotide encoding a protein to those preferentially used in a particular organism such that the encoded protein is efficiently expressed in the organism of interest. Although the genetic code is degenerate in that most amino acids are represented by several different "synonymous" codons, it is well known that codon usage by particular organisms is nonrandom and biased towards particular codon triplets. This codon usage bias may be higher in reference to a given gene, genes of common function or ancestral origin, highly expressed proteins versus low copy number proteins, and the aggregate protein coding regions of an organism's genome. In some embodiments, the polynucleotides encoding the imine reductase enzymes may be codon optimized for optimal production from the host organism selected for expression.

"Preferred, optimal, high codon usage bias codons" refers to codons that are used at higher frequency in the protein coding regions than other codons that code for the same amino acid. The preferred codons may be determined in relation to codon usage in a single gene, a set of genes of common function or origin, highly expressed genes, the codon frequency in the aggregate protein coding regions of the whole organism, codon frequency in the aggregate protein coding regions of related organisms, or combinations thereof. Codons whose frequency increases with the level of gene expression are typically optimal codons for expression. A variety of methods are known for determining the codon frequency (e.g., codon usage, relative synonymous codon usage) and codon preference in specific organisms, including multivariate analysis, for example, using cluster analysis or correspondence analysis, and the effective number of codons used in a gene (see GCG CodonPreference, Genetics Computer Group Wisconsin Package; CodonW, John Peden, University of Nottingham; McInerney, J. O, 1998, Bioinformatics 14:372-73; Stenico et al., 1994, Nucleic Acids Res. 222437-46; Wright, F., 1990, Gene 87:23-29). Codon usage tables are available for a growing list of organisms (see for example, Wada et al., 1992, Nucleic Acids Res. 20:2111-2118; Nakamura et al., 2000, Nucl. Acids Res. 28:292; Duret, et al., supra; Henaut and Danchin, "*Escherichia coli* and *Salmonella,*" 1996, Neidhardt, et al. Eds., ASM Press, Washington D.C., p. 2047-2066. The data source for obtaining codon usage may rely on any available nucleotide sequence capable of coding for a protein. These data sets include nucleic acid sequences actually known to encode expressed proteins (e.g., complete protein coding sequences-CDS), expressed sequence tags (ESTS), or predicted coding regions of genomic sequences (see for example, Mount, D., Bioinformatics: Sequence and Genome Analysis, Chapter 8, Cold Spring Harbor Laboratory Press, Cold Spring Harbor, N.Y., 2001; Uberbacher, E. C., 1996, Methods Enzymol. 266:259-281; Tiwari et al., 1997, Comput. Appl. Biosci. 13:263-270).

"Control sequence" as used herein refers to all sequences, which are necessary or advantageous for the expression of a polynucleotide and/or polypeptide as used in the present disclosure. Each control sequence may be native or foreign to the nucleic acid sequence encoding a polypeptide. Such control sequences include, but are not limited to, a leader, a promoter, a polyadenylation sequence, a pro-peptide sequence, a signal peptide sequence, and a transcription terminator. At a minimum, control sequences typically include a promoter, and transcriptional and translational stop signals. The control sequences may be provided with linkers for the purpose of introducing specific restriction sites facilitating ligation of the control sequences with the coding region of the nucleic acid sequence encoding a polypeptide.

"Operably linked" as used herein refers to a configuration in which a control sequence is appropriately placed (e.g., in a functional relationship) at a position relative to a polynucleotide sequence or polypeptide sequence of interest such that the control sequence directs or regulates the expression of the sequence of interest.

"Promoter sequence" refers to a nucleic acid sequence that is recognized by a host cell for expression of a polynucleotide of interest, such as a coding sequence. The promoter sequence contains transcriptional control sequences, which mediate the expression of a polynucleotide of interest. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

"Percentage of sequence identity," "percent sequence identity," "percentage homology," or "percent homology" are used interchangeably herein to refer to values quantifying comparisons of the sequences of polynucleotides or polypeptides, and are determined by comparing two optimally aligned sequences over a comparison window, wherein the portion of the polynucleotide or polypeptide sequence in the comparison window may comprise additions or deletions (or gaps) as compared to the reference sequence for optimal alignment of the two sequences. The percentage values may be calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Alternatively, the percentage may be calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Those of skill in the art appreciate that there are many established algorithms available to align two sequences. Optimal alignment of sequences for comparison can be conducted, e.g., by the local homology algorithm of Smith and Waterman, 1981, Adv. Appl. Math. 2:482, by the homology alignment algorithm of Needleman and Wunsch, 1970, J. Mol. Biol. 48:443, by the search for similarity method of Pearson and Lipman, 1988, Proc. Natl. Acad. Sci. USA 85:2444, by computerized implementations of these algorithms (GAP, BESTFIT, FASTA, and TFASTA in the GCG Wisconsin Software Package), or by visual inspection (see generally, Current Protocols in Molecular Biology, F. M. Ausubel et al., eds., Current Protocols, a joint venture between Greene Publishing Associates, Inc. and John Wiley & Sons, Inc., (1995 Supplement) (Ausubel)). Examples of algorithms that are suitable for determining percent sequence identity and sequence similarity are the BLAST and BLAST 2.0 algorithms, which are described in Altschul et al., 1990, J. Mol. Biol. 215:403-410 and Altschul et al., 1977, Nucleic Acids Res. 3389-3402, respectively. Software for performing BLAST analyses is publicly available through the National Center for Biotechnology Information website. This algorithm involves first identifying high scoring sequence pairs (HSPs) by identifying short words of length W in the query sequence, which either match or satisfy some positive-valued threshold score T when aligned with a word of the same length in a database sequence. T is referred to as, the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff and Henikoff, 1989, Proc Natl Acad Sci USA 89:10915). Exemplary determination of sequence alignment and % sequence identity can employ the BESTFIT or GAP programs in the GCG Wisconsin Software package (Accelrys, Madison Wis.), using default parameters provided.

"Reference sequence" refers to a defined sequence used as a basis for a sequence comparison. A reference sequence may be a subset of a larger sequence, for example, a segment of a full-length nucleic acid or polypeptide sequence. A reference sequence typically is at least 20 nucleotide or amino acid residue units in length, but can also be the full length of the nucleic acid or polypeptide. Since two polynucleotides or polypeptides may each (1) comprise a sequence (i.e., a portion of the complete sequence) that is similar between the two sequences, and (2) may further comprise a sequence that is divergent between the two sequences, sequence comparisons between two (or more) polynucleotides or polypeptide are typically performed by comparing sequences of the two polynucleotides or polypeptides over a "comparison window" to identify and compare local regions of sequence similarity. "Comparison window" refers to a conceptual segment of at least about 20 contiguous nucleotide positions or amino acids residues wherein a sequence may be compared to a reference sequence of at least 20 contiguous nucleotides or amino acids and wherein the portion of the sequence in the comparison window may comprise additions or deletions (or gaps) of 20 percent or less as compared to the reference sequence (which does not comprise additions or deletions) for optimal alignment of the two sequences.

"Substantial identity" or "substantially identical" refers to a polynucleotide or polypeptide sequence that has at least 70% sequence identity, at least 80% sequence identity, at least 85% sequence identity, at least 90% sequence identity, at least 95% sequence identity, or at least 99% sequence identity, as compared to a reference sequence over a comparison window of at least 20 nucleoside or amino acid residue positions, frequently over a window of at least 30-50 positions, wherein the percentage of sequence identity is calculated by comparing the reference sequence to a sequence that includes deletions or additions which total 20 percent or less of the reference sequence over the window of comparison.

"Corresponding to," "reference to," or "relative to" when used in the context of the numbering of a given amino acid or polynucleotide sequence refers to the numbering of the residues of a specified reference sequence when the given amino acid or polynucleotide sequence is compared to the reference sequence. In other words, the residue number or residue position of a given polymer is designated with respect to the reference sequence rather than by the actual numerical position of the residue within the given amino acid or polynucleotide sequence. For example, a given amino acid sequence, such as that of an engineered imine reductase, can be aligned to a reference sequence by introducing gaps to optimize residue matches between the two sequences. In these cases, although the gaps are present, the numbering of the residue in the given amino acid or polynucleotide sequence is made with respect to the reference sequence to which it has been aligned.

"Isolated" as used herein in reference to a molecule means that the molecule (e.g., cannabinoid, polynucleotide, polypeptide) is substantially separated from other compounds that naturally accompany it, e.g., protein, lipids, and polynucleotides. The term embraces nucleic acids which have been removed or purified from their naturally-occurring environment or expression system (e.g., host cell or in vitro synthesis).

"Substantially pure" refers to a composition in which a desired molecule is the predominant species present (i.e., on a molar or weight basis it is more abundant than any other individual macromolecular species in the composition), and is generally a substantially purified composition when the object species comprises at least about 50 percent of the macromolecular species present by mole or % weight.

"Recovered" as used herein in relation to an enzyme, protein, or cannabinoid compound, refers to a more or less pure form of the enzyme, protein, or cannabinoid.

Engineered Genes Encoding Recombinant Polypeptides with OAC Activity

The present disclosure provides engineered genes that encode recombinant polypeptides having olivetolic acid cyclase (OAC) activity, a carbon-sulfur lyase enzyme of class E.C. 4.4.1.26. When integrated into a recombinant host cell (e.g., *S. cerevisiae*) having a pathway capable of producing a tetraketide-CoA, such as 3,5,7-trioxododecanoyl-CoA, the presence of an engineered OAC gene expressing the recombinant polypeptides can result in the production of the cyclized aromatic cannabinoid precursor product, such as olivetolic acid (OA) with an enhanced yield. In at least one embodiment, when an engineered gene of the present disclosure is integrated in a recombinant host cell capable of producing the C-12 tetraketide-CoA compound, 3,5,7-trioxododecanoyl-CoA, the cyclized aromatic product OA, is produced by the host cell in greater yield relative to a comparable recombinant host cell integrated with a codon-optimized version of the gene encoding the wild-type *Cannabis sativa* OAC polypeptide of SEQ ID NO: 6 or 20.

The activity of the CsOAC polypeptide in the cannabinoid pathway of *C. sativa* is the cyclization of the C-12 tetraketide-CoA substrate, 3,5,7-trioxododecanoyl-CoA (compound (2)) to form the cannabinoid precursor product, olivetolic acid (compound (1)), as shown in Scheme 1.

Scheme 1

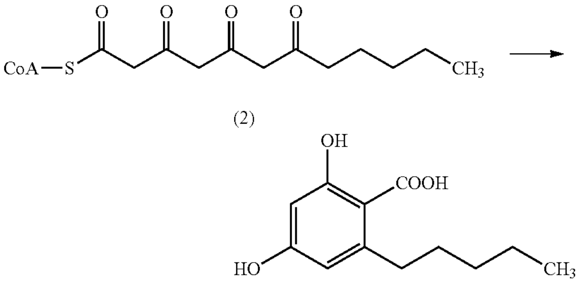

(2)

(1)

The engineered genes encoding recombinant polypeptides of the present disclosure exhibit the exemplary OAC activity of Scheme 1 when incorporated and expressed in a recombinant host cell comprising a pathway that produces the tetraketide-CoA cannabinoid precursor. Specifically, the recombinant polypeptides have OAC activity capable of hydrolyzing the CoA-thiol of 3,5,7-trioxododecanoyl-CoA (compound (2)) and cyclizing the tetraketide to form the cannabinoid precursor product, OA (compound (1)). The OAC activity resulting in the conversion of the tetraketide-CoA cannabinoid precursor substrate (e.g., compound (2)) to the cannabinoid precursor product (e.g., compound (1)) as in Scheme 1, when carried out by the engineered genes of the present disclosure integrated in a recombinant host cell results in a yield of OA the is comparable to or increased relative to a control recombinant host cell strain integrated with the yeast codon-optimized genes of either SEQ ID NO: 5 or 19 that encode the wild-type CsOAC polypeptide of SEQ ID NO: 6 or 20. Without intending to be bound by any particular theory or mechanism, the altered yield of the cyclized cannabinoid precursor product is correlated with the one or more residue differences in recombinant polypeptides of the present disclosure, as compared to the CsOAC amino acid sequence of SEQ ID NO: 6 or 20. Exemplary engineered genes and encoded recombinant polypeptides with OAC activity that exhibit the unexpected and surprising technical effect of comparable or increased cannabinoid or cannabinoid precursor yield when integrated in a recombinant host cell are summarized in Table 3 below (as well as in the following Examples and the accompanying Sequence Listing).

TABLE 3

Recombinant polypeptides with olivetolic acid cyclase (OAC) activity

| aa differences relative to CsOAC[1] | NT SEQ ID NO: | AA SEQ ID NO: |
|---|---|---|
| T16Q | 21 | 22 |
| P76V | 23 | 24 |
| L9V | 25 | 26 |
| K44P | 27 | 28 |
| I74S | 29 | 30 |
| H57G | 31 | 32 |
| K49R | 33 | 34 |
| E14G | 35 | 36 |
| D71G | 37 | 38 |
| K91E | 39 | 40 |
| L9V, E21V | 41 | 42 |
| T26N, K49R, D71G, K91E | 43 | 44 |
| K12L | 45 | 46 |
| A18S | 47 | 48 |
| L9V, E14G, T16Q, V40G, K49R, D71G, 174M, K91E | 49 | 50 |
| E17G, K44P | 51 | 52 |
| I94K | 53 | 54 |
| E64K | 55 | 56 |
| I33E, K49R, D71G, K91E | 57 | 58 |
| L9V, E21V, G82A | 59 | 60 |
| A77E | 61 | 62 |
| L9V, E14G, T16Q, K49R, D71G, K91E | 63 | 64 |
| T62G | 65 | 66 |
| F11L | 67 | 68 |
| S87K | 69 | 70 |
| D83R | 71 | 72 |
| L9V, E14G, T16Q, K49R, D71G, V84M, K91E | 73 | 74 |
| G82R | 75 | 76 |
| K25R, K49R, D71G, K91E | 77 | 78 |
| L9V, E14G, T16Q, A36E, K49R, D71G, K91E | 79 | 80 |
| K49R, D71G, K91E | 81 | 82 |
| L9V, E14G, T16Q, K49R, D71G, K91E | 83 | 84 |
| L9V, E14G, K49R, D71G, K91E | 85 | 86 |
| L9V, E14G, K49R, H57G, D71G, K91E | 87 | 88 |
| K25S, K49R, D71G, K91E | 89 | 90 |
| L9V, E14G, T16Q, K49R, D71G, K91E | 91 | 92 |
| L9V, E14G, K49R, D71G, K91E, Y97F | 93 | 94 |
| L9V, E14G, K49R, D71G, K91E, Y55W | 95 | 96 |
| L9I, E14G, K49R, D71G, K91E | 97 | 98 |
| L9V, E14G, K49R, D71G, K91E, V66L | 99 | 100 |
| L9V, E14G, V31S, K49R, D71G, K91E | 101 | 102 |
| L9V, E14G, K49R, D71G, K91E, V31M | 103 | 104 |
| L9V, E14G, K49R, D71G, K91E, V31E | 105 | 106 |
| L9V, E14G, K49R, D71G, K91E, V28C | 107 | 108 |
| L9V, E14G, K49R, D71G, K91E, T68S | 109 | 110 |
| L9V, E14G, K49R, D71G, K91E, T68Q | 111 | 112 |
| L9V, E14G, K49R, D71G, K91E, T68M | 113 | 114 |
| L9V, E14G, K49R, D71G, K91E, T68G | 115 | 116 |
| L9V, E14G, K49R, D71G, K91E, T68E | 117 | 118 |
| L9V, E14G, K49R, D71G, K91E, T68A | 119 | 120 |
| L9V, E14G, K49R, D71G, K91E, N29G | 121 | 122 |
| L9V, E14G, K49R, D71G, K91E, L6F | 123 | 124 |
| L9V, E14G, K49R, D71G, K91E, K25G, H78P | 125 | 126 |
| L9V, E14G, K49R, D71G, K91E, I74V | 127 | 128 |
| L9V, E14G, K49R, D71G, K91E, I74T | 129 | 130 |
| L9V, E14G, K49R, D71G, K91E, I74M | 131 | 132 |
| L9V, E14G, K49R, D71G, K91E, I74L | 133 | 134 |
| L9V, E14G, K49R, D71G, K91E, I74G | 135 | 136 |
| L9V, E14G, K49R, D71G, K91E, I33V | 137 | 138 |
| L9V, E14G, K49R, D71G, K91E, I33D | 139 | 140 |
| L9V, E14G, K49R, D71G, K91E, E64D | 141 | 142 |
| L9V, E14G, K49R, D71G, K91E, E53S | 143 | 144 |
| L9V, E14G, K49R, D71G, K91E, E53R, V84I | 145 | 146 |
| L9V, E14G, K49R, D71G, K91E, E53R | 147 | 148 |
| L9V, E14G, K49R, D71G, K91E, E53L | 149 | 150 |
| L9V, E14G, K49R, D71G, K91E, E53H | 151 | 152 |
| L9V, E14G, K49R, D71G, K91E, E53F | 153 | 154 |
| L9V, E14G, K49R, D71G, K91E, E53A | 155 | 156 |
| L9V, E14G, K49R, D71G, K91E, E52R | 157 | 158 |
| L9V, E14G, K49R, D71G, K91E, E52Q | 159 | 160 |
| L9V, E14G, K49R, D71G, K91E, D45V | 161 | 162 |
| L9V, E14G, K49R, D71G, K91E, A2G, I74N | 163 | 164 |
| L9V, E14G, K49R, E53S, D71G, G80K, K91E | 165 | 166 |

TABLE 3-continued

Recombinant polypeptides with olivetolic acid cyclase (OAC) activity

| aa differences relative to CsOAC[1] | NT SEQ ID NO: | AA SEQ ID NO: |
|---|---|---|
| L9V, E14G, K49R, E53S, T68H, D71G, K91E | 167 | 168 |
| L9V, E14G, K49R, E53S, D71G, I74S, K91E | 169 | 170 |
| L9V, E14G, K25D, K49R, E53S, D71G, K91E | 171 | 172 |
| L9V, E14G, K49R, E53S, D71G, S87H, K91E | 173 | 174 |
| L9V, E14G, K49R, E53S, T68C, D71G, K91E | 175 | 176 |
| L9V, E14G, K49R, E53S, D71G, F88Y, K91E | 177 | 178 |
| L9V, E14G, K49R, E53S, D71G, I74K, K91E | 179 | 180 |
| L9V, E14G, Y41Q, K49R, E53S, D71G, K91E | 181 | 182 |
| L9V, E14G, Y41T, K49R, E53S, D71G, K91E | 183 | 184 |
| L9V, E14G, K49R, E53S, T68G, D71G, K91E | 185 | 186 |
| L9V, E14G, K49R, E53S, D71G, D83R, K91E | 187 | 188 |
| L9V, E14G, Y41S, K49R, E53S, D71G, K91E | 189 | 190 |
| L9V, E14G, E21L, K49R, D71G, K91E | 191 | 192 |
| L9V, E14G, K49R, E52S, D71G, K91E | 193 | 194 |
| L9V, E14G, K49R, D71G, D83K, K91E | 195 | 196 |
| L9V, E14G, K49R, D71G, K91E, T98V | 197 | 198 |
| L9V, E14G, K49R, D71G, 174R, K91E | 199 | 200 |
| A2V, L9V, E14G, K49R, D71G, K91E | 201 | 202 |
| L9V, E14G, K49R, T68C, D71G, K91E | 203 | 204 |
| L9V, E14G, K49R, D71G, G82A, K91E | 205 | 206 |
| L9V, E14G, K49R, T68A, D71G, K91E | 207 | 208 |
| L9V, E14G, T47S, K49R, D71G, 174Q, K91E | 209 | 210 |
| L9V, E14G, T47G, K49R, D71G, K91E | 211 | 212 |
| L9V, E14G, K49R, D71G, F88W, K91E | 213 | 214 |
| L9V, E14G, V31A, K49R, D71G, K91E | 215 | 216 |
| A2S, L9V, E14G, K49R, D71G, K91E | 217 | 218 |
| L9V, E14G, A18E, K49R, D71G, K91E | 219 | 220 |
| L9V, E14G, K49R, D71G, R86S, K91E | 221 | 222 |
| L9V, E14G, K49R, D71G, I74H, K91E | 223 | 224 |
| L9V, E14G, K49R, D71G, I74Q, K91E | 225 | 226 |
| L9V, E14G, T47S, K49R, D71G, K91E | 227 | 228 |
| L9V, E14G, K49R, D71G, I74N, K91E | 229 | 230 |
| L9V, E14G, V46L, K49R, E53S, D71G, K91E | 231 | 232 |
| A2G, L9I, K25R | 233 | 234 |
| L9I, E53S, I94K | 235 | 236 |
| A36E | 237 | 238 |
| E53H, E64D | 239 | 240 |
| L9I, K25R, A36E, E53H, I94K | 241 | 242 |
| A2G, L9I, K25R, E53S, E64D, I94K | 243 | 244 |
| K25S, A36E | 245 | 246 |
| L9I, T16Q, K25R, E53S, E64D | 247 | 248 |
| K25S, I94K | 249 | 250 |
| A2G, L9I, K25G | 251 | 252 |
| E53A | 253 | 254 |
| A2G, L9V, T16P | 255 | 256 |
| E53A, E64D, I94K | 257 | 258 |
| L9I, K25S, A36E, E64D, I94K | 259 | 260 |
| L9I, K25S, A36E, E53R, I94K | 261 | 262 |
| K25E, A36E, E64D, I94K | 263 | 264 |
| K25R, E64D | 265 | 266 |
| K25R, A36E, E53S, E64D, I94K | 267 | 268 |
| A2G, L9I, A36E, E53S, E64D, I94K | 269 | 270 |
| A2G, L9V, Y27F, E52R, V66L, V84M | 271 | 272 |
| L9V, V66L | 273 | 274 |
| L9V, Y27F, V84M | 275 | 276 |
| A2G, L9V | 277 | 278 |
| L9I, Y27F, E53S, V66L, V84M | 279 | 280 |
| V66L, V84M | 281 | 282 |
| L9V, E52Q, V66L, P76V | 283 | 284 |
| L9I, Y27F, V66L, V84I | 285 | 286 |
| A2G, L9V, Y27F, V66L | 287 | 288 |
| Y27F | 289 | 290 |
| A2G, L9V, V66L, V84M | 291 | 292 |
| L9V, T26A, E52Q, P76V | 293 | 294 |
| L9V, E52R, V84M | 295 | 296 |
| L9V, Y27F, V66L, V84M | 297 | 298 |
| L9I, N29G, T62G, T68E, I94K | 299 | 300 |
| L9I, E14G, K44P, T68E, I94K | 301 | 302 |
| E14G, T68S, I94K | 303 | 304 |
| E14G, T68A, I94K | 305 | 306 |
| T62G, T68G, I94K | 307 | 308 |
| L9V, E14G, T68E, I94K | 309 | 310 |
| L9V, I94K | 311 | 312 |
| L9V, N29G, T68E, I94K | 313 | 314 |

TABLE 3-continued

Recombinant polypeptides with olivetolic acid cyclase (OAC) activity

| aa differences relative to CsOAC[1] | NT SEQ ID NO: | AA SEQ ID NO: |
|---|---|---|
| A2G, T16P, V31M, K49R, S87K | 315 | 316 |
| V31E, F63L, S87K | 317 | 318 |
| A2G, K49R | 319 | 320 |
| V31M, K49R, S87K | 321 | 322 |
| A2G, V31S, K49R, K91E | 323 | 324 |
| V31E, K49R, S87K | 325 | 326 |
| T16P, V31M, K49R | 327 | 328 |
| L9V, E14G, V31S, K49R, K91E | 329 | 330 |
| K12L, V31M, K49R | 331 | 332 |
| L9V, K91E | 333 | 334 |
| L9I, E14G, V40A, K49R | 335 | 336 |
| L9V, K49R, D71G, K91E | 337 | 338 |
| L9I, E14G, Y27F, D71G, K91E | 339 | 340 |
| E14G, K49R, D71G, K91E | 341 | 342 |
| L9I, Y27F, K91E | 343 | 344 |
| K49R, Y85F, K91E | 345 | 346 |
| L9I, E14G, D71G, K91E | 347 | 348 |
| L9V, K49R, K91E | 349 | 350 |
| L9I, E14G, K49R, D71G | 351 | 352 |
| E14G, Y27F, K49R | 353 | 354 |
| L9V, T16Q, K49R, K91E | 355 | 356 |
| L9I, K49R, K91E | 357 | 358 |
| L9V, E14G, Y27F, K49R, K91E | 359 | 360 |
| K49R, K91E | 361 | 362 |
| L9I, E14G, D71G | 363 | 364 |
| E14G, K49R, K91E | 365 | 366 |
| K49R, E64D, I74T | 367 | 368 |
| K12L, Y27F, K49R, I74M | 369 | 370 |
| A2G, Y27F, E64K, I74V | 371 | 372 |
| Y27F, K49R, E64D, I74V | 373 | 374 |
| Y27F, K49R, E64D, I74T | 375 | 376 |
| A2G, K49R, E64D, I74M | 377 | 378 |
| A2G, K49R, E64D, I74N | 379 | 380 |
| K49R, E64K, I74N | 381 | 382 |
| L9V, E14G, K25A, Q48P, I74N | 383 | 384 |
| K12L, K49R, I74V | 385 | 386 |
| Y27F, K49R, I74V | 387 | 388 |
| K49R, I74S | 389 | 390 |
| A2G, K12L, K49R, I74N | 391 | 392 |
| L9V, E14G, T47A, E64D, I74V | 393 | 394 |
| K12L, K49R, E64D, I74S | 395 | 396 |
| Y27F, K49R, I74N | 397 | 398 |
| A2G, E64K, I74M | 399 | 400 |
| V8I, L9I, I33V, K49R, T56S, D71T | 401 | 402 |
| V8I, L9I, I33D, K49R, T56S, I58V | 403 | 404 |
| V8I, L9I, K12N, K49R, Y55W, T56S | 405 | 406 |
| V8I, L9I, K12V, I33V, T56S, E64D | 407 | 408 |
| L9I, K12V, I33V, T56S, 158V, E64D | 409 | 410 |
| A2P, V81, L9I, E64D, T68S, R100G | 411 | 412 |
| V8I, K12V, T56S, I58V, E64D, Y97F | 413 | 414 |
| V31M, K49R, I58V, T62C, E64D, T68A | 415 | 416 |
| V8I, K49R, I58V, E64D, T68M, I74M | 417 | 418 |
| A36P, I58V, E64D, T68G, Q70K, I74M | 419 | 420 |
| E14G, A36Q, K49R, I58V, E64D, Q70K | 421 | 422 |
| A2P, V8I, L9I, I33V, E64D, I94K | 485 | 486 |
| V8I, L9I, A36S, Y55W, E64D, I94K | 487 | 488 |
| V8I, L9I, I33V, K49R, I58V, T62C | 489 | 490 |
| V8I, L9I, I33V, K49R, I58V, T62C | 491 | 492 |
| V8I, L9I, I33D, K49R, T56S, D71T | 493 | 494 |
| V8I, L9I, K12N, I33V, K49R, D71T | 495 | 496 |
| V8I, L9I, I33V, K49R, I58V, R100G | 497 | 498 |
| V8I, L9I, K12N, I33V, K49R, D71T | 499 | 500 |
| V8I, L9I, K49R, Y55W, I58V, R100G | 501 | 502 |
| V8I, L9I, I33V, K49R, T56S, R100G | 503 | 504 |
| V8I, L9I, I33V, A36L, K49R, I58V | 505 | 506 |
| L9I, I33V, A36Q, I58V, E64D, I94K | 507 | 508 |
| V8I, L9I, K10A, I33V, T56S, I58V | 509 | 510 |
| L9I, I33V, K49R, T56S, I58V, R100G | 511 | 512 |
| V8I, L9I, K12N, I33V, K49R, D71T | 513 | 514 |
| L9I, I33V, A36Q, I58V, E64D, I94K | 515 | 516 |
| V8I, L9I, K10A, N29D, I33V, I58V | 517 | 518 |
| L9I, I33V, K49R, T56S, I58V, R100G | 519 | 520 |
| V8I, L9I, I33D, T56S, I58V, E64D | 521 | 522 |
| V8I, L9I, I33D, K49R, T56S, D71T | 523 | 524 |

TABLE 3-continued

Recombinant polypeptides with olivetolic acid cyclase (OAC) activity

| aa differences relative to CsOAC[1] | NT SEQ ID NO: | AA SEQ ID NO: |
|---|---|---|
| V8I, L9I, I33D, K49R, T56S, D71T | 525 | 526 |
| L9I, A36Q, Y55W, I58V, E64D, I94K | 527 | 528 |
| V8I, L9I, I33V, T56S, I58V, Q70K | 529 | 530 |
| V8I, L9I, K49R, Y55W, T56S, R100G | 531 | 532 |
| V8I, L9I, I33D, K49R, T56S, D71T | 533 | 534 |
| V8I, L9I, K10A, N29D, I33V, T56S | 535 | 536 |
| V8I, L9I, K10A, N29D, I33V, T56S | 537 | 538 |
| A2P, V8I, L9I, Y55W, E64D, I94K | 539 | 540 |
| L9I, A36Q, Y55W, I58V, E64D, I94K | 541 | 542 |
| V8I, L9I, I33V, T56S, I58V, R100G | 543 | 544 |
| V8I, L9I, Y55W, T56S, I58V, R100G | 545 | 546 |
| L9I, A36Q, Y55W, I58V, E64D, I94K | 547 | 548 |
| V8I, L9I, K12N, T16Q, K49R, T56S | 549 | 550 |
| V8I, L9I, K49R, Y55W, I58V, T62C | 551 | 552 |
| A2P, V8I, L9I, T16Q, E64D, I94K | 553 | 554 |
| V8I, L9I, I33D, T56S, I58V, E64D | 555 | 556 |
| V8I, L9I, T16Q, A36F, K49R, I58V | 557 | 558 |
| V8I, I33V, K49R, T56S, I58V, R100G | 559 | 560 |
| V8I, L9I, T16Q, T56S, I58V, Q70K | 561 | 562 |
| V8I, L9I, T16Q, T56S, I58V, R100G | 563 | 564 |
| V8I, L9I, K10A, N29D, I33V, T56S | 565 | 566 |
| V8I, L9I, K10A, N29D, I33V, T56S | 567 | 568 |
| L9I, I33V, K49R, T56S, I58V, R100G | 569 | 570 |
| V8I, L9I, Y55W, T56S, I58V, R100G | 571 | 572 |
| L9I, A36Q, Y55W, I58V, E64D, I94K | 573 | 574 |
| V8I, L9I, K12V, I33V, T56S, I58V | 575 | 576 |
| V8I, L9I, T16Q, A36F, K49R, I58V | 577 | 578 |
| V8I, L9I, K12N, I33V, T56S, D71T | 579 | 580 |
| V8I, L9I, K49R, Y55W, T56S, R100G | 581 | 582 |
| V8I, L9I, I33V, A36S, T62C, E64D | 583 | 584 |
| V8I, K49R, Y55W, T56S, I58V, R100G | 585 | 586 |
| L9I, A36Q, I58V, E64D, T68S, I94K | 587 | 588 |
| V8I, L9I, T56S, I58V, T68S, R100G | 589 | 590 |
| V8I, L9I, K12V, T56S, E64D, T68S | 591 | 592 |
| L9I, A36Q, I58V, E64D, I94K, Y97F | 593 | 594 |
| V8I, L9I, V28C, K49R, T56S, I58V | 595 | 596 |
| V8I, L9I, K12V, I58V, E64D, T68G | 597 | 598 |
| V8I, L9I, A36S, E64D, I94K, Y97F | 599 | 600 |
| V8I, L9I, K12N, K49R, T68G, D71T | 601 | 602 |
| V8I, L9I, K49R, I58V, T62C, Y97F | 603 | 604 |
| V8I, L9I, V28C, K49R, T56S, D71T | 605 | 606 |
| V8I, L9I, K49R, I58V, T62C, Y97F | 607 | 608 |
| V8I, L9I, K10A, N29D, I58V, T68G | 609 | 610 |
| V8I, L9I, K49R, I58V, T68S, R100G | 611 | 612 |
| L9I, K49R, T56S, I58V, T68G, R100G | 613 | 614 |
| V8I, L9I, K12V, T56S, E64D, T68S | 615 | 616 |
| V8I, L9I, K10A, N29D, I58V, T68G | 617 | 618 |
| V8I, L9I, A36S, E64D, I94K, Y97F | 619 | 620 |
| V8I, L9I, K12N, K49R, T56S, Y97F | 621 | 622 |
| V8I, L9I, K12V, I58V, E64D, T68G | 623 | 624 |
| V8I, L9I, K12V, I58V, E64D, Y97F | 625 | 626 |
| V8I, L9I, T56S, I58V, T68S, R100G | 627 | 628 |
| V8I, L9I, K49R, I58V, T62C, T68G | 629 | 630 |
| V8I, L9I, K12V, T56S, E64D, T68S | 631 | 632 |
| V8I, K49R, T56S, I58V, T68S, R100G | 633 | 634 |
| V8I, L9I, T56S, I58V, T68G, Q70K | 635 | 636 |
| V8I, L9I, K49R, I58V, T62C, T68G | 637 | 638 |
| V8I, L9I, K12V, T56S, I58V, T68G | 639 | 640 |
| V8I, L9I, K12V, T56S, I58V, T68S | 641 | 642 |
| V8I, L9I, A36F, K49R, I58V, T68S | 643 | 644 |
| V8I, L9I, K49R, I58V, T62C, Y97F | 645 | 646 |
| V8I, L9I, A36F, K49R, I58V, Y97F | 647 | 648 |
| V8I, L9I, K12N, K49R, T68G, D71T | 649 | 650 |
| V8I, L9I, K12V, T56S, E64D, T68S | 651 | 652 |
| V8I, L9I, K49R, I58V, Y97F, R100G | 653 | 654 |
| V8I, L9I, A36F, K49R, I58V, Y97F | 655 | 656 |
| V8I, L9I, K12V, T56S, E64D, T68S | 657 | 658 |
| V8I, L9I, K10A, N29D, T56S, T68S | 659 | 660 |
| V8I, L9I, V28C, K49R, T56S, I58V | 661 | 662 |
| V8I, L9I, K10A, T56S, I58V, Y97F | 663 | 664 |
| V8I, L9I, K12V, E14G, K49R, E67S | 665 | 666 |
| L9I, A36S, K49R, E64D, T68M, I74M | 667 | 668 |
| L9I, Y41E, K49R, I58V, V66I, T68E | 669 | 670 |
| V8I, L9I, K12V, E14G, K49R, E67S | 671 | 672 |
| V8I, L9I, K12N, T16Q, K49R, I58V | 673 | 674 |
| V8I, L9I, K12V, E14G, K49R, E67S | 675 | 676 |
| V8I, L9I, K25N, K49R, I58V, T68S | 677 | 678 |
| V8, L9I, K49R, T56S, V66I, T68M | 679 | 680 |
| V8I, L9I, K12V, E14G, K49R, E67S | 681 | 682 |
| V8I, L9I, K25N, A36P, T68G, I74M | 683 | 684 |
| L9I, Y41E, K49R, I58V, V66I, T68E | 685 | 686 |
| V8I, L9I, K49R, E64D, Y97F, R100G | 687 | 688 |
| V8I, L9I, K12V, E14G, K49R, E67S | 689 | 690 |
| V8I, L9I, I33V, I58V, E64D, R100G | 691 | 692 |
| L9I, A36S, K49R, E64D, T68M, I74M | 693 | 694 |
| V8I, L9I, K49R, E64D, Y97F, R100G | 695 | 696 |
| V8I, L9I, Y41E, I58V, E64D, T68A | 697 | 698 |
| V8I, K12Q, V31M, V66I, T68S, I74M | 699 | 700 |
| V8I, L9I, Y41E, I58V, E64D, T68A | 701 | 702 |
| L9I, E14G, I58V, T62C, E64D, V66I | 703 | 704 |
| V8I, L9I, K49R, T56S, V66I, T68M | 705 | 706 |
| V8I, L9I, K25N, A36P, T68G, I74M | 707 | 708 |
| V8I, L9I, K25N, K49R, I58V, T68S | 709 | 710 |
| L9I, T16Q, K49R, I58V, E64D, R100G | 711 | 712 |
| V8I, K12Q, V31M, V66I, T68S, I74M | 713 | 714 |
| V8I, K12Q, I33V, K49R, I58V, I74M | 715 | 716 |
| V8I, L9I, K49R, E64D, Y97F, R100G | 717 | 718 |
| L9I, T16Q, K49R, I58V, E64D, R100G | 719 | 720 |
| L9I, E14G, I58V, T62C, E64D, V66I | 721 | 722 |
| V8I, L9I, K49R, E64D, Y97F, R100G | 723 | 724 |
| V8I, K12N, I33V, I58V, E64D, V66I | 725 | 726 |
| A2P, L9I, K25N, V31M, K49R, Y55W | 727 | 728 |
| V8I, L9I, K12N, T16Q, K49R, I58V | 729 | 730 |
| L9I, A36S, K49R, E64D, T68M, I74M | 731 | 732 |
| L9I, K49R, I58V, T68A, D71T, I94K | 733 | 734 |
| L9I, E14G, I58V, T62C, E64D, V66I | 735 | 736 |
| V8I, E14G, K49R, I58V, E64D, R100A | 737 | 738 |
| L9V, E14G, K49R, E53S, D71G, K91E | 739 | 740 |
| A2S, V8I, K49R, E53V, T56S, T68S | 741 | 742 |
| V8I, K12Q, V31M, V66I, T68S, I74M | 743 | 744 |
| V8I, K12Q, V31M, V66I, T68S, I74M | 745 | 746 |
| A2P, V8I, K49R, T62C, T68E, I74M | 747 | 748 |
| V8I, L9I, K12N, T16Q, K49R, I58V | 749 | 750 |
| V8I, L9I, I33V, K49R, T62C, E64D | 751 | 752 |
| V8I, K12Q, V31M, V66I, T68S, I74M | 753 | 754 |
| L9I, E53V, I58V, E64D, T68S, I74M | 755 | 756 |
| V8I, V28C, A36S, K49R, T56S, V66I | 757 | 758 |
| V8I, K12Q, V31M, V66I, T68S, I74M | 759 | 760 |
| V8I, L9I, K49R, E64D, Y97F, R100G | 761 | 762 |
| V8I, L9I, I33V, I58V, E64D, R100G | 763 | 764 |
| V8I, E14G, K49R, I58V, E64D, R100A | 765 | 766 |
| V8I, L9I, K25N, A36P, T68G, I74M | 767 | 768 |
| V8I, V31M, E64D, T68Q, Q70K, D71T | 769 | 770 |
| L9I, K25N, A36Q, K49R, V66I, T68Q | 771 | 772 |
| L9I, K25N, A36Q, K49R, V66I, T68Q | 773 | 774 |
| V8I, K49R, E64D, T68S, E90D, I94K | 775 | 776 |
| V8I, A36S, T56S, T68S, E90D, I94K | 777 | 778 |
| L9I, K49R, T62C, E64D, T68G, I74M | 779 | 780 |
| K12N, T56S, I58V, V66I, T68A, D71T | 781 | 782 |
| L9I, I33V, Q48M, I58V, E64D, I74M | 783 | 784 |
| L9I, V31M, K49R, N50Y, T68S, I74M | 785 | 786 |
| V8I, K25N, I33V, K49R, E64D, I74M | 787 | 788 |
| L9I, A18S, K25N, K49R, I58V, S87P | 789 | 790 |
| L9I, E22L, K49R, E64D, I74M, Y97F | 791 | 792 |
| V8I, K49R, E64D, T68S, E90D, I94K | 793 | 794 |
| L9I, E22L, V46I, E64D, I74M, Y97F | 795 | 796 |
| V8I, A18S, K49R, E64D, V66I, I94K | 797 | 798 |
| L9I, E22L, K49R, E64D, I74M, Y97F | 799 | 800 |
| A2S, V8I, T56S, T62C, T68S, I74M | 801 | 802 |
| Y41E, K49R, T56S, I58V, V66I, T68A | 803 | 804 |
| K10A, K49R, I58V, E64D, V66I, T68E | 805 | 806 |
| K12N, A18S, K49R, I58V, V66I, I74M | 807 | 808 |
| K49R, I58V, T62C, T68E, D71T, I74M | 809 | 810 |
| I33V, K49R, T62C, E64D, V661, I74M | 811 | 812 |
| T16Q, K25N, A36Q, K49R, V661, I74M | 813 | 814 |
| A2P, I58V, E64D, E67S, T68Q, R100G | 815 | 816 |
| I33V, K49R, T62C, E64D, V661, I74M | 817 | 818 |
| K49R, I58V, T68A, D71T, I74M, R100G | 819 | 820 |

TABLE 3-continued

Recombinant polypeptides with olivetolic acid cyclase (OAC) activity

| aa differences relative to CsOAC[1] | NT SEQ ID NO: | AA SEQ ID NO: |
|---|---|---|
| K25N, K49R, I58V, E64D, V66I, T68S | 821 | 822 |
| A36Q, K49R, I58V, E64D, V66I, K91E | 823 | 824 |
| K12N, A18S, K49R, I58V, V661, I74M | 825 | 826 |
| E21V, A36Q, I58V, V66I, E67S, I74M | 827 | 828 |
| A2P, E14G, Q48C, I58V, E64D, V66I | 829 | 830 |
| A2P, K12V, T16Q, K49R, I58V, V66I | 831 | 832 |
| A2P, K12V, T16Q, K49R, I58V, V66I | 833 | 834 |
| I33V, K49R, T62C, E64D, V66I, I74M | 835 | 836 |
| A2P, V31M, 158V, T62C, E64D, T68S | 837 | 838 |
| A36P, I58V, E67S, T68S, I74M, R100G | 839 | 840 |
| F23I, K49R, V66I, T68Q, Q70A, I74M | 841 | 842 |
| E22L, V31M, A36S, V66I, T68S, I74M | 843 | 844 |
| A36S, K49R, I58C, E64D, V66I, T68S | 845 | 846 |
| T16Q, A36Q, Q48H, I58V, E64D, I74M | 847 | 848 |
| K25N, K49R, Y55W, I58V, E64D, I74M | 849 | 850 |
| A36S, Q48C, E64D, T68E, I74M, S87P | 851 | 852 |
| K49R, V66I, T68Q, D71T, I74M, I94K | 853 | 854 |
| A2P, V8I, L9V, E64D, T68S, R100G | 855 | 856 |
| A2P, V8I, L9T, E64D, T68S, R100G | 857 | 858 |
| A2P, V8I, L9C, E64D, T68S, R100G | 859 | 860 |
| A2P, V8I, L9G, E64D, T68S, R100G | 861 | 862 |
| A2P, V8I, L9A, E64D, T68S, R100G | 863 | 864 |
| A2P, V8I, L9M, E64D, T68S, R100G | 865 | 866 |
| A2P, V8I, L9F, E64D, T68S, R100G | 867 | 868 |
| A2P, V8I, L9S, E64D, T68S, R100G | 869 | 870 |
| V8I, K49G, I58V, E64D, T68M, I74M | 871 | 872 |
| V8I, K49A, I58V, E64D, T68M, I74M | 873 | 874 |
| V8I, K49H, I58V, E64D, T68M, I74M | 875 | 876 |
| V8I, K49C, I58V, E64D, T68M, I74M | 877 | 878 |
| V8I, K49T, I58V, E64D, T68M, I74M | 879 | 880 |
| V8I, K49V, I58V, E64D, T68M, I74M | 881 | 882 |
| V8I, K49S, I58V, E64D, T68M, I74M | 883 | 884 |
| V8I, K49N, I58V, E64D, T68M, I74M | 885 | 886 |
| V8I, K49P, I58V, E64D, T68M, I74M | 887 | 888 |
| V8I, K49L, I58V, E64D, T68M, I74M | 889 | 890 |

[1]Amino acid differences relative to the wild-type CsOAC sequence of SEQ ID NO: 6 or 20 denoted by standard format of single letter amino acid and position number followed by substituted amino acid in single-letter-e.g., "179C".

[1]Amino acid differences relative to the wild-type CsOAC sequence of SEQ ID NO: 6 or 20 denoted by standard format of single letter amino acid and position number followed by substituted amino acid in single-letter-e.g., "179C".

In at least one embodiment, the recombinant polypeptides having OAC activity encoded by the engineered genes of the present disclosure have one or more residue differences as compared to the wild-type CsOAC polypeptide of SEQ ID NO: 6 or 20. In some embodiments, the recombinant polypeptides have one or more residue differences at residue positions selected from A2, L6, V8, L9, K10, F11, K12, E14, T16, E17, A18, E21, E22, F23, K25, T26, Y27, V28, N29, V31, I33, A36, V40, Y41, K44, D45, V46, T47, Q48, K49, N50, E52, E53, Y55, T56, H57, I58, T62, T62, E64, V66, T68, Q70, D71, I74, P76, A77, H78, G80, G82, D83, V84, Y85, R86, S87, F88, E90, K91, I94, Y97, T98, and R100.

In at least one embodiment, the polypeptide comprises an amino acid sequence of at least 80% identity to SEQ ID NO: 6, and an amino acid residue difference as compared to SEQ ID NO: 6 at each of a combination of six positions, wherein the combination of six positions are selected from the combinations listed in Table 4.

TABLE 4

Specific Combinations of Six Positions Amino Acid Residue Differences (relative to SEQ ID NO: 6 or 20)

| | |
|---|---|
| A2, V8, L9, E64, T68, R100 | V8, K49, I58, E64, T68, I74 |
| A2, I58, E64, E67, T68, R100 | V8, L9, T16, T56, I58, R100 |
| A2, K12, T16, K49, I58, V66 | V8, L9, T56, I58, T68, Q70 |

TABLE 4-continued

Specific Combinations of Six Positions Amino Acid Residue Differences (relative to SEQ ID NO: 6 or 20)

| | |
|---|---|
| A2, L9, E14, K49, D71, K91 | V8, L9, T56, I58, T68, R100 |
| A2, L9, K25, V31, K49, Y55 | V8, L9, V28, K49, T56, D71 |
| A2, V31, I58, T62, E64, T68 | V8, L9, V28, K49, T56, I58 |
| A2, V8, K49, E53, T56, T68 | V8, L9, Y41, I58, E64, T68 |
| A2, V8, K49, T62, T68, I74 | V8, L9, Y55, T56, I58, R100 |
| A2, E14, Q48, I58, E64, V66 | V8, V28, A36, K49, T56, V66 |
| A2, V8, L9, I33, E64, I94 | V8, V31, E64, T68, Q70, D71 |
| A2, V8, L9, T16, E64, I94 | L9, A18, K25, K49, I58, S87 |
| A2, V8, L9, Y55, E64, I94 | L9, A36, I58, E64, I94, Y97 |
| A2, V8, T56, T62, T68, I74 | L9, A36, I58, E64, T68, I94 |
| L6, L9, E14, K49, D71, K91 | L9, A36, K49, E64, T68, I74 |
| V8, A18, K49, E64, V66, I94 | L9, A36, Y55, I58, E64, I94 |
| V8, A36, T56, T68, E90, I94 | L9, E14, A18, K49, D71, K91 |
| V8, E14, K49, I58, E64, R100 | L9, E14, D45, K49, D71, K91 |
| V8, I33, K49, T56, I58, R100 | L9, E14, E21, K49, D71, K91 |
| V8, K12, I33, I58, E64, V66 | L9, E14, I33, K49, D71, K91 |
| V8, K12, I33, K49, I58, I74 | L9, E14, I58, T62, E64, V66 |
| V8, K12, T56, I58, E64, Y97 | L9, E14, K49, D71, D83, K91 |
| V8, K12, V31, V66, T68, I74 | L9, E14, K49, D71, F88, K91 |
| V8, K25, I33, K49, E64, I74 | L9, E14, K49, D71, G82, K91 |
| V8, K49, E64, T68, E90, I94 | L9, E14, K49, D71, I74, K91 |
| V8, L9, T16, T56, I58, Q70 | L9, E14, K49, D71, K91, T98 |
| V8, K49, T56, I58, T68, R100 | L9, E14, K49, D71, K91, Y97 |
| V8, K49, Y55, T56, I58, R100 | L9, E14, K49, D71, R86, K91 |
| V8, L9, A36, E64, I94, Y97 | L9, E14, K49, E52, D71, K91 |
| V8, L9, A36, K49, I58, T68 | L9, E14, K49, E53, D71, K91 |
| V8, L9, A36, K49, I58, Y97 | L9, E14, K49, E64, D71, K91 |
| V8, L9, A36, Y55, E64, I94 | L9, E14, K49, H57, D71, K91 |
| V8, L9, I33, A36, K49, I58 | L9, E14, K49, T68, D71, K91 |
| V8, L9, I33, A36, T62, E64 | L9, E14, K49, V66, D71, K91 |
| V8, L9, I33, I58, E64, R100 | L9, E14, K49, Y55, D71, K91 |
| V8, L9, I33, K49, I58, R100 | L9, E14, N29, K49, D71, K91 |
| V8, L9, I33, K49, I58, T62 | L9, E14, T16, K49, D71, K91 |
| V8, L9, I33, K49, T56, D71 | L9, E14, T47, K49, D71, K91 |
| V8, L9, I33, K49, T56, I58 | L9, E14, V28, K49, D71, K91 |
| V8, L9, I33, K49, T56, R100 | L9, E14, V31, K49, D71, K91 |
| V8, L9, I33, K49, T62, E64 | L9, E22, K49, E64, I74, Y97 |
| V8, L9, I33, T56, I58, E64 | L9, E22, V46, E64, I74, Y97 |
| V8, L9, I33, T56, I58, Q70 | L9, E53, I58, E64, T68, I74 |
| V8, L9, I33, T56, I58, R100 | L9, I33, A36, I58, E64, I94 |
| V8, L9, K10, I33, T56, I58 | L9, I33, K49, T56, I58, R100 |
| V8, L9, K10, N29, I33, I58 | L9, I33, Q48, I58, E64, I74 |
| V8, L9, K10, N29, I33, T56 | L9, K12, I33, T56, I58, E64 |
| V8, L9, K10, N29, I58, T68 | L9, K25, A36, K49, V66, T68 |
| V8, L9, K10, N29, T56, T68 | L9, K49, I58, T68, D71, I94 |
| V8, L9, K10, T56, I58, Y97 | L9, K49, T56, I58, T68, R100 |
| V8, L9, K12, E14, K49, E67 | L9, K49, T62, E64, T68, I74 |
| V8, L9, K12, I33, K49, D71 | L9, T16, K49, I58, E64, R100 |
| V8, L9, K12, I33, T56, D71 | L9, T16, T26, K49, D71, K91 |
| V8, L9, K12, I33, T56, E64 | L9, V31, K49, N50, T68, I74 |
| V8, L9, K12, I33, T56, I58 | L9, Y41, K49, I58, V66, T68 |
| V8, L9, K12, I58, E64, T68 | K10, K49, I58, E64, V66, T68 |
| V8, L9, K12, I58, E64, Y97 | K12, A18 K49, I58, V66, I74 |
| V8, L9, K12, K49, T56, Y97 | K12, T56, I58, V66, T68, D71 |
| V8, L9, K12, K49, T68, D71 | E14, A36, K49, I58, E64, Q70 |
| V8, L9, K12, K49, Y55, T56 | T16, A36, Q48, I58, E64, I74 |
| V8, L9, K12, T16, K49, I58 | T16, K25, A36, K49, V66, I74 |
| V8, L9, K12, T16, K49, T56 | E21, A36, I58, V66, E67, I74 |
| V8, L9, K12, T56, E64, T68 | E22, V31, A36, V66, T68, I74 |
| V8, L9, K12, T56, I58, T68 | F23, K49, V66, T68, Q70, I74 |
| V8, L9, K25, A36, T68, I74 | K25, K49, I58, E64, V66, T68 |
| V8, L9, K25, K49, I58, T68 | K25, K49, Y55, I58, E64, I74 |
| V8, L9, K49, E64, Y97, R100 | V31, K49, I58, T62, E64, T68 |
| V8, L9, K49, I58, T62, T68 | I33, K49, T62, E64, V66, I74 |
| V8, L9, K49, I58, T62, T68 | A36, I58, E64, T68, Q70, I74 |
| V8, L9, K49, I58, T62, Y97 | A36, I58, E67, T68, I74, R100 |
| V8, L9, K49, I58, T68, R100 | A36, K49, I58, E64, V66, K91 |
| V8, L9, K49, I58, Y97, R100 | A36, K49, I58, E64, V66, T68 |
| V8, L9, K49, T56, V66, T68 | A36, Q48, E64, T68, I74, S87 |
| V8, L9, K49, Y55, I58, R100 | Y41, K49, T56, I58, V66, T68 |
| V8, L9, K49, Y55, I58, T62 | K49, I58, T62, T68, D71, I74 |
| V8, L9, K49, Y55, T56, R100 | K49, I58, T68, D71, I74, R100 |
| V8, L9, T16, A36, K49, I58 | K49, V66, T68, D71, I74, I94 |

In at least one embodiment, the amino acid residue differences are selected from A2G, A2S, A2P, A2V, L6F, V8I, L9A, L9F, L9G, L9I, L9M, L9S, L9V, K10A, F11L, K12L, K12N, K12Q, K12V, E14G, T16P, T16Q, E17G, A18E, A18S, E21L, E21V, E22L, F23I, K25D, K25G, K25E, K25N, K25R, K25S, T26A, T26N, Y27F, V28C, N29D, N29G, V31A, V31E, V31M, V31S, I33D, I33E, I33V, A36E, A36F, A36L, A36Q, A36S, V40A, V40G, Y41E, Y41Q, Y41S, Y41T, K44P, D45V, V46I, V46L, T47A, T47G, T47S, T47S, Q48C, Q48H, Q48M, Q48P, K49A, K49C, K49G, K49H, K49L, K49N, K49P, K49R, K49S, K49T, K49V, N50Y, E52Q, E52R, E52S, E53A, E53F, E53H, E53L, E53R, E53S, E53V, Y55W, T56S, H57G, I58C, I58V, T62C, T62G, E64D, E64K, V66I, V66L, E67S, T68A, T68C, T68E, T68G, T68H, T68M, T68Q, T68S, Q70A, Q70K, D71G, I74G, I74H, I74K, I74L, I74M, I74N, I74Q, I74R, I74S, I74T, I74V, P76V, A77E, H78P, G80K, G82A, G82R, D83K, D83R, V84I, V84M, Y85F, R86S, S87H, S87K, S87P, F88W, F88Y, E90D, K91E, I94K, Y97F, T98V, R100A, and R100G.

It is contemplated that various combinations of the residue differences associated with comparable or increased OA production relative to the gene encoding the wild type CsOAC can be incorporated in further engineered genes to provide expression of further recombinant polypeptides having desirable functional characteristics in a recombinant host cell. In at least one embodiment, the desirable functional characteristic is increased titer produced of the cannabinoid precursor, OA, and/or the downstream cannabinoid compound, CBGA. Some exemplary combinations of residue differences are described in Tables 3, 5, 7, 8, 9, 10, 13, 14, and 15, and elsewhere herein. For example, the present disclosure provides a engineered genes encoding a recombinant polypeptide having combinations of two, three, four, five, six, or seven amino acid residue differences as compared to wild-type CsOAC (SEQ ID NO: 6 or 20) over a wide range of residue positions spanning the full length of the protein, including positions A2, L6, V8, L9, K10, F11, K12, E14, T16, E17, A18, E21, E22, F23, K25, T26, Y27, V28, N29, V31, I33, A36, V40, Y41, K44, D45, V46, T47, Q48, K49, N50, E52, E53, Y55, T56, H57, I58, T62, T62, E64, V66, T68, Q70, D71, I74, P76, A77, H78, G80, G82, D83, V84, Y85, R86, S87, F88, E90, K91, I94, Y97, T98, and R100. Combinations of amino acid residue differences relative to the wild-type CsOAC (SEQ ID NO: 6 or 20) exemplified in the recombinant OAC polypeptides of the present disclosure are provided in Table 3, and results demonstrating the OAC activity of these engineered polypeptides is provided in Tables 7, 8, 9, 10, 13, 14, and 15. Accordingly, in at least one embodiment, the engineered gene encodes a recombinant polypeptide having at least a combination of two, three, four, five, six, or seven amino acid residue differences relative to the polypeptide of SEQ ID NO: 6 or 20 selected from those combinations listed in Table 5 (below).

TABLE 5

| Specific Combinations Amino Acid Residue Differences (relative to SEQ ID NO: 6 or 20) | |
|---|---|
| A2G, K49R | L9V, K91E |
| A2G, L9V | L9V, V66L |
| A2G, E64K, I74M | L9V, E14G, K25A, Q48P, I74N |
| A2G, K12L, K49R, I74N | L9V, E14G, K25D, K49R, E53S, D71G, K91E |
| A2G, K49R, E64D, I74M | L9V, E14G, K25G, K49R, D71G, H78P, K91E |
| A2G, L9I, K25G | L9V, E14G, K49R, D71G, K91E |
| A2G, L9I, K25R | L9V, E14G, K49R, E53R, D71G, V84I, K91E |
| A2G, L9V, T16P | L9V, E14G, K49R, E53S, D71G, D83R, K91E |
| A2G, L9V, E14G, K49R, D71G, I74N, K91E | L9V, E14G, K49R, E53S, D71G, F88Y, K91E |
| A2G, L9V, V66L, V84M | L9V, E14G, K49R, E53S, D71G, G80K, K91E |
| A2G, L9V, Y27F, V66L | L9V, E14G, K49R, E53S, D71G, I74K, K91E |
| A2G, T16P, V31M, K49R, S87K | L9V, E14G, K49R, E53S, D71G, I74S, K91E |
| A2G, V31S, K49R, K91E | L9V, E14G, K49R, E53S, D71G, S87H, K91E |
| A2G, Y27F, E64K, I74V | L9V, E14G, K49R, E53S, T68C, D71G, K91E |
| E14G, K49R, K91E | L9V, E14G, K49R, E53S, T68G, D71G, K91E |
| E14G, K49R, D71G, K91E | L9V, E14G, K49R, E53S, T68H, D71G, K91E |
| E14G, T68A, I94K | L9V, E14G, T16Q, A36E, K49R, D71G, K91E |
| E14G, T68S, I94K | L9V, E14G, T16Q, K49R, D71G, V84M, K91E |
| E14G, Y27F, K49R | L9V, E14G, T47A, E64D, I74V |
| E17G, K44P | L9V, E14G, T47S, K49R, D71G, I74Q, K91E |
| E53A, E64D, I94K | L9V, E14G, T68E, I94K |
| E53H, E64D | L9V, E14G, V31S, K49R, K91E |
| K12L, K49R, I74V | L9V, E14G, V46L, K49R, E53S,D71G, K91E |
| K12L, K49R, E64D, I74S | L9V, E14G, Y27F, K49R, K91E |
| K12L, V31M, K49R | L9V, E14G, Y41Q, K49R, E53S, D71G, K91E |
| K12L, Y27F, K49R, I74M | L9V, E14G, Y41S, K49R, E53S, D71G, K91E |
| K25E, A36E, E64D, I94K | L9V, E14G, Y41T, K49R, E53S, D71G, K91E |
| K25R, A36E, E53S, E64D, I94K | L9V, E21V, G82A |
| K25R, E64D | L9V, E52Q, V66L, P76V |
| K25S, A36E | L9V, E52R, V84M |

TABLE 5-continued

| Specific Combinations Amino Acid Residue Differences (relative to SEQ ID NO: 6 or 20) | |
|---|---|
| K25S, I94K | L9V, K49R, K91E |
| K49R, I74S | L9V, K49R, D71G, K91E |
| K49R, K91E | L9V, N29G, T68E, I94K |
| K49R, E64D, I74T | L9V, T16Q, K49R, K91E |
| K49R, E64K, I74N | L9V, T26A, E52Q, P76V |
| K49R, Y85F, K91E | L9V, Y27F, V84M |
| L9I, E14G, D71G | L9V, Y27F, V66L, V84M |
| L9I, E14G, D71G, K91E | T16P, V31M, K49R |
| L9I, E14G, K44P, T68E, I94K | T62G, T68G, I94K |
| L9I, E14G, K49R, D71G | V31E, F63L, S87K |
| L9I, E14G, K49R, D71G, K91E | V31E, K49R, S87K |
| L9I, E14G, V40A, K49R | V31M, K49R, S87K |
| L9I, E14G, Y27F, D71G, K91E | V66L, V84M |
| L9I, E53S, I94K | Y27F, K49R, I74N |
| L9I, K25R, A36E, E53H, I94K | Y27F, K49R, I74V |
| L9I, K25S, A36E, E53R, I94K | Y27F, K49R, E64D, I74T |
| L9I, K25S, A36E, E64D, I94K | Y27F, K49R, E64D, I74V |
| L9I, K49R, K91E | L9I, Y27F, K91E |
| L9I, N29G, T62G, T68E, I94K | L9I, Y27F, E53S, V66L, V84M |
| L9I, T16Q, K25R, E53S, E64D | L9I, Y27F, V66L, V84I |
| L9V, I94K | L9V, E21V |
| A2P, V8I, L9V, E64D, T68S, R100G | V8I, K49R, I58V, E64D, T68M, I74M |
| A2P, I58V, E64D, E67S, T68Q, R100G | V8I, L9I, T56S, I58V, T68S, R100G |
| A2P, K12V, T16Q, K49R, I58V, V66I | V8I, L9I, V28C, K49R, T56S, D71T |
| A2P, L9I, K25N, V31M, K49R, Y55W | V8I, L9I, V28C, K49R, T56S, I58V |
| A2P, V31M, I58V, T62C, E64D, T68S | V8I, L9I, Y41E, I58V, E64D, T68A |
| A2P, V8I, K49R, T62C, T68E, I74M | V8I, L9I, Y55W, T56S, I58V, R100G |
| A2P, V8I, L9A, E64D, T68S, R100G | V8I, V28C, A36S, K49R, T56S, V66I |
| A2P, V8I, L9C, E64D, T68S, R100G | V8I, V31M, E64D, T68Q, Q70K, D71T |
| A2P, V8I, L9F, E64D, T68S, R100G | L9I, A18S, K25N, K49R, I58V, S87P |
| A2P, V8I, L9G, E64D, T68S, R100G | L9I, A36Q, I58V, E64D, I94K, Y97F |
| A2P, V8I, L9I, E64D, T68S, R100G | L9I, A36Q, I58V, E64D, T68S, I94K |
| A2P, V8I, L9I, I33V, E64D, I94K | L9I, A36Q, Y55W, I58V, E64D, I94K |
| A2P, V8I, L9I, T16Q, E64D, I94K | L9I, A36S, K49R, E64D, T68M, I74M |
| A2P, V8I, L9I, Y55W, E64D, I94K | L9I, E14G, I58V, T62C, E64D, V66I |
| A2P, V8I, L9M, E64D, T68S, R100G | L9I, E22L, K49R, E64D, I74M, Y97F |
| A2P, V8I, L9S, E64D, T68S, R100G | L9I, E22L, V46I, E64D, I74M, Y97F |
| A2P, V8I, L9T, E64D, T68S, R100G | L9I, E53V, I58V, E64D, T68S, I74M |
| A2P, E14G, Q48C, I58V, E64D, V66I | L9I, I33V, A36Q, I58V, E64D, I94K |
| A2S, L9V, E14G, K49R, D71G, K91E | L9I, I33V, K49R, T56S, I58V, R100G |
| A2S, V8I, K49R, E53V, T56S, T68S | L9I, I33V, Q48M, I58V, E64D, I74M |
| A2S, V8I, T56S, T62C, T68S, I74M | L9I, K12V, I33V, T56S, I58V, E64D |
| A2V, L9V, E14G, K49R, D71G, K91E | L9I, K25N, A36Q, K49R, V66I, T68Q |
| L6F, L9V, E14G, K49R, D71G, K91E | L9I, K49R, I58V, T68A, D71T, I94K |
| V8I, A18S, K49R, E64D, V66I, I94K | L9I, K49R, T56S, I58V, T68G, R100G |
| V8I, A36S, T56S, T68S, E90D, I94K | L9I, K49R, T62C, E64D, T68G, I74M |
| V8I, E14G, K49R, I58V, E64D, R100A | L9I, T16Q, K49R, I58V, E64D, R100G |
| V8I, E14G, K49R, I58V, E64D, R100A | L9I, V31M, K49R, N50Y, T68S, I74M |
| V8I, I33V, K49R, T56S, I58V, R100G | L9I, Y41E, K49R, I58V, V66I, T68E |
| V8I, K12N, I33V, I58V, E64D, V66I | L9V, E14G, A18E, K49R, D71G, K91E |
| V8I, K12Q, I33V, K49R, I58V, I74M | L9V, E14G, D45V, K49R, D71G, K91E |
| V8I, K12Q, V3IM, V66I, T68S, I74M | L9V, E14G, E21L, K49R, D71G, K91E |
| V8I, K12V, T56S, I58V, E64D, Y97F | L9V, E14G, I33D, K49R, D71G, K91E |
| V8I, K25N, I33V, K49R, E64D, I74M | L9V, E14G, I33V, K49R, D71G, K91E |
| V8I, K49A, I58V, E64D, T68M, I74M | L9V, E14G, K49R, D71G, D83K, K91E |
| V8I, K49C, I58V, E64D, T68M, I74M | L9V, E14G, K49R, D71G, F88W, K91E |
| V8I, K49G, I58V, E64D, T68M, I74M | L9V, E14G, K49R, D71G, G82A, K91E |
| V8I, K49H, I58V, E64D, T68M, I74M | L9V, E14G, K49R, D71G, I74G, K91E |
| V8I, K49L, I58V, E64D, T68M, I74M | L9V, E14G, K49R, D71G, I74H, K91E |
| V8I, K49N, I58V, E64D, T68M, I74M | L9V, E14G, K49R, D71G, I74L, K91E |
| V8I, K49P, I58V, E64D, T68M, I74M | L9V, E14G, K49R, D71G, I74M, K91E |
| V8I, K49R, E64D, T68S, E90D, I94K | L9V, E14G, K49R, D71G, I74N, K91E |
| V8I, K49R, T56S, I58V, T68S, R100G | L9V, E14G, K49R, D71G, I74Q, K91E |
| V8I, K49R, Y55W, T56S, I58V, R100G | L9V, E14G, K49R, D71G, I74R, K91E |
| V8I, K49S, I58V, E64D, T68M, I74M | L9V, E14G, K49R, D71G, I74T, K91E |
| V8I, K49T, I58V, E64D, T68M, I74M | L9V, E14G, K49R, D71G, I74V, K91E |
| V8I, K49V, I58V, E64D, T68M, I74M | L9V, E14G, K49R, D71G, K91E, T98V |
| V8I, L9I, A36F, K49R, I58V, T68S | L9V, E14G, K49R, D71G, K91E, Y97F |
| V8I, L9I, A36F, K49R, I58V, Y97F | L9V, E14G, K49R, D71G, R86S, K91E |
| V8I, L9I, A36S, E64D, I4K, Y97F | L9V, E14G, K49R, E52Q, D71G, K91E |
| V8I, L9I, A36S, Y55W, E64D, I94K | L9V, E14G, K49R, E52R, D71G, K91E |
| V8I, L9I, I33D, K49R, T56S, D71T | L9V, E14G, K49R, E52S, D71G, K91E |
| V8I, L9I, 133D, K49R, T56S, I58V | L9V, E14G, K49R, E53A, D71G, K91E |
| V8I, L9I, I33D, T56S, I58V, E64D | L9V, E14G, K49R, E53F, D71G, K91E |
| V8I, L9I, I33V, A36L, K49R, I58V | L9V, E14G, K49R, E53H, D71G, K91E |
| V8I, L9I, I33V, A36S, T62C, E64D | L9V, E14G, K49R, E53L, D71G, K91E |
| V8I, L9I, 133V, I58V, E64D, R100G | L9V, E14G, K49R, E53R, D71G, K91E |

TABLE 5-continued

| Specific Combinations Amino Acid Residue Differences (relative to SEQ ID NO: 6 or 20) | |
|---|---|
| V8I, L9I, I33V, K49R, I58V, R100G | L9V, E14G, K49R, E53S, D71G, K91E |
| V8I, L9I, I33V, K49R, I58V, T62C | L9V, E14G, K49R, E64D, D71G, K91E |
| V8I, L9I, I33V, K49R, T56S, D71T | L9V, E14G, K49R, H57G, D71G, K91E |
| V8I, L9I, I33V, K49R, T56S, R100G | L9V, E14G, K49R, T68A, D71G, K91E |
| V8I, L9I, I33V, K49R, T62C, E64D | L9V, E14G, K49R, T68C, D71G, K91E |
| V8I, L9I, I33V, T56S, I58V, Q70K | L9V, E14G, K49R, T68E, D71G, K91E |
| V8I, L9I, I33V, T56S, I58V, R100G | L9V, E14G, K49R, T68G, D71G, K91E |
| V8I, L9I, K10A, I33V, T56S, I58V | L9V, E14G, K49R, T68M, D71G, K91E |
| V8I, L9I, K10A, N29D, I33V, I58V | L9V, E14G, K49R, T68Q, D71G, K91E |
| V8I, L9I, K10A, N29D, I33V, T56S | L9V, E14G, K49R, T68S, D71G, K91E |
| V8I, L9I, K10A, N29D, I58V, T68G | L9V, E14G, K49R, V66L, D71G, K91E |
| V8I, L9I, K10A, N29D, T56S, T68S | L9V, E14G, K49R, Y55W, D71G, K91E |
| V8I, L9I, K10A, T56S, I58V, Y97F | L9V, E14G, N29G, K49R, D71G, K91E |
| V8I, L9I, K12N, I33V, K49R, D71T | L9V, E14G, T16Q, K49R, D71G, K91E |
| V8I, L9I, K12N, I33V, T56S, D71T | L9V, E14G, T47G, K49R, D71G, K91E |
| V8I, L9I, K12N, K49R, T56S, Y97F | L9V, E14G, T47S, K49R, D71G, K91E |
| V8I, L9I, K12N, K49R, T68G, D71T | L9V, E14G, V28C, K49R, D71G, K91E |
| V8I, L9I, K12N, K49R, Y55W, T56S | L9V, E14G, V31A, K49R, D71G, K91E |
| V8I, L9I, K12N, T16Q, K49R, I58V | L9V, E14G, V31E, K49R, D71G, K91E |
| V8I, L9I, K12N, T16Q, K49R, T56S | L9V, E14G, V31M, K49R, D71G, K91E |
| V8I, L9I, K12V, E14G, K49R, E67S | L9V, E14G, V31S, K49R, D71G, K91E |
| V8I, L9I, K12V, I33V, T56S, E64D | L9V, T16P, T26A, K49R, D71G, K91E |
| V8I, L9I, K12V, I33V, T56S, I58V | K10A, K49R, I58V, E64D, V66I, T68E |
| V8I, L9I, K12V, I58V, E64D, T68G | K12N, A18S, K49R, I58V, V66I, I74M |
| V8I, L9I, K12V, I58V, E64D, Y97F | K12N, T56S, I58V, V66I, T68A, D71T |
| V8I, L9I, K12V, T56S, E64D, T68S | E14G, A36Q, K49R, I58V, E64D, Q70K |
| V8I, L9I, K12V, T56S, I58V, T68G | T16Q, A36Q, Q48H, I58V, E64D, I74M |
| V8I, L9I, K12V, T56S, I58V, T68S | T16Q, K25N, A36Q, K49R, V66I, I74M |
| V8I, L9I, K25N, A36P, T68G, I74M | E21V, A36Q, I58V, V66I, E67S, I74M |
| V8I, L9I, K25N, K49R, I58V, T68S | E22L, V31M, A36S, V66I, T68S, I74M |
| V8I, L9I, K49R, E64D, Y97F, R100G | F23I, K49R, V66I, T68Q, Q70A, I74M |
| V8I, L9I, K49R, I58V, T62C, T68G | K25N, K49R, I58V, E64D, V66I, T68S |
| V8I, L9I, K49R, I58V, T62C, Y97F | K25N, K49R, Y55W, I58V, E64D, I74M |
| V8I, L9I, K49R, I58V, T68S, R100G | V31M, K49R, I58V, T62C, E64D, T68A |
| V8I, L9I, K49R, I58V, Y97F, R100G | I33V, K49R, T62C, E64D, V66I, I74M |
| V8I, L9I, K49R, T56S, V66I, T68M | A36P, I58V, E64D, T68G, Q70K, I74M |
| V8I, L9I, K49R, T56S, V66I, T68M | A36P, I58V, E67S, T68S, I74M, R100G |
| V8I, L9I, K49R, Y55W, I58V, R100G | A36Q, K49R, I58V, E64D, V66I, K91E |
| V8I, L9I, K49R, Y55W, I58V, T62C | A36S, K49R, I58C, E64D, V66I, T68S |
| V8I, L9I, K49R, Y55W, T56S, R100G | A36S, Q48C, E64D, T68E, I74M, S87P |
| V8I, L9I, T16Q, A36F, K49R, I58V | Y41E, K49R, T56S, I58V, V66I, T68A |
| V8I, L9I, T16Q, T56S, I58V, Q70K | K49R, I58V, T62C, T68E, D71T, 174M |
| V8I, L9I, T16Q, T56S, I58V, R100G | K49R, I58V, T68A, D71T, I74M, R100G |
| V8I, L9I, T56S, I58V, T68G, Q70K | K49R, V66I, T68Q, D71T, I74M, I94K |

Based on the correlation of recombinant polypeptide functional information provided herein with the sequence information provided in Tables 3, 7, 8, 9, 10, 13, 14, and 15, the accompanying Sequence Listing, one of ordinary skill can recognize that the present disclosure provides a range of recombinant polypeptides having OAC activity, wherein the polypeptide comprises an amino acid sequence comprising one or more of the amino acid differences or combinations of amino acid differences relative to CsOAC (SEQ ID NO: 6 or 20) disclosed in any one of SEQ ID NO: 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550, 552, 554, 556, 558, 560, 562, 564, 566, 568, 570, 572, 574, 576, 578, 580, 582, 584, 586, 588, 590, 592, 594, 596, 598, 600, 602, 604, 606, 608, 610, 612, 614, 616, 618, 620, 622, 624, 626, 628, 630, 632, 634, 636, 638, 640, 642, 644, 646, 648, 650, 652, 654, 656, 658, 660, 662, 664, 666, 668, 670, 672, 674, 676, 678, 680, 682, 684, 686, 688, 690, 692, 694, 696, 698, 700, 702, 704, 706, 708, 710, 712, 714, 716, 718, 720, 722, 724, 726, 728, 730, 732, 734, 736, 738, 740, 742, 744, 746, 748, 750, 752, 754, 756, 758, 760, 762, 764, 766, 768, 770, 772, 774, 776, 778, 780, 782, 784, 786, 788, 790, 792, 794, 796, 798, 800, 802, 804, 806, 808, 810, 812, 814, 816, 818, 820, 822, 824, 826, 828, 830, 832, 834, 836, 838, 840, 842, 844, 846, 848, 850, 852, 854, 856, 858, 860, 862, 864, 866, 868, 870, 872, 874, 876, 878, 880, 882, 884, 886, 888, and 890 (i.e., the sequences of even-numbered SEQ ID NOs: 22 to 890), and otherwise have at least 80%, at least 85% at least 90%, at least 95%, at least 97%, at least 98%, or at least 99% identity to a sequence selected from the group consisting of the even-numbered SEQ ID NOs: 22 to 890.

Thus, in at least one embodiment, a recombinant polypeptide of the present disclosure having OAC activity can have an amino acid sequence comprising one or more of the amino acid differences or sets of amino acid differences relative to CsOAC (SEQ ID NO: 6 or 20) disclosed in any one of the sequences of the even-numbered SEQ ID NOs: 22 to 890, and additionally have 1-2, 1-3, 1-4, 1-5, 1-6, 1-7, 1-8, 1-9, 1-10, 1-11, 1-12, 1-14, 1-15, 1-16, 1-18, or 1-20, residue differences at other residue positions. In some embodiments, the number of differences can be 1, 2, 3, 4, 5, 6, 7, 8, 9, 10, 11, 12, 14, 15, 16, 18, or 20 residue differences at the other residue positions.

In addition to the residue positions specified above, any of the engineered prenyltransferase polypeptides disclosed herein can further comprise other residue differences relative to the reference polypeptide of CsOAC (SEQ ID NO: 6 or 20) at other residue positions.

Residue differences at these other residue positions can provide for additional variations in the amino acid sequence without adversely affecting the ability of the recombinant polypeptide to carry out the desired biocatalytic conversion (e.g., conversion of compound (2) to compound (1). In some embodiments, the recombinant polypeptides can have additionally 1-2, 1-3, 1-4, 1-5, 1-6, 1-7, 1-8, 1-9, 1-10, 1-11, 1-12, 1-14, 1-15, 1-16, 1-18, or 1-20 residue differences at other amino acid residue positions as compared to SEQ ID NO: 6 or 20. In some embodiments, the number of differences can be 1, 2, 3, 4, 5, 6, 7, 8, 9, 10, 11, 12, 14, 15, 16, 18, or 20 residue differences at other residue positions. The residue difference at these other positions can include conservative changes or non-conservative changes. In some embodiments, the residue differences can comprise conservative substitutions and non-conservative substitutions as compared to the reference polypeptide of CsOAC (SEQ ID NO: 6 or 20).

In some embodiments, the recombinant polypeptides of the disclosure can be in the form of fusion polypeptides in which the engineered polypeptides are fused to other polypeptides, such as, by way of example and not limitation, antibody tags (e.g., myc epitope), purification sequences (e.g., His tags for binding to metals), and cell localization signals (e.g., secretion signals). Thus, the recombinant polypeptides described herein can be used with or without fusions to other polypeptides. It is also contemplated that the recombinant polypeptides described herein are not restricted to the genetically encoded amino acids. In addition to the genetically encoded amino acids, the polypeptides described herein may be comprised, either in whole or in part, of naturally-occurring and/or synthetic non-encoded amino acids.

In another aspect, the present disclosure provides polynucleotides encoding the recombinant polypeptides having OAC activity and increased activity and/or yield as described herein. In at least one embodiment, the polynucleotide encoding a recombinant polypeptide having OAC activity comprises an amino acid sequence that is at least about 80%, 85%, 90%, 91%, 92%, 93%, 94%, 95%, 96%, 97%, 98%, 99%, or more identical to the CsOAc polypeptide sequence of SEQ ID NO: 6 or 20. In some embodiments, the polynucleotide encodes a recombinant polypeptide comprising an amino acid sequence that has the percent identity described above and has one or more amino acid residue differences as compared to CsOAC (SEQ ID NO: 6 or 20) described elsewhere herein.

In at least one embodiment, the polynucleotide has a sequence encoding a recombinant polypeptide that includes an amino acid difference relative to CsOAC (SEQ ID NO: 6 or 20), and also has one or more codon differences relative to the SEQ ID NO: 5 or SEQ ID NO: 19, which codon differences result in increased yield of the cannabinoid precursor or cannabinoid product produced by a recombinant host cell in which the polynucleotide sequence is integrated. In at least one embodiment, the polynucleotide has a sequence of at least 80% identity to SEQ ID NO: 5 or 19, and a codon difference as compared to either of SEQ ID NO: 5 or 19 at a position not encoding an amino acid residue difference relative to CsOAC (SEQ ID NO: 6 or 20).

It is also contemplated that the polynucleotides encoding the recombinant polypeptides having OAC activity as described herein, can include a combination of one or more codon differences relative to SEQ ID NO: 5 or 19, wherein at least one the codon differences encodes an amino acid difference as compared to the CsOAC polypeptide (SEQ ID NO: 6 or 20) and at least one codon difference does not encode an amino acid difference as compared to SEQ ID NO: 6 or 20. Accordingly, in at least one embodiment, the present disclosure provides a engineered polynucleotide sequence encoding a recombinant polypeptide having OAC activity, wherein the polynucleotide sequence comprises a combination of a codon differences encoding an amino acid difference.

In at least one embodiment, the polynucleotide comprises a sequence encoding an exemplary recombinant polypeptide having OAC activity as disclosed in Tables 3, 5, 6, 7, 8, 11, 12, and 13, and the accompanying Sequence Listing. In at least one embodiment, the polynucleotide comprises a sequence of at least 80%, at least 85%, at least 90%, at least 95%, at least 97%, at least 98%, or at least 99% identity to a sequence selected from the group consisting of SEQ ID NO: 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 377, 379, 381, 383, 385, 387, 389, 391, 393, 395, 397, 399, 401, 403, 405, 407, 409, 411, 413, 415, 417, 419, 421, 485, 487, 489, 491, 493, 495, 497, 499, 501, 503, 505, 507, 509, 511, 513, 515, 517, 519, 521, 523, 525, 527, 529, 531, 533, 535, 537, 539, 541, 543, 545, 547, 549, 551, 553, 555, 557, 559, 561, 563, 565, 567, 569, 571, 573, 575, 577, 579, 581, 583, 585, 587, 589, 591, 593, 595, 597, 599, 601, 603, 605, 607, 609, 611, 613, 615, 617, 619, 621, 623, 625, 627, 629, 631, 633, 635, 637, 639, 641, 643, 645, 647, 649, 651, 653, 655, 657, 659, 661, 663, 665, 667, 669, 671, 673, 675, 677, 679, 681, 683, 685, 687, 689, 691, 693, 695, 697, 699, 701, 703, 705, 707, 709, 711, 713, 715, 717, 719, 721, 723, 725, 727, 729, 731, 733, 735, 737, 739, 741, 743, 745, 747, 749, 751, 753, 755, 757, 759, 761, 763, 765, 767, 769, 771, 773, 775, 777, 779, 781, 783, 785, 787, 789, 791, 793, 795, 797, 799, 801, 803, 805, 807, 809, 811, 813, 815, 817, 819, 821, 823, 825, 827, 829, 831, 833, 835, 837, 839, 841, 843, 845, 847, 849, 851, 853, 855, 857, 859, 861, 863, 865, 867, 869, 871, 873, 875, 877, 879, 881, 883, 885, 887, and 889 (i.e., the sequences of odd-numbered SEQ ID NOs: 21 to 889). In at least one embodiment, the polynucleotide comprises a codon degenerate sequence of a polynucleotide sequence selected from the group consisting of the odd-numbered SEQ ID NOs: 21 to 889.

The polynucleotide sequences encoding the recombinant polypeptides of the present disclosure may be operatively linked to one or more heterologous regulatory sequences that control gene expression to create a recombinant polynucleotide capable of expressing the polypeptide. Expression constructs containing a heterologous polynucleotide encoding the recombinant polypeptide can be introduced into appropriate host cells to express the corresponding polypeptide. Because of the knowledge of the codons corresponding to the various amino acids, availability of a protein sequence provides a description of all the polynucleotides capable of encoding the subject. The degeneracy of the genetic code, where the same amino acids are encoded by alternative or synonymous codons allows an extremely large number of nucleic acids to be made, all of which encode the improved transaminase enzymes disclosed herein. Thus, having identified a particular amino acid sequence, those skilled in the art could make any number of different nucleic acids by simply modifying the sequence of one or more codons in a way which does not change the amino acid sequence of the protein. In this regard, the present disclosure specifically contemplates each and every possible variation of polynucleotides that could be made by selecting combinations based on the possible codon choices, and all such variations are to be considered specifically disclosed for any polypeptide disclosed herein, including the amino acid sequences presented in Tables 3, 7, 8, 9, 10, 13, 14, and 15, and the accompanying Sequence Listing.

The codons can be selected to fit the host cell in which the protein is being produced. For example, preferred codons used in bacteria are used to express the gene in bacteria; preferred codons used in yeast are used for expression in yeast; and preferred codons used in mammals are used for expression in mammalian cells. It is contemplated that all codons need not be replaced to optimize the codon usage of the recombinant polypeptide since the natural sequence will comprise preferred codons and because use of preferred codons may not be required for all amino acid residues. Consequently, codon optimized polynucleotides encoding the recombinant polypeptide may contain preferred codons at about 40%, 50%, 60%, 70%, 80%, or greater than 90% of codon positions of the full length coding region.

The present disclosure also provides an expression vector comprising a polynucleotide encoding a recombinant polypeptide having OAC activity, and one or more expression regulating regions such as a promoter, a terminator, a replication origin, or the like, depending on the type of hosts into which they are to be introduced. The various nucleic acid and control sequences described above may be joined together to produce a recombinant expression vector which may include one or more convenient restriction sites to allow for insertion or substitution of the nucleic acid sequence encoding the recombinant polypeptide at such sites. Alternatively, a polynucleotide sequence of the present disclosure may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression. The recombinant expression vector may be any vector (e.g., a plasmid or virus), which can be conveniently subjected to recombinant DNA procedures and can bring about the expression of the polynucleotide sequence. The choice of the vector will typically depend on the compatibility of the vector with the host cell into which the vector is to be introduced. The vectors may be linear or closed circular plasmids.

The expression vector may be an autonomously replicating vector, i.e., a vector that exists as an extrachromosomal entity, the replication of which is independent of chromosomal replication, e.g., a plasmid, an extrachromosomal element, a mini-chromosome, or an artificial chromosome. The vector may contain any means for assuring self-replication. Alternatively, the vector may be one which, when introduced into the host cell, is integrated into the genome, and replicated together with the chromosome(s) into which it has been integrated. Furthermore, a single vector or plasmid or two or more vectors or plasmids which together contain the total DNA to be introduced into the genome of the host cell, or a transposon may be used. In at least one embodiment, the expression vector further comprises one or more selectable markers, which permit easy selection of transformed cells.

The present disclosure also provides host cell comprising a polynucleotide or expression vector encoding a recombinant polypeptide of the present disclosure, wherein the polynucleotide is operatively linked to one or more control sequences for expression of the polypeptide having OAC activity in the host cell. Host cells for use in expressing the polypeptides encoded by the expression vectors of the present invention are well known in the art and include but are not limited to, bacterial cells, such as *E. coli*, or fungal cells, such as *Saccharomyces cerevisiae* or *Pichia pastoris*, insect cells, such as Drosophila S2 and Spodoptera Sf9, animal cells, such as CHO, COS, BHK, 293, and plant cells. Appropriate culture mediums and growth conditions for the above-described host cells are well known in the art. Accordingly, in at least one embodiment, the present disclosure provides a method for producing a cannabinoid comprising: (a) culturing in a suitable medium a recombinant host cell of the present disclosure; and (b) recovering the produced cannabinoid.

Use in Recombinant Host Cells

The engineered genes that encode recombinant polypeptides having OAC activity can be incorporated into recombinant host cells for enhanced in vivo biosynthesis of cannabinoids and cannabinoid precursors. In the context of recombinant host cells, recombinant polynucleotides corresponding to the engineered genes can be integrated into a recombinant host cell that has a heterologous pathway capable of producing a cannabinoid or cannabinoid precursor. Generally, such a heterologous pathway integrated in a recombinant host cell includes a polynucleotide sequence encoding three, four, or five linked enzymes that are capable of converting a precursor molecule, such as hexanoic acid (HA) (and associated co-substrates such as malonyl CoA) to a cannabinoid precursor molecule, such as OA, then further convert that cannabinoid precursor to a prenylated cannabinoid compound, such as CBGA, and in some cases, where a fifth synthase enzyme is encoded, to a further cannabinoid molecule, such as THCA.

One exemplary cannabinoid pathway is depicted in FIG. 1. As shown in FIG. 1, this pathway is capable of converting hexanoic acid (HA) to the cannabinoid, cannabigerolic acid (CBGA). The pathway of FIG. 1 includes the sequence of four enzymes: (1) acyl activating enzyme (AAE), a CoA ligase enzyme of class E.C. 6.2.1.1, or a fatty acyl-CoA ligase (FACL) of class E.C.6.2.1.3 (e.g., FAA1 or FAA4); (2) olivetol synthase (OLS), a CoA synthase enzyme of class E.C. 2.3.1.206; (3) olivetolic acid cyclase (OAC), a carbon-sulfur lyase enzyme of class E.C. 4.4.1.26, and (4) prenyltransferase (PT), a transferase of class E.C. 2.5.1.102. The first two enzymes carry out the conversion of the HA starting compound to the precursor tetraketide-CoA compound, 3,5,7-trioxododecanoyl-CoA. The activity of the third enzyme, OAC, catalyzes the CoA lyase and cyclization of the tetraketide-CoA to provide the cannabinoid precursor, olivetolic acid (OA). The prenyltransferase activity of the fourth enzyme catalyzes the prenylation of OA with geranyl pyrophosphate (GPP), thereby forming the cannabinoid compound, CBGA. As illustrated by the FIG. 2, further enzymatic modification of the prenylated cannabinoid compound, CBGA, to provide cannabinoids, such as CBDA, THCA, and/or CBCA, can be carried out by including a cannabinoid synthase (e.g., CBDAS, THCAS) as a fifth enzyme in the pathway.

Exemplary cannabinoid pathway enzymes that can be introduced into a recombinant host cell to provide the pathways illustrated in FIGS. 1 and 2 include, but are not limited to, the enzymes derived from *C. sativa*, AAE1, OLS, OAC, PT4, CBDAS, and/or THCAS, listed in Table 6 (below), and homologs and variants of these enzymes, as described elsewhere herein.

TABLE 6

Exemplary cannabinoid pathway enzymes

| Name (type) | Source (accession) | SEQ ID NO: (nt) | SEQ ID NO: (aa) |
|---|---|---|---|
| AAE1 (acyl activating enzyme) | *Cannabis sativa* (AFD33345.1) | 1 | 2 |
| OLS (olivetol synthase) | *Cannabis sativa* (BAG14339.1) | 3 | 4 |
| CSOAC (olivetolic acid cyclase) | *Cannabis sativa* (AFN42527.1) | 5 | 6 |
| PT4 (aromatic prenyltransferase) | *Cannabis sativa* (DAC76710.1) | 7 | 8 |
| d82_PT4 (aromatic prenyltransferase) | 82 aa N-term truncation of SEQ ID NO: 8 | 9 | 10 |
| CBDAS (CBDA synthase) | *Cannabis sativa* (BAF65033.1) | 11 | 12 |
| d28_CBDAS (CBDA synthase) | 28 aa N-term truncation of SEQ ID NO: 12 | 13 | 14 |
| THCAS (THCA synthase) | *Cannabis sativa* (BAC41356.1) | 15 | 16 |
| d28_THCAS (THCA synthase) | 28 aa N-term truncation of SEQ ID NO: 16 | 17 | 18 |

The sequences of the exemplary cannabinoid pathway enzymes AAE1, OLS, CsOAC, PT4, CBDAS, and THCAS listed in Table 6 are naturally occurring sequences derived from the plant source, *Cannabis sativa*. In the recombinant host cell embodiments of the present disclosure, it is contemplated that the polynucleotide encoding the CsOAC enzyme of SEQ ID NO: 6 or 20 is replaced in the host cell by an engineered recombinant polynucleotide encoding a recombinant polypeptide having OAC activity. It is contemplated that the other heterologous cannabinoid pathway enzymes used in the recombinant host can include enzymes derived from naturally occurring sequence homologs of the *Cannabis sativa* enzymes, AAE1, OLS, PT4, CBDAS, THCAS, CBCAS. For example, based on the sequence, accession, and enzyme classification information provided herein, one of ordinary skill can identify known naturally occurring homologs to AAE1, OLS, PT4, CBDAS, THCAS, CBCAS, having activity in the desired biocatalytic reaction. In at least one embodiment, it is contemplated that a FACL enzyme, such as FAA1 from *S. cerevisiae* (UniProt entry: P30624) or FAA4 from *S. cerevisiae* (Uniprot entry: P47912), can be substituted for AAE1 or other AAE enzyme in a pathway.

Additionally, it is contemplated that the pathway enzymes AAE1, OLS, PT4, CBDAS, THCAS, CBCAS, or their homologs, as used in a recombinant host cell including an engineered gene of the present disclosure can include enzymes having non-naturally occurring sequences. For example, enzymes with amino acid sequences engineered to function optimally in a particular enzyme pathway, and/or optimally for production of particular cannabinoid, and/or optimally in a particular host. Methods for preparing such non-naturally occurring enzyme sequences are known in the art and include methods for enzyme engineering such as directed evolution (see, e.g., Stemmer, 1994, Proc Natl Acad Sci USA 91:10747-10751; PCT Publ. Nos. WO 95/22625, WO 97/0078, WO 97/35966, WO 98/27230, WO 00/42651, and WO 01/75767; U.S. Pat. Nos. 6,537,746; 6,117,679; 6,376,246; and 6,586,182; and U.S. Pat. Publ. Nos. 20080220990A1 and 20090312196A1; each of which is hereby incorporated by reference herein). Other modifications of cannabinoid pathway enzymes contemplated by the present disclosure include modification of the enzyme's amino acid sequence at either its N- or C-terminus by truncation or fusion. For example, in at least one embodiment of the pathway of producing a cannabinoid, versions of the AAE1, OLS, PT4, and/or CBDAS enzymes that are engineered with amino acid substitutions and/or truncated at the N- or C-terminus can be prepared using methods known in the art, and used in the compositions and methods of the present disclosure. In one embodiment, a CBDAS enzyme of SEQ ID NO: 12 that is truncated at the N-terminus by 28 amino acids to delete the native signal peptide can be used. The amino acid sequence of such a truncated CBDAS is provided herein as the d28_CBDAS enzyme of SEQ ID NO: 14. Accordingly, in at least one embodiment of the recombinant host cell, the pathway capable of producing a cannabinoid precursor or cannabinoid comprises at least enzymes having an amino acid sequence at least 90% identity to SEQ ID NO: 2 (AAE1), SEQ ID NO: 4 (OLS), SEQ ID NO: 8 (d82_PT4), and an amino acid sequence of at least 90% identity to recombinant polypeptide having OAC activity of the present disclosure as provided in Tables 3, 7, 8, 9, 10, 13, 14, and 15, and the accompanying Sequence Listing. Additionally, in at least one embodiment of the recombinant host cell, the pathway capable of producing a cannabinoid can further comprise a cannabinoid synthase of SEQ ID NO: 14 (d28_CBDAS) and/or SEQ ID NO: 18 (d28_THCAS).

The recombinant polypeptides having OAC activity encoded by the engineered genes of the present disclosure when integrated into recombinant host cells with a pathway capable of converting hexanoic acid (HA) to the C-12 tetraketide-CoA precursor, 3,5,7-trioxododecanoyl-CoA, can provide enhanced yields of the cannabinoid precursor, OA, which can be further converted to the cannabinoids, CBGA, CBDA, THCA, etc. It is contemplated that any of the engineered genes of the present disclosure that encode recombinant polypeptides having OAC activity can be incorporated into a four or five enzyme cannabinoid pathway as depicted in FIG. 1 and FIG. 2 to express the OAC activity needed for the biosynthesis of OA, and its downstream products, CBGA, CBDA, THCA, and/or CBCA Accordingly, in at least one embodiment, the present disclosure provides a recombinant host cell comprising recombinant polynucleotides encoding a pathway capable of producing a cannabinoid, wherein the pathway comprises enzymes capable of catalyzing reactions (i)-(iv):

(i)

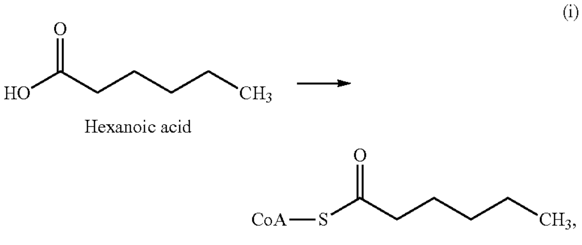

Hexanoic acid

Hexanoyl-CoA (ii)

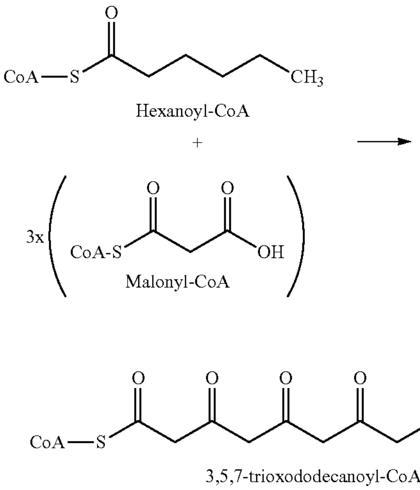

Hexanoyl-CoA

+

3x

Malonyl-CoA 3,5,7-trioxododecanoyl-CoA (iii)

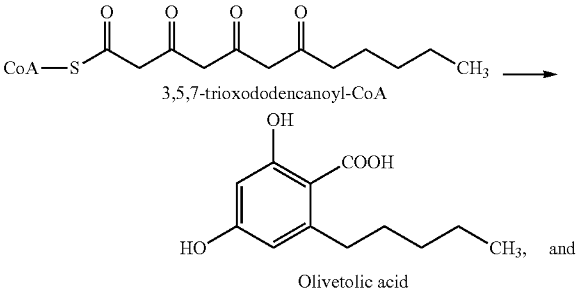

3,5,7-trioxododencanoyl-CoA

Olivetolic acid and (iv)

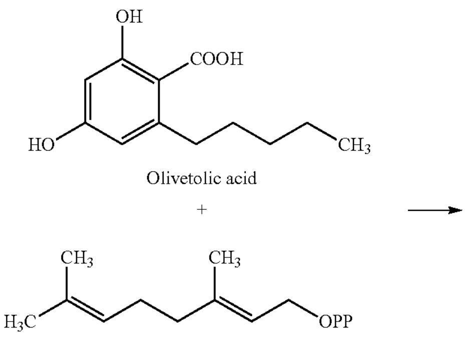

Olivetolic acid

+

Geranyldiphosphate

-continued

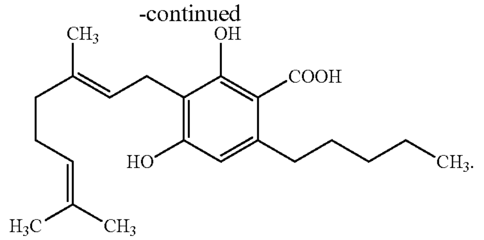

Cannabigerolic acid (CBGA

As shown in FIG. 1, exemplary enzymes capable of catalyzing reactions (i)-(iv) are: (i) acyl activating enzyme (AAE) or fatty acyl-CoA ligase (FACL); (ii) olivetol synthase (OLS); (iii) olivetolic acid cyclase (OAC); and (iv) prenyitransferase (PT). In at least one embodiment, the OAC of the pathway of the recombinant host cell is a recombinant polypeptide having OAC activity of the present disclosure, such as an exemplary recombinant polypeptide as disclosed in Tables 3, 7, 8, 9, 10, 13, 14, and 15.

In at least one embodiment, it is contemplated that a recombinant host cell comprising a pathway comprising the two enzymes, AAE, and OLS (or the two enzymes FACL, and OLS), could modified by integrating a recombinant polynucleotide of the present disclosure to provide expression of a recombinant polypeptide with the OAC activity to convert the C-12 tetraketide-CoA precursor, 3,5,7-trioxododecanoyl-CoA, to the cannabinoid precursor, OA, thereby providing a three enzyme cannabinoid pathway as illustrated by the first three steps depicted FIG. 1 corresponding to the reactions (i)-(iii) below:

(i)

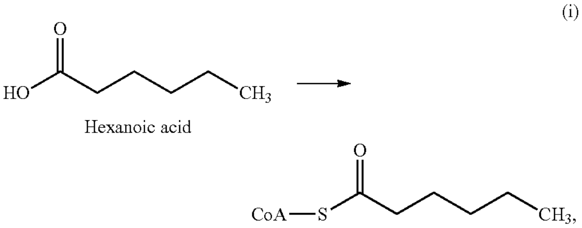

Hexanoic acid

Hexanoyl-CoA (ii)

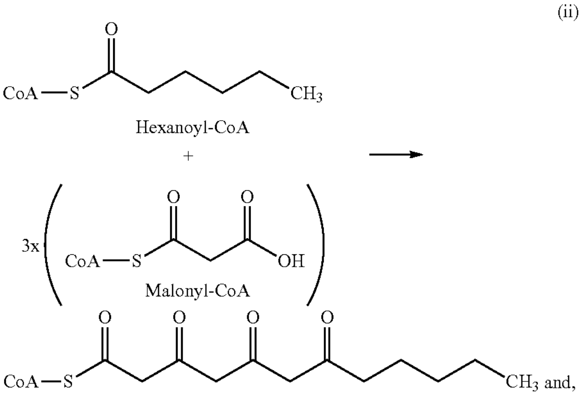

Hexanoyl-CoA

+

3x

Malonyl-CoA 3,5,7-trioxododecanoyl-CoA and, (iii)

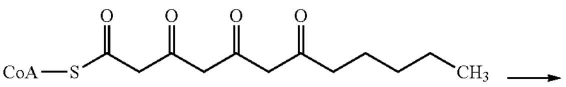

3,5,7-trioxododencanoyl-CoA

-continued

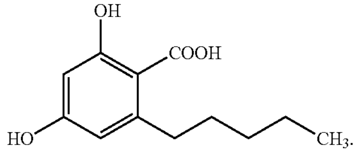

Olivetolic acid

Figure 2:
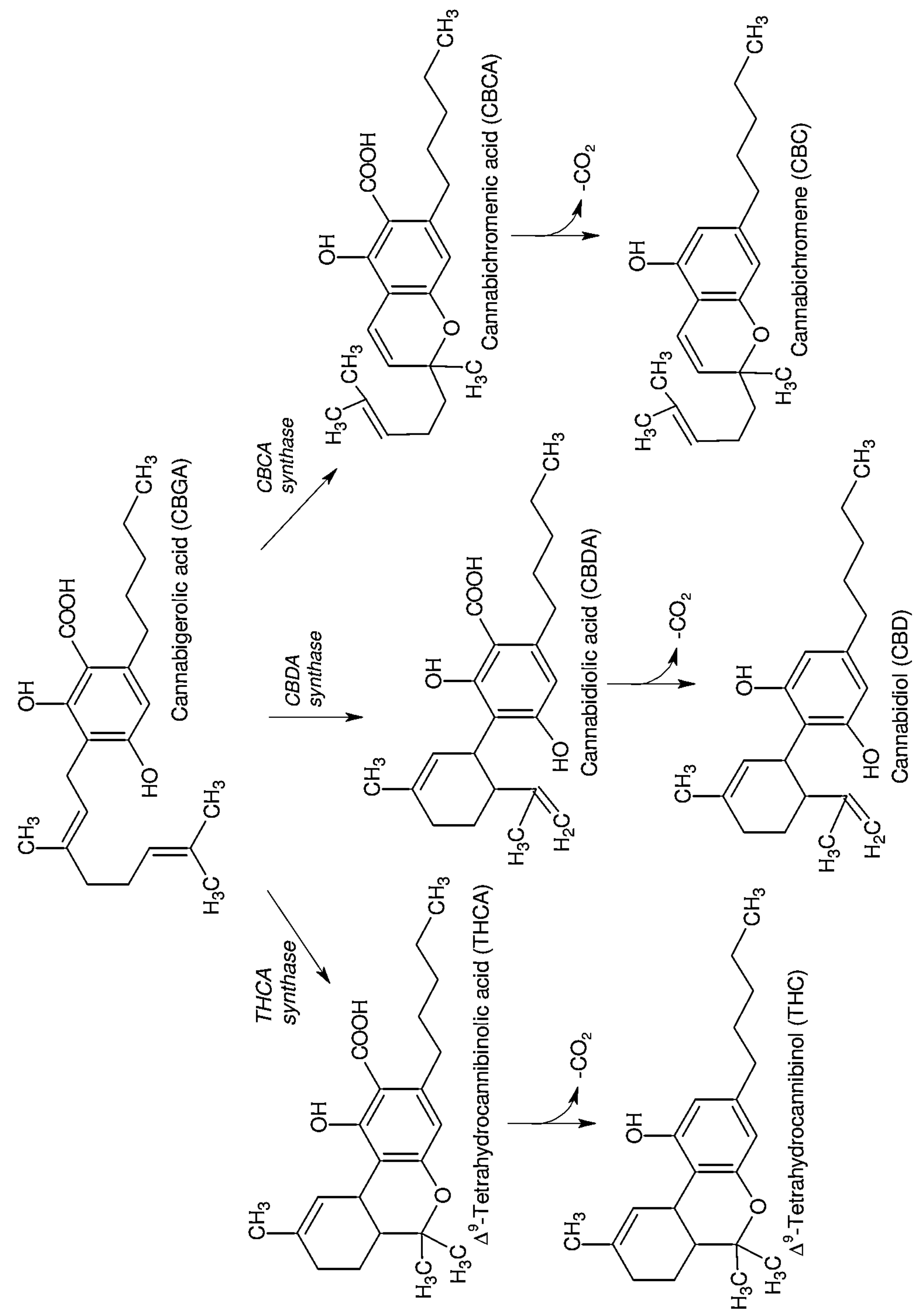
FIG. 2 depicts three exemplary two step pathways for converting the cannabinoid, CBGA, to one or more of the cannabinoids, $\Delta^9$-THCA, CBDA, and/or CBCA, and then, optionally, further converting them to the decarboxylated cannabinoids, $\Delta^9$-THC, CBD, and/or CBC. The first conversion from CBGA to $\Delta^9$-THCA, CBDA, and/or CBCA can be catalyzed by a cannabinoid synthase, CBDA synthase (CBDAS), THCA synthase (THCAS) and/or CBCA synthase (CBCAS), respectively. As described elsewhere herein, in some embodiments the single cannabinoid synthase (e.g., CBDAS) is capable of catalyzing not only the conversion of CBGA to its preferred product (e.g., CBDAS preferentially converts CBGA to CBDA), but also converts CBGA to one or both of the other cannabinoid acid products, typically in lesser amounts.

As shown in FIG. 2, the cannabinoid compound, CBGA, that is produced by the pathway of FIG. 1, can be further converted by a cannabinoid synthase to at least three other different cannabinoid compounds, $\Delta^9$-tetrahydrocannabinolic acid (THCA), cannabidiolic acid (CBDA), and/or cannabichromenic acid (CBCA). Accordingly, in at least one embodiment, the present disclosure provides a recombinant host cell comprising a pathway capable of converting hexanoic acid to CBGA and further comprising an enzyme capable of catalyzing the conversion of (v) CBGA to $\Delta^9$-THCA; (vi) CBGA to CBDA; and/or (vii) CBGA to CBCA. Thus, in at least one embodiment, the recombinant host cell comprises pathway capable of converting hexanoic acid to CBGA further comprises further comprises enzymes capable of catalyzing a reaction (v), (vi), and/or (vii):

(v)

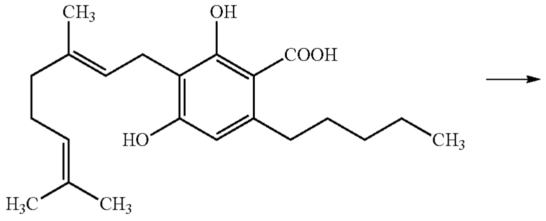

Cannabigerolic acid (CBGA)

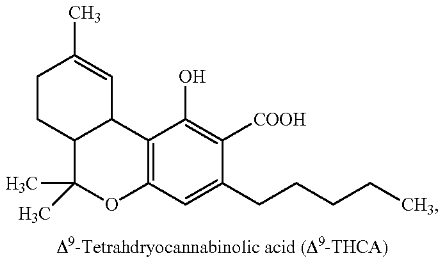

$\Delta^9$-Tetrahdryocannabinolic acid ($\Delta^9$-THCA)

(vi)

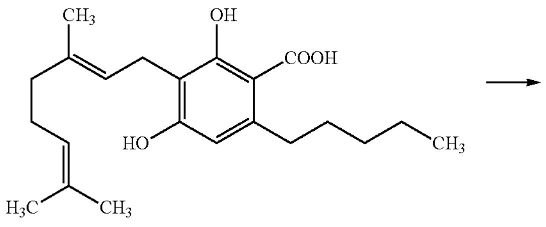

Cannabigerolic acid (CBGA)

-continued

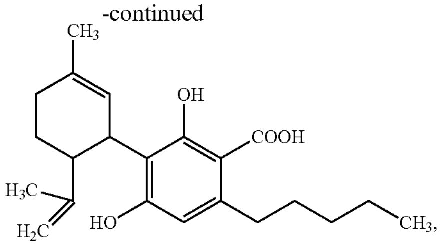

Cannabidiolic acid (CBDA)

(vii)

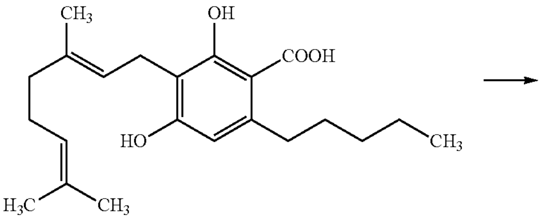

Cannabigerolic acid (CBGA)

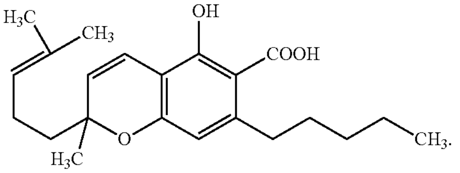

Cannabichromenic acid (CBCA)

As shown in FIG. 2, exemplary enzymes capable of catalyzing reaction (v)-(vii) are: (v) THCA synthase (THCAS); (vi) CBDA synthase (CBDAS); and (vii) CBCA synthase (CBCAS). The extension of the four enzyme exemplary pathway of FIG. 1 with polynucleotide sequence capable of expressing such a cannabinoid synthase (e.g., CBDAS, THCAS, and/or CBCAS) allows for the biosynthetic production of one or more of the cannabinoids, $\Delta^9$-THCA, CBDA, and/or CBCA. These cannabinoids can then be decarboxylated to provide the cannabinoids, $\Delta^9$-THC, CBD, and/or CBC. Accordingly, it is contemplated, that in some embodiments this further decarboxylation reaction can be carried out under in vitro reaction conditions using the cannabinoid acids separated and/or isolated from the recombinant host cells.

Other cannabinoid pathway enzymes useful in the recombinant host cells and associated methods of the present disclosure are known in the art, and can include naturally occurring enzymes obtained or derived from cannabis plants, or non-naturally occurring enzymes that have been engineered based on the naturally occurring cannabis plant sequences. It is also contemplated that enzymes obtained or derived from other organisms (e.g., microorganisms) having a catalytic activity related to a desired conversion activity useful in a cannabinoid pathway can be engineered for use in a recombinant host cell of the present disclosure.

A wide range of cannabinoid compounds can be produced biosynthetically by a recombinant host cell integrated with such a cannabinoid pathway. The cannabinoid pathways of FIGS. 1-2 depict the production of the more common naturally occurring cannabinoids, CBGA, $\Delta^9$-THCA, CBDA, and CBCA. It is also contemplated, however, that the engineered genes, recombinant polypeptides, cannabinoid pathways, recombinant host cells, and associated methods of the present disclosure can also be used to biosynthesize a range of additional rarely occurring, and/or synthetic cannabinoid compounds. Table 1 (above) lists the names and depicts the chemical structures of a wide range of exemplary rarely occurring, and/or synthetic cannabinoid compounds (e.g., CBGVA, CBDVA, THCVA) that are contemplated for production using the recombinant polypeptides, host cells, compositions, and methods of the present disclosure.

Similarly, Table 2 (above) depicts additional rarely occurring, and/or synthetic cannabinoid precursor compounds (e.g., DA) that could be produced by such recombinant host cells in the pathway for production of certain rarely occurring, and/or synthetic cannabinoid compounds of Table 1. Accordingly, in at least one embodiment, a recombinant host cell that includes a pathway to a cannabinoid precursor and that expresses a recombinant polypeptide having OAC activity of the present disclosure (e.g., as in Tables 3, 7, 8, 9, 10, 13, 14, and 15) can be used for the biosynthetic production of a rarely occurring, and/or synthetic cannabinoid compound, or a composition comprising such a cannabinoid compound. It is contemplated that the produced rarely occurring, and/or synthetic cannabinoid precursors and cannabinoids can include, but is not limited to, the compounds listed in Tables 1 and 2. Accordingly, in at least embodiment, a recombinant host cell of the present disclosure can be used for production of a cannabinoid compound selected from cannabigerolic acid (CBGA), cannabigerol (CBG), cannabidiolic acid (CBDA), cannabidiol (CBD), $\Delta^9$-tetrahydrocannabinolic acid ($\Delta^9$-THCA), $\Delta^9$-tetrahydrocannabinol ($\Delta^9$-THC), $\Delta^8$-tetrahydrocannabinolic acid ($\Delta^8$-THCA), $\Delta^8$-tetrahydrocannabinol ($\Delta^8$-THC), cannabichromenic acid (CBCA), cannabichromene (CBC), cannabinolic acid (CBNA), cannabinol (CBN), cannabidivarinic acid (CBDVA), cannabidivarin (CBDV), $\Delta^9$-tetrahydrocannabivarinic acid ($\Delta^9$-THCVA), $\Delta^9$-tetrahydrocannabivarin ($\Delta^9$-THCV), cannabidibutolic acid (CBDBA), cannabidibutol (CBDB), $\Delta^9$-tetrahydrocannabutolic acid ($\Delta^9$-THCBA), $\Delta^9$-tetrahydrocannabutol ($\Delta^9$-THCB), cannabidiphorolic acid (CBDPA), cannabidiphorol (CBDP), $\Delta^9$-tetrahydrocannabiphorolic acid ($\Delta^9$-THCPA), $\Delta^9$-tetrahydrocannabiphorol ($\Delta^9$-THCP), cannabichromevarinic acid (CBCVA), cannabichromevarin (CBCV), cannabigerovarinic acid (CBGVA), cannabigerovarin (CBGV), cannabicyclolic acid (CBLA), cannabicyclol (CBL), cannabielsoinic acid (CBEA), cannabielsoin (CBE), cannabicitranic acid (CBTA), cannabicitran (CBT), and any combination thereof.

Figure 3:
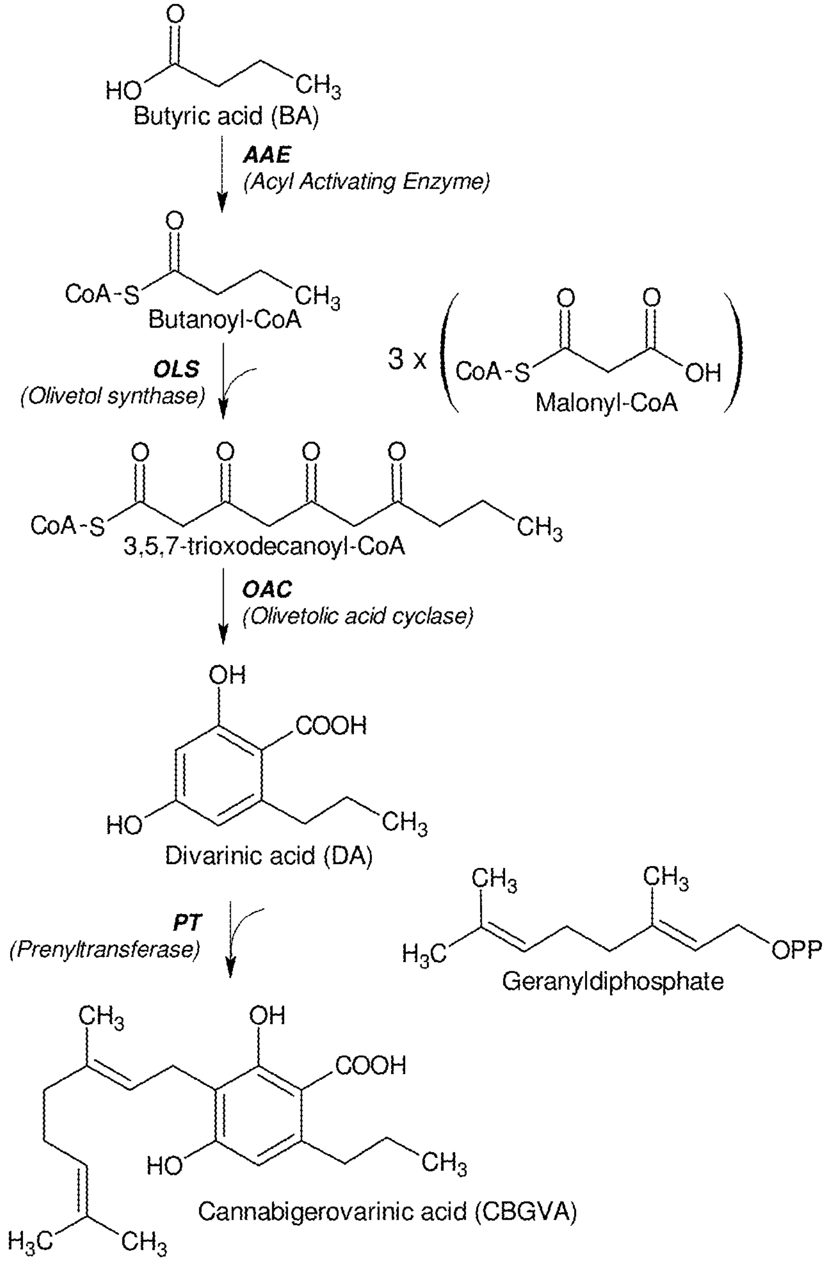
FIG. 3 depicts an exemplary four enzyme pathway capable of converting butyric acid (BA) to the rare cannabinoid precursor, divarinic acid (DA), and then further converting DA to the rare cannabinoid, cannabigerovarinic acid (CBGVA). The four enzymes catalyzing the steps in the biosynthetic pathway are AAE, OLS, OAC, and PT.

In at least one embodiment, the compositions and methods of the present disclosure can be used for the production of the rare varin series of cannabinoids, CBGVA, $\Delta^9$-THCVA, CBDVA, and CBCVA, and cannabinoid precursor, DA. As shown in Table 1, the varin cannabinoids feature a 3 carbon propyl side-chain rather than the 5 carbon pentyl side chain found in the common cannabinoids, CBGA, $\Delta^9$-THCA, CBDA, and CBCA. An exemplary cannabinoid pathway capable of producing the rare naturally occurring cannabinoid, cannabigerovarinic acid (CBGVA), is depicted in FIG. 3. Instead of starting with hexanoic acid, the pathway of FIG. 3 is fed butyric acid (BA) which is converted to cannabinoid precursor, divarinic acid (DA) via the same three enzyme pathway of AAE, OLS, and OAC. The cannabinoid precursor DA is then converted by an prenyltransferase to the rare cannabinoid, CBGVA. In at least one embodiment of the present disclosure, the OAC of the pathway of the recombinant host cell is a recombinant polypeptide having OAC activity of the present disclosure, such as an exemplary recombinant polypeptide as disclosed in Tables 3, 7, 8, 9, 10, 13, 14, and 15. Accordingly, in at least one embodiment of the recombinant host cell, the pathway capable of producing a cannabinoid comprises enzymes capable of catalyzing reactions (i)-(iv):

(i)

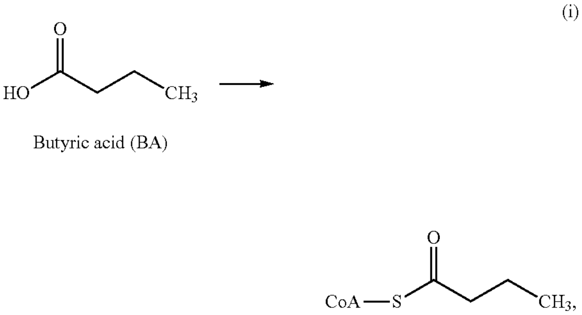

Butyric acid (BA)

Butanoyl-CoA (ii)

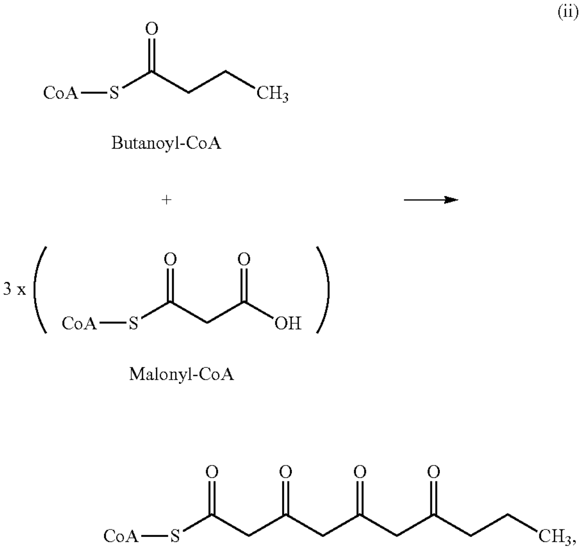

Butanoyl-CoA

Malonyl-CoA 3,5,7-trioxodecanoyl-CoA (iii)

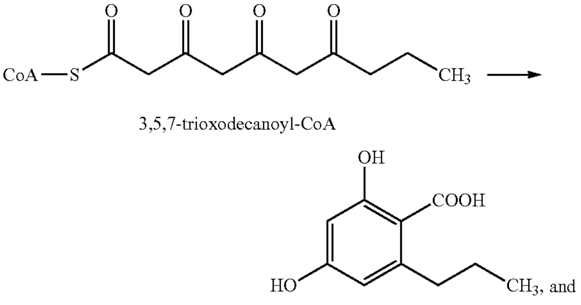

3,5,7-trioxodecanoyl-CoA and

Divarinic acid (DA)

-continued (iv)

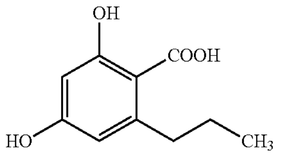

Divarinic acid (DA)

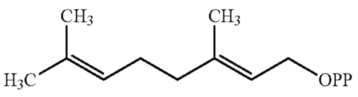

Geranyldiphosphate

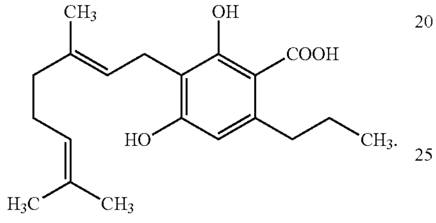

Cannabigerovarinic acid (CBGVA)

Exemplary enzymes capable of catalyzing reactions (i), (ii), (iii) and (iv) are: (i) acyl activating enzyme (AAE) or fatty acyl-CoA ligase (FACL); (ii) olivetol synthase (OLS); (iii) a recombinant polypeptide having OAC activity as disclosed herein (e.g., a polypeptide of Tables 3, 7, 8, 9, 10, 13, 14, and 15); and (iv) prenyltransferase (PT4). Exemplary enzymes, AAE1, OLS, and PT4, derived from *C. sativa* are known in the art and also provided in Table 1, and the accompanying Sequence Listing. In at least one embodiment, it is contemplated that FAA1 from *S. cerevisiae* (UniProt entry: P30624) or FAA4 from *S. cerevisiae* (Uniprot entry: P47912) can be used to catalyze reaction (i) rather than an AAE enzyme in a pathway with OLS, and PT4.

Figure 4:
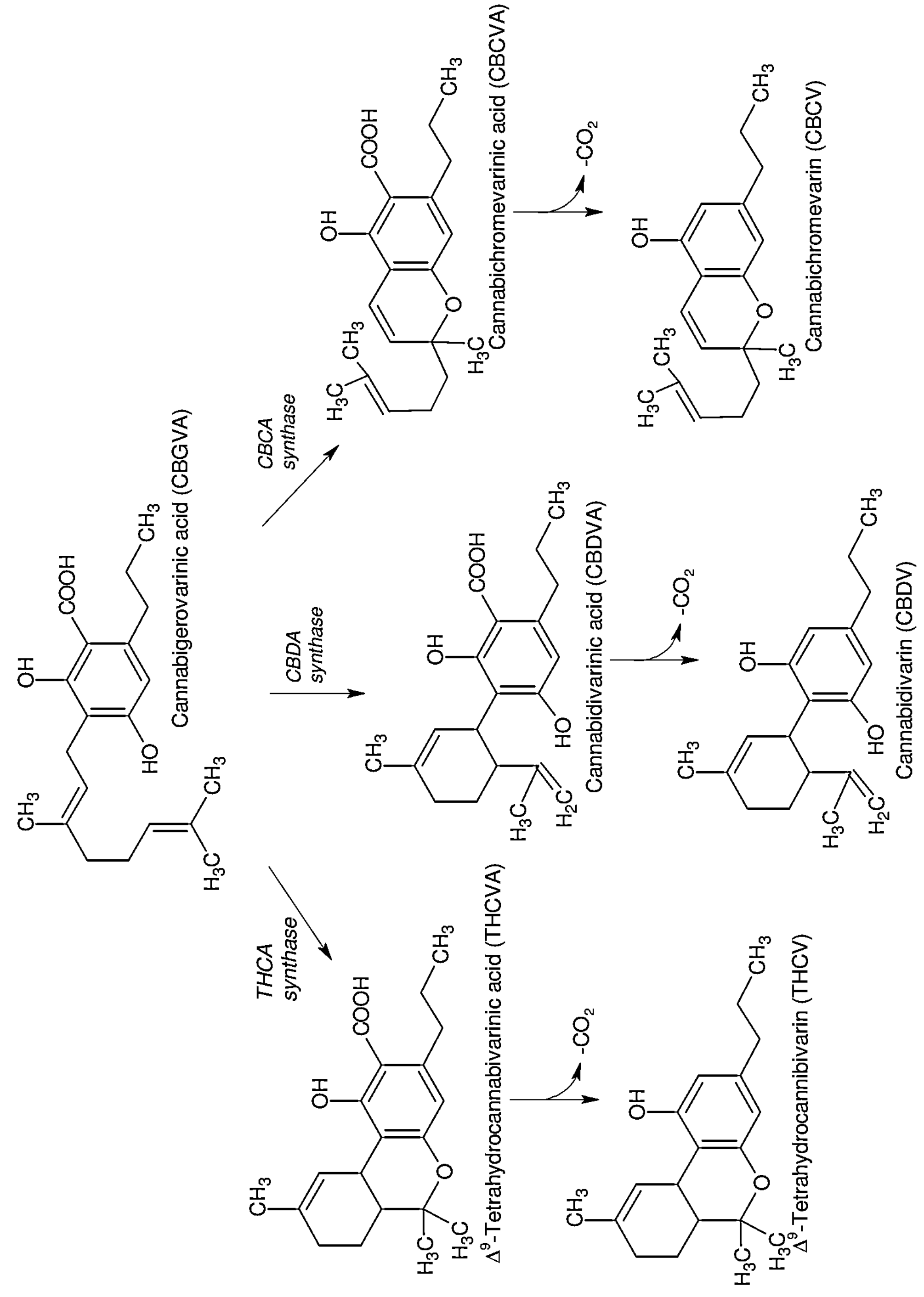
FIG. 4 depicts three exemplary two step pathways for converting the rare cannabinoid, CBGVA, to one or more of the rare cannabinoids, $\Delta^9$-THCVA, CBDVA, and/or CBCVA, and then, optionally, further converting them to the decarboxylated cannabinoids, $\Delta^9$-THCV, CBDV, and/or CBCV. The first conversion from CBGVA to $\Delta^9$-THCVA, CBDVA, and/or CBCVA can be catalyzed by a single cannabinoid synthase, CBDAs, THCAs and/or CBCAs, respectively. As described elsewhere herein, in some embodiments the single cannabinoid synthase (e.g., CBDAs) is capable of catalyzing not only the conversion of CBGVA to its preferred product (e.g., CBDAs preferentially converts CBGVA to CBDVA), but also converts CBGVA to one or both of the other cannabinoid acid products, typically in lesser amounts.

As further illustrated in FIG. 4, the heterologous pathway depicted in FIG. 3 which is capable of producing a rare cannabinoid, such as CBGVA, can be further modified to include one or more cannabinoid synthase enzymes (e.g., CBDAS, THCAS, CBCAS). As shown by the exemplary pathway of FIG. 4, with the incorporation of one or more synthase enzymes, the rare varin cannabinoid, CBGVA, can be converted to the rare varin cannabinoids, cannabidivarinic acid (CBDVA), $\Delta^9$-tetrahydrocannabivarinic acid ($\Delta^9$-THCVA), and cannabichromevarinic acid (CBCVA). Enzymes capable of carrying out these conversions include the *C. sativa* CBDA synthase, THCA synthase, and CBCA synthase, respectively. Accordingly, in at least one embodiment, the present disclosure provides a recombinant host cell comprising a pathway capable of converting BA to CBGVA and further comprising an enzyme capable of catalyzing the conversion of (v) CBGVA to $\Delta^9$-THCVA; (vi) CBGVA to CBDVA; and/or (vii) CBGVA to CBCVA. Thus, in at least one embodiment, the recombinant host cell comprises pathway capable of converting BA to CBGVA further comprises further comprises enzymes capable of catalyzing a reaction (v), (vi), and/or (vii):

(v)

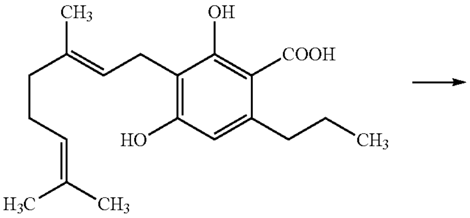

Cannabigerovarinic acid (CBGVA)

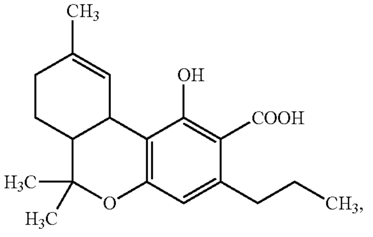

$\Delta^9$-Tetrahdryocannabivarinic acid($\Delta^9$-THCVA)

(vi)

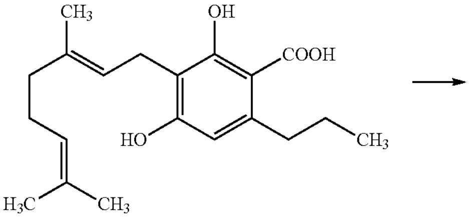

Cannabigerovarinic acid (CBGVA)

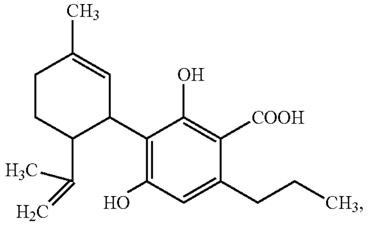

Cannabidivarinic acid (CBDVA)

(vii)

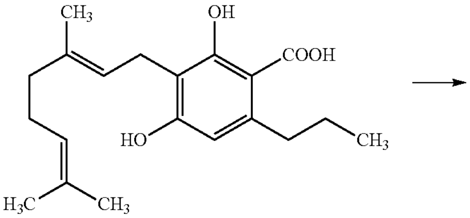

Cannabigerovarinic acid (CBGVA)

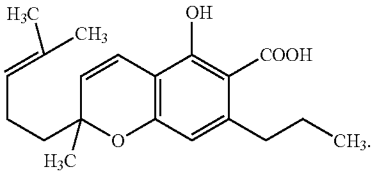

Cannabichromevarinic acid (CBCVA)

Exemplary enzymes capable of catalyzing reaction (v)-(vii) as shown above are: (v) THCA synthase (THCAS); (vi) CBDA synthase (CBDAS); and (vii) CBCA synthase (CBCAS). Exemplary THCAS, CBDAS, and CBCAS enzymes are provided in Table 1.

Furthermore, as shown in FIG. 4, the rare cannabinoid acids, CBDVA, $\Delta^9$-THCVA, and CBCVA, can undergo a further decarboxylation reaction to provide the varin cannabinoid products, cannabidivarin (CBDV). $\Delta^9$-tetrahydrocannabivarin ($\Delta^9$-THCV), and cannabichromevarin (CBCV), respectively. In some embodiments, this further decarboxylation can be carried out under in vitro reaction conditions using the cannabinoid acids isolated from the recombinant host cells.

Similarly, as shown in FIGS. 1 and 3, a heterologous cannabinoid pathway comprising the sequence of at least the four enzymes AAE, OLS, OAC, and PT (wherein, the OAC is a recombinant polypeptide having OAC activity of the present disclosure) is capable of converting a precursor substrate compound, such as hexanoic acid (HA) to an initial cannabinoid compound, such as CBGA or CBGVA. These initial cannabinoid product compounds can themselves be used as a substrate for the in vitro biosynthesis of a range of further cannabinoid product compounds, such as THCA and THCVA, as shown in FIGS. 2 and 4. A wide range of cannabinoid compounds, such as those shown in Table 1, are contemplated for in vivo biosynthetic production in a recombinant host cell of the present disclosure or via a partial or full in vitro biosynthesis process using recombinant polypeptides of the present disclosure.

As described herein, the heterologous cannabinoid pathways of the present disclosure can be incorporated into a range of host cells to provide a system for biosynthetic production of cannabinoids (e.g., CBGA, CBGVA, CBDA, CBDVA, THCA, THCVA). Methods and techniques for integrating polynucleotides into recombinant host cells, such as yeast, so that they express functional pathways of enzymes are well known in the art and described elsewhere herein including the Examples. Generally, the host cell used in the recombinant host cells of the present disclosure can be any cell that can be recombinantly modified with nucleic acids and cultured to express the recombinant products of those nucleic acids, including polypeptides and metabolites produced by the activity of the recombinant polypeptides. A wide range of suitable sources of host cells are known in the art, and exemplary host cell sources useful as recombinant host cells of the present disclosure include, but are not limited to, *Saccharomyces cerevisiae, Yarrowia lipolytica, Pichia pastoris*, and *Escherichia coli*. It is also contemplated that the host cell source for a recombinant host cell of the present disclosure can include a non-naturally occurring cell source, e.g., an engineered host cell. For example, a non-naturally occurring source host cell, such as a yeast cell previously engineered for improved production of recombinant genes, may be used to prepare the recombinant host cell of the present disclosure.

The recombinant host cells of the present disclosure comprise heterologous nucleic acids encoding a pathway of enzymes capable of producing a tetraketide-CoA precursor compound (e.g., 3,5,7-trioxododecanoyl-CoA or 3,5,7-trioxodecanoyl-CoA), and a heterologous nucleic acid comprising a sequence encoding a recombinant polypeptide having OAC activity capable of cyclizing this tetraketide-CoA to form a cannabinoid precursor product (e.g., OA or DA). As described elsewhere herein, nucleic acid sequences encoding the cannabinoid pathway enzymes, are known in the art, and provided herein, and can readily be used in accordance with the present disclosure. Typically, the nucleic acid sequence encoding enzymes which form a part of a cannabinoid pathway, further include one or more additional nucleic acid sequences, for example, a nucleic acid sequence controlling expression of the enzymes which form a part of a cannabinoid biosynthetic enzyme pathway, and these one or more additional nucleic acid sequences together with the nucleic acid sequence encoding the enzyme can be considered a heterologous nucleic acid sequence. A variety of techniques and methodologies are available and well known in the art for introducing heterologous nucleic acid sequences, such as nucleic acid sequences encoding the cannabinoid pathway enzymes (e.g., AAE, OLS, OAC, and PT), into a host cell so as to attain expression the host cell. Such techniques are well known to the skilled artisan and can, for example, be found in Sambrook et al., Molecular Cloning, a Laboratory Manual, Cold Spring Harbor Laboratory Press, 2012, Fourth Ed.

One of ordinary skill will recognize that the heterologous nucleic acids encoding the recombinant olivetolic acid cyclase enzymes and/or other pathway enzymes will further comprise transcriptional promoters capable of controlling expression of the enzymes in the recombinant host cell. Generally, the transcriptional promoters are selected to be compatible with the host cell, so that promoters obtained from bacterial cells are used when a bacterial host cell is selected in accordance herewith, while a fungal promoter is used when a fungal host cell is selected, a plant promoter is used when a plant cell is selected, and so on. Promoters useful in the recombinant host cells of the present disclosure may be constitutive or inducible, provided such promoters are operable in the host cells. Promoters that may be used to control expression in fungal host cells, such as *Saccharomyces cerevisiae*, are well known in the art and include, but are not limited to: inducible promoters, such as a Gal1 promoter or Gal10 promoter, a constitutive promoter, such as an alcohol dehydrogenase (ADH) promoter, a glyceraldehyde-3-phosphate dehydrogenase (GPD) promoter, or an *S. pombe* Nmt, or ADH promoter. Exemplary promoters that may be used to control expression in bacterial cells can include the *Escherichia coli* promoters lac, tac, trc, trp or the 77 promoter. Exemplary promoters that may be used to control expression in plant cells include, for example, a Cauliflower Mosaic Virus 35S promoter (Odell et al. (1985) Nature 313:810-812), a ubiquitin promoter (U.S. Pat. No. 5,510,474; Christensen et al. (1989)), or a rice actin promoter (McElroy et al. (1990) Plant Cell 2:163-171). Exemplary promoters that can be used in mammalian cells include, a viral promoter such as an SV40 promoter or a metallothionine promoter. All of these host cell promoters are well known by and readily available to one of ordinary skill in the art. Further nucleic acid control elements useful for controlling expression in a recombinant host cell can include transcriptional terminators, enhancers, and the like, all of which may be used with the heterologous nucleic acids incorporate in the recombinant host cells of the present disclosure.

A wide variety of techniques are well known in the art for linking transcriptional promoters and other control elements to heterologous nucleic acid sequences encoding cannabinoid pathway genes. Such techniques are described in e.g., Sambrook et al., Molecular Cloning, a Laboratory Manual, Cold Spring Harbor Laboratory Press, 2012, Fourth Ed. Accordingly, in at least one embodiment, the heterologous nucleic acid sequences of the present disclosure comprise a promoter capable of controlling expression in a host cell, wherein the promoter is linked to a nucleic acid sequence encoding a recombinant polypeptide having OAC activity of the present disclosure, and as necessary, other enzymes constituting a cannabinoid pathway (e.g., AAE, OLS, OAC). This heterologous nucleic acid sequence can be integrated into a recombinant expression vector which ensures good expression in the desired host cell, wherein the expression vector is suitable for expression in a host cell, meaning that the recombinant expression vector comprises the heterologous nucleic acid sequence linked to any genetic elements required to achieve expression in the host cell. Genetic elements that may be included in the expression vector in this regard include a transcriptional termination region, one or more nucleic acid sequences encoding marker genes, one or more origins of replication, and the like. In some embodiments, the expression vector further comprises genetic elements required for the integration of the vector or a portion thereof in the host cell's genome.

It is also contemplated that in some embodiments an expression vector comprising a heterologous nucleic acid of the present disclosure may further contain a marker gene. Marker genes useful in accordance with the present disclosure include any genes that allow the distinction of transformed cells from non-transformed cells, including all selectable and screenable marker genes. A marker gene may be a resistance marker such as an antibiotic resistance marker against, for example, kanamycin or ampicillin. Screenable markers that may be employed to identify transformants through visual inspection include β-glucuronidase (GUS) (U.S. Pat. Nos. 5,268,463 and 5,599,670) and green fluorescent protein (GFP) (Niedz et al., 1995, Plant Cell Rep., 14:403).

In at least one embodiment, the present disclosure also provides of a method for producing a cannabinoid, wherein a heterologous nucleic acid encoding a recombinant polypeptide having OAC activity (e.g., an exemplary engineered polypeptide of Tables 3, 7, 8, 9, 10, 13, 14, and 15) can be introduced into a recombinant host cell. The recombinant host cell can then be used for production of the polypeptide, or incorporated in a biocatalytic process that utilized the OAC activity of the recombinant polypeptide expressed by the host cell for the catalytic cyclization of a tetraketide-CoA substrate, e.g., the cyclization of 3,5,7-trioxododecanoyl-CoA to produce OA. In at least one embodiment, the recombinant host cell can further comprise a pathway of enzymes capable of producing a tetraketide-CoA precursor (e.g., 3,5,7-trioxododecanoyl-CoA) which can act as a substrate for the recombinant polypeptide with OAC activity. It is contemplated that a recombinant host cell comprising a heterologous nucleic acid encoding a recombinant polypeptide having OAC activity of the present disclosure can provide improved biosynthesis of a desired cannabinoid precursor (e.g., OA) or a cannabinoid (e.g., CBGA) product in terms of titer, yield, and production rate, due to the improved characteristics of the expressed OAC activity in the cell associated with the amino acid and codon differences engineered in the gene.

Accordingly, in at least one embodiment, the present disclosure provides a method of producing a cannabinoid derivative, wherein the method comprises: (a) culturing in a suitable medium a recombinant host cell of the present disclosure; and (b) recovering the produced cannabinoid derivative. In at least one embodiment, the method of producing a cannabinoid derivative further contacting a cell-free extract of the culture containing the produced cannabinoid with a biocatalytic reagent or chemical reagent capable of converting the cannabinoid to a cannabinoid derivative. In at least one embodiment, the biocatalytic reagent is an enzyme capable of converting the produced cannabinoid to a different cannabinoid or a cannabinoid derivative compound. In at least one embodiment, the chemical reagent is capable of chemically modifying the produced cannabinoid to produce a different cannabinoid or a cannabinoid derivative compound. In at least one embodiment of the method for producing a cannabinoid, the method can further comprise contacting a cell-free extract of the culture containing the produced cannabinoid with a biocatalytic reagent or chemical reagent.

It is contemplated that the cannabinoid, or cannabinoid derivative produced using the methods of the present disclosure can be produced and/or recovered from the reaction in the form of a salt. In at least one embodiment, the recovered salt of the cannabinoid, cannabinoid precursor, cannabinoid precursor derivative, or cannabinoid derivative is a pharmaceutically acceptable salt. Such pharmaceutically acceptable salts retain the biological effectiveness and properties of the free base compound.

It also is contemplated the recombinant polypeptides with OAC activity of the present disclosure can be incorporated in any biosynthesis method requiring a OAC catalyzed biocatalytic step. Thus, in at least one embodiment, the recombinant polypeptides having OAC activity (e.g., exemplary polypeptides of Tables 3, 7, 8, 9, 10, 13, 14, and 15) can be used in a method for preparing a cannabinoid precursor compound of structural formula (I)

(I)

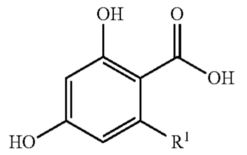

wherein, $R^1$ is C1-C7 alkyl, wherein the method comprises contacting an recombinant polypeptide having OAC activity of the present disclosure (e.g., an exemplary recombinant of Table 3) under suitable reactions conditions, with tetraketide-CoA cannabinoid precursor compound of structural formula (II)

(II)

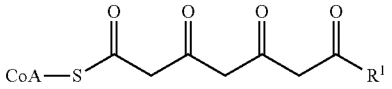

wherein, $R^1$ is C1-C7 alkyl.

Exemplary conversions of cannabinoid precursor compounds of structural formula (II) to cannabinoid compounds of structural formula (I) that are catalyzed by the recombinant polypeptides having OAC activity of the present disclosure include: (1) conversion of 3,5,7-trioxododecanoyl-CoA to olivetolic acid (OA); and (2) conversion 3,5,7-trioxodecanoyl-CoA to divarinic acid (DA).

It is contemplated that the recombinant polypeptides having OAC activity of the present disclosure (e.g., polypeptides disclosed in Tables 3, 7, 8, 9, 10, 13, 14, and 15) can catalyze the cyclization of other cannabinoid precursor compounds that are structural analogs of the tetraketide-CoA, 3,5,7-trioxododecanoyl-CoA. Accordingly, in at least one embodiment of the biosynthesis method for conversion a cannabinoid precursor compound of structural formula (II) to a cannabinoid compound of structural formula (I), the compound of structure formula (I) is olivetolic acid (OA) and the compound of structural formula (II) is 3,5,7-trioxododecanoyl-CoA. In at least one embodiment, the compound of structure formula (I) is divarinic acid (DA) and the compound of structural formula (II) is 3,5,7-trioxodecanoyl-CoA acid.

Suitable reaction conditions for the biosynthesis of cannabinoid precursors and cannabinoids are known in the art, and can be used with the recombinant polypeptides having OAC activity of the present disclosure. Additionally, suitable reaction conditions for the exemplary polypeptides of the present disclosure can be determined using routine techniques known in the art for optimizing biocatalytic reactions. It is contemplated that various ranges of suitable reaction conditions with the recombinant polypeptides of the present disclosure, including but not limited to ranges of pH, temperature, buffer, solvent system, substrate loading, polypeptide loading, co-substrate or co-factor loading, atmosphere, and reaction time. Suitable reaction conditions can be readily determined and optimized for particular reactions by routine experimentation that includes, but is not limited to, contacting the recombinant polypeptide and substrate under experimental reaction conditions of concentration, pH, temperature, solvent conditions, and detecting the production of the desired compound of structural formula (I). In at least one embodiment, the suitable reaction conditions comprise a reaction solution of ~pH 7-8, a temperature of 25 C to 37 C; optionally, the reaction conditions comprise a reaction solution of ~PH 7 and a temperature of ~30 C. In at least one embodiment, the reaction solution is allowed to incubate at a temperature of 25 C to 37 C for a reaction time of at least 1, 6, 12, 24, or 48 hours, before the amount of reaction product is determined.

The present disclosure also contemplates that the methods for biocatalytic conversion of a cannabinoid precursor compound of structural formula (II) to a cannabinoid compound of structural formula (I) using an recombinant polypeptide having OAC activity of the present disclosure can comprise additional chemical or biocatalytic steps carried out on the product compound of structural formula (II), including steps of product compound work-up, extraction, isolation, purification, and/or crystallization, each of which can be carried out under a range of conditions.

EXAMPLES

Various features and embodiments of the disclosure are illustrated in the following representative examples, which are intended to be illustrative, and not limiting. Those skilled in the art will readily appreciate that the specific examples are only illustrative of the invention as described more fully in the claims which follow thereafter. Every embodiment and feature described in the application should be understood to be interchangeable and combinable with every embodiment contained within.

Example 1: Preparation and Screening of Engineered Genes Encoding Recombinant Polypeptides with Olivetolic Acid Cyclase Activity This example illustrates preparation and screening of libraries of engineered genes expressing OAC activity when integrated in a yeast strain already engineered with the *C. sativa* genes, AAE1 (SEQ ID NO: 1) and OLS (SEQ ID NO: 3). An initial library was generated by site saturation mutagenesis (SSM) of an OAC parent gene with SEQ ID NO: 5, a synthesized yeast codon-optimized variant of CsOAC. A further codon optimization library was designed for increased expression in yeast on SEQ ID NO 5, from which SEQ ID NO 19 was identified to have 1.6-fold improvement in gene expression and or transcript stability. Codon usage can affect secondary structure of mRNA and translation efficiency. SEQ ID NO: 5 and SEQ ID NO 19 encode the wild-type CsOAC polypeptide sequence of SEQ ID NO: 6 or 20. Both the SSM and codon optimization libraries based on SEQ ID NO. 5 were integrated in yeast strains already engineered with the *C. sativa* genes, AAE1 (SEQ ID NO: 1) and OLS (SEQ ID NO: 3) and screened for OA production indicating expression of a recombinant polypeptide having OAC activity.

Materials and Methods

A. Site Saturation Mutagenesis Library Build:

A yeast codon-optimized gene encoding the wild-type *C. sativa* OAC polypeptide of SEQ ID NO: 6 or 20 was synthesized as the polynucleotide of SEQ ID NO: 5. Further codon optimization of SEQ NO ID NO: 5 identified an alternative yeast codon-optimized version of the gene encoding the wild-type *C. sativa* OAC as polynucleotide of SEQ ID NO: 19. It was found that yeast strains integrated with this alternative codon-optimized gene of SEQ ID NO: 19 exhibited increased OA titer (~1.6-fold) likely due to enhanced expression or transcript stability.

The synthetic gene of SEQ ID NO: 5 was integrated into a parent yeast strain as a knock-in using CRISPR-Cas9 at the XI-2 locus. The integrated OAC gene was expressed under the bidirectional Gal1/10 promoter and the PGK1 terminator sequences. The parent strain was previously engineered to include the two *C. sativa* genes, AAE1 (SEQ ID NO: 1) and OLS (SEQ ID NO: 3), which form a pathway capable of converting hexanoic acid to 3,5,7-trioxododecanoyl-CoA, the precursor for olivetolic acid (OA) synthesis. The resulting control strain (MV005), integrated with the OAC gene thus included a pathway of the genes AAE1, OLS, and OAC capable of converting hexanoic acid to OA. The MV005 control strain was further modified to build a screening strain for integration of the saturation mutagenesis and codon optimization libraries. A screening strain (EVO002), was built by integrating the m-Venus cassette at the XI-2 site under control of the bidirectional Gal1/10 promoter and PGK1 terminator, thereby replacing the previous integrated OAC gene. The EVO002 strain was no longer capable of converting hexanoic acid to OA.

Genomic DNA from the control strain MV005, was used as the template to generate two overlapping PCR products: (1) a first PCR product (Fragment A), which does not harbor any degenerate codons, and (2) a second PCR product (Fragment B), which has sequence overlap with the Fragment A, and is amplified harboring one NNK degenerate codon only. Primers used for amplification of Fragments A and B and overlap extension were designed according to standard site-saturation mutagenesis protocols. Fragment B was amplified with a series of forward primers that included the single NNK degenerate codon scanned across the various desired positions and a single reverse primer: 5'-CTAAGTCTAGCCACGAAAACTGCAA-3' (SEQ ID NO: 423). Fragment A was amplified using a single forward primer: 5'-GGTTATGAAGAGGAAAAAT-TGGCAGTAACC-3' (SEQ ID NO: 424) and a series of reverse primers designed according to the location of the mutagenesis site. The two fragments A and B were assembled by overlap extension PCR using the forward primer: 5'-GAACGAATCAAATTAACAACCATAG-GATGA-3' (SEQ ID NO: 425) and reverse primer: 5'-GCACCAAAAGTAAGAAACGACAAAGTTT-3' (SEQ ID NO: 426).

The assembled OE-PCR products were then pooled together, and gel purified to provide a saturation mutagenesis library for integration as linear donor DNA.

B. Codon Optimization Library Build:

A total of 96 codon optimized variants were designed based on SEQ ID NO 5 using an AFIAK python script developed in house using the preferred *Saccharomyces cerevisiae* codon usage table and optimization optimal GC count. To facilitate efficient integration, a 50-nucleotide 5' flanking sequence, 5'-CAAAAAATTGTTAATATACCTC-TATACTTTAACGTCAAGGAGAAAAAACC-3' (SEQ ID NO: 427), and a 50-nucleotide 3' flanking sequence, 5'-TAAATTGAATTGAATTGAAATCGATAGATCAAT-TTTTTTCTTTTCTCTTT-3' (SEQ ID NO: 428), were introduced into each codon variant. This sequence provided the overlap homology to build longer DNA donors including the pGal1 promoter: 5'-TTTTCAAAAATTCT-TACTTTTTTTTTGGATGGACGCAAAGAAGTT-TAATAATCATATTACATG GCATTACCACCATATA-CATATCCATATACATATCCATATCTAATCTTACTTATAT GTTGTGGA AATGTAAAGAGCCCCATTATCT-TAGCCTAAAAAAACCTTCTCTTTG-GAACTTTCAGTAATAC GCTTAACTGCTCATTGCTAT-ATTGAAGTACGGATTAGAAGCCGCCGAGCGGGTGA CAGCC CTCCGAAGGAA-GACTCTCCTCCGTGCGTCCTCGTCTT-CACCGGTCGCGTTCCTGAAACGC AGATGTGCCTCGCGCCGCACTGCTCCGAACAATAAA-GATTCTACAATACTAGCTTTTATGG TTATGAAGAG-GAAAAATTGGCAGTAACCTGGCCCCACAAACCTT-CAAATGAACGAATCAAA TTAACAACCATAGGATGATAATGCGATTAGTTTTT-TAGCCTTATTTCTGGGGTAATTAATCA GCGAAGC-GATGATTTTTGATCTATTAACAGA-TATATAAATGCAAAAACTGCATAACCACTTT AACTAATACTTTCAACATTTTCGGTTTGTAT-TACTTCTTATTCAAATGTAATAAAAGTATCAAC AAAAAATTGTTAATATACCTCTATACTTTAACGT-CAAGGAGAAAAAACC-3' (SEQ ID NO: 429) and the PGK1t terminator: 5'-ATTGAATTGAATTGAAATCGATA-GATCAATTTTTTTCTTTTCTCTTTCCCCATCCTT-TACGCT AAAATAATAGTTTATTTTATTTTTTGAATAT-TTTTTATTTATATACGTATATATAGACTATTATT TATCTTTTAATGATTATTAAGATTTTTAT-TAAAAAAAAATTCGCTCCTCTTTTAATGCCTTTAT GCAGTTTTTTTTTCCCATTCGATATTTCTATGT-3' (SEQ ID NO: 430). The codon optimized variants including the flanking sequences were synthesized by Twist. The individual codon optimized variants, promoter and terminator DNA pieces were assembled by overlap extension PCR using the forward primer: 5'-GAACGAATCAAAT-TAACAACCATAGGATGA-3' (SEQ ID NO: 425) and reverse primer: 5'-GCAC-CAAAAGTAAGAAACGACAAAGTTT-3' (SEQ ID NO: 426).

The assembled OE-PCR products were then pooled together, and gel purified to provide a codon optimization library for integration as linear donor DNA.

Both the saturation mutagenesis and codon optimization libraries consisting of linear donor DNA were transformed separately into the screening strain (EVO002), along with sequence specific guide to integrate the library in place of the m-Venus cassette using CRISPR-Cas9 at the XI-2 site in a yeast strain that already had integrated genes encoding the *C. sativa* enzymes, AAE1, and OLS. The resulting libraries would contain integrated OAC mutants integrated at the XI-2 site under control of the bidirectional Gal1/10 promoter and PGK1 terminator, in place of the m-Venus cassette and therefore restoring ability to convert hexanoic acid to OA. The resulting libraries integrated into the EVO002 strain were plated on selective YPD agar to select for strains with positive integration events.

C. Screening of Site Saturation Mutagenesis and Codon Optimization Libraries for Olivetolic Acid Biosynthesis:

Individual colonies from the saturation mutagenesis and codon optimization libraries integrated in EVO002 and the respective MV005 control strain were grown in 0.3 mL YPD in 96-well microtiter plates. The microtiter plates were incubated in shaking incubators for 48 h at 30 C. 85% humidity, and 250 rpm. The resulting liquid cultures were then sub-cultured into additional 96 well plates with 0.27 mL fresh YPD and hexanoic acid (HA) was added to 2 mM final concentration. Subculture microtiter plates were then incubated in shaking incubators for an additional 48 hours at 30 C, 85% humidity, and 250 rpm. The whole broth from these subculture plates was extracted and analyzed for the presence of the cannabinoid precursor compound, OA, using HPLC, as described below.

1. HPLC sample preparation: The whole broth of each culture within the 96 well plates were extracted and diluted with MeOH for sample preparation. The extracted samples were loaded onto RapidFire365 coupled with a triple quadrupole mass spectrometry detector. The cannabinoid precursor compound, OA, was detected using MRM mode. A calibration curve of OA was generated by running serial dilutions of standards, and then used to calculate the concentration of the cultures within the library plates.

2. HPLC instrumentation and parameters: HPLC system: Agilent RapidFire 365; Column: Agilent Cartridge C18 (12 μl, type C): Mobile phase: Pump 1 uses 95:5 H2O: acetonitrile with 0.1% formic acid at 1 mL/min". Pump 2 uses 20:80 acetonitrile: $H_2O$ at 0.8 mL/min; Pump 3 uses MeOH with 0.1% formic acid, at 0.8 mL/min.; Aqueous wash uses $H_2O$; Organic wash uses acetonitrile; RapidFire cycle time: Aspiration 600 ms; Load/wash 3000 ms; Extra wash 2000 ms; Elute 4000 ms; Re-equilibration 500 ms.

D. Sequencing

Those clones from the saturation mutagenesis and codon optimization libraries determined by screening to exhibit an OA titer were re-tested and sequenced using Sanger sequencing technology to determine the specific codon differences (relative to SEQ ID NO 5) and amino acid differences (relative to SEQ ID NO 6).

E. Results

Results for relative OA titer and corresponding amino acid changes of the SSM library strains, and nucleotide changes of the codon optimized library generated from the parent codon-optimized gene of SEQ ID NO: 5 are summarized in Table 7 (below).

TABLE 7

| NT SEQ ID NO: | AA SEQ ID NO: | aa substitution(s) relative to CsOAC | Relative OA titer[1] |
|---|---|---|---|
| 5 | 6 | n/a | 1 |
| 19 | 20 | n/a | 1.58 |
| 21 | 22 | T16Q | 1.6 |
| 23 | 24 | P76V | 1.11 |
| 25 | 26 | L9V | 1.07 |
| 27 | 28 | K44P | 1.01 |
| 29 | 30 | I74S | 1.00 |
| 31 | 32 | H57G | 0.93 |

TABLE 7-continued

| NT SEQ ID NO: | AA SEQ ID NO: | aa substitution(s) relative to CsOAC | Relative OA titer[1] |
|---|---|---|---|
| 33 | 34 | K49R | 0.90 |
| 35 | 36 | E14G | 0.90 |
| 37 | 38 | D71G | 0.90 |
| 39 | 40 | K91E | 0.89 |
| 41 | 42 | L9V, E21V | 0.74 |
| 45 | 46 | K12L | 0.49 |
| 47 | 48 | A18S | 0.67 |
| 51 | 52 | E17G, K44P | 0.44 |
| 53 | 54 | I94K | 0.44 |
| 55 | 56 | E64K | 0.40 |
| 61 | 62 | A77E | 0.29 |
| 65 | 66 | T62G | 0.27 |
| 67 | 68 | F11L | 0.26 |
| 69 | 70 | S87K | 0.29 |
| 71 | 72 | D83R | 0.26 |
| 75 | 76 | G82R; | 0.25 |

[1]The OA titer for the MV005 control strain integrated with codon optimized OAC gene of SEQ ID NO: 5 was set as 1, and the values for "Relative OA titer" for each library strain clone were determined by comparison to this MV005 control strain.

Example 2: Preparation and Screening of Engineered Genes Encoding Recombinant Polypeptides with Olivetolic Acid Cyclase Activity This example illustrates preparation and screening of additional libraries of engineered genes expressing OAC activity when integrated in a yeast strain already engineered with the *C. sativa* genes, AAE1 (SEQ ID NO: 1) and OLS (SEQ ID NO: 3). A combinatorial library of 56 variant sequences was synthesized using diversity identified in Table 5. 26 combinatorial variants were synthesized based on SEQ ID NO. 5 and 26 variants were synthesized based on the codon optimized SEQ ID NO. 19. One combinatorial variant synthesized based on SEQ ID NO 19 was further used as a parent for SSM to introduce additional genetic diversity (SEQ ID NO 85).

Materials and Methods

A. Combinatorial Library Build:

The synthetic codon-optimized genes of SEQ ID NO: 5 and SEQ ID NO. 19 described in Example 1 were used as parent backbones to design and synthesize 56 variants incorporating combinations of amino acid changes selected from Table 1. As in Example 1, to facilitate efficient integration, the 50-mer 5' and 3' flanking sequences of SEQ ID NO: 427 and SEQ ID NO: 428 were introduced into each combinatorial variant. As in Example 1, these flanking sequences provided the overlap homology to build longer DNA donors including the pGal1 promoter and the PGK1t terminator. The combinatorial variants including the flanking sequence were synthesized by Twist. The individual combinatorial variants, promoter and terminator DNA pieces were assembled by overlap extension PCR using the forward primer: 5'-GAACGAATCAAATTAACAACCATAGGATGA-3' (SEQ ID NO: 425) and reverse primer: 5'-GCACCAAAAGTAAGAAACGACAAAGTTT-3' (SEQ ID NO: 426). The integrated synthesized genes were expressed under the bidirectional Gal1/10 promoter and the PGK1 terminator sequences. As in Example 1, The parent strain was previously engineered to include the two *C. sativa* genes, AAE1 (SEQ ID NO: 1) and OLS (SEQ ID NO: 3), which form a pathway capable of converting hexanoic acid to 3,5,7-trioxododecanoyl-CoA, the precursor for olivetolic acid (OA) synthesis. The control strain was (MV005) thus included a pathway of the genes AAE1, OLS, and OAC capable of converting hexanoic acid to OA. As in Example 1, the MV005 control strain was further modified to build a screening strain for integration of the combinatorial and additional site saturation mutagenesis libraries. The screening strain (EVO002), was built by integrating the m-Venus cassette at the XI-2 site under control of the bidirectional Gal1/10 promoter and PGK1 terminator, thereby replacing the previous integrated OAC gene. The EVO002 strain was no longer capable of converting hexanoic acid to OA.

The pooled combinatorial library of linear donor DNA was transformed into the screening strain (EVO002), along with sequence specific guide to integrate the library in place of the m-Venus cassette using CRISPR-Cas9 at the XI-2 site in a yeast strain that already had integrated genes encoding the *C. sativa* enzymes, AAE1, and OLS. The resulting libraries would contain integrated OAC mutants from the combinatorial library integrated at the XI-2 site under control of the bidirectional Gal1/10 promoter and PGK1 terminator, in place of the m-Venus cassette and therefore restoring ability to convert hexanoic acid to OA. The resulting combinatorial libraries integrated into the EVO002 strain were plated on selective YPD agar to select for strains with positive integration events.

B. Additional SSM Library Build

The combinatorial variant, SEQ ID NO. 85 (derived from the codon-optimized parent gene of SEQ ID NO 19) was used as a parent gene to build an additional SSM library introducing additional genetic diversity along with the 5 amino acid changes L9V, E14G, K49R, D71G, K91E already encoded by SEQ ID NO: 85 in the variant polypeptide sequence of SEQ ID NO: 86.

Genomic DNA from the combinatorial variant with SEQ ID NO. 85 was used as the template to generate two overlapping PCR products: (1) a first PCR product (Fragment A), which does not harbor any degenerate codons, and (2) a second PCR product (Fragment B), which has sequence overlap with the Fragment A, and is amplified harboring one NNK degenerate codon only. Primers used for amplification of Fragments A and B and overlap extension were designed according to standard site-saturation mutagenesis protocols. Fragment B was amplified with a series of forward primers that included the single NNK degenerate codon scanned across the various desired positions and a single reverse primer: 5'-CTAAGTCTAGCCACGAAAACTGCAA-3' (SEQ ID NO: 423). Fragment A was amplified using a single forward primer: 5'-GGTTATGAAGAGGAAAAATTGGCAGTAACC-3' (SEQ ID NO: 424) and a series of reverse primers designed according to the location of the mutagenesis site. The two fragments A and B were assembled by overlap extension PCR using the forward primer: 5'-GAACGAATCAAATTAACAACCATAGGATGA-3' (SEQ ID NO: 425) and reverse primer: 5'-GCACCAAAAGTAAGAAACGACAAAGTTT-3' (SEQ ID NO: 426). The assembled OE-PCR products were then pooled together, and gel purified to provide a saturation mutagenesis library for integration as linear donor DNA.

C. Screening of Combinatorial and Additional SSM Libraries for Olivetolic Acid Biosynthesis:

Individual colonies from the combinatorial libraries in EVO002 (section A above) and additional SSM libraries in EVO002 (section B above) and the respective MV005 control strain were grown in 0.3 mL YPD in 96-well microtiter plates and screened as described in Example 1. Whole broth culture samples were extracted and screened using HPLC as described in Example 1.

D. Sequencing

Clones determined by screening to exhibit an OA titer were re-tested and sequenced using Sanger sequencing technology to determine their nucleotide and amino acid differences compared to SEQ ID NO 5 and SEQ ID NO 6, respectively.

E. Results

Results for relative OA titer and corresponding amino acid changes of the combinatorial and additional SSM libraries is summarized in Table 8 (below).

TABLE 8

| NT SEQ ID NO: | AA SEQ ID NO: | aa substitution(s) relative to CsOAC | Relative OA titer[1] |
|---|---|---|---|
| 5 | 6 | n/a | 1 |
| 19 | 20 | n/a | 1.58 |
| 43 | 44 | T26N, K49R, D71G, K91E | 0.5 |
| 49 | 50 | L9V, E14G, T16Q, V40G, K49R, D71G, I74M, K91E | 0.44 |
| 57 | 58 | I33E, K49R, D71G, K91E | 0.3 |
| 59 | 60 | L9V, E21V, G82A | 0.3 |
| 73 | 74 | L9V, E14G, T16Q, K49R, D71G, V84M, K91E | 0.26 |
| 77 | 78 | K25R, K49R, D71G, K91E | 0.23 |
| 79 | 80 | L9V, E14G, T16Q, A36E, K49R, D71G, K91E | 0.23 |
| 81 | 82 | K49R, D71G, K91E | 0.23 |
| 85 | 86 | L9V, E14G, K49R, D71G, K91E | 0.54 |
| 87 | 88 | L9V, K49R, E14G, D71G, H57G, K91E | 0.24 |
| 89 | 90 | K25S, K49R, D71G, K91E | 0.26 |
| 91 | 92 | L9V, E14G, T16Q, K49R, D71G, K91E | 0.2 |
| 93 | 94 | L9V, E14G, K49R, D71G, K91E, Y97F | 0.34 |
| 95 | 96 | L9V, E14G, K49R, D71G, K91E, Y55W | 0.37 |
| 97 | 98 | L9I, E14G, K49R, D71G, K91E | 0.47 |
| 99 | 100 | L9V, E14G, K49R, D71G, K91E, V66L | 0.38 |
| 101 | 102 | L9V, E14G, K49R, D71G, K91E, V31S | 0.38 |
| 103 | 104 | L9V, E14G, K49R, D71G, K91E, V31M | 0.34 |
| 105 | 106 | L9V, E14G, K49R, D71G, K91E, V31E | 0.31 |
| 107 | 108 | L9V, E14G, K49R, D71G, K91E, V28C | 0.34 |
| 109 | 110 | L9V, E14G, K49R, D71G, K91E, T68S | 0.4 |
| 111 | 112 | L9V, E14G, K49R, D71G, K91E, T68Q | 0.32 |
| 113 | 114 | L9V, E14G, K49R, D71G, K91E, T68M | 0.45 |
| 115 | 116 | L9V, E14G, K49R, D71G, K91E, T68G | 0.4 |
| 117 | 118 | L9V, E14G, K49R, D71G, K91E, T68E | 0.42 |
| 119 | 120 | L9V, E14G, K49R, D71G, K91E, T68A | 0.38 |
| 121 | 122 | L9V, E14G, K49R, D71G, K91E, N29G | 0.31 |
| 123 | 124 | L9V, E14G, K49R, D71G, K91E, L6F | 0.35 |
| 125 | 126 | L9V, E14G, K49R, D71G, K91E, K25G, H78P | 0.53 |
| 127 | 128 | L9V, E14G, K49R, D71G, K91E, I74V | 0.36 |
| 129 | 130 | L9V, E14G, K49R, D71G, K91E, I74T | 0.42 |
| 131 | 132 | L9V, E14G, K49R, D71G, K91E, I74M | 0.41 |
| 133 | 134 | L9V, E14G, K49R, D71G, K91E, I74L | 0.4 |
| 135 | 136 | L9V, E14G, K49R, D71G, K91E, I74G | 0.32 |
| 137 | 138 | L9V, E14G, K49R, D71G, K91E, I33V | 0.43 |
| 139 | 140 | L9V, E14G, K49R, D71G, K91E, I33D | 0.41 |
| 141 | 142 | L9V, E14G, K49R, D71G, K91E, E64D | 0.38 |
| 143 | 144 | L9V, E14G, K49R, D71G, K91E, E53S | 0.37 |
| 145 | 146 | L9V, E14G, K49R, D71G, K91E, E53R, V84I | 0.26 |
| 147 | 148 | L9V, E14G, K49R, D71G, K91E, E53R | 0.35 |
| 149 | 150 | L9V, E14G, K49R, D71G, K91E, E53L | 0.37 |
| 151 | 152 | L9V, E14G, K49R, D71G, K91E, E53H | 0.36 |
| 153 | 154 | L9V, E14G, K49R, D71G, K91E, E53F | 0.27 |
| 155 | 156 | L9V, E14G, K49R, D71G, K91E, E53A | 0.38 |
| 157 | 158 | L9V, E14G, K49R, D71G, K91E, E52R | 0.34 |
| 159 | 160 | L9V, E14G, K49R, D71G, K91E, E52Q | 0.43 |
| 161 | 162 | L9V, E14G, K49R, D71G, K91E, D45V | 0.36 |
| 163 | 164 | L9V, E14G, K49R, D71G, K91E, A2G, I74N | 0.42 |

[1]The OA titer for the MV005 control strain integrated with codon optimized OAC gene of SEQ ID NO: 5 was set as 1, and the values for "Relative OA titer" for each library strain clone (including parent of SEQ ID NO 85), were determined by comparison to this MV005 control strain.

Example 3: Preparation and Screening of Engineered Genes Encoding Recombinant Polypeptides with Olivetolic Acid Cyclase Activity This example illustrates preparation and screening of libraries of engineered genes expressing OAC activity when integrated in a yeast strain already engineered with the *C. sativa* genes, AAE1 (SEQ ID NO: 1). OLS (SEQ ID NO: 3) and d82PT4 (SEQ ID NO: 9). The libraries were generated by site saturation mutagenesis (SSM) of two parent OAC variant genes from Example 2, SEQ ID NO. 85 and SEQ ID. NO 143 which encode the polypeptides of SEQ ID NO: 86 and 143, each of which has either 5 or 6 amino acid changes relative to the wild-type OAC polypeptide sequence of SEQ ID NO: 6. These SSM libraries were integrated in a yeast strain similar to EVO002 but engineered to include the *C.*

*sativa* genes, AAE1 (SEQ ID NO: 1), OLS (SEQ ID NO: 3), and d82PT4 (SEQ ID NO: 9) and screened for OA production indicating expression of a recombinant polypeptide having OAC activity.

Materials and Methods

A. Site Saturation Mutagenesis Library Builds:

Each of the two OAC parent genes, SEQ ID NO: 143 and SEQ ID. NO: 85 was integrated into a parent yeast strain using CRISPR-Cas9 at the XI-2 site to create the control strains EVO038 and EVO039, respectively. The integrated OAC genes were expressed under the bidirectional Gal1/10 promoter and the PGK1 terminator sequences. The parent strain was previously engineered to include the genes, AAE1 (SEQ ID NO: 1), OLS (SEQ ID NO: 3), and d82PT4 (SEQ ID NO: 9). The resulting control strains (EVO038 and EVO039) integrated with the variant OAC genes of SEQ ID NO. 143 and 85, respectively, thus included a pathway of the genes AAE1, OLS, and OAC capable of converting hexanoic acid to OA, as well as PT4 capable of converting OA to CBGA. As in Examples 1 and 2, the control strain was further modified to build a screening strain for integration of the site saturation mutagenesis libraries. This screening strain (EVO029), was built by integrating the m-Venus cassette at the XI-2 site under control of the bidirectional Gal1/10 promoter and PGK1 terminator, thereby replacing the previous integrated OAC gene. The EVO029 strain was no longer capable of converting hexanoic acid to OA or further to CBGA.

The EVO038 and EVO039 control strains were used to calculate fold-improvement in OA titer in each respective library as described below.

Genomic DNA from the control strains were used as the template to generate two PCR products: (1) a first PCR product (Fragment A), which does not harbor any degenerate codons, and (2) a second PCR product (Fragment B), which has sequence overlap with the Fragment A, and is amplified harboring one NNK degenerate codon only. Primers used for amplification of Fragments A and B and overlap extension were designed according to standard site-saturation mutagenesis protocols. Fragment B was amplified with a series of forward primers that included the single NNK degenerate codon scanned across the various desired positions and a single reverse primer: 5'-CTAAGTCTAGCCACGAAAACTGCAA-3' (SEQ ID NO: 423). Fragment A was amplified using a single forward primer: 5'-GGTTATGAAGAGGAAAAATTGGCAGTAACC-3' (SEQ ID NO: 424) and a series of reverse primers designed according to the location of the mutagenesis site. The two fragments A and B were assembled by overlap extension PCR using the forward primer: 5'-GAACGAATCAAATTAACAACCATAGGATGA-3' (SEQ ID NO: 425) and reverse primer: 5'-GCACCAAAAGTAAGAAACGACAAAGTTT-3' (SEQ ID NO: 426).

The assembled OE-PCR products were then pooled together per template and gel purified to provide two saturation mutagenesis libraries of linear donor DNA.

The two pooled saturation mutagenesis libraries of linear donor DNA were transformed and integrated as a knock-in using CRISPR-Cas9 into an m-Venus cassette located at the XI-2 site in a yeast strain that already had integrated genes encoding the *C. sativa* enzymes, AAE1, OLS and PT4 (EVO029). The m-Venus cassette was integrated at the XI-2 site under control of the bidirectional Gal1/10 promoter and PGK1 terminator.

B. Screening of Site Saturation Mutagenesis Libraries for Olivetolic Acid Biosynthesis:

Individual clones from the saturation mutagenesis libraries integrated in EVO029 and the respective EVO038 or EVO039 control strains were grown in 0.3 mL YPD in 96-well microtiter plates and screened as described in Example 1. Whole broth culture samples were extracted and screened using HPLC as described in Example 1.

C. Sequencing

Clones determined by screening to exhibit an OA titer were re-tested and sequenced using Sanger sequencing technology to determine their nucleotide and amino acid differences compared to SEQ ID NO 5 and SEQ ID NO 6, respectively.

D. Results

Results for relative OA titer and corresponding amino acid changes of the SSM libraries generated from the parent codon-optimized genes of SEQ ID NO: 85 and 143 is summarized in Tables 9 and 10 respectively (below).

TABLE 9

| NT SEQ ID NO: | AA SEQ ID NO: | aa substitution(s) relative to CsOAC | aa substitution relative to SEQ ID NO: 144 | Relative OA titer[1] |
|---|---|---|---|---|
| 143 | 144 | L9V, E14G, K49R, E53S, D71G, K91E | n/a | 1 |
| 165 | 166 | L9V, E14G, K49R, E53S, D71G, G80K, K91E | G80K | 1.12 |
| 167 | 168 | L9V, E14G, K49R, E53S, T68H, D71G, K91E | T68H | 1.15 |
| 169 | 170 | L9V, E14G, K49R, E53S, D71G, I74S, K91E | I74S | 1.08 |
| 171 | 172 | L9V, E14G, K25D, K49R, E53S, D71G, K91E | K25D | 1.02 |
| 173 | 174 | L9V, E14G, K49R, E53S, D71G, S87H, K91E | S87H | 1 |
| 175 | 176 | L9V, E14G, K49R, E53S, T68C, D71G, K91E | T68C | 0.96 |
| 177 | 178 | L9V, E14G, K49R, E53S, D71G, F88Y, K91E | F88Y | 1.05 |
| 179 | 180 | L9V, E14G, K49R, E53S, D71G, I74K, K91E | I74K | 1.12 |
| 181 | 182 | L9V, E14G, Y41Q, K49R, E53S, D71G, K91E | Y41Q | 0.96 |
| 183 | 184 | L9V, E14G, Y41T, K49R, E53S, D71G, K91E | Y41T | 1.05 |
| 185 | 186 | L9V, E14G, K49R, E53S, T68G, D71G, K91E | T68G | 1.05 |
| 187 | 188 | L9V, E14G, K49R, E53S, D71G, D83R, K91E | D83R | 0.92 |
| 189 | 190 | L9V, E14G, Y41S, K49R, E53S, D71G, K91E | Y41S | 1.08 |
| 231 | 232 | L9V, E14G, V46L, K49R, E53S, D71G, K91E | V46L | 0.9 |

[1]The OA titer for the EVO038 control strain integrated with codon optimized OAC gene of SEQ ID NO: 143 was set as 1, and the values for "Relative OA titer" for each library strain clone was determined by comparison to this control strain.

TABLE 10

| NT SEQ ID NO: | AA SEQ ID NO: | aa substitution(s) relative to CsOAC | aa substitution (s) relative to SEQ ID NO: 86 | Relative OA titer[1] |
|---|---|---|---|---|
| 85 | 86 | L9V, E14G, K49R, D71G, K91E | n/a | 1 |
| 191 | 192 | L9V, E14G, E21L, K49R, D71G, K91E | E21L | 0.58 |
| 193 | 194 | L9V, E14G, K49R, E52S, D71G, K91E | E52S | 0.84 |
| 195 | 196 | L9V, E14G, K49R, D71G, D83K, K91E | D83K | 0.69 |
| 197 | 198 | L9V, E14G, K49R, D71G, K91E, T98V | T98V | 1.21 |
| 199 | 200 | L9V, E14G, K49R, D71G, I74R, K91E | I74R | 1.17 |
| 201 | 202 | A2V, L9V, E14G, K49R, D71G, K91E | A2V | 1.24 |
| 203 | 204 | L9V, E14G, K49R, T68C, D71G, K91E | T68C | 1.16 |
| 205 | 206 | L9V, E14G, K49R, D71G, G82A, K91E | G82A | 0.99 |
| 207 | 208 | L9V, E14G, K49R, T68A, D71G, K91E | T68A | 1.43 |
| 209 | 210 | L9V, E14G, T47S, K49R, D71G, I74Q, K91E | T47S, I74Q | 1.49 |
| 211 | 212 | L9V, E14G, T47G, K49R, D71G, K91E | T47G | 1.26 |
| 213 | 214 | L9V, E14G, K49R, D71G, F88W, K91E | F88W | 0.86 |
| 215 | 216 | L9V, E14G, V31A, K49R, D71G, K91E | V31A | 1.29 |
| 217 | 218 | A2S, L9V, E14G, K49R, D71G, K91E | A2S | 1.01 |
| 219 | 220 | L9V, E14G, A18E, K49R, D71G, K91E | A18E | 0.99 |
| 221 | 222 | L9V, E14G, K49R, D71G, R86S, K91E | R86S | 0.9 |
| 223 | 224 | L9V, E14G, K49R, D71G, I74H, K91E | I74H | 1.19 |
| 225 | 226 | L9V, E14G, K49R, D71G, I74Q, K91E | I74Q | 1.28 |
| 227 | 228 | L9V, E14G, T47S, K49R, D71G, K91E | T47S | 1.38 |
| 229 | 230 | L9V, E14G, K49R, D71G, I74N, K91E | I74N | 1.49 |

[1]The OA titer for the EVO039 control strain integrated with codon optimized OAC gene of SEQ ID NO: 85 was set as 1, and the values for "Relative OA titer" for each library strain clone was determined by comparison to this control strain.

Example 4: Preparation and Screening of Engineered Genes Encoding Recombinant Polypeptides with Olivetolic Acid Cyclase Activity This example illustrates preparation and screening of libraries of engineered genes expressing OAC activity when integrated in a yeast strain already engineered with the *C. sativa* genes, AAE1 (SEQ ID NO: 1), OLS (SEQ ID NO: 3), and d82PT4 (SEQ ID NO: 9). Combinatorial libraries were generated by two methods: (1) a semi-synthetic method of introducing mutations into a codon-optimized OAC parent gene of SEQ ID NO. 5, using oligonucleotides harboring specific amino acid mutations; and (2) synthesis of 576 combinatorial variants of SEQ ID NO: 5 that contain encode six amino acid mutations relative to the parent sequence. These semi-synthetic and synthesized combinatorial libraries were integrated into yeast strains engineered with the *C. sativa* genes, AAE1, OLS, and PT4 and screened for OA production indicating expression of a recombinant polypeptide having OAC activity.

Materials and Methods

A. Semi Synthetic Combinatorial Library Builds:

The yeast codon-optimized gene of SEQ ID NO: 5 encoding the wild-type *C. sativa* OAC polypeptide of SEQ ID NO: 6 was synthesized. Oligonucleotides were synthesized to randomly introduce mutations into the parent gene of SEQ ID NO: 5 via PCR amplification. The OAC parent gene of SEQ ID NO: 5 was integrated into a parent yeast strain using CRISPR-Cas9 at the XI-2 site to create the control strain EVO033. The integrated OAC gene was expressed under the bidirectional Gal1/10 promoter and the PGK1 terminator sequences. The parent strain was previously engineered to include the three *C. sativa* genes, AAE1 (SEQ ID NO: 1), OLS (SEQ ID NO: 3), and d82PT4 (SEQ ID NO: 9), which form a pathway capable of converting hexanoic acid to 3,5,7-trioxododecanoyl-CoA, the precursor for olivetolic acid (OA) synthesis and further to CBGA. The resulting control strain (EVO033) integrated with the OAC gene of SEQ ID NO. 5 thus included a pathway of the genes AAE1, OLS, and OAC capable of converting hexanoic acid to OA, as well as PT4 capable of converting OA to CBGA. As in Example 3, the screening strain for integration of the semi synthetic combinatorial libraries was EVO029, a strain was built by integrating the m-Venus cassette at the XI-2 site under control of the bidirectional Gal1/10 promoter and PGK1 terminator, thereby replacing the previous integrated OAC gene. The EVO029 strain was no longer capable of converting hexanoic acid to OA or further to CBGA. The EVO033 control strain was used to calculate fold-improvement in OA titer in each respective library as described below.

Genomic DNA from the control strain EVO033 was used as the template to generate a PCR product of SEQ ID NO. 5 including 5' and 3' flanking sequences using forward primer: 5'-GGTTATGAAGAGGAAAAAT-TGGCAGTAACC-3' (SEQ ID NO: 424) and reverse primer: 5'-CTAAGTCTAGCCACGAAAACTGCAA-3' (SEQ ID NO: 423). The PCR product was then digested into smaller fragments according to standard DNA shuffling protocols. The smaller fragments were gel purified, mixed with a 2 mM pool of oligonucleotides encoding combinations of mutations, and re-assembled by overlap extension PCR using the forward primer: 5'-GAACGAATCAAATTAACAACCAT-AGGATGA-3' (SEQ ID NO: 425) and reverse primer: 5'-GCACCAAAAGTAAGAAACGACAAAGTTT-3' (SEQ ID NO: 426). The combinations of mutations introduced per library are listed in Table 11 below:

TABLE 11

| | | | | | | | | |
|---|---|---|---|---|---|---|---|---|
| Combi 1 | A2G | L9V/I | T16Q/P | K25S/G/R | A36E | E53F/S/R/ L/H/A | E64D/K | I94K |
| Combi 2 | A2G | L9V/I | Y27F | E52R/Q | V66L | P76V | V84/I/M | |
| Combi 3 | L9V/I | E14G | N29G | K44P | T62G | T68/S/G/A/ E/Q/M/ | I94k | |
| Combi 4 | A2G | K12L | T16Q/P | V31M/E/S | K49R | S87K | K91E | |
| Combi 5 | L9V/I | E14G | T16Q | Y27F | K49R | H57G | D71G | K91E |
| Combi 6 | A2G | K12L | Y27F | K49R | E64D/K | I74/V/T/N/ M/L/G/S | | |

The oligonucleotide primers used to incorporate mutations are listed in Table 12 below.

TABLE 12

| Mutation | Primer | SEQ ID NO: |
|---|---|---|
| A2G | TACGATAAGGTGCTTGACACCCATGGTTTTTCTCCTTGACG | 431 |
| T16Q | TTCTTCTTTCTGGGCTTCTTGAATTTCGTCCTTGAATTTCAG | 432 |
| E53R | GACGATGTGAGTGTAACCTCTTTCTTTGTTTTTTTGGGTGAC | 433 |
| T62G | CGTCTCTACTGACTCGAAACCGACTTCGACGATGTGAGTGTA | 434 |
| T68E | TATTATGTAATCTTGGATTTCCTCTACTGACTCGAAAGTGAC | 435 |
| I74M | TCCCACATGGGCCGGGTGCATTATGTAATCTTGGATCGTCTC | 436 |
| V84I | TTCCCAGAAGCTACGGTAAATGTCTCCGAATCCCACATGGGC | 437 |
| A36E | CCAATAAACATCTTTCATTTCAGGGATGATATTCACCAGGTT | 438 |
| E53F | GACGATGTGAGTGTAACCAAATTCTTTGTTTTTTTGGGTGAC | 439 |
| E64K | TTGGATCGTCTCTACTGATTTGAAAGTGACTTCGACGATGTG | 440 |
| T68S | TATTATGTAATCTTGGATAGACTCTACTGACTCGAAAGTGAC | 441 |
| I74G | TCCCACATGGGCCGGGTGACCTATGTAATCTTGGATCGTCTC | 442 |
| V84M | TTCCCAGAAGCTACGGTACATGTCTCCGAATCCCACATGGGC | 443 |
| L9V | AATTTCGTCCTTGAATTTAACTACGATAAGGTGCTTGACAGC | 444 |
| N29G | AGGGATGATATTCACCAGACCTACATAGGTCTTGAAAAATTC | 445 |
| E53S | GACGATGTGAGTGTAACCAGATTCTTTGTTTTTTTGGGTGAC | 446 |
| E64D | TTGGATCGTCTCTACTGAATCGAAAGTGACTTCGACGATGTG | 447 |
| D71G | GGCCGGGTGTATTATGTAACCTTGGATCGTCTCTACTGACTC | 448 |
| S87K | CAAAAGTTTTTCCCAGAATTTACGGTAAACGTCTCCGAATCC | 449 |
| L9I | AATTTCGTCCTTGAATTTAATTACGATAAGGTGCTTGACAGC | 450 |
| V31S | CATCGCAGGGATGATATTAGACAGGTTTACATAGGTCTTGAA | 451 |
| K44P | GTTTTTTTGGGTGACGTCTGGGCCCCAATAAACATCTTTCAT | 452 |
| E53L | GACGATGTGAGTGTAACCCAATTCTTTGTTTTTTTGGGTGAC | 453 |
| V66L | GTAATCTTGGATCGTCTCCAATGACTCGAAAGTGACTTCGAC | 454 |
| I74N | TCCCACATGGGCCGGGTGATTTATGTAATCTTGGATCGTCTC | 455 |
| K91E | ATAGTCGAAAATCAAAAGTTCTTCCCAGAAGCTACGGTAAAC | 456 |
| K25S | CACCAGGTTTACATAGGTAGAGAAAAATTCTTCTTTCTGGGC | 457 |
| V31M | CATCGCAGGGATGATATTCATCAGGTTTACATAGGTCTTGAA | 458 |
| E53H | GACGATGTGAGTGTAACCATGTTCTTTGTTTTTTTGGGTGAC | 459 |
| T68Q | TATTATGTAATCTTGGATTTGCTCTACTGACTCGAAAGTGAC | 460 |

TABLE 12-continued

| Mutation | Primer | SEQ ID NO: |
|---|---|---|
| I74V | TCCCACATGGGCCGGGTGAACTATGTAATCTTGGATCGTCTC | 461 |
| I94K | TCTCGGGGTATAGTCGAATTTCAAAAGTTTTTCCCAGAAGCT | 462 |
| K12L | GGCTTCTGTAATTTCGTCCAAGAATTTCAGTACGATAAGGTG | 463 |
| K25G | CACCAGGTTTACATAGGTACCGAAAAATTCTTCTTTCTGGGC | 464 |
| V31E | CATCGCAGGGATGATATTTTCCAGGTTTACATAGGTCTTGAA | 465 |
| K49R | GTAACCTTCTTCTTTGTTTCTTTGGGTGACGTCTTTGCCCCA | 466 |
| E53A | GACGATGTGAGTGTAACCAGCTTCTTTGTTTTTTTGGGTGAC | 467 |
| T68A | TATTATGTAATCTTGGATAGCCTCTACTGACTCGAAAGTGAC | 468 |
| I74T | TCCCACATGGGCCGGGTGAGTTATGTAATCTTGGATCGTCTC | 469 |
| E14G | TTTCTGGGCTTCTGTAATACCGTCCTTGAATTTCAGTACGAT | 470 |
| K25R | CACCAGGTTTACATAGGTTCTGAAAAATTCTTCTTTCTGGGC | 471 |
| E52Q | GATGTGAGTGTAACCTTCTTGTTTGTTTTTTTGGGTGACGTC | 472 |
| T68G | TATTATGTAATCTTGGATACCCTCTACTGACTCGAAAGTGAC | 473 |
| I74S | TCCCACATGGGCCGGGTGAGATATGTAATCTTGGATCGTCTC | 474 |
| T16P | TTCTTCTTTCTGGGCTTCTGGAATTTCGTCCTTGAATTTCAG | 475 |
| E52R | GATGTGAGTGTAACCTTCTCTTTTGTTTTTTTGGGTGACGTC | 476 |
| H57G | GAAAGTGACTTCGACGATACCAGTGTAACCTTCTTCTTTGTT | 477 |
| T68M | TATTATGTAATCTTGGATCATCTCTACTGACTCGAAAGTGAC | 478 |
| I74L | TACGATAAGGTGCTTGACACCCATGGTTTTTTCTCCTTGACG | 479 |

The final libraries were assembled by overlap extension PCR using the forward primer: 5'-GAACGAATCAAATTAACAACCATAGGATGA-3' (SEQ ID NO: 425) and reverse primer: 5'-GCACCAAAAGTAAGAAACGACAAAGTTT-3' (SEQ ID NO: 426). The assembled OE-PCR products were then pooled together per library and gel purified to provide six semi-synthetic combinatorial libraries of linear donor DNA. The six pooled semi-synthetic combinatorial libraries of linear donor DNA were transformed and integrated as a knock-in using CRISPR-Cas9 into an m-Venus cassette located at the XI-2 site in a yeast strain that already had integrated genes encoding the *C. sativa* enzymes, AAE1, OLS and PT4 (EVO029). The m-Venus cassette was integrated at the XI-2 site under control of the bidirectional Gal1/10 promoter and PGK1 terminator. B. Synthesis of 576 Combinatorial Variants The synthetic gene of SEQ ID NO: 5 was used to design and synthesize 576 variants each with six amino acid changes with respect to SEQ ID NO: 6. As in Example 1, to facilitate efficient integration, the 50-mer 5' and 3' flanking sequences of SEQ ID NO: 427 and SEQ ID NO: 428 were introduced into each combinatorial variant. As in Example 1, these flanking sequences provided the overlap homology to build longer DNA donors including the pGal1 promoter and the PGK1t terminator. The combinatorial variants including the flanking sequence were synthesized by Twist.

A first PCR product (Fragment A) that has sequence overlap with the 5' end of each of the OAC variants was amplified from EVO029 genomic DNA using the following primers 5'-GGTTATGAAGAGGAAAAATTGGCAGTAACC-3' (SEQ ID NO: 480), and 5'-CTTTAACACTATCAAGTGCTTTACAGCCATGGTTTTTTCTCCTTGACGTTAAAGTATAGA-3' (SEQ ID NO: 481). A second PCR product (Fragment B) that has sequence overlap with the 3' end of each of the OAC was amplified from EVO029 genomic DNA using the following primers 5'-GGAAACCTCTACACATAGAAATATCGAATGGG-3' (SEQ ID NO: 482) and 5'-TTGTTAATTTTTGATTACACTCCAAGGAAGTAAATTGAATTGAATTGAAATCGATAGATC-3' (SEQ ID NO: 483). The third product, OAC Variants (Fragment C) was synthesized as described above with between 47 and 50 base pair sequence overlap with the 3' end of Fragment A (amplified from gDNA template) and overlap with the 5' end of Fragment B (amplified from gDNA template). The three Fragments A, B, and C were assembled by overlap extension PCR using the forward primer 5'-GAACGAATCAAATTAACAACCATAGGATGA-3' (SEQ ID NO: 425) and reverse primer 5'-GAGGAGCGAATTTTTTTTAATAAAAATCT-3' (SEQ ID NO: 484). Thus, the integrated synthesized genes were expressed under the bidirectional Gal1/10 promoter and the PGK1 terminator sequences. The parent strain was previously engineered to include the three *C. sativa* genes, AAE1 (SEQ ID NO: 1), OLS (SEQ ID NO: 3), and d82PT4 (SEQ ID NO: 9), which form a pathway capable of converting hexanoic acid to 3,5,7-trioxododecanoyl-CoA, the precursor for olivetolic acid (OA) synthesis and further to CBGA. The resulting control strain (EVO033) integrated with the OAC gene of SEQ ID NO. 5, thus included a pathway of the genes AAE1, OLS, and OAC capable of converting hexanoic acid to OA, as well as PT4 capable of converting OA to CBGA. As in Example 3, the screening strain for integration of the semi synthetic combinatorial libraries was EVO029, a strain was built by integrating the m-Venus cassette at the XI-2 site under control of the bidirectional Gal1/10 promoter and PGK1 terminator, thereby replacing the previous integrated OAC gene. The EVO029 strain was no longer capable of converting hexanoic acid to OA or further to CBGA. The EVO033 control strain was used to calculate fold-improvement in OA titer in each respective library as described below.

C. Screening of the Semi-Synthetic and Synthesized Combinatorial Libraries for Olivetolic Acid Biosynthesis:

Individual clones from the semi-synthetic and synthesized combinatorial libraries were integrated in EVO029 and the respective EVO033 control strains were grown in 0.3 mL YPD in 96-well microtiter plates and screened as described in Example 1. Whole broth culture samples were extracted and screened using HPLC as described in Example 1.

C. Sequencing

Clones determined by screening to exhibit an OA titer were re-tested and sequenced using Sanger sequencing technology to determine their nucleotide and amino acid differences compared to SEQ ID NO 5 and SEQ ID NO 6, respectively.

D. Results

Results for relative OA titer and corresponding amino acid changes of the semi-synthetic combinatorial libraries generated from the parent codon-optimized genes of SEQ ID NO: 5 are summarized in Table 13 (below).

TABLE 13

| NT SEQ ID NO: | AA SEQ ID NO: | aa substitution(s) relative to CsOAC | Relative OA titer[1] |
|---|---|---|---|
| 233 | 234 | A2G, L9I, K25R | 0.87 |
| 235 | 236 | L9I, E53S, I94K | 1.16 |
| 237 | 238 | A36E | 1.15 |
| 239 | 240 | E53H, E64D | 0.97 |
| 241 | 242 | L9I, K25R, A36E, E53H, I94K | 1.32 |
| 243 | 244 | A2G, L9I, K25R, E53S, E64D, I94K | 0.9 |
| 245 | 246 | K25S, A36E | 1.23 |
| 247 | 248 | L9I, T16Q, K25R, E53S, E64D | 1.17 |
| 249 | 250 | K25S, I94K | 1.04 |
| 251 | 252 | A2G, L9I, K25G | 1.04 |
| 253 | 254 | E53A | 0.93 |
| 255 | 256 | A2G, L9V, T16P | 0.23 |
| 257 | 258 | E53A, E64D, I94K | 0.9 |
| 259 | 260 | L9I, K25S, A36E, E64D, I94K | 1.39 |
| 261 | 262 | L9I, K25S, A36E, E53R, I94K | 1.11 |
| 263 | 264 | K25E, A36E, E64D, I94K | 1.22 |
| 265 | 266 | K25R, E64D | 1.1 |
| 267 | 268 | K25R, A36E, E53S, E64D, I94K | 1.2 |
| 269 | 270 | A2G, L9I, A36E, E53S, E64D, I94K | 1.09 |
| 271 | 272 | A2G, L9V, Y27F, E52R, V66L, V84M | 1.36 |
| 273 | 274 | L9V, V66L | 1.27 |
| 275 | 276 | L9V, Y27F, V84M | 1.18 |
| 277 | 278 | A2G, L9V | 1.06 |
| 279 | 280 | L9I, Y27F, E53S, V66L, V84M | 0.71 |
| 281 | 282 | V66L, V84M | 1.05 |
| 283 | 284 | L9V, E52Q, V66L, P76V | 0.55 |
| 285 | 286 | L9I, Y27F, V66L, V84I | 0.94 |
| 287 | 288 | A2G, L9V, Y27F, V66L | 0.85 |
| 289 | 290 | Y27F | 0.82 |
| 291 | 292 | A2G, L9V, V66L, V84M | 1.01 |
| 293 | 294 | L9V, T26A, E52Q, P76V | 1.05 |
| 295 | 296 | L9V, E52R, V84M | 1.18 |
| 297 | 298 | L9V, Y27F, V66L, V84M | 1.14 |
| 299 | 300 | L9I, N29G, T62G, T68E, I94K | 0.86 |
| 301 | 302 | L9I, E14G, K44P, T68E, I94K | 1 |

TABLE 13-continued

| NT SEQ ID NO: | AA SEQ ID NO: | aa substitution(s) relative to CsOAC | Relative OA titer[1] |
|---|---|---|---|
| 303 | 304 | E14G, T68S, I94K | 1.19 |
| 305 | 306 | E14G, T68A, I94K | 1.24 |
| 307 | 308 | T62G, T68G, I94K | 0.49 |
| 309 | 310 | L9V, E14G, T68E, I94K | 1.14 |
| 311 | 312 | L9V, I94K | 1 |
| 313 | 314 | L9V, N29G, T68E, I94K | 1.16 |
| 315 | 316 | A2G, T16P, V31M, K49R, S87K | 0.23 |
| 317 | 318 | V31E, F63L, S87K | 1.16 |
| 319 | 320 | A2G, K49R | 1.09 |
| 321 | 322 | V31M, K49R, S87K | 1.1 |
| 323 | 324 | A2G, V31S, K49R, K91E | 0.5 |
| 325 | 326 | V31E, K49R, S87K | 0.84 |
| 327 | 328 | T16P, V31M, K49R | 1.05 |
| 329 | 330 | L9V, E14G, V31S, K49R, K91E | 1.01 |
| 331 | 332 | K12L, V31M, K49R | 0.98 |
| 333 | 334 | L9V, K91E | 0.72 |
| 335 | 336 | L9I, E14G, V40A, K49R | 1.01 |
| 337 | 338 | L9V, K49R, D71G, K91E | 0.49 |
| 339 | 340 | L9I, E14G, Y27F, D71G, K91E | 0.28 |
| 341 | 342 | E14G, K49R, D71G, K91E | 0.37 |
| 343 | 344 | L9I, Y27F, K91E | 0.74 |
| 345 | 346 | K49R, Y85F, K91E | 0.86 |
| 347 | 348 | L9I, E14G, D71G, K91E | 0.65 |
| 349 | 350 | L9V, K49R, K91E | 1.05 |
| 351 | 352 | L9I, E14G, K49R, D71G | 1.21 |
| 353 | 354 | E14G, Y27F, K49R | 0.93 |
| 355 | 356 | L9V, T16Q, K49R, K91E | 0.85 |
| 357 | 358 | L9I, K49R, K91E | 1.1 |
| 359 | 360 | L9V, E14G, Y27F, K49R, K91E | 0.75 |
| 361 | 362 | K49R, K91E | 0.85 |
| 363 | 364 | L91, E14G, D71G | 1.15 |
| 365 | 366 | E14G, K49R, K91E | 0.72 |
| 367 | 368 | K49R, E64D, I74T | 1.15 |
| 369 | 370 | K12L, Y27F, K49R, I74M | 0.94 |
| 371 | 372 | A2G, Y27F, E64K, I74V | 0.3 |
| 373 | 374 | Y27F, K49R, E64D, I74V | 1 |
| 375 | 376 | Y27F, K49R, E64D, I74T | 0.9 |
| 377 | 378 | A2G, K49R, E64D, I74M | 1.11 |
| 379 | 380 | A2G, K49R, E64D, I74N | 1 |
| 381 | 382 | K49R, E64K, I74N | 1.1 |
| 383 | 384 | L9V, E14G, K25A, Q48P, I74N | 0.99 |
| 385 | 386 | K12L, K49R, I74V | 1.19 |
| 387 | 388 | Y27F, K49R, I74V | 1.02 |
| 389 | 390 | K49R, I74S | 1.16 |
| 391 | 392 | A2G, K12L, K49R, I74N | 0.68 |
| 393 | 394 | L9V, E14G, T47A, E64D, I74V | 1.37 |
| 395 | 396 | K12L, K49R, E64D, I74S | 1.08 |
| 397 | 398 | Y27F, K49R, I74N | 0.97 |
| 399 | 400 | A2G, E64K, I74M | 0.54 |
| 401 | 402 | V8I, L9I, I33V, K49R, T56S, D71T | 1.35 |
| 403 | 404 | V8I, L9I, I33D, K49R, T56S, I58V | 1.27 |
| 405 | 406 | V8I, L9I, K12N, K49R, Y55W, T56S | 1 |
| 407 | 408 | V8I, L9I, K12V, I33V, T56S, E64D | 1.29 |
| 409 | 410 | L9I, K12V, I33V, T56S, I58V, E64D | 1.24 |
| 411 | 412 | A2P, V8I, L9I, E64D, T68S, R100G | 1.33 |
| 413 | 414 | V8I, K12V, T56S, I58V, E64D, Y97F | 0.86 |
| 415 | 416 | V31M, K49R, I58V, T62C, E64D, T68A | 1.08 |
| 417 | 418 | V8I, K49R, I58V, E64D, T68M, I74M | 1.25 |
| 419 | 420 | A36P, I58V, E64D, T68G, Q70K, I74M | 1.14 |
| 421 | 422 | E14G, A36Q, K49R, I58V, E64D, Q70K | 1.28 |
| 485 | 486 | A2P, V8I, L91, I33V, E64D, I94K | 1.51 |
| 487 | 488 | V8I, L9I, A36S, Y55W, E64D, I94K | 1.48 |
| 489 | 490 | V8I, L9I, I33V, K49R, I58V, T62C | 1.46 |
| 491 | 492 | V8I, L9I, I33V, K49R, I58V, T62C | 1.45 |
| 493 | 494 | V8I, L9I, I33D, K49R, T56S, D71T | 1.44 |
| 495 | 496 | V8I, L9I, K12N, I33V, K49R, D71T | 1.42 |
| 497 | 498 | V8I, L9I, I33V, K49R, I58V, R100G | 1.39 |
| 499 | 500 | V8I, L9I, K12N, I33V, K49R, D71T | 1.38 |
| 501 | 502 | V8I, L9I, K49R, Y55W, I58V, R100G | 1.38 |
| 503 | 504 | V8I, L9I, I33V, K49R, T56S, R100G | 1.38 |
| 505 | 506 | V8I, L9I, I33V, A36L, K49R, I58V | 1.37 |
| 507 | 508 | L9I, I33V, A36Q, I58V, E64D, I94K | 1.36 |
| 509 | 510 | V8I, L9I, K10A, I33V, T56S, I58V | 1.35 |
| 511 | 512 | L9I, I33V, K49R, T56S, I58V, R100G | 1.34 |
| 513 | 514 | V8I, L9I, K12N, I33V, K49R, D71T | 1.33 |
| 515 | 516 | L9I, I33V, A36Q, I58V, E64D, I94K | 1.32 |

TABLE 13-continued

| NT SEQ ID NO: | AA SEQ ID NO: | aa substitution(s) relative to CsOAC | Relative OA titer[1] |
|---|---|---|---|
| 517 | 518 | V8I, L9I, K10A, N29D, I33V, I58V | 1.32 |
| 519 | 520 | L9I, I33V, K49R, T56S, I58V, R100G | 1.32 |
| 521 | 522 | V8I, L9I, I33D, T56S, I58V, E64D | 1.30 |
| 523 | 524 | V8I, L9I, I33D, K49R, T56S, D71T | 1.30 |
| 525 | 526 | V8I, L9I, I33D, K49R, T56S, D71T | 1.28 |
| 527 | 528 | L9I, A36Q, Y55W, I58V, E64D, I94K | 1.27 |
| 529 | 530 | V8I, L9I, I33V, T56S, I58V, Q70K | 1.27 |
| 531 | 532 | V8I, L9I, K49R, Y55W, T56S, R100G | 1.26 |
| 533 | 534 | V8I, L9I, I33D, K49R, T56S, D71T | 1.25 |
| 535 | 536 | V8I, L9I, K10A, N29D, I33V, T56S | 1.25 |
| 537 | 538 | V8I, L9I, K10A, N29D, I33V, T56S | 1.25 |
| 539 | 540 | A2P, V8I, L9I, Y55W, E64D, I94K | 1.24 |
| 541 | 542 | L9I, A36Q, Y55W, I58V, E64D, I94K | 1.24 |
| 543 | 544 | V8I, L9I, I33V, T56S, I58V, R100G | 1.23 |
| 545 | 546 | V8I, L9I, Y55W, T56S, I58V, R100G | 1.22 |
| 547 | 548 | L9I, A36Q, Y55W, I58V, E64D, I94K | 1.22 |
| 549 | 550 | V8I, L9I, K12N, T16Q, K49R, T56S | 1.21 |
| 551 | 552 | V8I, L9I, K49R, Y55W, I58V, T62C | 1.21 |
| 553 | 554 | A2P, V8I, L9I, T16Q, E64D, I94K | 1.20 |
| 555 | 556 | V8I, L9I, I33D, T56S, I58V, E64D | 1.19 |
| 557 | 558 | V8I, L9I, T16Q, A36F, K49R, I58V | 1.19 |
| 559 | 560 | V8I, I33V, K49R, T56S, I58V, R100G | 1.19 |
| 561 | 562 | V8I, L9I, T16Q, T56S, I58V, Q70K | 1.19 |
| 563 | 564 | V8I, L9I, T16Q, T56S, I58V, R100G | 1.18 |
| 565 | 566 | V8I, L9I, K10A, N29D, I33V, T56S | 1.17 |
| 567 | 568 | V8I, L9I, K10A, N29D, I33V, T56S | 1.17 |
| 569 | 570 | L9I, I33V, K49R, T56S, I58V, R100G | 1.17 |
| 571 | 572 | V8I, L9I, Y55W, T56S, I58V, R100G | 1.16 |
| 573 | 574 | L9I, A36Q, Y55W, I58V, E64D, I94K | 1.16 |
| 575 | 576 | V8I, L9I, K12V, I33V, T56S, I58V | 1.15 |
| 577 | 578 | V8I, L9I, T16Q, A36F, K49R, I58V | 1.14 |
| 579 | 580 | V8I, L9I, K12N, I33V, T56S, D71T | 1.14 |
| 581 | 582 | V8I, L9I, K49R, Y55W, T56S, R100G | 1.13 |
| 583 | 584 | V8I, L9I, I33V, A36S, T62C, E64D | 1.13 |
| 585 | 586 | V8I, K49R, Y55W, T56S, I58V, R100G | 1.13 |
| 587 | 588 | L9I, A36Q, I58V, E64D, T68S, I94K | 1.64 |
| 589 | 590 | V8I, L9I, T56S, I58V, T68S, R100G | 1.52 |
| 591 | 592 | V8I, L9I, K12V, T56S, E64D, T68S | 1.47 |
| 593 | 594 | L9I, A36Q, I58V, E64D, I94K, Y97F | 1.46 |
| 595 | 596 | V8I, L9I, V28C, K49R, T56S, I58V | 1.44 |
| 597 | 598 | V8I, L9I, K12V, I58V, E64D, T68G | 1.44 |
| 599 | 600 | V8I, L9I, A36S, E64D, I94K, Y97F | 1.44 |
| 601 | 602 | V8I, L9I, K12N, K49R, T68G, D71T | 1.39 |
| 603 | 604 | V8I, L9I, K49R, I58V, T62C, Y97F | 1.38 |
| 605 | 606 | V8I, L9I, V28C, K49R, T56S, D71T | 1.36 |
| 607 | 608 | V8I, L9I, K49R, I58V, T62C, Y97F | 1.36 |
| 609 | 610 | V8I, L9I, K10A, N29D, I58V, T68G | 1.35 |
| 611 | 612 | V8I, L9I, K49R, I58V, T68S, R100G | 1.35 |
| 613 | 614 | L9I, K49R, T56S, I58V, T68G, R100G | 1.32 |
| 615 | 616 | V8I, L9I, K12V, T56S, E64D, T68S | 1.31 |
| 617 | 618 | V8I, L9I, K10A, N29D, I58V, T68G | 1.30 |
| 619 | 620 | V8I, L9I, A36S, E64D, I94K, Y97F | 1.29 |
| 621 | 622 | V8I, L9I, K12N, K49R, T56S, Y97F | 1.28 |
| 623 | 624 | V8I, L9I, K12V, I58V, E64D, T68G | 1.28 |
| 625 | 626 | V8I, L9I, K12V, I58V, E64D, Y97F | 1.27 |
| 627 | 628 | V8I, L9I, T56S, I58V, T68S, R100G | 1.27 |
| 629 | 630 | V8I, L9I, K49R, I58V, T62C, T68G | 1.27 |
| 631 | 632 | V8I, L9I, K12V, T56S, E64D, T68S | 1.27 |
| 633 | 634 | V8I, K49R, T56S, I58V, T68S, R100G | 1.25 |
| 635 | 636 | V8I, L9I, T56S, I58V, T68G, Q70K | 1.25 |
| 637 | 638 | V8I, L9I, K49R, I58V, T62C, T68G | 1.24 |
| 639 | 640 | V8I, L9I, K12V, T56S, I58V, T68G | 1.24 |
| 641 | 642 | V8I, L9I, K12V, T56S, I58V, T68S | 1.24 |
| 643 | 644 | V8I, L9I, A36F, K49R, I58V, T68S | 1.23 |
| 645 | 646 | V8I, L9I, K49R, I58V, T62C, Y97F | 1.23 |
| 647 | 648 | V8I, L9I, A36F, K49R, I58V, Y97F | 1.23 |
| 649 | 650 | V8I, L9I, K12N, K49R, T68G, D71T | 1.23 |
| 651 | 652 | V8I, L9I, K12V, T56S, E64D, T68S | 1.22 |
| 653 | 654 | V8I, L9I, K49R, I58V, Y97F, R100G | 1.22 |
| 655 | 656 | V8I, L9I, A36F, K49R, I58V, Y97F | 1.22 |
| 657 | 658 | V8I, L9I, K12V, T56S, E64D, T68S | 1.21 |
| 659 | 660 | V8I, L9I, K10A, N29D, T56S, I58S | 1.21 |
| 661 | 662 | V8I, L9I, V28C, K49R, T56S, I58V | 1.21 |
| 663 | 664 | V8I, L9I, K10A, T56S, I58V, Y97F | 1.19 |
| 665 | 666 | V8I, L9I, K12V, E14G, K49R, E67S | 1.60 |
| 667 | 668 | L9I, A36S, K49R, E64D, T68M, I74M | 1.57 |
| 669 | 670 | L9I, Y41E, K49R, I58V, V66I, T68E | 1.54 |
| 671 | 672 | V8I, L9I, K12V, E14G, K49R, E67S | 1.53 |
| 673 | 674 | V8I, L9I, K12N, T16Q, K49R, I58V | 1.49 |
| 675 | 676 | V8I, L9I, K12V, E14G, K49R, E67S | 1.47 |
| 677 | 678 | V8I, L9I, K25N, K49R, I58V, T68S | 1.46 |
| 679 | 680 | V8I, L9I, K49R, T56S, V66I, T68M | 1.44 |
| 681 | 682 | V8I, L9I, K12V, E14G, K49R, E67S | 1.43 |
| 683 | 684 | V8I, L9I, K25N, A36P, T68G, I74M | 1.43 |
| 685 | 686 | L9I, Y41E, K49R, I58V, V66I, T68E | 1.42 |
| 687 | 688 | V8I, L9I, K49R, E64D, Y97F, R100G | 1.41 |
| 689 | 690 | V8I, L9I, K12V, E14G, K49R, E67S | 1.40 |
| 691 | 692 | V8I, L9I, I33V, 158V, E64D, R100G | 1.40 |
| 693 | 694 | L9I, A36S, K49R, E64D, T68M, I74M | 1.40 |
| 695 | 696 | V8I, L9I, K49R, E64D, Y97F, R100G | 1.37 |
| 697 | 698 | V8I, L9I, Y41E, I58V, E64D, T68A | 1.36 |
| 699 | 700 | V8I, K12Q, V31M, V66I, T68S, I74M | 1.35 |
| 701 | 702 | V8I, L9I, Y41E, I58V, E64D, T68A | 1.35 |
| 703 | 704 | L9I, E14G, I58V, T62C, E64D, V66I | 1.35 |
| 705 | 706 | V8I, L9I, K49R, T56S, V66I, T68M | 1.35 |
| 707 | 708 | V8I, L9I, K25N, A36P, T68G, I74M | 1.34 |
| 709 | 710 | V8I, L9I, K25N, K49R, I58V, T68S | 1.34 |
| 711 | 712 | L9I, T16Q, K49R, I58V, E64D, R100G | 1.34 |
| 713 | 714 | V8I, K12Q, V31M, V661, T68S, I74M | 1.33 |
| 715 | 716 | V8I, K12Q, I33V, K49R, I58V, I74M | 1.33 |
| 717 | 718 | V8I, L9I, K49R, E64D, Y97F, R100G | 1.33 |
| 719 | 720 | L9I, T16Q, K49R, I58V, E64D, R100G | 1.31 |
| 721 | 722 | L9I, E14G, I58V, T62C, E64D, V66I | 1.29 |
| 723 | 724 | V8I, L9I, K49R, E64D, Y97F, R100G | 1.29 |
| 725 | 726 | V8I, K12N, I33V, I58V, E64D, V66I | 1.29 |
| 727 | 728 | A2P, L9I, K25N, V31M, K49R, Y55W | 1.29 |
| 729 | 730 | V8I, L9I, K12N, T16Q, K49R, I58V | 1.28 |
| 731 | 732 | L9I, A36S, K49R, E64D, T68M, I74M | 1.28 |
| 733 | 734 | L9I, K49R, I58V, T68A, D71T, I94K | 1.27 |
| 735 | 736 | L9I, E14G, I58V, T62C, E64D, V66I | 1.27 |
| 737 | 738 | V8I, E14G, K49R, I58V, E64D, R100A | 1.26 |
| 739 | 740 | L9V, E14G, K49R, E53S, D71G, K91E | 1.26 |
| 741 | 742 | A2S, V8I, K49R, E53V, T56S, T68S | 1.26 |
| 743 | 744 | V8I, K12Q, V31M, V66I, T68S, I74M | 1.26 |
| 745 | 746 | V8I, K12Q, V31M, V66I, T68S, I74M | 1.25 |
| 747 | 748 | A2P, V8I, K49R, T62C, T68E, I74M | 1.25 |
| 749 | 750 | V8I, L9I, K12N, T16Q, K49R, I58V | 1.25 |
| 751 | 752 | V8I, L9I, I33V, K49R, T62C, E64D | 1.23 |
| 753 | 754 | V8I, K12Q, V31M, V66I, T68S, I74M | 1.23 |
| 755 | 756 | L9I, E53V, I58V, E64D, T68S, I74M | 1.22 |
| 757 | 758 | V8I, V28C, A36S, K49R, T56S, V66I | 1.22 |
| 759 | 760 | V8I, K12Q, V31M, V66I, T68S, I74M | 1.22 |
| 761 | 762 | V8I, L9I, K49R, E64D, Y97F, R100G | 1.21 |
| 763 | 764 | V8I, L9I, I33V, I58V, E64D, R100G | 1.21 |
| 765 | 766 | V8I, E14G, K49R, I58V, E64D, R100A | 1.20 |
| 767 | 768 | V8I, L9I, K25N, A36P, T68G, I74M | 1.19 |
| 769 | 770 | V8I, V31M, E64D, T68Q, Q70K, D71T | 1.19 |
| 771 | 772 | L9I, K25N, A36Q, K49R, V66I, T68Q | 1.50 |
| 773 | 774 | L9I, K25N, A36Q, K49R, V66I, T68Q | 1.44 |
| 775 | 776 | V8I, K49R, E64D, T68S, E90D, I94K | 1.39 |
| 777 | 778 | V8I, A36S, T56S, T68S, E90D, I94K | 1.35 |
| 779 | 780 | L9I, K49R, T62C, E64D, T68G, I74M | 1.31 |
| 781 | 782 | K12N, T56S, I58V, V66I, T68A, D71T | 1.29 |
| 783 | 784 | L9I, I33V, Q48M, I58V, E64D, I74M | 1.28 |
| 785 | 786 | L9I, V31M, K49R, N50Y, T68S, I74M | 1.27 |
| 787 | 788 | V8I, K25N, I33V, K49R, E64D, I74M | 1.26 |
| 789 | 790 | L9I, A18S, K25N, K49R, I58V, S87P | 1.24 |
| 791 | 792 | L9I, E22L, K49R, E64D, I74M, Y97F | 1.21 |
| 793 | 794 | V8I, K49R, E64D, T68S, E90D, I94K | 1.19 |
| 795 | 796 | L9I, E22L, V46I, E64D, I74M, Y97F | 1.17 |
| 797 | 798 | V8I, A18S, K49R, E64D, V66I, I94K | 1.15 |
| 799 | 800 | L9I, E22L, K49R, E64D, I74M, Y97F | 1.14 |
| 801 | 802 | A2S, V8I, T56S, T62C, T68S, I74M | 1.10 |
| 803 | 804 | Y41E, K49R, T56S, I58V, V66I, T68A | 1.09 |
| 805 | 806 | K10A, K49R, I58V, E64D, V66I, T68E | 1.45 |
| 807 | 808 | K12N, A18S, K49R, I58V, V66I, I74M | 1.31 |
| 809 | 810 | K49R, 158V, T62C, T68E, D71T, I74M | 1.21 |
| 811 | 812 | I33V, K49R, T62C, E64D, V66I, I74M | 1.20 |
| 813 | 814 | T16Q, K25N, A36Q, K49R, V66I, I74M | 1.16 |
| 815 | 816 | A2P, I58V, E64D, E67S, T68Q, R100G | 1.14 |
| 817 | 818 | I33V, K49R, T62C, E64D, V66I, I74M | 1.14 |
| 819 | 820 | K49R, I58V, T68A, D71T, I74M, R100G | 1.14 |

TABLE 13-continued

| NT SEQ ID NO: | AA SEQ ID NO: | aa substitution(s) relative to CsOAC | Relative OA titer[1] |
|---|---|---|---|
| 821 | 822 | K25N, K49R, I58V, E64D, V66I, T68S | 1.13 |
| 823 | 824 | A36Q, K49R, I58V, E64D, V66I, K91E | 1.10 |
| 825 | 826 | K12N, A18S, K49R, I58V, V66I, I74M | 1.07 |
| 827 | 828 | E21V, A36Q, I58V, V66I, E67S, I74M | 1.06 |
| 829 | 830 | A2P, E14G, Q48C, I58V, E64D, V66I | 1.05 |
| 831 | 832 | A2P, K12V, T16Q, K49R, I58V, V66I | 1.03 |
| 833 | 834 | A2P, K12V, T16Q, K49R, I58V, V66I | 1.02 |
| 835 | 836 | I33V, K49R, T62C, E64D, V66I, I74M | 1.01 |
| 837 | 838 | A2P, V31M, I58V, T62C, E64D, T68S | 0.91 |
| 839 | 840 | A36P, I58V, E67S, T68S, I74M, R100G | 0.90 |
| 841 | 842 | F23I, K49R, V66I, T68Q, Q70A, I74M | 0.90 |
| 843 | 844 | E22L, V31M, A36S, V66I, T68S, I74M | 0.85 |
| 845 | 846 | A36S, K49R, 158C, E64D, V66I, T68S | 1.23 |
| 847 | 848 | T16Q, A36Q, Q48H, I58V, E64D, I74M | 1.16 |
| 849 | 850 | K25N, K49R, Y55W, 158V, E64D, I74M | 1.12 |
| 851 | 852 | A36S, Q48C, E64D, T68E, I74M, S87P | 1.05 |
| 853 | 854 | K49R, V66I, T68Q, D71T, I74M, 194K | 0.92 |

[1]The OA titer for the EVO033 control strain integrated with codon optimized OAC gene of SEQ ID NO: 5 was set as 1, and the values for "Relative OA titer" for each library strain clone was determined by comparison to this control strain.

Example 5: Preparation and Screening of Engineered Genes Encoding Recombinant Polypeptides with Olivetolic Acid Cyclase Activity This example illustrates preparation and screening of libraries of engineered genes expressing OAC activity when integrated in a yeast strain already engineered with the *C. sativa* genes, AAE1 (SEQ ID NO: 1), OLS (SEQ ID NO: 3) and d82PT4 (SEQ ID NO: 9). The libraries were generated by site saturation mutagenesis (SSM) of two parent OAC variant genes from Example 5, SEQ ID NO. 411 and SEQ ID. NO 417 which encode the polypeptides of SEQ ID NO: 412 and 418, each of which has 6 amino acid changes relative to the wild-type OAC polypeptide sequence of SEQ ID NO: 6. These SSM libraries were integrated in a yeast strain similar to EVO002 but engineered to include the *C. sativa* genes, AAE1 (SEQ ID NO: 1), OLS (SEQ ID NO: 3), and d82PT4 (SEQ ID NO: 9) and screened for OA production indicating expression of a recombinant polypeptide having OAC activity.

Materials and Methods

A. Site Saturation Mutagenesis Library Builds:

Each of the two OAC parent genes, SEQ ID NO: 411 and SEQ ID. NO: 417 was integrated into a parent yeast strain using CRISPR-Cas9 at the XI-2 site to create the control strains EVO067 and EVO068, respectively. The integrated OAC genes were expressed under the bidirectional Gal1/10 promoter and the PGK1 terminator sequences. The parent strain was previously engineered to include the genes, AAE1 (SEQ ID NO: 1), OLS (SEQ ID NO: 3), and d82PT4 (SEQ ID NO: 9). The resulting control strains (EVO067 and EVO068) integrated with the variant OAC genes of SEQ ID NO. 411 and 417, respectively, thus included a pathway of the genes AAE1, OLS, and OAC capable of converting hexanoic acid to OA, as well as PT4 capable of converting OA to CBGA. As in Examples 1 and 2, the screening strain EVO029, was built by integrating the m-Venus cassette at the XI-2 site under control of the bidirectional Gal1/10 promoter and PGK1 terminator, thereby replacing the previous integrated OAC gene. The EVO029 strain was no longer capable of converting hexanoic acid to OA or further to CBGA.

The EVO067 and EVO068 control strains were used to calculate fold-improvement in OA titer in each respective library as described below.

Genomic DNA from the control strains (EVO067 and EVO068) were used as the template to generate two PCR products: (1) a first PCR product (Fragment A), which does not harbor any degenerate codons, and (2) a second PCR product (Fragment B), which has sequence overlap with the Fragment A, and is amplified harboring one NNK degenerate codon only. Primers used for amplification of Fragments A and B and overlap extension were designed according to standard site-saturation mutagenesis protocols. Fragment B was amplified with a single forward primer that included the single NNK degenerate codon at either position 9 or position 49 respectively and a single reverse primer: 5'-CTAAGTCTAGCCACGAAAACTGCAA-3' (SEQ ID NO: 423). Fragment A was amplified using a single forward primer: 5'-GGTTATGAAGAGGAAAAAT-TGGCAGTAACC-3' (SEQ ID NO: 424) and a single primer designed according to the location of the mutagenesis site, in this case position 9 or 49 respectively. The two fragments A and B were assembled by overlap extension PCR using the forward primer: 5'-GAACGAATCAAATTAACAACCAT-AGGATGA-3' (SEQ ID NO: 425) and reverse primer: 5'-GCACCAAAAGTAAGAAACGACAAAGTTT-3' (SEQ ID NO: 426).

The assembled OE-PCR products were then pooled together per template and gel purified to provide two saturation mutagenesis libraries of linear donor DNA.

The two pooled saturation mutagenesis libraries of linear donor DNA were transformed and integrated as a knock-in using CRISPR-Cas9 into an m-Venus cassette located at the XI-2 site in a yeast strain that already had integrated genes encoding the *C. sativa* enzymes, AAE1, OLS and PT4 (EVO029). The m-Venus cassette was integrated at the XI-2 site under control of the bidirectional Gal1/10 promoter and PGK1 terminator.

B. Screening of Site Saturation Mutagenesis Libraries for Olivetolic Acid Biosynthesis:

Individual clones from the saturation mutagenesis libraries integrated in EVO029 and the respective EVO067 or EVO068 control strains were grown in 0.3 mL YPD in 96-well microtiter plates and screened as described in Example 1. Whole broth culture samples were extracted and screened using HPLC as described in Example 1.

C. Sequencing

Clones determined by screening to exhibit an OA titer were re-tested and sequenced using Sanger sequencing technology to determine their nucleotide and amino acid differences compared to SEQ ID NO 5 and SEQ ID NO 6, respectively.

D. Results

Results for relative OA titer and corresponding amino acid changes of the SSM libraries generated from the parent codon-optimized genes of SEQ ID NO: 411 and 417 is summarized in Tables 14 and 15 respectively (below).

TABLE 14

| NT SEQ ID NO: | AA SEQ ID NO: | aa substitution(s) relative to CsOAC | aa substitution (s) relative to SEQ ID NO: 412 | Relative OA titer[1] |
|---|---|---|---|---|
| 411 | 412 | A2P, V8I, L9I, E64D, T68S, R100G | n/a | 1 |
| 855 | 856 | A2P, V8I, L9V, E64D, T68S, R100G | L9V | 1.171 |
| 857 | 858 | A2P, V8I, L9T, E64D, T68S, R100G | L9T | 0.774 |

TABLE 14-continued

| NT SEQ ID NO: | AA SEQ ID NO: | aa substitution(s) relative to CsOAC | aa substitution (s) relative to SEQ ID NO: 412 | Relative OA titer[1] |
|---|---|---|---|---|
| 859 | 860 | A2P, V8I, L9C, E64D, T68S, R100G | L9C | 1.046 |
| 861 | 862 | A2P, V8I, L9G, E64D, T68S, R100G | L9G | 0.185 |
| 863 | 864 | A2P, V8I, L9A, E64D, T68S, R100G | L9A | 0.916 |
| 865 | 866 | A2P, V8I, L9M, E64D, T68S, R100G | L9M | 0.951 |
| 867 | 868 | A2P, V8I, L9F, E64D, T68S, R100G | L9F | 0.951 |
| 869 | 870 | A2P, V8I, L9S, E64D, T68S, R100G | L9S | 0.191 |

[1]The OA titer for the EVO067 control strain integrated with codon optimized OAC gene of SEQ ID NO: 411 was set as 1, and the values for "Relative OA titer" for each library strain clone was determined by comparison to this control strain.

TABLE 15

| NT SEQ ID NO: | AA SEQ ID NO: | aa substitution(s) relative to CsOAC | aa substitution (s) relative to SEQ ID NO: 418 | Relative OA titer[1] |
|---|---|---|---|---|
| 417 | 418 | V8I, K49R, I58V, E64D, T68M, I74M | n/a | 1 |
| 871 | 872 | V8I, K49G, I58V, E64D, T68M, I74M | K49G | 0.83 |
| 873 | 874 | V8I, K49A, I58V, E64D, T68M, I74M | K49A | 0.74 |
| 875 | 876 | V8I, K49H, I58V, E64D, T68M, I74M | K49H | 1.07 |
| 877 | 878 | V8I, K49C, I58V, E64D, T68M, I74M | K49C | 0.78 |
| 879 | 880 | V8I, K49T, I58V, E64D, T68M, I74M | K49T | 0.76 |
| 881 | 882 | V8I, K49V, I58V, E64D, T68M, I74M | K49V | 0.78 |
| 883 | 884 | V8I, K49S, I58V, E64D, T68M, I74M | K49S | 0.86 |
| 885 | 886 | V8I, K49N, I58V, E64D, T68M, I74M | K49N | 0.75 |
| 887 | 888 | V8I, K49P, I58V, E64D, T68M, I74M | K49P | 0.78 |
| 889 | 890 | V8I, K49L, I58V, E64D, T68M, I74M | K49L | 0.74 |

[1]The OA titer for the EVO068 control strain integrated with codon optimized OAC gene of SEQ ID NO: 417 was set as 1, and the values for "Relative OA titer" for each library strain clone was determined by comparison to this control strain.

As shown by the results in Tables 3, 7, 8, 9, 10, 13, 14, and 15, the presence of the following amino acid differences in the recombinant polypeptides having OAC activity expressed in the strains from the various SSM, combinatorial and codon optimization libraries resulted in substantial OA titer produced by the yeast strain: A2G, A2S, A2P, A2V, L6F, V8I, L9A, L9F, L9G, L9I, L9M, L9S, L9V, K10A, F11L, K12L, K12N, K12Q, K12V, E14G, T16P, T16Q, E17G, A18E, A18S, E21L, E21V, E22L, F23I, K25D, K25G, K25E, K25N, K25R, K25S, T26A, T26N, Y27F, V28C, N29D, N29G, V31A, V31E, V31M, V31S, I33D, I33E, I33V, A36E, A36F, A36L, A36Q, A36S, V40A, V40G, Y41E, Y41Q, Y41S, Y41T, K44P, D45V, V46I, V46L, T47A, T47G, T47S, T47S, Q48C, Q48H, Q48M, Q48P, K49A, K49C, K49G, K49H, K49L, K49N, K49P, K49R, K49S, K49T, K49V, N50Y, E52Q, E52R, E52S, E53A, E53F, E53H, E53L, E53R, E53S, E53V, Y55W, T56S, H57G, 158C, 158V, T62C, T62G, E64D, E64K, V66I, V66L, E67S, T68A, T68C, T68E, T68G, T68H, T68M, T68Q, T68S, Q70A, Q70K, D71G, I74G, I74H, I74K, I74L, I74M, I74N, I74Q, I74R, I74S, I74T, I74V, P76V, A77E, H78P, G80K, G82A, G82R, D83K, D83R, V84I, V84M, Y85F, R86S, S87H, S87K, S87P, F88W, F88Y, E90D, K91E, I94K, Y97F, T98V, R100A, and R100G. Additionally, at least the combinations of two, three, four, five, six, seven, or more amino acid residue differences listed for the specific variant polypeptides listed in Tables 7, 8, 9, 10, 13, 14, and 15 when engineered in the gene encoding the OAC polypeptides result in substantial OA titer produced by the yeast strain.

While the foregoing disclosure of the present invention has been described in some detail by way of example and illustration for purposes of clarity and understanding, this disclosure including the examples, descriptions, and embodiments described herein are for illustrative purposes, are intended to be exemplary, and should not be construed as limiting the present disclosure. It will be clear to one skilled in the art that various modifications or changes to the examples, descriptions, and embodiments described herein can be made and are to be included within the spirit and purview of this disclosure and the appended claims. Further, one of skill in the art will recognize a number of equivalent methods and procedure to those described herein. All such equivalents are to be understood to be within the scope of the present disclosure and are covered by the appended claims.

Additional embodiments of the invention are set forth in the following claims.

The disclosures of all publications, patent applications, patents, or other documents mentioned herein are expressly incorporated by reference in their entirety for all purposes to the same extent as if each such individual publication, patent, patent application or other document were individually specifically indicated to be incorporated by reference herein in its entirety for all purposes and were set forth in its entirety herein. In case of conflict, the present specification, including specified terms, will control.

What is claimed is:

1. A recombinant polypeptide having olivetolic acid cyclase activity, wherein the polypeptide comprises an amino acid sequence of at least 90% identity to SEQ ID NO: 6, and an amino acid residue difference as compared to SEQ ID NO: 6 at each of a combination of six positions, wherein the combination of six positions are selected from V8, K49, 158, E64, T68, and 174, and the amino acid residue differences at the positions are selected from: V8I, K49A, K49C, K49G, K49H, K49L, K49N, K49P, K49R, K49S, K49T, K49V, 158C, I58V, E64D, E64K, T68A, T68C, T68E, T68G, T68H, T68M, T68Q, T68S, 174G, 174H, I74K, I74L, 174M, 174N, 174Q, I74R, I74S, I74T, and I74V.

2. The polypeptide of claim 1, wherein the combination of six amino acid differences selected from the following:

| |
|---|
| V8I, K49R, I58V, E64D, T68M, I74M |
| V8I, K49G, I58V, E64D, T68M, I74M |
| V8I, K49A, I58V, E64D, T68M, I74M |
| V8I, K49H, I58V, E64D, T68M, I74M |
| V8I, K49C, I58V, E64D, T68M, I74M |
| V8I, K49T, I58V, E64D, T68M, I74M |
| V8I, K49V, I58V, E64D, T68M, I74M |
| V8I, K49S, I58V, E64D, T68M, I74M |
| V8I, K49N, I58V, E64D, T68M, I74M |
| V8I, K49P, I58V, E64D, T68M, I74M |
| V8I, K49L, I58V, E64D, T68M, I74M. |

3. The polypeptide of claim 1 in which the polypeptide comprises an amino acid sequence of at least 90% identity to a sequence selected from the group consisting of even-numbered SEQ ID NOs: 22 to 890.

4. The polypeptide of claim 1 in which the olivetolic acid cyclase activity of the polypeptide as compared to a polypeptide consisting of SEQ ID NO: 20 is at least 0.2-fold.

5. A polynucleotide encoding the polypeptide of claim 1.

6. The polynucleotide of claim 5 in which the polynucleotide sequence comprises:

(a) a sequence of at least 80% identity to a sequence selected from the group consisting of odd-numbered SEQ ID NOs: 21 to 889; or (b) a codon degenerate sequence of a sequence selected from the group consisting of odd-numbered SEQ ID NOs: 21 to 889.

7. An expression vector comprising the polynucleotide of claim 5.

8. An isolated host cell comprising the polynucleotide of claim 5 or the expression vector of claim 7.

9. An isolated host cell comprising a nucleic acid encoding a recombinant polypeptide having olivetolic acid cyclase activity of claim 1.

10. The host cell of claim 9, wherein the host cell further comprises a pathway of enzymes capable of producing a tetraketide cannabinoid precursor; optionally, wherein the tetraketide cannabinoid precursor is 3,5,7-trioxododecanoyl-CoA.

11. The host cell of claim 9, wherein the cell further comprises a nucleic acid encoding an enzyme capable of catalyzing the conversion of OA to CBGA.

12. The host cell of claim 9, wherein the cell further comprises a nucleic acid encoding an enzyme capable of catalyzing the conversion of CBGA to A9-THCA, CBDA, and/or CBCA.

13. The host cell of claim 11, wherein the cell produces a cannabinoid selected from cannabigerolic acid (CBGA), cannabigerol (CBG), cannabidiolic acid (CBDA), cannabidiol (CBD), $\Delta^9$-tetrahydrocannabinolic acid (49-THCA), $\Delta^9$-tetrahydrocannabinol ($\Delta^9$-THC), $\Delta^8$-tetrahydrocannabinolic acid (48-THCA), $\Delta^8$-tetrahydrocannabinol (48-THC), cannabichromenic acid (CBCA), cannabichromene (CBC), cannabinolic acid (CBNA), cannabinol (CBN), cannabidivarinic acid (CBDVA), cannabidivarin (CBDV), $\Delta^9$-tetrahydrocannabivarinic acid ($\Delta^9$-THCVA), $\Delta^9$-tetrahydrocannabivarin (49-THCV), cannabidibutolic acid (CBDBA), cannabidibutol (CBDB), $\Delta^9$-tetrahydrocannabutolic acid (49-THCBA), $\Delta^9$-tetrahydrocannabutol (49-THCB), cannabidiphorolic acid (CBDPA), cannabidiphorol (CBDP), 49-tetrahydrocannabiphorolic acid (49-THCPA), $\Delta^9$-tetrahydrocannabiphorol (49-THCP), cannabichromevarinic acid (CBCVA), cannabichromevarin (CBCV), cannabigerovarinic acid (CBGVA), cannabigerovarin (CBGV), cannabicyclolic acid (CBLA), cannabicyclol (CBL), cannabielsoinic acid (CBEA), cannabielsoin (CBE), cannabicitranic acid (CBTA), cannabicitran (CBT), and any combination thereof.

14. The host cell of claim 9, wherein recombinant host cell source is selected from *Saccharomyces cerevisiae, Yarrowia lipolytica, Pichia pastoris*, and *Escherichia coli.*

15. A method for producing a cannabinoid or cannabinoid precursor comprising:

(a) culturing in a suitable medium a recombinant host cell of claim 9; and (b) recovering the produced cannabinoid or cannabinoid precursor.

16. The method of claim 15, wherein the method further comprises contacting a cell-free extract of the culture with a biocatalytic reagent or chemical reagent.

17. A method for preparing a compound of structural formula (I)

(I)

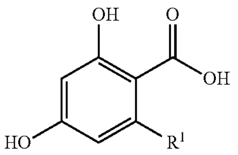

wherein, $R^1$ is $C_1$-$C_7$ alkyl, comprising contacting under suitable reactions conditions a compound of structural formula (II)

(II)

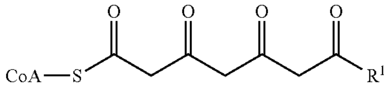

wherein, $R^1$ is $C_1$-$C_7$ alkyl, and a recombinant polypeptide of claim 1.

18. The method of claim 17, wherein:

(a) the compound of structure formula (I) is olivetolic acid (OA) and the compound of structural formula (II) is 3,5,7-trioxododecanoyl-CoA; or (b) the compound of structure formula (I) is divarinic acid (DA) and the compound of structural formula (II) is 3,5,7-trioxodecanoyl-CoA acid.

* * * * *

SEQUENCE LISTING

```
Sequence total quantity: 890
SEQ ID NO: 1            moltype = DNA  length = 2163
FEATURE                 Location/Qualifiers
misc_feature            1..2163
                        note = Synthetic biopolymer
source                  1..2163
                        mol_type = other DNA
                        organism = synthetic construct
SEQUENCE: 1
atgggaaaaa attataagtc acttgacagt gtggttgcta gtgatttcat agccttgggt  60
atcacatctg aggtagcgga gactcttcat gggcgtttag ctgagattgt gtgtaattac  120
ggggcggcca cccctcagac ttggatcaat atagcaaacc acatcttatc tcctgatcta  180
ccctttctc tacaccaaat gctgttctat gggtgttaca aagatttcgg gcccgcaccg  240
cccgcatgga taccggatcc agagaaagtc aaatccacca acttaggcgc gttgcttgaa  300
aaaagaggca aggaattcct gggcgtcaag tacaaggacc ccatctcatc tttctcccac  360
ttccaagagt tctctgtacg taatccggag gtttactggc gtaccgtcct tatggatgag  420
atgaagatat cattctccaa ggacccggaa tgtatactaa gaagggatga cattaacaac  480
ccagggggca gtgagtggct tccgggtgga taccttaata gtgcaaaaaa ctgtcttaac  540
gtgaactcaa acaaaaagtt aaacgataca atgatcgtgt ggcgtgatga gggcaatgat  600
gaccttccgc taaataagtt gacgcttgat cagctaagaa agcgtgtctg gcttgtcgga  660
tatgccctag aggagatggg ccttgagaag ggatgcgcga tcgccataga tatgcctatg  720
```

-continued

```
catgtcgatg ctgtggttat atatctggcc atcgttctag cgggctatgt tgttgtgagt  780
attgccgata gcttcagtgc acccgaaata tcaacgagac tgcgtttgtc caaagccaaa  840
gcaatattca cacaggatca tatcattaga ggaaagaagc gtattccgct atattcaagg  900
gtggtggagg ccaaaagccc gatggctata gtgataccct gttcaggcag caacatcgga  960
gctgaattaa gagatggaga tatatcctgg gactattttt tagagagggc gaaagaattt  1020
aagaactgcg agttcaccgc aagggaacag ccagtggatg cgtatacaaa catactattc  1080
agttcaggta ctacgggaga accaaaggct ataccctgga cgcaggcaac cccgctaaaa  1140
gctgccgctg acgggtggtc tcatttggat atcaggaagg gtgatgttat cgtatggcca  1200
acaaatcttg gatggatgat gggaccgtgg cttgtgtacg ctagcttgtt aaatggagct  1260
tcaatcgctc tatataatgg ttcccctctt gtcagcggtt ttgcgaagtt cgtacaggat  1320
gccaaggtaa ctatgctggg agtcgttcct agcatcgtca ggagttggaa atcaactaac  1380
tgtgtgtctg gttacgactg gtccactatc agatgtttta gctccagtgg tgaggcctcc  1440
aacgtagatg agtacctttg gcttatggga cgtgccaact ataaaccggt aatagagatg  1500
tgtgggggta ctgaaatagg aggagcgttt tcagctggca gtttcttcca ggctcaaagc  1560
ttgtctagtt tctcttcaca gtgtatgggc tgtacgttat acattcttga taagaacggt  1620
tatccaatgc ccaaaaacaa accaggtata ggagaattgg cgctgggtcc agtcatgttt  1680
ggcgctagta aaactctact gaacggaaat catcacgacg tttactttaa aggtatgcct  1740
actcttaatg gagaagtact taggcgtcat ggcgatatct ttgagttgac atccaatggc  1800
tactatcacg cccatggcag ggcggatgac accatgaaca tcggggggat caaaatctcc  1860
agtatagaga tcgagagagt gtgtaacgag gtagacgacc gtgtattcga gacaacagcc  1920
attggggttc caccccctagg tggtggcccc gaacaacttg ttatcttttt tgtgctgaag  1980
gactcaaatg acactaccat tgatttaaat caactacgtt tgtcattcaa tctgggatta  2040
caaaagaagt tgaatccttt attcaaggtc acaagagtag taccccttag ttccctgcca  2100
agaactgcga caaacaagat aatgcgtaga gtgctaaggc agcagtttag tcattttgag  2160
taa                                                                2163

SEQ ID NO: 2            moltype = AA  length = 720
FEATURE                 Location/Qualifiers
source                  1..720
                        mol_type = protein
                        organism = Cannabis sativa
SEQUENCE: 2
MGKNYKSLDS VVASDFIALG ITSEVAETLH GRLAEIVCNY GAATPQTWIN IANHILSPDL  60
PFSLHQMLFY GCYKDFGPAP PAWIPDPEKV KSTNLGALLE KRGKEFLGVK YKDPISSFSH  120
FQEFSVRNPE VYWRTVLMDE MKISFSKDPE CILRRDDINN PGGSEWLPGG YLNSAKNCLN  180
VNSNKKLNDT MIVWRDEGND DLPLNKLTLD QLRKRVWLVG YALEEMGLEK GCAIAIDMPM  240
HVDAVVIYLA IVLAGYVVVS IADSFSAPEI STRLRLSKAK AIFTQDHIIR GKKRIPLYSR  300
VVEAKSPMAI VIPCSGSNIG AELRDGDISW DYFLERAKEF KNCEFTAREQ PVDAYTNILF  360
SSGTTGEPKA IPWTQATPLK AAADGWSHLD IRKGDVIVWP TNLGWMMGPW LVYASLLNGA  420
SIALYNGSPL VSGFAKFVQD AKVTMLGVVP SIVRSWKSTN CVSGYDWSTI RCFSSSGEAS  480
NVDEYLWLMG RANYKPVIEM CGGTEIGGAF SAGSFLQAQS LSSFSSQCMG CTLYILDKNG  540
YPMPKNKPGI GELALGPVMF GASKTLLNGN HHDVYFKGMP TLNGEVLRRH GDIFELTSNG  600
YYHAHGRADD TMNIGGIKIS SIEIERVCNE VDDRVFETTA IGVPPLGGGP EQLVIFFVLK  660
DSNDTTIDLN QLRLSFNLGL QKKLNPLFKV TRVVPLSSLP RTATNKIMRR VLRQQFSHFE  720

SEQ ID NO: 3            moltype = DNA  length = 1158
FEATURE                 Location/Qualifiers
misc_feature            1..1158
                        note = Synthetic biopolymer
source                  1..1158
                        mol_type = other DNA
                        organism = synthetic construct
SEQUENCE: 3
atgaaccact tgagagcaga agggccggcc agtgtactgg ctatagggac agccaacccc  60
gaaaatatac tgttgcaaga tgagttccca gattattact ttagagtgac taaatccgag  120
cacatgacgc aacttaagga gaaattcagg aaaatatgcg acaaatctat gattagaaaa  180
agaaattgtt tcttaaatga ggagcatcta aagcagaatc cccgtctggt agaacatgaa  240
atgcaaactt tggacgcgcg tcaagacatg ctagttgtcg aagtgcctaa attaggcaaa  300
gacgcgtgtg caaaggctat aaaagagtgg ggccaaccga agtccaaaat tacacaccta  360
atattcactt ctgcgtccac caccgacatg cccggagccg actaccactg tgcgaaactt  420
ctaggcctat ccccttcagt caagcgtgta atgatgtatc aactggggtg ctacggagga  480
ggcaccgttt tgaggattgc aaaggatatc gctgaaaata acaagggggc tcgtgtactt  540
gctgtgtgct gtgatatcat ggcctgcctt ttcagaggcc cctcagagtc agatcttgaa  600
ctgttagtag gtcaggctat cttcggagat ggcgctgcag ccgtcatagt tggggcggag  660
cctgacgaat cagttgggga gaggcccatt ttcgagctgg tcagtacggg acagaccatc  720
ttgccaaata gcgagggcac gatcggaggc cacataaggg aggcgggttt gatatttgac  780
cttcataagg atgtaccgat gttgatctcc aataatattg agaagtgtct tattgaagca  840
tttacccctca ttggtatttc agactggaac agtatcttct ggattacgca tccgggaggt  900
aaggcgattc ttgataaagt cgaagaaaag ctacacctga agtcagacaa gttcgttgac  960
tccagacacg ttctttcaga gcacggcaac atgagttctt ccaccgtcct tttcgtaatg  1020
gacgagctga ggaaacgtag ccttgaggaa ggtaaaagta cgacaggaga tgggtttgag  1080
tggggagtgt tgtttggctt cggcccaggg ttaacagttg aacgtgtagt cgttagatct  1140
gtccctatta aatactaa                                                1158

SEQ ID NO: 4            moltype = AA  length = 385
FEATURE                 Location/Qualifiers
source                  1..385
                        mol_type = protein
                        organism = Cannabis sativa
```

```
SEQUENCE: 4
MNHLRAEGPA SVLAIGTANP ENILLQDEFP DYYFRVTKSE HMTQLKEKFR KICDKSMIRK  60
RNCFLNEEHL KQNPRLVEHE MQTLDARQDM LVVEVPKLGK DACAKAIKEW GQPKSKITHL  120
IFTSASTTDM PGADYHCAKL LGLSPSVKRV MMYQLGCYGG GTVLRIAKDI AENNKGARVL  180
AVCCDIMACL FRGPSESDLE LLVGQAIFGD GAAAVIVGAE PDESVGERPI FELVSTGQTI  240
LPNSEGTIGG HIREAGLIFD LHKDVPMLIS NNIEKCLIEA FTPIGISDWN SIFWITHPGG  300
KAILDKVEEK LHLKSDKFVD SRHVLSEHGN MSSSTVLFVM DELRKRSLEE GKSTTGDGFE  360
WGVLFGFGPG LTVERVVVRS VPIKY                                      385

SEQ ID NO: 5            moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 5
atggctgtca agcaccttat cgtactgaaa ttcaaggacg aaattacaga agcccagaaa  60
gaagaatttt tcaagaccta tgtaaacctg gtgaatatca tccctgcgat gaaagatgtt  120
tattggggca aagacgtcac ccaaaaaaac aaagaagaag gttacactca catcgtcgaa  180
gtcactttcg agtcagtaga gacgatccaa gattacataa tacacccggc ccatgtggga  240
ttcggagacg tttaccgtag cttctgggaa aaactttttga ttttcgacta taccccgaga  300
aaa                                                              303

SEQ ID NO: 6            moltype = AA  length = 101
FEATURE                 Location/Qualifiers
source                  1..101
                        mol_type = protein
                        organism = Cannabis sativa
SEQUENCE: 6
MAVKHLIVLK FKDEITEAQK EEFFKTYVNL VNIIPAMKDV YWGKDVTQKN KEEGYTHIVE  60
VTFESVETIQ DYIIHPAHVG FGDVYRSFWE KLLIFDYTPR K                    101

SEQ ID NO: 7            moltype = DNA  length = 1517
FEATURE                 Location/Qualifiers
source                  1..1517
                        mol_type = genomic DNA
                        organism = Cannabis sativa
SEQUENCE: 7
atcaataata atcttcatgg gactctcatt agtttgtacc ttttcatttc aaactaatta  60
tcatacttta ttaaaccctc ataataagaa tcccaaaaac tcattattat cttatcaaca  120
ccccaaaaca ccaataatta aatcctctta tgataatttt ccctctaaat attgcttaac  180
caagaacttt catttacttg gactcaattc acacaacaga ataagctcac aatcaaggtc  240
cattagggca ggtagcgatc aaattgaagg ttctcctcat catgaatctg ataattcaat  300
agcaactaaa attttaaatt ttggacatac ttgttggaaa cttcaaagac catatgtagt  360
aaaagggatg atttcaatcg cttgtggttt gtttgggaga gagttgttca ataacagaca  420
tttattcagt tggggtttga tgtggaaggc attctttgct ttggtgccta tattgtcctt  480
caatttcttt gcagcaatca tgaatcaaat ttacgatgtg gacatcgaca ggataaacaa  540
gcctgatcta ccactagttt caggggaaat gtcaattgaa acagcttgga ttttgagcat  600
aattgtggca ctaactgggt tgatagtaac tataaaattg aaatctgcac cactttttgt  660
tttcatttac atttttggta tatttgctgg gtttgcctat tctgttccac caattagatg  720
gaagcaatat ccttttacca attttctaat taccatatcg agtcatgtgg gcttagcttt  780
cacatcatat tctgcaacca catcagctct tggtttacca tttgtgtgga ggcctgcttt  840
tagtttcatc atagcattca tgacagttat gggtatgact attgcttttg ccaaagatat  900
ttcagatatt gaaggcgacg ccaaatatgg ggtatcaact gttgcaacca aattaggtgc  960
taggaacatg acatttgttg tttctggagt tcttcttcta aactacttgg tttctatatc  1020
tattgggata atttggcctc aggttttcaa gagtaacata atgatacttt ctcatgcaat  1080
cttagcattt tgcttaatct tccagactcg tgagcttgct ctagcaaatt acgcctcggc  1140
gccaagcaga caattcttcg agtttatctg gttgctatat tatgctgaat actttgtata  1200
tgtatttata taagaccata atataacata tatatgttta ttacataaaa ttgggacaca  1260
aaaacgtcaa ttatttggac aaaagtactc agaaagacct ctttcactac aaggggaggc  1320
catttagtta tacttgggtt tcaatcaaca aatttataaa tttttaagat tttatttaca  1380
aaacattttc atgtgtaatt aaatcgatcg tcatttattt tttggataca acttggttca  1440
acttatttta attagagtgc ttcgtaattt aactacaatt atagaagggc attttataaa  1500
aatactggat ttggggt                                               1517

SEQ ID NO: 8            moltype = AA  length = 398
FEATURE                 Location/Qualifiers
source                  1..398
                        mol_type = protein
                        organism = Cannabis sativa
SEQUENCE: 8
MGLSLVCTFS FQTNYHTLLN PHNKNPKNSL LSYQHPKTPI IKSSYDNFPS KYCLTKNFHL  60
LGLNSHNRIS SQSRSIRAGS DQIEGSPHHE SDNSIATKIL NFGHTCWKLQ RPYVVKGMIS  120
IACGLFGREL FNNRHLFSWG LMWKAFFALV PILSFNFFAA IMNQIYDVDI DRINKPDLPL  180
VSGEMSIETA WILSIIVALT GLIVTIKLKS APLFVFIYIF GIFAGFAYSV PPIRWKQYPF  240
TNFLITISSH VGLAFTSYSA TTSALGLPFV WRPAFSFIIA FMTVMGMTIA FAKDISDIEG  300
DAKYGVSTVA TKLGARNMTF VVSGVLLLNY LVSISIGIIW PQVFKSNIMI LSHAILAFCL  360
IFQTRELALA NYASAPSRQF FEFIWLLYYA EYFVYVFI                         398
```

```
SEQ ID NO: 9            moltype = DNA  length = 954
FEATURE                 Location/Qualifiers
misc_feature            1..954
                        note = Synthetic biopolymer
source                  1..954
                        mol_type = other DNA
                        organism = synthetic construct
SEQUENCE: 9
atgatcgaag gttcacctca tcatgaaagt gataacagca tagccacgaa gattttgaat  60
ttcggccata cttgttggaa gctacagagg ccgtacgtcg ttaaggggat gatttccatt  120
gcgtgcggtc tgtttggcag ggaattattt aacaacagac acttattcag ttggggcctg  180
atgtggaagg ccttcttcgc tcttgtaccc attctgtcct tcaacttttt tgcagcgatc  240
atgaatcaaa tatacgatgt agacatcgat agaataaaca agcccgattt acctctggta  300
tcaggcgaaa tgagcatcga aactgcgtgg attttatcaa tcatcgttgc attgactggg  360
ctgatagtga ccataaagtt aaagtcagcc ccgttgtttg tcttcatata catcttcggc  420
attttcgcgg gctttgcgta tagtgtacct cccattagat ggaagcagta cccgtttact  480
aactttctta ttacaattag cagccatgtc ggtcttgcat tcacgtccta ctcagccacc  540
acatccgcac tggggctacc gtttgtgtgg cgtccagcct tcagcttcat catcgcattc  600
atgacagtaa tgggtatgac gatagctttt gcaaaggata taagtgatat cgagggtgac  660
gctaagtatg gagtgtctac tgtggccacg aagctggggg cccgtaatat gactttcgtg  720
gtatcaggtg tactattgct taattacctt gtttctatat caatcggaat tatttggcca  780
caagttttca aatccaatat aatgatccta tcacacgcta ttttagcgtt ttgtttgata  840
tttcagacta gagagcttgc actagcgaat tacgcgagtg ccccgagtag gcagtttttc  900
gagttcatat ggctattata ctatgctgag tactttgttt acgtatttat ttaa        954

SEQ ID NO: 10           moltype = AA  length = 317
FEATURE                 Location/Qualifiers
REGION                  1..317
                        note = Synthetic biopolymer
source                  1..317
                        mol_type = protein
                        organism = synthetic construct
SEQUENCE: 10
MIEGSPHHES DNSIATKILN FGHTCWKLQR PYVVKGMISI ACGLFGRELF NNRHLFSWGL  60
MWKAFFALVP ILSFNFFAAI MNQIYDVDID RINKPDLPLV SGEMSIETAW ILSIIVALTG  120
LIVTIKLKSA PLFVFIYIFG IFAGFAYSVP PIRWKQYPFT NFLITISSHV GLAFTSYSAT  180
TSALGLPFVW RPAFSFIIAF MTVMGMTIAF AKDISDIEGD AKYGVSTVAT KLGARNMTFV  240
VSGVLLLNYL VSISIGIIWP QVFKSNIMIL SHAILAFCLI FQTRELALAN YASAPSRQFF  300
EFIWLLYYAE YFVYVFI                                                 317

SEQ ID NO: 11           moltype = DNA  length = 1635
FEATURE                 Location/Qualifiers
source                  1..1635
                        mol_type = genomic DNA
                        organism = Cannabis sativa
SEQUENCE: 11
atgaagtgct caacattctc cttttggttt gtttgcaaga taatattttt ctttttctca  60
ttcaatatcc aaacttccat tgctaatcct cgagaaaact tccttaaatg cttctcgcaa  120
tatattccca ataatgcaac aaatctaaaa ctcgtataca ctcaaaacaa cccattgtat  180
atgtctgtcc taaattcgac aatacacaat cttagattca cctctgacac aaccccaaaa  240
ccacttgtta tcgtcactcc ttcacatgtc tctcatatcc aaggcactat tctatgctcc  300
aagaaagttg gcttgcagat tcgaactcga agtggtggtc atgattctga gggcatgtcc  360
tacatatctc aagtcccatt tgttatagta gacttgagaa acatgcgttc aatcaaaata  420
gatgttcata gccaaactgc atgggttgaa gccggagcta cccttggaga agtttattat  480
tgggttaatg agaaaaatga gaatcttagt ttggcggctg ggtattgccc tactgtttgc  540
gcaggtggac actttggtgg aggaggctat ggaccattga tgagaaacta tggcctcgcg  600
gctgataata tcattgatgc acacttagtc aacgttcatg gaaaagtgct agatcgaaaa  660
tctatggggg aagatctctt ttgggcttta cgtggtggtg gagcagaaag cttcggaatc  720
attgtagcat ggaaaattag actggttgct gtcccaaagt ctactatgtt tagtgttaaa  780
aagatcatgg agatacatga gcttgtcaag ttagttaaca aatggcaaaa tattgcttac  840
aagtatgaca aagatttatt actcatgact cacttcataa ctaggaacat tacagataat  900
caagggaaga ataagacagc aatacacact tacttctctt cagttttcct tggtggagtg  960
gatagtctag tcgacttgat gaacaagagt tttcctgagt tgggtattaa aaaaacggat  1020
tgcagacaat tgagctggat tgatactatc atcttctata gtggtgttgt aaattacgac  1080
actgataatt ttaacaagga aattttgctt gatagatccg ctgggcagaa cggtgctttc  1140
aagattaagt tagactacgt taagaaacca attccagaat ctgtatttgt ccaaattttg  1200
gaaaaattat atgaagaaga tataggagct gggatgtatg cgttgtaccc ttacggtggt  1260
ataatggatg agatttcaga atcagcaatt ccattccctc atcgagctgg aatcttgtat  1320
gagttatggt acatatgtag ttgggagaag caagaagata acgaaaagca tctaaactgg  1380
attagaaata tttataactt catgactcct tatgtgtcca aaaatccaag attggcatat  1440
ctcaattata gagaccttga tataggaata aatgatccca agaatccaaa taattacaca  1500
caagcacgta tttggggtga gaagtatttt ggtaaaaatt ttgacaggct agtaaaagtg  1560
aaaaccctgg ttgatcccaa taactttttt agaaacgaac aaagcatccc acctcttcca  1620
cggcatcgtc attaa                                                   1635

SEQ ID NO: 12           moltype = AA  length = 544
FEATURE                 Location/Qualifiers
source                  1..544
```

```
                        mol_type = protein
                        organism = Cannabis sativa
SEQUENCE: 12
MKCSTFSFWF VCKIIFFFFS FNIQTSIANP RENFLKCFSQ YIPNNATNLK LVYTQNNPLY  60
MSVLNSTIHN LRFTSDTTPK PLVIVTPSHV SHIQGTILCS KKVGLQIRTR SGGHDSEGMS  120
YISQVPFVIV DLRNMRSIKI DVHSQTAWVE AGATLGEVYY WVNEKNENLS LAAGYCPTVC  180
AGGHFGGGGY GPLMRNYGLA ADNIIDAHLV NVHGKVLDRK SMGEDLFWAL RGGGAESFGI  240
IVAWKIRLVA VPKSTMFSVK KIMEIHELVK LVNKWQNIAY KYDKDLLLMT HFITRNITDN  300
QGKNKTAIHT YFSSVFLGGV DSLVDLMNKS FPELGIKKTD CRQLSWIDTI IFYSGVVNYD  360
TDNFNKEILL DRSAGQNGAF KIKLDYVKKP IPESVFVQIL EKLYEEDIGA GMYALYPYGG  420
IMDEISESAI PFPHRAGILY ELWYICSWEK QEDNEKHLNW IRNIYNFMTP YVSKNPRLAY  480
LNYRDLDIGI NDPKNPNNYT QARIWGEKYF GKNFDRLVKV KTLVDPNNFF RNEQSIPPLP  540
RHRH                                                             544

SEQ ID NO: 13           moltype = DNA  length = 1554
FEATURE                 Location/Qualifiers
misc_feature            1..1554
                        note = Synthetic biopolymer
source                  1..1554
                        mol_type = other DNA
                        organism = synthetic construct
SEQUENCE: 13
atgaaccccc gtgaaaattt tttgaaatgt ttctctcaat acatacccaa caatgcaacc  60
aacttaaagc tggtatatac tcaaaacaac cccctatata tgtctgttct aaatagtact  120
atccataact tacgtttcac ctcagatacc acccctaaac cgctggtcat cgtgactccg  180
tctcatgttt cacacataca gggcacgata ttgtgctcaa aaaaggtcgg gttacagatt  240
cgtacccgtt caggaggtca tgatagtgag ggaatgtctt acatctccca ggtccctttt  300
gtaattgtcg accttcgtaa tatgagatcc ataaagatcg acgttcattc acagacggcg  360
tgggtagagg ctggtgcaac cctaggtgaa gtctactact gggtcaacga aaaaaacgag  420
aacttatcat tagctgcggg gtattgccct acagtttgtg ccggaggtca ttttggaggt  480
ggaggctacg ggccactgat gaggaactac ggtctggcag cagacaacat tatagatgca  540
cacctagtga acgtgcatgg taaagtttta gatagaaagt ccatgggaga agatttgttt  600
tgggcactac gtggaggagg ggctgagtca ttcgggatta ttgtagcgtg gaagatccgt  660
ctggtcgcag tccctaaatc tacgatgttt tccgtgaaaa agattatgga aattcacgag  720
ctagtgaaac ttgtcaataa gtggcagaat atagcataca aatatgacaa ggatctattg  780
ttgatgacgc atttcatcac aagaaacatt acggacaatc aaggtaagaa taagacggct  840
attcacactt acttcagctc cgtttttcta ggaggggtag attccctagt tgacctgatg  900
aataagagtt ttcccgagtt gggtattaaa aaaactgatt gtagacagct gtcttggatc  960
gacacaatca tattctactc tggtgtggta aactatgaca ccgataattt caacaaagaa  1020
atcttactgg atagatcagc cggtcaaaac ggcgcgttta aaatcaagct ggattacgta  1080
aagaagccta tacccgaatc cgtatttgta cagattctgg aaaagttata cgaggaagac  1140
attggggcgg gtatgtacgc tctttaccct tacggcggga tcatggatga gatttccgaa  1200
agtgctatcc cgttccctca tcgtgctggc attctgtacg agttatggta tatttgcagt  1260
tgggagaagc aggaggataa tgaaaagcac ctaaattgga ttcgtaatat tttataatttc  1320
atgactccct atgttagtaa gaaccccaga ctggcctacc ttaattatag agacctggac  1380
atcgggataa atgatccgaa gaacccaaat aactatacgc aggccaggat ttggggggaa  1440
aagtatttcg gaaagaactt tgacagactg gtgaaagtta agaccctggt ggatccaaat  1500
aattttttca ggaacgagca gagtattccc ccgcttccac gtcacaggca ttaa        1554

SEQ ID NO: 14           moltype = AA  length = 517
FEATURE                 Location/Qualifiers
REGION                  1..517
                        note = Synthetic biopolymer
source                  1..517
                        mol_type = protein
                        organism = synthetic construct
SEQUENCE: 14
MNPRENFLKC FSQYIPNNAT NLKLVYTQNN PLYMSVLNST IHNLRFTSDT TPKPLVIVTP  60
SHVSHIQGTI LCSKKVGLQI RTRSGGHDSE GMSYISQVPF VIVDLRNMRS IKIDVHSQTA  120
WVEAGATLGE VYYWVNEKNE NLSLAAGYCP TVCAGGHFGG GGYGPLMRNY GLAADNIIDA  180
HLVNVHGKVL DRKSMGEDLF WALRGGGAES FGIIVAWKIR LVAVPKSTMF SVKKIMEIHE  240
LVKLVNKWQN IAYKYDKDLL LMTHFITRNI TDNQGKNKTA IHTYFSSVFL GGVDSLVDLM  300
NKSFPELGIK KTDCRQLSWI DTIIFYSGVV NYDTDNFNKE ILLDRSAGQN GAFKIKLDYV  360
KKPIPESVFV QILEKLYEED IGAGMYALYP YGGIMDEISE SAIPFPHRAG ILYELWYICS  420
WEKQEDNEKH LNWIRNIYNF MTPYVSKNPR LAYLNYRDLD IGINDPKNPN NYTQARIWGE  480
KYFGKNFDRL VKVKTLVDPN NFFRNEQSIP PLPRHRH                          517

SEQ ID NO: 15           moltype = DNA  length = 1638
FEATURE                 Location/Qualifiers
source                  1..1638
                        mol_type = genomic DNA
                        organism = Cannabis sativa
SEQUENCE: 15
atgaattgct cagcattttc cttttggttt gtttgcaaaa taatattttt ctttctctca  60
ttccatatcc aaatttcaat agctaatcct cgagaaaact tccttaaatg cttctcaaaa  120
catattccca acaatgtagc aaatccaaaa ctcgtataca ctcaacacga ccaattgtat  180
atgtctatcc tgaattcgac aatacaaaat cttagattca tctctgatac aaccccaaaa  240
ccactcgtta ttgtcactcc ttcaaataac tcccatatcc aagcaactat tttatgctct  300
aagaaagttg gcttgcagat tcgaactcga agcggtggcc atgatgctga gggtatgtcc  360
```

-continued

```
tacatatctc aagtcccatt tgttgtagta gacttgagaa acatgcattc gatcaaaata  420
gatgttcata gccaaactgc gtgggttgaa gccggagcta cccttggaga agtttattat  480
tggatcaatg agaagaatga gaatcttagt tttcctggtg ggtattgccc tactgttggc  540
gtaggtggac actttagtgg aggaggctat ggagcattga tgcgaaatta tggccttgcg  600
gctgataata ttattgatgc acacttagtc aatgttgatg gaaaagttct agatcgaaaa  660
tccatgggag aagatctgtt ttgggctata cgtggtggtg gaggagaaaa ctttggaatc  720
attgcagcat ggaaaatcaa actggttgct gtcccatcaa agtctactat attcagtgtt  780
aaaaagaaca tggagataca tgggcttgtc aagttattta acaaatggca aaatattgct  840
tacaagtatg acaaagattt agtactcatg actcacttca taacaaagaa tattacagat  900
aatcatggga agaataagac tacagtacat ggttacttct cttcaatttt tcatggtgga  960
gtggatagtc tagtcgactt gatgaacaag agctttcctg agttgggtat taaaaaaact  1020
gattgcaaag aatttagctg gattgataca accatcttct acagtggtgt tgtaaatttt  1080
aacactgcta attttaaaaa ggaaattttg cttgatagat cagctgggaa gaagacggct  1140
ttctcaatta agttagacta tgttaagaaa ccaattccag aaactgcaat ggtcaaaatt  1200
ttggaaaaat tatatgaaga agatgtagga gctgggatgt atgtgttgta cccttacggt  1260
ggtataatgg aggagatttc agaatcagca attccattcc ctcatcgagc tggaataatg  1320
tatgaacttt ggtacactgc ttcctgggag aagcaagaag ataatgaaaa gcatataaac  1380
tgggttcgaa gtgtttataa ttttacgact ccttatgtgt cccaaaatcc aagattggcg  1440
tatctcaatt atagggacct tgatttagga aaaactaatc atgcgagtcc taataattac  1500
acacaagcac gtatttgggg tgaaaagtat tttggtaaaa attttaacag gttagttaag  1560
gtgaaaacta aagttgatcc caataatttt tttagaaacg aacaaagtat cccacctctt  1620
ccaccgcatc atcattaa                                                1638

SEQ ID NO: 16          moltype = AA  length = 545
FEATURE                Location/Qualifiers
source                 1..545
                       mol_type = protein
                       organism = Cannabis sativa
SEQUENCE: 16
MNCSAFSFWF VCKIIFFFLS FHIQISIANP RENFLKCFSK HIPNNVANPK LVYTQHDQLY  60
MSILNSTIQN LRFISDTTPK PLVIVTPSNN SHIQATILCS KKVGLQIRTR SGGHDAEGMS  120
YISQVPFVVV DLRNMHSIKI DVHSQTAWVE AGATLGEVYY WINEKNENLS FPGGYCPTVG  180
VGGHFSGGGY GALMRNYGLA ADNIIDAHLV NVDGKVLDRK SMGEDLFWAI RGGGGENFGI  240
IAAWKIKLVA VPSKSTIFSV KKNMEIHGLV KLFNKWQNIA YKYDKDLVLM THFITKNITD  300
NHGKNKTTVH GYFSSIFHGG VDSLVDLMNK SFPELGIKKT DCKEFSWIDT TIFYSGVVNF  360
NTANFKKEIL LDRSAGKKTA FSIKLDYVKK PIPETAMVKI LEKLYEEDVG AGMYVLYPYG  420
GIMEEISESA IPFPHRAGIM YELWYTASWE KQEDNEKHIN WVRSVYNFTT PYVSQNPRLA  480
YLNYRDLDLG KTNHASPNNY TQARIWGEKY FGKNFNRLVK VKTKVDPNNF FRNEQSIPPL  540
PPHHH                                                              545

SEQ ID NO: 17          moltype = DNA  length = 1557
FEATURE                Location/Qualifiers
misc_feature           1..1557
                       note = Synthetic biopolymer
source                 1..1557
                       mol_type = other DNA
                       organism = synthetic construct
SEQUENCE: 17
atgaatcctc gagaaaactt ccttaaatgc ttctcaaaac atattcccaa caatgtagca  60
aatccaaaac tcgtatacac tcaacacgac caattgtata tgtctatcct gaattcgaca  120
atacaaaatc ttagattcat ctctgataca accccaaaac cactcgttat tgtcactcct  180
tcaaataact cccatatcca agcaactatt ttatgctcta agaaagttgg cttgcagatt  240
cgaactcgaa gcggtggcca tgatgctgag ggtatgtcct acatatctca agtcccattt  300
gttgtagtag acttgagaaa catgcattcg atcaaaatag atgttcatag ccaaactgcg  360
tgggttgaag ccggagctac ccttggagaa gtttattatt ggatcaatga gaagaatgag  420
aatcttagtt ttcctggtgg gtattgccct actgttggcg taggtggaca ctttagtgga  480
ggaggctatg gagcattgat gcgaaattat ggccttgcgg ctgataatat tattgatgca  540
cacttagtca atgttgatgg aaaagttcta gatcgaaaat ccatgggaga agatctgttt  600
tgggctatac gtggtggtgg aggagaaaac tttggaatca ttgcagcatg gaaaatcaaa  660
ctggttgctg tcccatcaaa gtctactata ttcagtgtta aaaagaacat ggagatacat  720
gggcttgtca agttatttaa caaatggcaa aatattgctt acaagtatga caaagattta  780
gtactcatga ctcacttcat aacaaagaat attacagata atcatgggaa gaataagact  840
acagtacatg gttacttctc ttcaattttt catggtggag tggatagtct agtcgacttg  900
atgaacaaga gctttcctga gttgggtatt aaaaaaactg attgcaaaga atttagctgg  960
attgatacaa ccatcttcta cagtggtgtt gtaaatttta acactgctaa ttttaaaaag  1020
gaaattttgc ttgatagatc agctgggaag aagacggctt tctcaattaa gttagactat  1080
gttaagaaac caattccaga aactgcaatg gtcaaaattt tggaaaaatt atatgaagaa  1140
gatgtaggag ctgggatgta tgtgttgtac ccttacggtg gtataatgga ggagatttca  1200
gaatcagcaa ttccattccc tcatcgagct ggaataatgt atgaactttg gtacactgct  1260
tcctgggaga agcaagaaga taatgaaaag catataaact gggttcgaag tgtttataat  1320
tttacgactc cttatgtgtc ccaaaatcca agattggcgt atctcaatta tagggacctt  1380
gatttaggaa aaactaatca tgcgagtcct aataattaca cacaagcacg tatttggggt  1440
gaaaagtatt ttggtaaaaa ttttaacagg ttagttaagg tgaaaactaa agttgatccc  1500
aataattttt ttagaaacga acaaagtatc ccacctcttc caccgcatca tcattaa     1557

SEQ ID NO: 18          moltype = AA  length = 518
FEATURE                Location/Qualifiers
REGION                 1..518
                       note = Synthetic biopolymer
```

```
source                  1..518
                        mol_type = protein
                        organism = synthetic construct
SEQUENCE: 18
MNPRENFLKC FSKHIPNNVA NPKLVYTQHD QLYMSILNST IQNLRFISDT TPKPLVIVTP  60
SNNSHIQATI LCSKKVGLQI RTRSGGHDAE GMSYISQVPF VVVDLRNMHS IKIDVHSQTA  120
WVEAGATLGE VYYWINEKNE NLSFPGGYCP TVGVGGHFSG GGYGALMRNY GLAADNIIDA  180
HLVNVDGKVL DRKSMGEDLF WAIRGGGGEN FGIIAAWKIK LVAVPSKSTI FSVKKNMEIH  240
GLVKLFNKWQ NIAYKYDKDL VLMTHFITKN ITDNHGKNKT TVHGYFSSIF HGGVDSLVDL  300
MNKSFPELGI KKTDCKEFSW IDTTIFYSGV VNFNTANFKK EILLDRSAGK KTAFSIKLDY  360
VKKPIPETAM VKILEKLYEE DVGAGMYVLY PYGGIMEEIS ESAIPFPHRA GIMYELWYTA  420
SWEKQEDNEK HINWVRSVYN FTTPYVSQNP RLAYLNYRDL DLGKTNHASP NNYTQARIWG  480
EKYFGKNFNR LVKVKTKVDP NNFFRNEQSI PPLPPHHH                         518

SEQ ID NO: 19           moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 19
atggccgtca agcatttaat cgtcttaaaa tttaaggacg aaatcacaga agctcaaaag  60
gaggaattct tcaaaaccta tgtaaactta gtgaacataa ttcctgctat gaaagacgtt  120
tattggggta aggatgttac gcaaaaaaat aaggaagaag gatacaccca cattgtagaa  180
gtcacttttg aatcagtgga aaccatacaa gattatatca ttcaccctgc acatgttggg  240
ttcggtgatg tctacagatc attttgggaa aagttattga tctttgatta cacacctaga  300
aaa                                                               303

SEQ ID NO: 20           moltype = AA  length = 101
FEATURE                 Location/Qualifiers
source                  1..101
                        mol_type = protein
                        organism = Cannabis sativa
SEQUENCE: 20
MAVKHLIVLK FKDEITEAQK EEFFKTYVNL VNIIPAMKDV YWGKDVTQKN KEEGYTHIVE  60
VTFESVETIQ DYIIHPAHVG FGDVYRSFWE KLLIFDYTPR K                     101

SEQ ID NO: 21           moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 21
atggctgtca agcaccttat cgtactgaaa ttcaaggacg aaattcagga agcccagaaa  60
gaagaatttt tcaagaccta tgtaaacctg gtgaatatca tccctgcgat gaaagatgtt  120
tattggggca aagacgtcac ccaaaaaaac aaagaagaag gttacactca catcgtcgaa  180
gtcactttcg agtcagtaga gacgatccaa gattacataa tacacccggc ccatgtggga  240
ttcggagacg tttaccgtag cttctgggaa aaacttttga ttttcgacta taccccgaga  300
aaa                                                               303

SEQ ID NO: 22           moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 22
MAVKHLIVLK FKDEIQEAQK EEFFKTYVNL VNIIPAMKDV YWGKDVTQKN KEEGYTHIVE  60
VTFESVETIQ DYIIHPAHVG FGDVYRSFWE KLLIFDYTPR K                     101

SEQ ID NO: 23           moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 23
atggctgtca agcaccttat cgtactgaaa ttcaaggacg aaattacaga agcccagaaa  60
gaagaatttt tcaagaccta tgtaaacctg gtgaatatca tccctgcgat gaaagatgtt  120
tattggggca aagacgtcac ccaaaaaaac aaagaagaag gttacactca catcgtcgaa  180
gtcactttcg agtcagtaga gacgatccaa gattacataa tacacgtggc ccatgtggga  240
ttcggagacg tttaccgtag cttctgggaa aaacttttga ttttcgacta taccccgaga  300
aaa                                                               303
```

```
SEQ ID NO: 24          moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 24
MAVKHLIVLK FKDEITEAQK EEFFKTYVNL VNIIPAMKDV YWGKDVTQKN KEEGYTHIVE  60
VTFESVETIQ DYIIHVAHVG FGDVYRSFWE KLLIFDYTPR K                      101

SEQ ID NO: 25          moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 25
atggctgtca agcaccttat cgtagttaaa ttcaaggacg aaattacaga agcccagaaa  60
gaagaatttt tcaagaccta tgtaaacctg gtgaatatca tccctgcgat gaaagatgtt  120
tattggggca aagacgtcac ccaaaaaaac aaagaagaag gttacactca catcgtcgaa  180
gtcactttcg agtcagtaga gacgatccaa gattacataa tacacccggc ccatgtggga  240
ttcggagacg tttaccgtag cttctgggaa aaacttttga ttttcgacta taccccgaga  300
aaa                                                                303

SEQ ID NO: 26          moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 26
MAVKHLIVVK FKDEITEAQK EEFFKTYVNL VNIIPAMKDV YWGKDVTQKN KEEGYTHIVE  60
VTFESVETIQ DYIIHPAHVG FGDVYRSFWE KLLIFDYTPR K                      101

SEQ ID NO: 27          moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 27
atggctgtca agcaccttat cgtactgaaa ttcaaggacg aaattacaga agcccagaaa  60
gaagaatttt tcaagaccta tgtaaacctg gtgaatatca tccctgcgat gaaagatgtt  120
tattggggcc cggacgtcac ccaaaaaaac aaagaagaag gttacactca catcgtcgaa  180
gtcactttcg agtcagtaga gacgatccaa gattacataa tacacccggc ccatgtggga  240
ttcggagacg tttaccgtag cttctgggaa aaacttttga ttttcgacta taccccgaga  300
aaa                                                                303

SEQ ID NO: 28          moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 28
MAVKHLIVLK FKDEITEAQK EEFFKTYVNL VNIIPAMKDV YWGPDVTQKN KEEGYTHIVE  60
VTFESVETIQ DYIIHPAHVG FGDVYRSFWE KLLIFDYTPR K                      101

SEQ ID NO: 29          moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 29
atggctgtca agcaccttat cgtactgaaa ttcaaggacg aaattacaga agcccagaaa  60
gaagaatttt tcaagaccta tgtaaacctg gtgaatatca tccctgcgat gaaagatgtt  120
tattggggca aagacgtcac ccaaaaaaac aaagaagaag gttacactca catcgtcgaa  180
gtcactttcg agtcagtaga gacgatccaa gattacatat ctcacccggc ccatgtggga  240
ttcggagacg tttaccgtag cttctgggaa aaacttttga ttttcgacta taccccgaga  300
aaa                                                                303

SEQ ID NO: 30          moltype = AA  length = 101
```

```
FEATURE                 Location/Qualifiers
REGION                  1..101
                        note = Synthetic biopolymer
source                  1..101
                        mol_type = protein
                        organism = synthetic construct
SEQUENCE: 30
MAVKHLIVLK FKDEITEAQK EEFFKTYVNL VNIIPAMKDV YWGKDVTQKN KEEGYTHIVE  60
VTFESVETIQ DYISHPAHVG FGDVYRSFWE KLLIFDYTPR K                     101

SEQ ID NO: 31           moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 31
atggctgtca agcaccttat cgtactgaaa ttcaaggacg aaattacaga agcccagaaa  60
gaagaatttt tcaagaccta tgtaaacctg gtgaatatca tccctgcgat gaaagatgtt  120
tattggggca aagacgtcac ccaaaaaaac aaagaagaag gttacactgg tatcgtcgaa  180
gtcactttcg agtcagtaga gacgatccaa gattacataa tacacccggc ccatgtggga  240
ttcggagacg tttaccgtag cttctgggaa aaacttttga ttttcgacta taccccgaga  300
aaa                                                                303

SEQ ID NO: 32           moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 32
MAVKHLIVLK FKDEITEAQK EEFFKTYVNL VNIIPAMKDV YWGKDVTQKN KEEGYTGIVE  60
VTFESVETIQ DYIIHPAHVG FGDVYRSFWE KLLIFDYTPR K                     101

SEQ ID NO: 33           moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 33
atggctgtca agcaccttat cgtactgaaa ttcaaggacg aaattacaga agcccagaaa  60
gaagaatttt tcaagaccta tgtaaacctg gtgaatatca tccctgcgat gaaagatgtt  120
tattggggca aagacgtcac ccaacgtaac aaagaagaag gttacactca catcgtcgaa  180
gtcactttcg agtcagtaga gacgatccaa gattacataa tacacccggc ccatgtggga  240
ttcggagacg tttaccgtag cttctgggaa aaacttttga ttttcgacta taccccgaga  300
aaa                                                                303

SEQ ID NO: 34           moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 34
MAVKHLIVLK FKDEITEAQK EEFFKTYVNL VNIIPAMKDV YWGKDVTQRN KEEGYTHIVE  60
VTFESVETIQ DYIIHPAHVG FGDVYRSFWE KLLIFDYTPR K                     101

SEQ ID NO: 35           moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 35
atggctgtca agcaccttat cgtactgaaa ttcaaggacg ggattacaga agcccagaaa  60
gaagaatttt tcaagaccta tgtaaacctg gtgaatatca tccctgcgat gaaagatgtt  120
tattggggca aagacgtcac ccaaaaaaac aaagaagaag gttacactca catcgtcgaa  180
gtcactttcg agtcagtaga gacgatccaa gattacataa tacacccggc ccatgtggga  240
ttcggagacg tttaccgtag cttctgggaa aaacttttga ttttcgacta taccccgaga  300
aaa                                                                303

SEQ ID NO: 36           moltype = AA  length = 101
FEATURE                 Location/Qualifiers
```

```
REGION                  1..101
                        note = Synthetic biopolymer
source                  1..101
                        mol_type = protein
                        organism = synthetic construct
SEQUENCE: 36
MAVKHLIVLK FKDGITEAQK EEFFKTYVNL VNIIPAMKDV YWGKDVTQKN KEEGYTHIVE  60
VTFESVETIQ DYIIHPAHVG FGDVYRSFWE KLLIFDYTPR K                     101

SEQ ID NO: 37           moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 37
atggctgtca agcaccttat cgtactgaaa ttcaaggacg aaattacaga agcccagaaa  60
gaagaatttt tcaagaccta tgtaaacctg gtgaatatca tccctgcgat gaaagatgtt  120
tattggggca aagacgtcac ccaaaaaaac aaagaagaag gttacactca catcgtcgaa  180
gtcactttcg agtcagtaga gacgatccaa gggtacataa tacacccggc ccatgtggga  240
ttcggagacg tttaccgtag cttctgggaa aaacttttga ttttcgacta taccccgaga  300
aaa                                                                303

SEQ ID NO: 38           moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 38
MAVKHLIVLK FKDEITEAQK EEFFKTYVNL VNIIPAMKDV YWGKDVTQKN KEEGYTHIVE  60
VTFESVETIQ GYIIHPAHVG FGDVYRSFWE KLLIFDYTPR K                     101

SEQ ID NO: 39           moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 39
atggctgtca agcaccttat cgtactgaaa ttcaaggacg aaattacaga agcccagaaa  60
gaagaatttt tcaagaccta tgtaaacctg gtgaatatca tccctgcgat gaaagatgtt  120
tattggggca aagacgtcac ccaaaaaaac aaagaagaag gttacactca catcgtcgaa  180
gtcactttcg agtcagtaga gacgatccaa gattacataa tacacccggc ccatgtggga  240
ttcggagacg tttaccgtag cttctgggaa gagcttttga ttttcgacta taccccgaga  300
aaa                                                                303

SEQ ID NO: 40           moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 40
MAVKHLIVLK FKDEITEAQK EEFFKTYVNL VNIIPAMKDV YWGKDVTQKN KEEGYTHIVE  60
VTFESVETIQ DYIIHPAHVG FGDVYRSFWE ELLIFDYTPR K                     101

SEQ ID NO: 41           moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 41
atggctgtca agcaccttat cgtagtgaaa ttcaaggacg aaattacaga agcccagaaa  60
gttgaatttt tcaagaccta tgtaaacctg gtgaatatca tccctgcgat gaaagatgtt  120
tattggggca aagacgtcac ccaaaaaaac aaagaagaag gttacactca catcgtcgaa  180
gtcactttcg agtcagtaga gacgatccaa gattacataa tacacccggc ccatgtggga  240
ttcggagacg tttaccgtag cttctgggaa aaacttttga ttttcgacta taccccgaga  300
aaa                                                                303

SEQ ID NO: 42           moltype = AA  length = 101
FEATURE                 Location/Qualifiers
REGION                  1..101
```

```
                         note = Synthetic biopolymer
source                   1..101
                         mol_type = protein
                         organism = synthetic construct
SEQUENCE: 42
MAVKHLIVVK FKDEITEAQK VEFFKTYVNL VNIIPAMKDV YWGKDVTQKN KEEGYTHIVE  60
VTFESVETIQ DYIIHPAHVG FGDVYRSFWE KLLIFDYTPR K                      101

SEQ ID NO: 43            moltype = DNA  length = 303
FEATURE                  Location/Qualifiers
misc_feature             1..303
                         note = Synthetic biopolymer
source                   1..303
                         mol_type = other DNA
                         organism = synthetic construct
SEQUENCE: 43
atggctgtca agcaccttat cgtactgaaa ttcaaggacg aaattacaga agcccagaaa  60
gaagaatttt tcaagaatta tgtaaacctg gtgaatatca tccctgcgat gaaagatgtt  120
tattggggca aagacgtcac ccaacgtaac aaagaagaag gttacactca catcgtcgaa  180
gtcactttcg agtcagtaga gacgatccaa ggctacataa tacacccggc ccatgtggga  240
ttcggagacg tttaccgtag cttctgggaa gaacttttga ttttcgacta taccccgaga  300
aaa                                                                303

SEQ ID NO: 44            moltype = AA  length = 101
FEATURE                  Location/Qualifiers
REGION                   1..101
                         note = Synthetic biopolymer
source                   1..101
                         mol_type = protein
                         organism = synthetic construct
SEQUENCE: 44
MAVKHLIVLK FKDEITEAQK EEFFKNYVNL VNIIPAMKDV YWGKDVTQRN KEEGYTHIVE  60
VTFESVETIQ GYIIHPAHVG FGDVYRSFWE ELLIFDYTPR K                      101

SEQ ID NO: 45            moltype = DNA  length = 303
FEATURE                  Location/Qualifiers
misc_feature             1..303
                         note = Synthetic biopolymer
source                   1..303
                         mol_type = other DNA
                         organism = synthetic construct
SEQUENCE: 45
atggctgtca agcaccttat cgtactgaaa ttcttggacg aaattacaga agcccagaaa  60
gaagaatttt tcaagaccta tgtaaacctg gtgaatatca tccctgcgat gaaagatgtt  120
tattggggca aagacgtcac ccaaaaaaac aaagaagaag gttacactca catcgtcgaa  180
gtcactttcg agtcagtaga gacgatccaa gattacataa tacacccggc ccatgtggga  240
ttcggagacg tttaccgtag cttctgggaa aaacttttga ttttcgacta taccccgaga  300
aaa                                                                303

SEQ ID NO: 46            moltype = AA  length = 101
FEATURE                  Location/Qualifiers
REGION                   1..101
                         note = Synthetic biopolymer
source                   1..101
                         mol_type = protein
                         organism = synthetic construct
SEQUENCE: 46
MAVKHLIVLK FLDEITEAQK EEFFKTYVNL VNIIPAMKDV YWGKDVTQKN KEEGYTHIVE  60
VTFESVETIQ DYIIHPAHVG FGDVYRSFWE KLLIFDYTPR K                      101

SEQ ID NO: 47            moltype = DNA  length = 303
FEATURE                  Location/Qualifiers
misc_feature             1..303
                         note = Synthetic biopolymer
source                   1..303
                         mol_type = other DNA
                         organism = synthetic construct
SEQUENCE: 47
atggctgtca agcaccttat cgtactgaaa ttcaaggacg aaattacaga atcgcagaaa  60
gaagaatttt tcaagaccta tgtaaacctg gtgaatatca tccctgcgat gaaagatgtt  120
tattggggca aagacgtcac ccaaaaaaac aaagaagaag gttacactca catcgtcgaa  180
gtcactttcg agtcagtaga gacgatccaa gattacataa tacacccggc ccatgtggga  240
ttcggagacg tttaccgtag cttctgggaa aaacttttga ttttcgacta taccccgaga  300
aaa                                                                303

SEQ ID NO: 48            moltype = AA  length = 101
FEATURE                  Location/Qualifiers
REGION                   1..101
                         note = Synthetic biopolymer
```

```
source                  1..101
                        mol_type = protein
                        organism = synthetic construct
SEQUENCE: 48
MAVKHLIVLK FKDEITESQK EEFFKTYVNL VNIIPAMKDV YWGKDVTQKN KEEGYTHIVE  60
VTFESVETIQ DYIIHPAHVG FGDVYRSFWE KLLIFDYTPR K                      101

SEQ ID NO: 49           moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 49
atggctgtaa agcaccttat cgtagtcaaa ttcaaggacg gcattcagga agcccagaaa  60
gaagaatttt tcaagaccta tgtaaacctg gtgaatatca tccctgcgat gaaagatggg  120
tattggggca aagacgtcac ccaacgtaac aaagaagaag gttacactca catcgtcgaa  180
gtcactttcg agtcagtaga gacgatccaa ggctacataa tgcacccggc ccatgtggga  240
ttcggagacg tttaccgtag cttctgggaa gaacttttga ttttcgacta taccccgaga  300
aaa                                                                303

SEQ ID NO: 50           moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 50
MAVKHLIVVK FKDGIQEAQK EEFFKTYVNL VNIIPAMKDG YWGKDVTQRN KEEGYTHIVE  60
VTFESVETIQ GYIMHPAHVG FGDVYRSFWE ELLIFDYTPR K                      101

SEQ ID NO: 51           moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 51
atggctgtca agcaccttat cgtactgaaa ttcaaggacg aaattacagg agcccagaaa  60
gaagaatttt tcaagaccta tgtaaacctg gtgaatatca tccctgcgat gaaagatgtt  120
tattggggcc cggacgtcac ccaaaaaaac aaagaagaag gttacaccca catcgtcgaa  180
gtcactttcg agtcagtaga gacgatccaa gattacataa tacacccggc ccatgtggga  240
ttcggagacg tttaccgtag cttctgggaa aaacttttga ttttcgacta taccccgaga  300
aaa                                                                303

SEQ ID NO: 52           moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 52
MAVKHLIVLK FKDEITGAQK EEFFKTYVNL VNIIPAMKDV YWGPDVTQKN KEEGYTHIVE  60
VTFESVETIQ DYIIHPAHVG FGDVYRSFWE KLLIFDYTPR K                      101

SEQ ID NO: 53           moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 53
atggctgtca agcaccttat cgtactgaaa ttcaaggacg aaattacaga agcccagaaa  60
gaagaatttt tcaagaccta tgtaaacctg gtgaatatca tccctgcgat gaaagatgtt  120
tattggggca aagacgtcac ccaaaaaaac aaagaagaag gttacactca catcgtcgaa  180
gtcactttcg agtcagtaga gacgatccaa gattacataa tacacccggc ccatgtggga  240
ttcggagacg tttaccgtag cttctgggaa aaacttttga agttcgacta taccccgaga  300
aaa                                                                303

SEQ ID NO: 54           moltype = AA  length = 101
FEATURE                 Location/Qualifiers
REGION                  1..101
                        note = Synthetic biopolymer
source                  1..101
```

```
                        mol_type = protein
                        organism = synthetic construct
SEQUENCE: 54
MAVKHLIVLK FKDEITEAQK EEFFKTYVNL VNIIPAMKDV YWGKDVTQKN KEEGYTHIVE  60
VTFESVETIQ DYIIHPAHVG FGDVYRSFWE KLLKFDYTPR K                      101

SEQ ID NO: 55           moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 55
atggctgtca agcaccttat cgtactgaaa ttcaaggacg aaattacaga agcccagaaa  60
gaagaatttt tcaagaccta tgtaaacctg gtgaatatca tccctgcgat gaaagatgtt  120
tattggggca aagacgtcac ccaaaaaaac aaagaagaag gttacactca catcgtcgaa  180
gtcactttca agtcagtaga gacgatccag gattacataa tacacccggc ccatgtggga  240
ttcggagacg tttaccgtag cttctgggaa aaacttttga ttttcgacta taccccgaga  300
aaa                                                                303

SEQ ID NO: 56           moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 56
MAVKHLIVLK FKDEITEAQK EEFFKTYVNL VNIIPAMKDV YWGKDVTQKN KEEGYTHIVE  60
VTFKSVETIQ DYIIHPAHVG FGDVYRSFWE KLLIFDYTPR K                      101

SEQ ID NO: 57           moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 57
atggctgtca agcaccttat cgtactgaaa ttcaaggacg aaattacaga agcccagaaa  60
gaagaatttt tcaagaccta tgtaaacctg gtgaatgaga tccctgcgat gaaagatgtt  120
tattggggca aagacgtcac ccaacgtaac aaagaagaag gttacactca catcgtcgaa  180
gtcactttcg agtcagtaga gacgatccaa ggctacataa tacacccggc ccatgtggga  240
ttcggagacg tttaccgtag cttctgggaa gaacttttga ttttcgacta taccccgaga  300
aaa                                                                303

SEQ ID NO: 58           moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 58
MAVKHLIVLK FKDEITEAQK EEFFKTYVNL VNEIPAMKDV YWGKDVTQRN KEEGYTHIVE  60
VTFESVETIQ GYIIHPAHVG FGDVYRSFWE ELLIFDYTPR K                      101

SEQ ID NO: 59           moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 59
atggctgtca agcaccttat cgtagtgaaa ttcaaggacg aaattacaga agcccagaaa  60
gttgaatttt tcaagaccta tgtaaacctg gtgaatatca tccctgcgat gaaagatgtt  120
tattggggca aagacgtcac ccaaaaaaac aaagaagaag gttacactca catcgtcgaa  180
gtcactttcg agtcagtaga gacgatccaa gattacataa tacacccggc ccatgtggga  240
ttcgctgacg tttaccgtag cttctgggaa aaacttttga ttttcgacta taccccgaga  300
aaa                                                                303

SEQ ID NO: 60           moltype = AA  length = 101
FEATURE                 Location/Qualifiers
REGION                  1..101
                        note = Synthetic biopolymer
source                  1..101
                        mol_type = protein
```

```
                         organism = synthetic construct
SEQUENCE: 60
MAVKHLIVVK FKDEITEAQK VEFFKTYVNL VNIIPAMKDV YWGKDVTQKN KEEGYTHIVE  60
VTFESVETIQ DYIIHPAHVG FADVYRSFWE KLLIFDYTPR K                     101

SEQ ID NO: 61            moltype = DNA  length = 303
FEATURE                  Location/Qualifiers
misc_feature             1..303
                         note = Synthetic biopolymer
source                   1..303
                         mol_type = other DNA
                         organism = synthetic construct
SEQUENCE: 61
atggctgtca agcaccttat cgtactgaaa ttcaaggacg aaattacaga agcccagaaa  60
gaagaatttt tcaagaccta tgtaaacctg gtgaatatca tccctgcgat gaaagatgtt  120
tattggggca aagacgtcac ccaaaaaaac aaagaagaag gttacactca catcgtcgaa  180
gtcactttcg agtcagtaga gacgatccaa gattacataa tacacccgga gcatgtggga  240
ttcggagacg tttaccgtag cttctgggaa aaacttttga ttttcgacta taccccgaga  300
aaa                                                               303

SEQ ID NO: 62            moltype = AA  length = 101
FEATURE                  Location/Qualifiers
REGION                   1..101
                         note = Synthetic biopolymer
source                   1..101
                         mol_type = protein
                         organism = synthetic construct
SEQUENCE: 62
MAVKHLIVLK FKDEITEAQK EEFFKTYVNL VNIIPAMKDV YWGKDVTQKN KEEGYTHIVE  60
VTFESVETIQ DYIIHPEHVG FGDVYRSFWE KLLIFDYTPR K                     101

SEQ ID NO: 63            moltype = DNA  length = 303
FEATURE                  Location/Qualifiers
misc_feature             1..303
                         note = Synthetic biopolymer
source                   1..303
                         mol_type = other DNA
                         organism = synthetic construct
SEQUENCE: 63
atggctgtca agcaccttat cgtagtcaaa ttcaaggacg gcattcagga agcccagaaa  60
gaagaatttt tcaagaccta tgtaaacctg gtgaatatca tccctgcgat gaaagatgtt  120
tattggggca aagacgtcac ccaacgtaac aaagaagaag gttacactca catcgtcgaa  180
gtcactttcg agtcagtaga gacgatccaa ggctacataa tacacccggc ccatgtggga  240
ttcggagacg tttaccgtag cttctgggaa gaacttttga ttttcgacta taccccgaga  300
aaa                                                               303

SEQ ID NO: 64            moltype = AA  length = 101
FEATURE                  Location/Qualifiers
REGION                   1..101
                         note = Synthetic biopolymer
source                   1..101
                         mol_type = protein
                         organism = synthetic construct
SEQUENCE: 64
MAVKHLIVVK FKDGIQEAQK EEFFKTYVNL VNIIPAMKDV YWGKDVTQRN KEEGYTHIVE  60
VTFESVETIQ GYIIHPAHVG FGDVYRSFWE ELLIFDYTPR K                     101

SEQ ID NO: 65            moltype = DNA  length = 303
FEATURE                  Location/Qualifiers
misc_feature             1..303
                         note = Synthetic biopolymer
source                   1..303
                         mol_type = other DNA
                         organism = synthetic construct
SEQUENCE: 65
atggctgtca agcaccttat cgtactgaaa ttcaaggacg aaattacaga agcccagaaa  60
gaagaatttt tcaagaccta tgtaaacctg gtgaatatca tccctgcgat gaaagatgtt  120
tattggggca aagacgtcac ccaaaaaaac aaagaagaag gttacactca catcgtcgaa  180
gtcgggttcg agtcagtaga gacgatccaa gattacataa tacacccggc ccatgtggga  240
ttcggagacg tttaccgtag cttctgggaa aaacttttga ttttcgacta taccccgaga  300
aaa                                                               303

SEQ ID NO: 66            moltype = AA  length = 101
FEATURE                  Location/Qualifiers
REGION                   1..101
                         note = Synthetic biopolymer
source                   1..101
                         mol_type = protein
                         organism = synthetic construct
```

```
SEQUENCE: 66
MAVKHLIVLK FKDEITEAQK EEFFKTYVNL VNIIPAMKDV YWGKDVTQKN KEEGYTHIVE  60
VGFESVETIQ DYIIHPAHVG FGDVYRSFWE KLLIFDYTPR K                      101

SEQ ID NO: 67          moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 67
atggctgtca agcaccttat cgtactgaaa ttgaaggacg aaattacaga agcccagaaa  60
gaagaatttt tcaagaccta tgtaaacctg gtgaatatca tccctgcgat gaaagatgtt  120
tattggggca aagacgtcac ccaaaaaaac aaagaagaag gttacactca catcgtcgaa  180
gtcactttcg agtcagtaga gacgatccaa gattacataa tacacccggc ccatgtggga  240
ttcggagacg tttaccgtag cttctgggaa aaacttttga ttttcgacta taccccgaga  300
aaa                                                                303

SEQ ID NO: 68          moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 68
MAVKHLIVLK LKDEITEAQK EEFFKTYVNL VNIIPAMKDV YWGKDVTQKN KEEGYTHIVE  60
VTFESVETIQ DYIIHPAHVG FGDVYRSFWE KLLIFDYTPR K                      101

SEQ ID NO: 69          moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 69
atggctgtca agcaccttat cgtactgaaa ttcaaggacg aaattacaga agcccagaaa  60
gaagaatttt tcaagaccta tgtaaacctg gtgaatatca tccctgcgat gaaagatgtt  120
tattggggca aagacgtcac ccaaaaaaac aaagaagaag gttacactca catcgtcgaa  180
gtcactttcg agtcagtaga gacgatccaa gattacataa tacacccggc ccatgtggga  240
ttcggagacg tttaccgtaa gttctgggaa aaacttttga ttttcgacta taccccgaga  300
aaa                                                                303

SEQ ID NO: 70          moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 70
MAVKHLIVLK FKDEITEAQK EEFFKTYVNL VNIIPAMKDV YWGKDVTQKN KEEGYTHIVE  60
VTFESVETIQ DYIIHPAHVG FGDVYRKFWE KLLIFDYTPR K                      101

SEQ ID NO: 71          moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 71
atggctgtca agcaccttat cgtactgaaa ttcaaggacg aaattacaga agcccagaaa  60
gaagaatttt tcaagaccta tgtaaacctg gtgaatatca tccctgcgat gaaagatgtt  120
tattggggca aagacgtcac ccaaaaaaac aaagaagaag gttacactca catcgtcgaa  180
gtcactttcg agtcagtaga gacgatccaa gattacataa tacacccggc ccatgtggga  240
ttcggacggg tttaccgtag cttctgggaa aaacttttga ttttcgacta taccccgaga  300
aaa                                                                303

SEQ ID NO: 72          moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 72
```

-continued

```
MAVKHLIVLK FKDEITEAQK EEFFKTYVNL VNIIPAMKDV YWGKDVTQKN KEEGYTHIVE  60
VTFESVETIQ DYIIHPAHVG FGRVYRSFWE KLLIFDYTPR K                      101

SEQ ID NO: 73          moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 73
atggctgtca agcaccttat cgtagtcaaa ttcaaggacg gcattcagga agcccagaaa  60
gaagaatttt tcaagaccta tgtaaacctg gtgaatatca tccctgcgat gaaagatgtt  120
tattggggca aagacgtcac ccaacgtaac aaagaagaag gttacactca catcgtcgaa  180
gtcactttcg agtcagtaga gacgatccaa ggctacataa tacacccggc ccatgtggga  240
ttcggagaca tgtaccgtag cttctgggaa gaacttttga ttttcgacta taccccgaga  300
aaa                                                                303

SEQ ID NO: 74          moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 74
MAVKHLIVVK FKDGIQEAQK EEFFKTYVNL VNIIPAMKDV YWGKDVTQRN KEEGYTHIVE  60
VTFESVETIQ GYIIHPAHVG FGDMYRSFWE ELLIFDYTPR K                      101

SEQ ID NO: 75          moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 75
atggctgtca agcaccttat cgtactgaaa ttcaaggacg aaattacaga agcccagaaa  60
gaagaatttt tcaagaccta tgtaaacctg gtgaatatca tccctgcgat gaaagatgtt  120
tattggggca aagacgtcac ccaaaaaaac aaagaagaag gttacactca catcgtcgaa  180
gtcactttcg agtcagtaga gacgatccaa gattacataa tacacccggc ccatgtggga  240
ttccgggacg tttaccgtag cttctgggaa aaacttttga ttttcgacta taccccgaga  300
aaa                                                                303

SEQ ID NO: 76          moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 76
MAVKHLIVLK FKDEITEAQK EEFFKTYVNL VNIIPAMKDV YWGKDVTQKN KEEGYTHIVE  60
VTFESVETIQ DYIIHPAHVG FRDVYRSFWE KLLIFDYTPR K                      101

SEQ ID NO: 77          moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 77
atggctgtca agcaccttat cgtactgaaa ttcaaggacg aaattacaga agcccagaaa  60
gaagaatttt tccggaccta tgtaaacctg gtgaatatca tccctgcgat gaaagatgtt  120
tattggggca aagacgtcac ccaacgtaac aaagaagaag gttacactca catcgtcgaa  180
gtcactttcg agtcagtaga gacgatccaa ggctacataa tacacccggc ccatgtggga  240
ttcggagacg tttaccgtag cttctgggaa gaacttttga ttttcgacta taccccgaga  300
aaa                                                                303

SEQ ID NO: 78          moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 78
MAVKHLIVLK FKDEITEAQK EEFFRTYVNL VNIIPAMKDV YWGKDVTQRN KEEGYTHIVE  60
```

-continued

```
VTFESVETIQ GYIIHPAHVG FGDVYRSFWE ELLIFDYTPR K                101

SEQ ID NO: 79           moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 79
atggctgtaa agcaccttat cgtagtcaaa ttcaaggacg gcattcagga agcccagaaa  60
gaagaatttt tcaagaccta tgtaaacctg gtgaatatca tccctgagat gaaagatgtt  120
tattggggca aagacgtcac ccaacgtaac aaagaagaag gttacactca catcgtcgaa  180
gtcactttcg agtcagtaga gacgatccaa ggctacataa tacacccggc ccatgtggga  240
ttcggagacg tttaccgtag cttctgggaa gaacttttga ttttcgacta taccccgaga  300
aaa                                                          303

SEQ ID NO: 80           moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 80
MAVKHLIVVK FKDGIQEAQK EEFFKTYVNL VNIIPEMKDV YWGKDVTQRN KEEGYTHIVE  60
VTFESVETIQ GYIIHPAHVG FGDVYRSFWE ELLIFDYTPR K                101

SEQ ID NO: 81           moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 81
atggctgtca agcaccttat cgtagtgaaa ttcaaggacg aaattccaga agcccagaaa  60
gaagaatttt tcaaggctta tgtaaacctg gtgaatatca tccctgcgat gaaagatgtt  120
tattggggca aagacgtcac ccaacgtaac aaagaagaag gttacactca catcgtcgaa  180
gtcactttcg agtcagtaga gacgatccaa ggctacataa tacacccggc ccatgtggga  240
ttcggagacg tttaccgtag cttctgggaa gaacttttga ttttcgacta taccccgaga  300
aaa                                                          303

SEQ ID NO: 82           moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 82
MAVKHLIVVK FKDEIPEAQK EEFFKAYVNL VNIIPAMKDV YWGKDVTQRN KEEGYTHIVE  60
VTFESVETIQ GYIIHPAHVG FGDVYRSFWE ELLIFDYTPR K                101

SEQ ID NO: 83           moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 83
atggctgtca agcaccttat cgtagtcaaa ttcaaggacg gcattcagga agcccagaaa  60
gaagaatttt tcaagaccta tgtaaacctg gtgaatatca tccctgcgat gaaagatgtt  120
tattggggca aagacgtcac ccaacgtaac aaagaagaag gttacactca catcgtcgaa  180
gtcactttcg agtcagtaga gacgatccaa ggctacataa tacacccggc ccatgtggga  240
ttcggagacg tttaccgtag cttctgggaa gaacttttga ttttcgacta taccccgaga  300
aaa                                                          303

SEQ ID NO: 84           moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 84
MAVKHLIVVK FKDGIQEAQK EEFFKTYVNL VNIIPAMKDV YWGKDVTQRN KEEGYTHIVE  60
VTFESVETIQ GYIIHPAHVG FGDVYRSFWE ELLIFDYTPR K                101
```

```
SEQ ID NO: 85          moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 85
atggccgtca agcatttaat cgtcgtcaaa tttaaggacg gtatcacaga agctcaaaag  60
gaggaattct tcaaaaccta tgtaaactta gtgaacataa ttcctgctat gaaagacgtt  120
tattggggta aggatgttac gcaaagaaat aaggaagaag gatacaccca cattgtagaa  180
gtcacttttg aatcagtgga aaccatacaa ggttatatca ttcaccctgc acatgttggg  240
ttcggtgatg tctacagatc attttgggaa gaattattga tctttgatta cactccaagg  300
aag                                                                303

SEQ ID NO: 86          moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 86
MAVKHLIVVK FKDGITEAQK EEFFKTYVNL VNIIPAMKDV YWGKDVTQRN KEEGYTHIVE  60
VTFESVETIQ GYIIHPAHVG FGDVYRSFWE ELLIFDYTPR K                      101

SEQ ID NO: 87          moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 87
atggccgtca agcatttaat cgtcgtcaaa tttaaggacg gtatcacaga agctcaaaag  60
gaggaattct tcaaaaccta tgtaaactta gtgaacataa ttcctgctat gaaagacgtt  120
tattggggta aggatgttac gcaaagaaat aaggaagaag gatacaccgg tattgtagaa  180
gtcacttttg aatcagtgga aaccatacaa ggttatatca ttcaccctgc acatgttggg  240
ttcggtgatg tctacagatc attttgggaa gaattattga tctttgatta cacacctaga  300
aaa                                                                303

SEQ ID NO: 88          moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 88
MAVKHLIVVK FKDGITEAQK EEFFKTYVNL VNIIPAMKDV YWGKDVTQRN KEEGYTGIVE  60
VTFESVETIQ GYIIHPAHVG FGDVYRSFWE ELLIFDYTPR K                      101

SEQ ID NO: 89          moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 89
atggctgtca agcaccttat cgtactgaaa ttcaaggacg aaattacaga agcccagaaa  60
gaagaatttt tctcgaccta tgtaaactta gtgaacataa ttcctgctat gaaagacgtt  120
tattggggta aggatgttac gcaaagaaat aaggaagaag gatacaccca cattgtagaa  180
gtcacttttg aatcagtgga aaccatacaa ggttatatca ttcaccctgc acatgttggg  240
ttcggtgatg tctacagatc attttgggaa gaattattga tctttgatta cactccaagg  300
aag                                                                303

SEQ ID NO: 90          moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 90
MAVKHLIVLK FKDEITEAQK EEFFSTYVNL VNIIPAMKDV YWGKDVTQRN KEEGYTHIVE  60
VTFESVETIQ GYIIHPAHVG FGDVYRSFWE ELLIFDYTPR K                      101
```

-continued

```
SEQ ID NO: 91          moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 91
atggccgtca agcatttaat cgtcgtcaaa tttaaggacg gtatccaaga agctcaaaag  60
gaggaattct tcaaaaccta tgtaaactta gtgaacataa ttcctgctat gaaagacgtt  120
tattggggta aggatgttac gcaaagaaat aaggaagaag gatacaccca cattgtagaa  180
gtcacttttg aatcagtgga aaccatacaa ggttatatca ttcaccctgc acatgttggg  240
ttcggtgatg tctacagatc attttgggaa gaattattga tctttgatta cacacctaga  300
aaa                                                               303

SEQ ID NO: 92          moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 92
MAVKHLIVVK FKDGIQEAQK EEFFKTYVNL VNIIPAMKDV YWGKDVTQRN KEEGYTHIVE  60
VTFESVETIQ GYIIHPAHVG FGDVYRSFWE ELLIFDYTPR K                     101

SEQ ID NO: 93          moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 93
atggccgtca agcatttaat cgtcgtcaaa tttaaggacg gtatcacaga agctcaaaag  60
gaggaattct tcaaaaccta tgtaaactta gtgaacataa ttcctgctat gaaagacgtt  120
tattggggta aggatgttac gcaaagaaat aaggaagaag gatacaccca cattgtagaa  180
gtcacttttg aatcagtgga aaccatacaa ggttatatca ttcaccctgc acatgttggg  240
ttcggtgatg tctacagatc attttgggaa gaattattga tctttgattt tactccaagg  300
aag                                                               303

SEQ ID NO: 94          moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 94
MAVKHLIVVK FKDGITEAQK EEFFKTYVNL VNIIPAMKDV YWGKDVTQRN KEEGYTHIVE  60
VTFESVETIQ GYIIHPAHVG FGDVYRSFWE ELLIFDFTPR K                     101

SEQ ID NO: 95          moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 95
atggccgtca agcatttaat cgtcgtcaaa tttaaggacg gtatcacaga agctcaaaag  60
gaggaattct tcaaaaccta tgtaaactta gtgaacataa ttcctgctat gaaagacgtt  120
tattggggta aggatgttac gcaaagaaat aaggaagaag gatggaccca cattgtagaa  180
gtcacttttg aatcagtgga aaccatacaa ggttatatca ttcaccctgc acatgttggg  240
ttcggtgatg tctacagatc attttgggaa gaattattga tctttgatta cactccaagg  300
aag                                                               303

SEQ ID NO: 96          moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 96
MAVKHLIVVK FKDGITEAQK EEFFKTYVNL VNIIPAMKDV YWGKDVTQRN KEEGWTHIVE  60
VTFESVETIQ GYIIHPAHVG FGDVYRSFWE ELLIFDYTPR K                     101

SEQ ID NO: 97          moltype = DNA  length = 303
```

```
FEATURE               Location/Qualifiers
misc_feature          1..303
                      note = Synthetic biopolymer
source                1..303
                      mol_type = other DNA
                      organism = synthetic construct
SEQUENCE: 97
atggccgtca agcatttaat cgtcatcaaa tttaaggacg gtatcacaga agctcaaaag  60
gaggaattct tcaaaaccta tgtaaactta gtgaacataa ttcctgctat gaaagacgtt  120
tattggggta aggatgttac gcaaagaaat aaggaagaag gatacaccca cattgtagaa  180
gtcacttttg aatcagtgga aaccatacaa ggttatatca ttcaccctgc acatgttggg  240
ttcggtgatg tctacagatc attttgggaa gaattattga tctttgatta cactccaagg  300
aag                                                                303

SEQ ID NO: 98         moltype = AA  length = 101
FEATURE               Location/Qualifiers
REGION                1..101
                      note = Synthetic biopolymer
source                1..101
                      mol_type = protein
                      organism = synthetic construct
SEQUENCE: 98
MAVKHLIVIK FKDGITEAQK EEFFKTYVNL VNIIPAMKDV YWGKDVTQRN KEEGYTHIVE  60
VTFESVETIQ GYIIHPAHVG FGDVYRSFWE ELLIFDYTPR K                      101

SEQ ID NO: 99         moltype = DNA  length = 303
FEATURE               Location/Qualifiers
misc_feature          1..303
                      note = Synthetic biopolymer
source                1..303
                      mol_type = other DNA
                      organism = synthetic construct
SEQUENCE: 99
atggccgtca agcatttaat cgtcgtcaaa tttaaggacg gtatcacaga agctcaaaag  60
gaggaattct tcaaaaccta tgtaaactta gtgaacataa ttcctgctat gaaagacgtt  120
tattggggta aggatgttac gcaaagaaat aaggaagaag gatacaccca cattgtagaa  180
gtcacttttg aatcactgga aaccatacaa ggttatatca ttcaccctgc acatgttggg  240
ttcggtgatg tctacagatc attttgggaa gaattattga tctttgatta cactccaagg  300
aag                                                                303

SEQ ID NO: 100        moltype = AA  length = 101
FEATURE               Location/Qualifiers
REGION                1..101
                      note = Synthetic biopolymer
source                1..101
                      mol_type = protein
                      organism = synthetic construct
SEQUENCE: 100
MAVKHLIVVK FKDGITEAQK EEFFKTYVNL VNIIPAMKDV YWGKDVTQRN KEEGYTHIVE  60
VTFESLETIQ GYIIHPAHVG FGDVYRSFWE ELLIFDYTPR K                      101

SEQ ID NO: 101        moltype = DNA  length = 303
FEATURE               Location/Qualifiers
misc_feature          1..303
                      note = Synthetic biopolymer
source                1..303
                      mol_type = other DNA
                      organism = synthetic construct
SEQUENCE: 101
atggccgtca agcatttaat cgtcgtcaaa tttaaggacg gtatcacaga agctcaaaag  60
gaggaattct tcaaaaccta tgtaaactta tcgaacataa ttcctgctat gaaagacgtt  120
tattggggta aggatgttac gcaaagaaat aaggaagaag gatacaccca cattgtagaa  180
gtcacttttg aatcagtgga aaccatacaa ggttatatca ttcaccctgc acatgttggg  240
ttcggtgatg tctacagatc attttgggaa gaattattga tctttgatta cactccaagg  300
aag                                                                303

SEQ ID NO: 102        moltype = AA  length = 101
FEATURE               Location/Qualifiers
REGION                1..101
                      note = Synthetic biopolymer
source                1..101
                      mol_type = protein
                      organism = synthetic construct
SEQUENCE: 102
MAVKHLIVVK FKDGITEAQK EEFFKTYVNL SNIIPAMKDV YWGKDVTQRN KEEGYTHIVE  60
VTFESVETIQ GYIIHPAHVG FGDVYRSFWE ELLIFDYTPR K                      101

SEQ ID NO: 103        moltype = DNA  length = 303
FEATURE               Location/Qualifiers
```

```
misc_feature           1..303
                       note = Synthetic biopolymer
source                 1..303
                       mol_type = other DNA
                       organism = synthetic construct
SEQUENCE: 103
atggccgtca agcatttaat cgtcgtcaaa tttaaggacg gtatcacaga agctcaaaag  60
gaggaattct tcaaaaccta tgtaaactta atgaacataa ttcctgctat gaaagacgtt  120
tattggggta aggatgttac gcaaagaaat aaggaagaag gatacaccca cattgtagaa  180
gtcacttttg aatcagtgga aaccatacaa ggttatatca ttcaccctgc acatgttggg  240
ttcggtgatg tctacagatc attttgggaa gaattattga tctttgatta cactccaagg  300
aag                                                                303

SEQ ID NO: 104         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 104
MAVKHLIVVK FKDGITEAQK EEFFKTYVNL MNIIPAMKDV YWGKDVTQRN KEEGYTHIVE  60
VTFESVETIQ GYIIHPAHVG FGDVYRSFWE ELLIFDYTPR K                      101

SEQ ID NO: 105         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 105
atggccgtca agcatttaat cgtcgtcaaa tttaaggacg gtatcacaga agctcaaaag  60
gaggaattct tcaaaaccta tgtaaactta gagaacataa ttcctgctat gaaagacgtt  120
tattggggta aggatgttac gcaaagaaat aaggaagaag gatacaccca cattgtagaa  180
gtcacttttg aatcagtgga aaccatacaa ggttatatca ttcaccctgc acatgttggg  240
ttcggtgatg tctacagatc attttgggaa gaattattga tctttgatta cactccaagg  300
aag                                                                303

SEQ ID NO: 106         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 106
MAVKHLIVVK FKDGITEAQK EEFFKTYVNL ENIIPAMKDV YWGKDVTQRN KEEGYTHIVE  60
VTFESVETIQ GYIIHPAHVG FGDVYRSFWE ELLIFDYTPR K                      101

SEQ ID NO: 107         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 107
atggccgtca agcatttaat cgtcgtcaaa tttaaggacg gtatcacaga agctcaaaag  60
gaggaattct tcaaaaccta ttgtaactta gtgaacataa ttcctgctat gaaagacgtt  120
tattggggta aggatgttac gcaaagaaat aaggaagaag gatacaccca cattgtagaa  180
gtcacttttg aatcagtgga aaccatacaa ggttatatca ttcaccctgc acatgttggg  240
ttcggtgatg tctacagatc attttgggaa gaattattga tctttgatta cactccaagg  300
aag                                                                303

SEQ ID NO: 108         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 108
MAVKHLIVVK FKDGITEAQK EEFFKTYCNL VNIIPAMKDV YWGKDVTQRN KEEGYTHIVE  60
VTFESVETIQ GYIIHPAHVG FGDVYRSFWE ELLIFDYTPR K                      101

SEQ ID NO: 109         moltype = DNA  length = 303
FEATURE                Location/Qualifiers
misc_feature           1..303
```

-continued

```
                         note = Synthetic biopolymer
source                   1..303
                         mol_type = other DNA
                         organism = synthetic construct
SEQUENCE: 109
atggccgtca agcatttaat cgtcgtcaaa tttaaggacg gtatcacaga agctcaaaag  60
gaggaattct tcaaaaccta tgtaaactta gtgaacataa ttcctgctat gaaagacgtt  120
tattggggta aggatgttac gcaaagaaat aaggaagaag gatacaccca cattgtagaa  180
gtcacttttg aatcagtgga aagtatacaa ggttatatca tacacccggc ccatgtggga  240
ttcggtgatg tctacagatc attttgggaa gaattattga tctttgatta cactccaagg  300
aag                                                                303

SEQ ID NO: 110           moltype = AA  length = 101
FEATURE                  Location/Qualifiers
REGION                   1..101
                         note = Synthetic biopolymer
source                   1..101
                         mol_type = protein
                         organism = synthetic construct
SEQUENCE: 110
MAVKHLIVVK FKDGITEAQK EEFFKTYVNL VNIIPAMKDV YWGKDVTQRN KEEGYTHIVE  60
VTFESVESIQ GYIIHPAHVG FGDVYRSFWE ELLIFDYTPR K                      101

SEQ ID NO: 111           moltype = DNA  length = 303
FEATURE                  Location/Qualifiers
misc_feature             1..303
                         note = Synthetic biopolymer
source                   1..303
                         mol_type = other DNA
                         organism = synthetic construct
SEQUENCE: 111
atggccgtca agcatttaat cgtcgtcaaa tttaaggacg gtatcacaga agctcaaaag  60
gaggaattct tcaaaaccta tgtaaactta gtgaacataa ttcctgctat gaaagacgtt  120
tattggggta aggatgttac gcaaagaaat aaggaagaag gatacaccca cattgtagaa  180
gtcacttttg aatcagtgga acagatacaa ggttatatca ttcaccctgc acatgttggg  240
ttcggtgatg tctacagatc attttgggaa gaattattga tctttgatta cactccaagg  300
aag                                                                303

SEQ ID NO: 112           moltype = AA  length = 101
FEATURE                  Location/Qualifiers
REGION                   1..101
                         note = Synthetic biopolymer
source                   1..101
                         mol_type = protein
                         organism = synthetic construct
SEQUENCE: 112
MAVKHLIVVK FKDGITEAQK EEFFKTYVNL VNIIPAMKDV YWGKDVTQRN KEEGYTHIVE  60
VTFESVEQIQ GYIIHPAHVG FGDVYRSFWE ELLIFDYTPR K                      101

SEQ ID NO: 113           moltype = DNA  length = 303
FEATURE                  Location/Qualifiers
misc_feature             1..303
                         note = Synthetic biopolymer
source                   1..303
                         mol_type = other DNA
                         organism = synthetic construct
SEQUENCE: 113
atggccgtca agcatttaat cgtcgtcaaa tttaaggacg gtatcacaga agctcaaaag  60
gaggaattct tcaaaaccta tgtaaactta gtgaacataa ttcctgctat gaaagacgtt  120
tattggggta aggatgttac gcaaagaaat aaggaagaag gatacaccca cattgtagaa  180
gtcacttttg aatcagtgga aatgatacaa ggttatatca ttcaccctgc acatgttggg  240
ttcggtgatg tctacagatc attttgggaa gaattattga tctttgatta cactccaagg  300
aag                                                                303

SEQ ID NO: 114           moltype = AA  length = 101
FEATURE                  Location/Qualifiers
REGION                   1..101
                         note = Synthetic biopolymer
source                   1..101
                         mol_type = protein
                         organism = synthetic construct
SEQUENCE: 114
MAVKHLIVVK FKDGITEAQK EEFFKTYVNL VNIIPAMKDV YWGKDVTQRN KEEGYTHIVE  60
VTFESVEMIQ GYIIHPAHVG FGDVYRSFWE ELLIFDYTPR K                      101

SEQ ID NO: 115           moltype = DNA  length = 303
FEATURE                  Location/Qualifiers
misc_feature             1..303
                         note = Synthetic biopolymer
```

```
source                  1..303
                        mol_type = other DNA
                        organism = synthetic construct
SEQUENCE: 115
atggccgtca agcatttaat cgtcgtcaaa tttaaggacg gtatcacaga agctcaaaag  60
gaggaattct tcaaaaccta tgtaaactta gtgaacataa ttcctgctat gaaagacgtt  120
tattggggta aggatgttac gcaaagaaat aaggaagaag gatacaccca cattgtagaa  180
gtcacttttg aatcagtgga aggtatacaa ggttatatca ttcaccctgc acatgttggg  240
ttcggtgatg tctacagatc attttgggaa gaattattga tctttgatta cactccaagg  300
aag                                                                303

SEQ ID NO: 116          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 116
MAVKHLIVVK FKDGITEAQK EEFFKTYVNL VNIIPAMKDV YWGKDVTQRN KEEGYTHIVE  60
VTFESVEGIQ GYIIHPAHVG FGDVYRSFWE ELLIFDYTPR K                      101

SEQ ID NO: 117          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 117
atggccgtca agcatttaat cgtcgtcaaa tttaaggacg gtatcacaga agctcaaaag  60
gaggaattct tcaaaaccta tgtaaactta gtgaacataa ttcctgctat gaaagacgtt  120
tattggggta aggatgttac gcaaagaaat aaggaagaag gatacaccca cattgtagaa  180
gtcacttttg aatcagtgga agagatacaa ggttatatca ttcaccctgc acatgttggg  240
ttcggtgatg tctacagatc attttgggaa gaattattga tctttgatta cactccaagg  300
aag                                                                303

SEQ ID NO: 118          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 118
MAVKHLIVVK FKDGITEAQK EEFFKTYVNL VNIIPAMKDV YWGKDVTQRN KEEGYTHIVE  60
VTFESVEEIQ GYIIHPAHVG FGDVYRSFWE ELLIFDYTPR K                      101

SEQ ID NO: 119          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 119
atggccgtca agcatttaat cgtcgtcaaa tttaaggacg gtatcacaga agctcaaaag  60
gaggaattct tcaaaaccta tgtaaactta gtgaacataa ttcctgctat gaaagacgtt  120
tattggggta aggatgttac gcaaagaaat aaggaagaag gatacaccca cattgtagaa  180
gtcacttttg aatcagtgga agcgatacaa ggttatatca ttcaccctgc acatgttggg  240
ttcggtgatg tctacagatc attttgggaa gaattattga tctttgatta cactccaagg  300
aag                                                                303

SEQ ID NO: 120          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 120
MAVKHLIVVK FKDGITEAQK EEFFKTYVNL VNIIPAMKDV YWGKDVTQRN KEEGYTHIVE  60
VTFESVEAIQ GYIIHPAHVG FGDVYRSFWE ELLIFDYTPR K                      101

SEQ ID NO: 121          moltype = DNA  length = 303
FEATURE                 Location/Qualifiers
misc_feature            1..303
                        note = Synthetic biopolymer
source                  1..303
```

```
                        mol_type = other DNA
                        organism = synthetic construct
SEQUENCE: 121
atggccgtca agcatttaat cgtcgtcaaa tttaaggacg gtatcacaga agctcaaaag  60
gaggaattct tcaaaaccta tgtagggtta gtgaacataa ttcctgctat gaaagacgtt  120
tattggggta aggatgttac gcaaagaaat aaggaagaag gatacaccca cattgtagaa  180
gtcacttttg aatcagtgga aaccatacaa ggttatatca ttcaccctgc acatgttggg  240
ttcggtgatg tctacagatc attttgggaa gaattattga tctttgatta cactccaagg  300
aag                                                                303

SEQ ID NO: 122          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 122
MAVKHLIVVK FKDGITEAQK EEFFKTYVGL VNIIPAMKDV YWGKDVTQRN KEEGYTHIVE  60
VTFESVETIQ GYIIHPAHVG FGDVYRSFWE ELLIFDYTPR K                      101

SEQ ID NO: 123          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 123
atggccgtca agcattttat tgtcgtcaaa tttaaggacg gtatcacaga agctcaaaag  60
gaggaattct tcaaaaccta tgtaaactta gtgaacataa ttcctgctat gaaagacgtt  120
tattggggta aggatgttac gcaaagaaat aaggaagaag gatacaccca cattgtagaa  180
gtcacttttg aatcagtgga aaccatacaa ggttatatca ttcaccctgc acatgttggg  240
ttcggtgatg tctacagatc attttgggaa gaattattga tctttgatta cactccaagg  300
aag                                                                303

SEQ ID NO: 124          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 124
MAVKHFIVVK FKDGITEAQK EEFFKTYVNL VNIIPAMKDV YWGKDVTQRN KEEGYTHIVE  60
VTFESVETIQ GYIIHPAHVG FGDVYRSFWE ELLIFDYTPR K                      101

SEQ ID NO: 125          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 125
atggccgtca agcatttaat cgtcgtcaaa tttaaggacg gtatcacaga agctcaaaag  60
gaggaattct tcgggaccta tgtaaactta gtgaacataa ttcctgctat gaaagacgtt  120
tattggggta aggatgttac gcaaagaaat aaggaagaag gatacaccca cattgtagaa  180
gtcacttttg aatcagtgga aaccatacaa ggttatatca ttcaccctgc accggttggg  240
ttcggtgatg tctacagatc attttgggaa gaattattga tctttgatta cactccaagg  300
aag                                                                303

SEQ ID NO: 126          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 126
MAVKHLIVVK FKDGITEAQK EEFFGTYVNL VNIIPAMKDV YWGKDVTQRN KEEGYTHIVE  60
VTFESVETIQ GYIIHPAPVG FGDVYRSFWE ELLIFDYTPR K                      101

SEQ ID NO: 127          moltype = DNA  length = 303
FEATURE                 Location/Qualifiers
misc_feature            1..303
                        note = Synthetic biopolymer
source                  1..303
                        mol_type = other DNA
```

```
                         organism = synthetic construct
SEQUENCE: 127
atggccgtca agcatttaat cgtcgtcaaa tttaaggacg gtatcacaga agctcaaaag  60
gaggaattct tcaaaaccta tgtaaactta gtgaacataa ttcctgctat gaaagacgtt  120
tattggggta aggatgttac gcaaagaaat aaggaagaag gatacaccca cattgtagaa  180
gtcacttttg aatcagtgga aaccatacaa ggttatatcg tgcaccctgc acatgttggg  240
ttcggtgatg tctacagatc attttgggaa gaattattga tctttgatta cactccaagg  300
aag                                                               303

SEQ ID NO: 128          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 128
MAVKHLIVVK FKDGITEAQK EEFFKTYVNL VNIIPAMKDV YWGKDVTQRN KEEGYTHIVE  60
VTFESVETIQ GYIVHPAHVG FGDVYRSFWE ELLIFDYTPR K                     101

SEQ ID NO: 129          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 129
atggccgtca agcatttaat cgtcgtcaaa tttaaggacg gtatcacaga agctcaaaag  60
gaggaattct tcaaaaccta tgtaaactta gtgaacataa ttcctgctat gaaagacgtt  120
tattggggta aggatgttac gcaaagaaat aaggaagaag gatacaccca cattgtagaa  180
gtcacttttg aatcagtgga aaccatacaa ggttatatca cgcaccctgc acatgttggg  240
ttcggtgatg tctacagatc attttgggaa gaattattga tctttgatta cactccaagg  300
aag                                                               303

SEQ ID NO: 130          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 130
MAVKHLIVVK FKDGITEAQK EEFFKTYVNL VNIIPAMKDV YWGKDVTQRN KEEGYTHIVE  60
VTFESVETIQ GYITHPAHVG FGDVYRSFWE ELLIFDYTPR K                     101

SEQ ID NO: 131          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 131
atggccgtca agcatttaat cgtcgtcaaa tttaaggacg gtatcacaga agctcaaaag  60
gaggaattct tcaaaaccta tgtaaactta gtgaacataa ttcctgctat gaaagacgtt  120
tattggggta aggatgttac gcaaagaaat aaggaagaag gatacaccca cattgtagaa  180
gtcacttttg aatcagtgga aaccatacaa ggttatatca tgcaccctgc acatgttggg  240
ttcggtgatg tctacagatc attttgggaa gaattattga tctttgatta cactccaagg  300
aag                                                               303

SEQ ID NO: 132          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 132
MAVKHLIVVK FKDGITEAQK EEFFKTYVNL VNIIPAMKDV YWGKDVTQRN KEEGYTHIVE  60
VTFESVETIQ GYIMHPAHVG FGDVYRSFWE ELLIFDYTPR K                     101

SEQ ID NO: 133          moltype = DNA  length = 303
FEATURE                 Location/Qualifiers
misc_feature            1..303
                        note = Synthetic biopolymer
source                  1..303
                        mol_type = other DNA
                        organism = synthetic construct
```

```
SEQUENCE: 133
atggccgtca agcatttaat cgtcgtcaaa tttaaggacg gtatcacaga agctcaaaag  60
gaggaattct tcaaaaccta tgtaaactta gtgaacataa ttcctgctat gaaagacgtt  120
tattggggta aggatgttac gcaaagaaat aaggaagaag gatacaccca cattgtagaa  180
gtcacttttg aatcagtgga aaccatacaa ggttatatct tgcaccctgc acatgttggg  240
ttcggtgatg tctacagatc attttgggaa gaattattga tctttgatta cactccacgg  300
aag                                                               303

SEQ ID NO: 134         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 134
MAVKHLIVVK FKDGITEAQK EEFFKTYVNL VNIIPAMKDV YWGKDVTQRN KEEGYTHIVE  60
VTFESVETIQ GYILHPAHVG FGDVYRSFWE ELLIFDYTPR K                     101

SEQ ID NO: 135         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 135
atggccgtca agcatttaat cgtcgtcaaa tttaaggacg gtatcacaga agctcaaaag  60
gaggaattct tcaaaaccta tgtaaactta gtgaacataa ttcctgctat gaaagacgtt  120
tattggggta aggatgttac gcaaagaaat aaggaagaag gatacaccca cattgtagaa  180
gtcacttttg aatcagtgga aaccatacaa ggttatatcg ggcaccctgc acatgttggg  240
ttcggtgatg tctacagatc attttgggaa gaattattga tctttgatta cactccaagg  300
aag                                                               303

SEQ ID NO: 136         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 136
MAVKHLIVVK FKDGITEAQK EEFFKTYVNL VNIIPAMKDV YWGKDVTQRN KEEGYTHIVE  60
VTFESVETIQ GYIGHPAHVG FGDVYRSFWE ELLIFDYTPR K                     101

SEQ ID NO: 137         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 137
atggccgtca agcatttaat cgtcgtcaaa tttaaggacg gtatcacaga agctcaaaag  60
gaggaattct tcaaaaccta tgtaaactta gtgaacgtga ttcctgctat gaaagacgtt  120
tattggggta aggatgttac gcaaagaaat aaggaagaag gatacaccca cattgtagaa  180
gtcacttttg aatcagtgga aaccatacaa ggttatatca ttcaccctgc acatgttggg  240
ttcggtgatg tctacagatc attttgggaa gaattattga tctttgatta cactccaagg  300
aag                                                               303

SEQ ID NO: 138         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 138
MAVKHLIVVK FKDGITEAQK EEFFKTYVNL VNVIPAMKDV YWGKDVTQRN KEEGYTHIVE  60
VTFESVETIQ GYIIHPAHVG FGDVYRSFWE ELLIFDYTPR K                     101

SEQ ID NO: 139         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 139
```

-continued

```
atggccgtca agcatttaat cgtcgtcaaa tttaaggacg gtatcacaga agctcaaaag  60
gaggaattct tcaaaaccta tgtaaactta gtgaacgata ttcctgctat gaaagacgtt  120
tattggggta aggatgttac gcaaagaaat aaggaagaag gatacaccca cattgtagaa  180
gtcacttttg aatcagtgga aaccatacaa ggttatatca ttcaccctgc acatgttggg  240
ttcggtgatg tctacagatc attttgggaa gaattattga tctttgatta cactccaagg  300
aag                                                                303

SEQ ID NO: 140         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 140
MAVKHLIVVK FKDGITEAQK EEFFKTYVNL VNDIPAMKDV YWGKDVTQRN KEEGYTHIVE  60
VTFESVETIQ GYIIHPAHVG FGDVYRSFWE ELLIFDYTPR K                      101

SEQ ID NO: 141         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 141
atggccgtca agcatttaat cgtcgtcaaa tttaaggacg gtatcacaga agctcaaaag  60
gaggaattct tcaaaaccta tgtaaactta gtgaacataa ttcctgctat gaaagacgtt  120
tattggggta aggatgttac gcaaagaaat aaggaagaag gatacaccca cattgtagaa  180
gtcacttttg attcagtgga aaccatacaa ggttatatca ttcaccctgc acatgttggg  240
ttcggtgatg tctacagatc attttgggaa gaattattga tctttgatta cactccaagg  300
aag                                                                303

SEQ ID NO: 142         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 142
MAVKHLIVVK FKDGITEAQK EEFFKTYVNL VNIIPAMKDV YWGKDVTQRN KEEGYTHIVE  60
VTFDSVETIQ GYIIHPAHVG FGDVYRSFWE ELLIFDYTPR K                      101

SEQ ID NO: 143         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 143
atggccgtca agcatttaat cgtcgtcaaa tttaaggacg gtatcacaga agctcaaaag  60
gaggaattct tcaaaaccta tgtaaactta gtgaacataa ttcctgctat gaaagacgtt  120
tattggggta aggatgttac gcaaagaaat aaggaatcgg gatacaccca cattgtagaa  180
gtcacttttg aatcagtgga aaccatacaa ggttatatca tacaccctgc acatgttggg  240
ttcggtgatg tctacagatc attttgggaa gaattattga tctttgatta cactccaagg  300
aag                                                                303

SEQ ID NO: 144         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 144
MAVKHLIVVK FKDGITEAQK EEFFKTYVNL VNIIPAMKDV YWGKDVTQRN KESGYTHIVE  60
VTFESVETIQ GYIIHPAHVG FGDVYRSFWE ELLIFDYTPR K                      101

SEQ ID NO: 145         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 145
atggccgtca agcatttaat cgtcgtcaaa tttaaggacg gtatcacaga agctcaaaag  60
```

```
gaggaattct tcaaaaccta tgtaaactta gtgaacataa ttcctgctat gaaagacgtt  120
tattggggta aggatgttac gcaaagaaat aaggaacggg gatacaccca cattgtagaa  180
gtcacttttg aatcagtgga aaccatacaa ggttatatca tacaccctgc acatgttggg  240
ttcggtgata tctacagatc attttgggaa gaattattga tctttgatta cactccaagg  300
aag                                                                303

SEQ ID NO: 146          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 146
MAVKHLIVVK FKDGITEAQK EEFFKTYVNL VNIIPAMKDV YWGKDVTQRN KERGYTHIVE  60
VTFESVETIQ GYIIHPAHVG FGDIYRSFWE ELLIFDYTPR K                      101

SEQ ID NO: 147          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 147
atggccgtca agcatttaat cgtcgtcaaa tttaaggacg gtatcacaga agctcaaaag  60
gaggaattct tcaaaaccta tgtaaactta gtgaacataa ttcctgctat gaaagacgtt  120
tattggggta aggatgttac gcaaagaaat aaggaacgtg gatacaccca cattgtagaa  180
gtcacttttg aatcagtgga aaccatacaa ggttatatca ttcaccctgc acatgttggg  240
ttcggtgatg tctacagatc attttgggaa gaattattga tctttgatta cactccaagg  300
aag                                                                303

SEQ ID NO: 148          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 148
MAVKHLIVVK FKDGITEAQK EEFFKTYVNL VNIIPAMKDV YWGKDVTQRN KERGYTHIVE  60
VTFESVETIQ GYIIHPAHVG FGDVYRSFWE ELLIFDYTPR K                      101

SEQ ID NO: 149          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 149
atggccgtca agcatttaat cgtcgtcaaa tttaaggacg gtatcacaga agctcaaaag  60
gaggaattct tcaaaaccta tgtaaactta gtgaacataa ttcctgctat gaaagacgtt  120
tattggggta aggatgttac gcaaagaaat aaggaactgg gatacaccca cattgtagaa  180
gtcacttttg aatcagtgga aaccatacaa ggttatatca tacacccggc ccatgtggga  240
ttcggtgatg tctacagatc attttgggaa gaattattga tctttgatta cactccaagg  300
aag                                                                303

SEQ ID NO: 150          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 150
MAVKHLIVVK FKDGITEAQK EEFFKTYVNL VNIIPAMKDV YWGKDVTQRN KELGYTHIVE  60
VTFESVETIQ GYIIHPAHVG FGDVYRSFWE ELLIFDYTPR K                      101

SEQ ID NO: 151          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 151
atggccgtca agcatttaat cgtcgtcaaa tttaaggacg gtatcacaga agctcaaaag  60
gaggaattct tcaaaaccta tgtaaactta gtgaacataa ttcctgctat gaaagacgtt  120
```

-continued

```
tattggggta aggatgttac gcaaagaaat aaggaacatg gatacaccca cattgtagaa  180
gtcacttttg aatcagtgga aaccatacaa ggttatatca ttcaccctgc acatgttggg  240
ttcggtgatg tctacagatc attttgggaa gaattattga tctttgatta cactccaagg  300
aag                                                                303

SEQ ID NO: 152         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 152
MAVKHLIVVK FKDGITEAQK EEFFKTYVNL VNIIPAMKDV YWGKDVTQRN KEHGYTHIVE  60
VTFESVETIQ GYIIHPAHVG FGDVYRSFWE ELLIFDYTPR K                      101

SEQ ID NO: 153         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 153
atggccgtca agcatttaat cgtcgtcaaa tttaaggacg gtatcacaga agctcaaaag  60
gaggaattct tcaaaaccta tgtaaactta gtgaacataa ttcctgctat gaaagacgtt  120
tattggggta aggatgttac gcaaagaaat aaggaatttg gatacaccca cattgtagaa  180
gtcacttttg aatcagtgga aaccatacaa ggttatatca tacaccctgc acatgttggg  240
ttcggtgatg tctacagatc attttgggaa gaattattga tctttgatta cactccaagg  300
aag                                                                303

SEQ ID NO: 154         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 154
MAVKHLIVVK FKDGITEAQK EEFFKTYVNL VNIIPAMKDV YWGKDVTQRN KEFGYTHIVE  60
VTFESVETIQ GYIIHPAHVG FGDVYRSFWE ELLIFDYTPR K                      101

SEQ ID NO: 155         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 155
atggccgtca agcatttaat cgtcgtcaaa tttaaggacg gtatcacaga agctcaaaag  60
gaggaattct tcaaaaccta tgtaaactta gtgaacataa ttcctgctat gaaagacgtt  120
tattggggta aggatgttac gcaaagaaat aaggaagcgg gatacaccca cattgtagaa  180
gtcacttttg aatcagtgga aaccatacaa ggttatatca ttcaccctgc acatgttggg  240
ttcggtgatg tctacagatc attttgggaa gaattattga tctttgatta cactccaagg  300
aag                                                                303

SEQ ID NO: 156         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 156
MAVKHLIVVK FKDGITEAQK EEFFKTYVNL VNIIPAMKDV YWGKDVTQRN KEAGYTHIVE  60
VTFESVETIQ GYIIHPAHVG FGDVYRSFWE ELLIFDYTPR K                      101

SEQ ID NO: 157         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 157
atggccgtca agcatttaat cgtcgtcaaa tttaaggacg gtatcacaga agctcaaaag  60
gaggaattct tcaaaaccta tgtaaactta gtgaacataa ttcctgctat gaaagacgtt  120
tattggggta aggatgttac gcaaagaaat aagagggaag gatacaccca cattgtagaa  180
```

-continued

```
gtcacttttg aatcagtgga aaccatacaa ggttatatca ttcaccctgc acatgttggg  240
ttcggtgatg tctacagatc attttgggaa gaattattga tctttgatta cactccaagg  300
aag                                                                303

SEQ ID NO: 158         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 158
MAVKHLIVVK FKDGITEAQK EEFFKTYVNL VNIIPAMKDV YWGKDVTQRN KREGYTHIVE  60
VTFESVETIQ GYIIHPAHVG FGDVYRSFWE ELLIFDYTPR K                      101

SEQ ID NO: 159         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 159
atggccgtca agcatttaat cgtcgtcaaa tttaaggacg gtatcacaga agctcaaaag  60
gaggaattct tcaaaaccta tgtaaactta gtgaacataa ttcctgctat gaaagacgtt  120
tattggggta aggatgttac gcaaagaaat aagcaggaag gatacaccca cattgtagaa  180
gtcacttttg aatcagtgga aaccatacaa ggttatatca ttcaccctgc acatgttggg  240
ttcggtgatg tctacagatc attttgggaa gaattattga tctttgatta cactccaagg  300
aag                                                                303

SEQ ID NO: 160         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 160
MAVKHLIVVK FKDGITEAQK EEFFKTYVNL VNIIPAMKDV YWGKDVTQRN KQEGYTHIVE  60
VTFESVETIQ GYIIHPAHVG FGDVYRSFWE ELLIFDYTPR K                      101

SEQ ID NO: 161         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 161
atggccgtca agcatttaat cgtcgtcaaa tttaaggacg gtatcacaga agctcaaaag  60
gaggaattct tcaaaaccta tgtaaactta gtgaacataa ttcctgctat gaaagacgtt  120
tattggggta aggtggttac gcaaagaaat aaggaagaag gatacaccca cattgtagaa  180
gtcacttttg aatcagtgga aaccatacaa ggttatatca ttcaccctgc acatgttggg  240
ttcggtgatg tctacagatc attttgggaa gaattattga tctttgatta cactccaagg  300
aag                                                                303

SEQ ID NO: 162         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 162
MAVKHLIVVK FKDGITEAQK EEFFKTYVNL VNIIPAMKDV YWGKVVTQRN KEEGYTHIVE  60
VTFESVETIQ GYIIHPAHVG FGDVYRSFWE ELLIFDYTPR K                      101

SEQ ID NO: 163         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 163
atgggcgtca agcatttaat cgtcgtcaaa tttaaggacg gtatcacaga agctcaaaag  60
gaggaattct tcaaaaccta tgtaaactta gtgaacataa ttcctgctat gaaagacgtt  120
tattggggta aggatgttac gcaaagaaat aaggaagaag gatacaccca cattgtagaa  180
gtcacttttg aatcagtgga aaccatacaa ggttatatca atcaccctgc acatgttggg  240
```

```
ttcggtgatg tctacagatc attttgggaa gaattattga tctttgatta cactccaagg  300
aag                                                                303

SEQ ID NO: 164         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 164
MGVKHLIVVK FKDGITEAQK EEFFKTYVNL VNIIPAMKDV YWGKDVTQRN KEEGYTHIVE  60
VTFESVETIQ GYINHPAHVG FGDVYRSFWE ELLIFDYTPR K                      101

SEQ ID NO: 165         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 165
atggccgtca agcatttaat cgtcgtcaaa tttaaggacg gtatcacaga agctcaaaag  60
gaggaattct tcaaaaccta tgtaaactta gtgaacataa ttcctgctat gaaagacgtt  120
tattggggta aggatgttac gcaaagaaat aaggaatcgg gatacaccca cattgtagaa  180
gtcacttttg aatcagtgga aaccatacaa ggttatatca ttcaccctgc acatgttaag  240
ttcggtgatg tctacagatc attttgggaa gaattattga tctttgatta cactccaagg  300
aag                                                                303

SEQ ID NO: 166         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 166
MAVKHLIVVK FKDGITEAQK EEFFKTYVNL VNIIPAMKDV YWGKDVTQRN KESGYTHIVE  60
VTFESVETIQ GYIIHPAHVK FGDVYRSFWE ELLIFDYTPR K                      101

SEQ ID NO: 167         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 167
atggccgtca agcatttaat cgtcgtcaaa tttaaggacg gtatcacaga agctcaaaag  60
gaggaattct tcaaaaccta tgtaaactta gtgaacataa ttcctgctat gaaagacgtt  120
tattggggta aggatgttac gcaaagaaat aaggaatcgg gatacaccca cattgtagaa  180
gtcacttttg aatcagtgga acatatacaa ggttatatca tacaccctgc acatgttggg  240
ttcggtgatg tctacagatc attttgggaa gaattattga tctttgatta cactccaagg  300
aag                                                                303

SEQ ID NO: 168         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 168
MAVKHLIVVK FKDGITEAQK EEFFKTYVNL VNIIPAMKDV YWGKDVTQRN KESGYTHIVE  60
VTFESVEHIQ GYIIHPAHVG FGDVYRSFWE ELLIFDYTPR K                      101

SEQ ID NO: 169         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 169
atggccgtca agcatttaat cgtcgtcaaa tttaaggacg gtatcacaga agctcaaaag  60
gaggaattct tcaaaaccta tgtaaactta gtgaacataa ttcctgctat gaaagacgtt  120
tattggggta aggatgttac gcaaagaaat aaggaatcgg gatacaccca cattgtagaa  180
gtcacttttg aatcagtgga aaccatacaa ggttatatct ctcaccctgc acatgttggg  240
ttcggtgatg tctacagatc attttgggaa gaattattga tctttgatta cactccaagg  300
```

```
aag                                                            303

SEQ ID NO: 170         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 170
MAVKHLIVVK FKDGITEAQK EEFFKTYVNL VNIIPAMKDV YWGKDVTQRN KESGYTHIVE  60
VTFESVETIQ GYISHPAHVG FGDVYRSFWE ELLIFDYTPR K                     101

SEQ ID NO: 171         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 171
atggccgtca agcatttaat cgtcgtcaaa tttaaggacg gtatcacaga agctcaaaag  60
gaggaattct tcgataccta tgtaaactta gtgaacataa ttcctgctat gaaagacgtt  120
tattggggta aggatgttac gcaaagaaat aaggaatcgg gatacaccca cattgtagaa  180
gtcacttttg aatcagtgga aaccatacaa ggttatatca tacaccctgc acatgttggg  240
ttcggtgatg tctacagatc attttgggaa gaattattga tctttgatta cactccaagg  300
aag                                                            303

SEQ ID NO: 172         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 172
MAVKHLIVVK FKDGITEAQK EEFFDTYVNL VNIIPAMKDV YWGKDVTQRN KESGYTHIVE  60
VTFESVETIQ GYIIHPAHVG FGDVYRSFWE ELLIFDYTPR K                     101

SEQ ID NO: 173         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 173
atggccgtca agcatttaat cgtcgtcaaa tttaaggacg gtatcacaga agctcaaaag  60
gaggaattct tcaaaaccta tgtaaactta gtgaacataa ttcctgctat gaaagacgtt  120
tattggggta aggatgttac gcaaagaaat aaggaatcgg gatacaccca cattgtagaa  180
gtcacttttg aatcagtgga aaccatacaa ggttatatca tacaccctgc acatgttggg  240
ttcggtgatg tctacagaca tttttgggaa gaattattga tctttgatta cactccaagg  300
aag                                                            303

SEQ ID NO: 174         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 174
MAVKHLIVVK FKDGITEAQK EEFFKTYVNL VNIIPAMKDV YWGKDVTQRN KESGYTHIVE  60
VTFESVETIQ GYIIHPAHVG FGDVYRHFWE ELLIFDYTPR K                     101

SEQ ID NO: 175         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 175
atggccgtca agcatttaat cgtcgtcaaa tttaaggacg gtatcacaga agctcaaaag  60
gaggaattct tcaaaaccta tgtaaactta gtgaacataa ttcctgctat gaaagacgtt  120
tattggggta aggatgttac gcaaagaaat aaggaatcgg gatacaccca cattgtagaa  180
gtcacttttg aatcagtgga atgtatacaa ggttatatca tacaccctgc acatgttggg  240
ttcggtgatg tctacagatc attttgggaa gaattattga tctttgatta cactccaagg  300
aag                                                            303
```

```
SEQ ID NO: 176         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 176
MAVKHLIVVK FKDGITEAQK EEFFKTYVNL VNIIPAMKDV YWGKDVTQRN KESGYTHIVE  60
VTFESVECIQ GYIIHPAHVG FGDVYRSFWE ELLIFDYTPR K                     101

SEQ ID NO: 177         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 177
atggccgtca agcatttaat cgtcgtcaaa tttaaggacg gtatcacaga agctcaaaag  60
gaggaattct tcaaaaccta tgtaaactta gtgaacataa ttcctgctat gaaagacgtt  120
tattggggta aggatgttac gcaaagaaat aaggaatcgg gatacaccca cattgtagaa  180
gtcacttttg aatcagtgga aaccatacaa ggttatatca tacaccctgc acatgttggg  240
ttcggtgatg tctacagatc atattgggaa gaattattga tctttgatta cactccaagg  300
aag                                                               303

SEQ ID NO: 178         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 178
MAVKHLIVVK FKDGITEAQK EEFFKTYVNL VNIIPAMKDV YWGKDVTQRN KESGYTHIVE  60
VTFESVETIQ GYIIHPAHVG FGDVYRSYWE ELLIFDYTPR K                     101

SEQ ID NO: 179         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 179
atggccgtca agcatttaat cgtcgtcaaa tttaaggacg gtatcacaga agctcaaaag  60
gaggaattct tcaaaaccta tgtaaactta gtgaacataa ttcctgctat gaaagacgtt  120
tattggggta aggatgttac gcaaagaaat aaggaatcgg gatacaccca cattgtagaa  180
gtcacttttg aatcagtgga aaccatacaa ggttatatca agcaccctgc acatgttggg  240
ttcggtgatg tctacagatc attttgggaa gaattattga tctttgatta cactccaagg  300
aag                                                               303

SEQ ID NO: 180         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 180
MAVKHLIVVK FKDGITEAQK EEFFKTYVNL VNIIPAMKDV YWGKDVTQRN KESGYTHIVE  60
VTFESVETIQ GYIKHPAHVG FGDVYRSFWE ELLIFDYTPR K                     101

SEQ ID NO: 181         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 181
atggccgtca agcatttaat cgtcgtcaaa tttaaggacg gtatcacaga agctcaaaag  60
gaggaattct tcaaaaccta tgtaaactta gtgaacataa ttcctgctat gaaagacgtt  120
cagtggggta aggatgttac gcaaagaaat aaggaatcgg gatacaccca cattgtagaa  180
gtcacttttg aatcagtgga aaccatacaa ggttatatca tacaccctgc acatgttggg  240
ttcggtgatg tctacagatc attttgggaa gaattattga tctttgatta cactccaagg  300
aag                                                               303
```

-continued

```
SEQ ID NO: 182         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 182
MAVKHLIVVK FKDGITEAQK EEFFKTYVNL VNIIPAMKDV QWGKDVTQRN KESGYTHIVE  60
VTFESVETIQ GYIIHPAHVG FGDVYRSFWE ELLIFDYTPR K                     101

SEQ ID NO: 183         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 183
atggccgtca agcatttaat cgtcgtcaaa tttaaggacg gtatcacaga agctcaaaag  60
gaggaattct tcaaaaccta tgtaaactta gtgaacataa ttcctgctat gaaagacgtt  120
acgtggggta aggatgttac gcaaagaaat aaggaatcgg gatacaccca cattgtagaa  180
gtcacttttg aatcagtgga aaccatacaa ggttatatca tacaccctgc acatgttggg  240
ttcggtgatg tctacagatc attttgggaa gaattattga tctttgatta cactccaagg  300
aag                                                                303

SEQ ID NO: 184         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 184
MAVKHLIVVK FKDGITEAQK EEFFKTYVNL VNIIPAMKDV TWGKDVTQRN KESGYTHIVE  60
VTFESVETIQ GYIIHPAHVG FGDVYRSFWE ELLIFDYTPR K                     101

SEQ ID NO: 185         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 185
atggccgtca agcatttaat cgtcgtcaaa tttaaggacg gtatcacaga agctcaaaag  60
gaggaattct tcaaaaccta tgtaaactta gtgaacataa ttcctgctat gaaagacgtt  120
tattggggta aggatgttac gcaaagaaat aaggaatcgg gatacaccca cattgtagaa  180
gtcacttttg aatcagtgga agggatacaa ggttatatca tacaccctgc acatgttggg  240
ttcggtgatg tctacagatc attttgggaa gaattattga tctttgatta cactccaagg  300
aag                                                                303

SEQ ID NO: 186         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 186
MAVKHLIVVK FKDGITEAQK EEFFKTYVNL VNIIPAMKDV YWGKDVTQRN KESGYTHIVE  60
VTFESVEGIQ GYIIHPAHVG FGDVYRSFWE ELLIFDYTPR K                     101

SEQ ID NO: 187         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 187
atggccgtca agcatttaat cgtcgtcaaa tttaaggacg gtatcacaga agctcaaaag  60
gaggaattct tcaaaaccta tgtaaactta gtgaacataa ttcctgctat gaaagacgtt  120
tattggggta aggatgttac gcaaagaaat aaggaatcgg gatacaccca cattgtagaa  180
gtcacttttg aatcagtgga aaccatacaa ggttatatca ttcaccctgc acatgttggg  240
ttcggtaggg tctacagatc attttgggaa gaattattga tctttgatta cactccaagg  300
aag                                                                303

SEQ ID NO: 188         moltype = AA  length = 101
```

```
FEATURE                Location/Qualifiers
REGION                 1..101
                       note = Synthetic biopolymer
source                 1..101
                       mol_type = protein
                       organism = synthetic construct
SEQUENCE: 188
MAVKHLIVVK FKDGITEAQK EEFFKTYVNL VNIIPAMKDV YWGKDVTQRN KESGYTHIVE  60
VTFESVETIQ GYIIHPAHVG FGRVYRSFWE ELLIFDYTPR K                     101

SEQ ID NO: 189         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 189
atggccgtca agcatttaat cgtcgtcaaa tttaaggacg gtatcacaga agctcaaaag  60
gaggaattct tcaaaaccta tgtaaactta gtgaacataa ttcctgctat gaaagacgtt  120
tcttggggta aggatgttac gcaaagaaat aaggaatcgg gatacaccca cattgtagaa  180
gtcacttttg aatcagtgga aaccatacaa ggttatatca tacaccctgc acatgttggg  240
ttcggtgatg tctacagatc attttgggaa gaattattga tctttgatta cactccaagg  300
aag                                                               303

SEQ ID NO: 190         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 190
MAVKHLIVVK FKDGITEAQK EEFFKTYVNL VNIIPAMKDV SWGKDVTQRN KESGYTHIVE  60
VTFESVETIQ GYIIHPAHVG FGDVYRSFWE ELLIFDYTPR K                     101

SEQ ID NO: 191         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 191
atggccgtca agcatttaat cgtcgtcaaa tttaaggacg gtatcacaga agctcaaaag  60
ttggaattct tcaaaaccta tgtaaactta gtgaacataa ttcctgctat gaaagacgtt  120
tattggggta aggatgttac gcaaagaaat aaggaagaag gatacaccca cattgtagaa  180
gtcacttttg aatcagtgga aaccatacaa ggttatatca ttcaccctgc acatgttggg  240
ttcggtgatg tctacagatc attttgggaa gaattattga tctttgatta cactccaagg  300
aag                                                               303

SEQ ID NO: 192         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 192
MAVKHLIVVK FKDGITEAQK LEFFKTYVNL VNIIPAMKDV YWGKDVTQRN KEEGYTHIVE  60
VTFESVETIQ GYIIHPAHVG FGDVYRSFWE ELLIFDYTPR K                     101

SEQ ID NO: 193         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 193
atggccgtca agcatttaat cgtcgtcaaa tttaaggacg gtatcacaga agctcaaaag  60
gaggaattct tcaaaaccta tgtaaactta gtgaacataa ttcctgctat gaaagacgtt  120
tattggggta aggatgttac gcaaagaaat aagtcggaag gatacaccca cattgtagaa  180
gtcacttttg aatcagtgga aaccatacaa ggttatatca ttcaccctgc acatgttggg  240
ttcggtgatg tctacagatc attttgggaa gaattattga tctttgatta cactccaagg  300
aag                                                               303

SEQ ID NO: 194         moltype = AA  length = 101
FEATURE                Location/Qualifiers
```

```
REGION                 1..101
                       note = Synthetic biopolymer
source                 1..101
                       mol_type = protein
                       organism = synthetic construct
SEQUENCE: 194
MAVKHLIVVK FKDGITEAQK EEFFKTYVNL VNIIPAMKDV YWGKDVTQRN KSEGYTHIVE  60
VTFESVETIQ GYIIHPAHVG FGDVYRSFWE ELLIFDYTPR K                      101

SEQ ID NO: 195         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 195
atggccgtca agcatttaat cgtcgtcaaa tttaaggacg gtatcacaga agctcaaaag  60
gaggaattct tcaaaaccta tgtaaactta gtgaacataa ttcctgctat gaaagacgtt  120
tattggggta aggatgttac gcaaagaaat aaggaagaag gatacaccca cattgtagaa  180
gtcacttttg aatcagtgga aaccatacaa ggttatatca ttcaccctgc acatgttggg  240
ttcggtaagg tctacagatc attttgggaa gaattattga tctttgatta cactccaagg  300
aag                                                                303

SEQ ID NO: 196         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 196
MAVKHLIVVK FKDGITEAQK EEFFKTYVNL VNIIPAMKDV YWGKDVTQRN KEEGYTHIVE  60
VTFESVETIQ GYIIHPAHVG FGKVYRSFWE ELLIFDYTPR K                      101

SEQ ID NO: 197         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 197
atggccgtca agcatttaat cgtcgtcaaa tttaaggacg gtatcacaga agctcaaaag  60
gaggaattct tcaaaaccta tgtaaactta gtgaacataa ttcctgctat gaaagacgtt  120
tattggggta aggatgttac gcaaagaaat aaggaagaag gatacaccca cattgtagaa  180
gtcacttttg aatcagtgga aaccatacaa ggttatatca ttcaccctgc acatgttggg  240
ttcggtgatg tctacagatc attttgggaa gaattattga tctttgatta cgttccaagg  300
aag                                                                303

SEQ ID NO: 198         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 198
MAVKHLIVVK FKDGITEAQK EEFFKTYVNL VNIIPAMKDV YWGKDVTQRN KEEGYTHIVE  60
VTFESVETIQ GYIIHPAHVG FGDVYRSFWE ELLIFDYVPR K                      101

SEQ ID NO: 199         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 199
atggccgtca agcatttaat cgtcgtcaaa tttaaggacg gtatcacaga agctcaaaag  60
gaggaattct tcaaaaccta tgtaaactta gtgaacataa ttcctgctat gaaagacgtt  120
tattggggta aggatgttac gcaaagaaat aaggaagaag gatacaccca cattgtagaa  180
gtcacttttg aatcagtgga aaccatacaa ggttatatca ggcaccctgc acatgttggg  240
ttcggtgatg tctacagatc attttgggaa gaattattga tctttgatta cactccaagg  300
aag                                                                303

SEQ ID NO: 200         moltype = AA  length = 101
FEATURE                Location/Qualifiers
REGION                 1..101
```

```
                        note = Synthetic biopolymer
source                  1..101
                        mol_type = protein
                        organism = synthetic construct
SEQUENCE: 200
MAVKHLIVVK FKDGITEAQK EEFFKTYVNL VNIIPAMKDV YWGKDVTQRN KEEGYTHIVE  60
VTFESVETIQ GYIRHPAHVG FGDVYRSFWE ELLIFDYTPR K                    101

SEQ ID NO: 201          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 201
atggtggtca agcatttaat cgtcgtcaaa tttaaggacg gtatcacaga agctcaaaag  60
gaggaattct tcaaaaccta tgtaaactta gtgaacataa ttcctgctat gaaagacgtt  120
tattggggta aggatgttac gcaaagaaat aaggaagaag gatacaccca cattgtagaa  180
gtcacttttg aatcagtgga aaccatacaa ggttatatca ttcaccctgc acatgttggg  240
ttcggtgatg tctacagatc attttgggaa gaattattga tctttgatta cactccaagg  300
aag                                                               303

SEQ ID NO: 202          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 202
MVVKHLIVVK FKDGITEAQK EEFFKTYVNL VNIIPAMKDV YWGKDVTQRN KEEGYTHIVE  60
VTFESVETIQ GYIIHPAHVG FGDVYRSFWE ELLIFDYTPR K                    101

SEQ ID NO: 203          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 203
atggccgtca agcatttaat cgtcgtcaaa tttaaggacg gtatcacaga agctcaaaag  60
gaggaattct tcaaaaccta tgtaaactta gtgaacataa ttcctgctat gaaagacgtt  120
tattggggta aggatgttac gcaaagaaat aaggaagaag gatacaccca cattgtagaa  180
gtcacttttg aatcagtgga atgtatacaa ggttatatca ttcaccctgc acatgttggg  240
ttcggtgatg tctacagatc attttgggaa gaattattga tctttgatta cactccaagg  300
aag                                                               303

SEQ ID NO: 204          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 204
MAVKHLIVVK FKDGITEAQK EEFFKTYVNL VNIIPAMKDV YWGKDVTQRN KEEGYTHIVE  60
VTFESVECIQ GYIIHPAHVG FGDVYRSFWE ELLIFDYTPR K                    101

SEQ ID NO: 205          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 205
atggccgtca agcatttaat cgtcgtcaaa tttaaggacg gtatcacaga agctcaaaag  60
gaggaattct tcaaaaccta tgtaaactta gtgaacataa ttcctgctat gaaagacgtt  120
tattggggta aggatgttac gcaaagaaat aaggaagaag gatacaccca cattgtagaa  180
gtcacttttg aatcagtgga aaccatacaa ggttatatca ttcaccctgc acatgttggg  240
ttcgctgatg tctacagatc attttgggaa gaattattga tctttgatta cactccaagg  300
aag                                                               303

SEQ ID NO: 206          moltype = AA  length = 101
FEATURE                 Location/Qualifiers
REGION                  1..101
                        note = Synthetic biopolymer
```

```
source                  1..101
                        mol_type = protein
                        organism = synthetic construct
SEQUENCE: 206
MAVKHLIVVK FKDGITEAQK EEFFKTYVNL VNIIPAMKDV YWGKDVTQRN KEEGYTHIVE  60
VTFESVETIQ GYIIHPAHVG FADVYRSFWE ELLIFDYTPR K                      101

SEQ ID NO: 207          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 207
atggccgtca agcatttaat cgtcgtcaaa tttaaggacg gtatcacaga agctcaaaag  60
gaggaattct tcaaaaccta tgtaaactta gtgaacataa ttcctgctat gaaagacgtt  120
tattggggta aggatgttac gcaaagaaat aaggaagaag gatacaccca cattgtagaa  180
gtcacttttg aatcagtgga agcgatacaa ggttatatca ttcaccctgc acatgttggg  240
ttcggtgatg tctacagatc attttgggaa gaattattga tctttgatta cactccaagg  300
aag                                                                303

SEQ ID NO: 208          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 208
MAVKHLIVVK FKDGITEAQK EEFFKTYVNL VNIIPAMKDV YWGKDVTQRN KEEGYTHIVE  60
VTFESVEAIQ GYIIHPAHVG FGDVYRSFWE ELLIFDYTPR K                      101

SEQ ID NO: 209          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 209
atggccgtca agcatttaat cgtcgtcaaa tttaaggacg gtatcacaga agctcaaaag  60
gaggaattct tcaaaaccta tgtaaactta gtgaacataa ttcctgctat gaaagacgtt  120
tattggggta aggatgtttc tcaaagaaat aaggaagaag gatacaccca cattgtagaa  180
gtcacttttg aatcagtgga aaccatacaa ggttatatcc agcaccctgc acatgttggg  240
ttcggtgatg tctacagatc attttgggaa gaattattga tctttgatta cactccaagg  300
aag                                                                303

SEQ ID NO: 210          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 210
MAVKHLIVVK FKDGITEAQK EEFFKTYVNL VNIIPAMKDV YWGKDVSQRN KEEGYTHIVE  60
VTFESVETIQ GYIQHPAHVG FGDVYRSFWE ELLIFDYTPR K                      101

SEQ ID NO: 211          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 211
atggccgtca agcatttaat cgtcgtcaaa tttaaggacg gtatcacaga agctcaaaag  60
gaggaattct tcaaaaccta tgtaaactta gtgaacataa ttcctgctat gaaagacgtt  120
tattggggta aggatgttgg gcaaagaaat aaggaagaag gatacaccca cattgtagaa  180
gtcacttttg aatcagtgga aaccatacaa ggttatatca ttcaccctgc acatgttggg  240
ttcggtgatg tctaccgttc attttgggaa gaattattga tctttgatta cactccaagg  300
aag                                                                303

SEQ ID NO: 212          moltype = AA  length = 101
FEATURE                 Location/Qualifiers
REGION                  1..101
                        note = Synthetic biopolymer
source                  1..101
```

```
                        mol_type = protein
                        organism = synthetic construct
SEQUENCE: 212
MAVKHLIVVK FKDGITEAQK EEFFKTYVNL VNIIPAMKDV YWGKDVGQRN KEEGYTHIVE  60
VTFESVETIQ GYIIHPAHVG FGDVYRSFWE ELLIFDYTPR K                      101

SEQ ID NO: 213          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 213
atggccgtca agcatttaat cgtcgtcaaa tttaaggacg gtatcacaga agctcaaaag  60
gaggaattct tcaaaaccta tgtaaactta gtgaacataa ttcctgctat gaaagacgtt  120
tattggggta aggatgttac gcaaagaaat aaggaagaag gatacaccca cattgtagaa  180
gtcacttttg aatcagtgga aaccatacaa ggttatatca ttcaccctgc acatgttggg  240
ttcggtgatg tctacagatc atggtgggaa gaattattga tctttgatta cactccaagg  300
aag                                                                303

SEQ ID NO: 214          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 214
MAVKHLIVVK FKDGITEAQK EEFFKTYVNL VNIIPAMKDV YWGKDVTQRN KEEGYTHIVE  60
VTFESVETIQ GYIIHPAHVG FGDVYRSWWE ELLIFDYTPR K                      101

SEQ ID NO: 215          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 215
atggccgtca agcatttaat cgtcgtcaaa tttaaggacg gtatcacaga agctcaaaag  60
gaggaattct tcaaaaccta tgtaaactta gctaacataa ttcctgctat gaaagacgtt  120
tattggggta aggatgttac gcaaagaaat aaggaagaag gatacaccca cattgtagaa  180
gtcacttttg aatcagtgga aaccatacaa ggttatatca ttcaccctgc acatgttggg  240
ttcggtgatg tctacagatc attttgggaa gaattattga tctttgatta cactccaagg  300
aag                                                                303

SEQ ID NO: 216          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 216
MAVKHLIVVK FKDGITEAQK EEFFKTYVNL ANIIPAMKDV YWGKDVTQRN KEEGYTHIVE  60
VTFESVETIQ GYIIHPAHVG FGDVYRSFWE ELLIFDYTPR K                      101

SEQ ID NO: 217          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 217
atgtcggtca agcatttaat cgtcgtcaaa tttaaggacg gtatcacaga agctcaaaag  60
gaggaattct tcaaaaccta tgtaaactta gtgaacataa ttcctgctat gaaagacgtt  120
tattggggta aggatgttac gcaaagaaat aaggaagaag gatacaccca cattgtagaa  180
gtcacttttg aatcagtgga aaccatacaa ggttatatca ttcaccctgc acatgttggg  240
ttcggtgatg tctacagatc attttgggaa gaattattga tctttgatta cactccaagg  300
aag                                                                303

SEQ ID NO: 218          moltype = AA  length = 101
FEATURE                 Location/Qualifiers
REGION                  1..101
                        note = Synthetic biopolymer
source                  1..101
                        mol_type = protein
```

```
                         organism = synthetic construct
SEQUENCE: 218
MSVKHLIVVK FKDGITEAQK EEFFKTYVNL VNIIPAMKDV YWGKDVTQRN KEEGYTHIVE  60
VTFESVETIQ GYIIHPAHVG FGDVYRSFWE ELLIFDYTPR K                      101

SEQ ID NO: 219           moltype = DNA  length = 303
FEATURE                  Location/Qualifiers
misc_feature             1..303
                         note = Synthetic biopolymer
source                   1..303
                         mol_type = other DNA
                         organism = synthetic construct
SEQUENCE: 219
atggccgtca agcatttaat cgtcgtcaaa tttaaggacg gtatcacaga agagcaaaag  60
gaggaattct tcaaaaccta tgtaaactta gtgaacataa ttcctgctat gaaagacgtt  120
tattggggta aggatgttac gcaaagaaat aaggaagaag gatacaccca cattgtagaa  180
gtcacttttg aatcagtgga aaccatacaa ggttatatca ttcaccctgc acatgttggg  240
ttcggtgatg tctacagatc attttgggaa gaattattga tctttgatta cactccaagg  300
aag                                                                303

SEQ ID NO: 220           moltype = AA  length = 101
FEATURE                  Location/Qualifiers
REGION                   1..101
                         note = Synthetic biopolymer
source                   1..101
                         mol_type = protein
                         organism = synthetic construct
SEQUENCE: 220
MAVKHLIVVK FKDGITEEQK EEFFKTYVNL VNIIPAMKDV YWGKDVTQRN KEEGYTHIVE  60
VTFESVETIQ GYIIHPAHVG FGDVYRSFWE ELLIFDYTPR K                      101

SEQ ID NO: 221           moltype = DNA  length = 303
FEATURE                  Location/Qualifiers
misc_feature             1..303
                         note = Synthetic biopolymer
source                   1..303
                         mol_type = other DNA
                         organism = synthetic construct
SEQUENCE: 221
atggccgtca agcatttaat cgtcgtcaaa tttaaggacg gtatcacaga agctcaaaag  60
gaggaattct tcaaaaccta tgtaaactta gtgaacataa ttcctgctat gaaagacgtt  120
tattggggta aggatgttac gcaaagaaat aaggaagaag gatacaccca cattgtagaa  180
gtcacttttg aatcagtgga aaccatacaa ggttatatca ttcaccctgc acatgttggg  240
ttcggtgatg tctacagttc attttgggaa gaattattga tctttgatta cactccaagg  300
aag                                                                303

SEQ ID NO: 222           moltype = AA  length = 101
FEATURE                  Location/Qualifiers
REGION                   1..101
                         note = Synthetic biopolymer
source                   1..101
                         mol_type = protein
                         organism = synthetic construct
SEQUENCE: 222
MAVKHLIVVK FKDGITEAQK EEFFKTYVNL VNIIPAMKDV YWGKDVTQRN KEEGYTHIVE  60
VTFESVETIQ GYIIHPAHVG FGDVYSSFWE ELLIFDYTPR K                      101

SEQ ID NO: 223           moltype = DNA  length = 303
FEATURE                  Location/Qualifiers
misc_feature             1..303
                         note = Synthetic biopolymer
source                   1..303
                         mol_type = other DNA
                         organism = synthetic construct
SEQUENCE: 223
atggccgtca agcatttaat cgtcgtcaaa tttaaggacg gtatcacaga agctcaaaag  60
gaggaattct tcaaaaccta tgtaaactta gtgaacataa ttcctgctat gaaagacgtt  120
tattggggta aggatgttac gcaaagaaat aaggaagaag gatacaccca cattgtagaa  180
gtcacttttg aatcagtgga aaccatacaa ggttatatcc atcaccctgc acatgttggg  240
ttcggtgatg tctacagatc attttgggaa gaattattga tctttgatta cactccaagg  300
aag                                                                303

SEQ ID NO: 224           moltype = AA  length = 101
FEATURE                  Location/Qualifiers
REGION                   1..101
                         note = Synthetic biopolymer
source                   1..101
                         mol_type = protein
                         organism = synthetic construct
```

```
SEQUENCE: 224
MAVKHLIVVK FKDGITEAQK EEFFKTYVNL VNIIPAMKDV YWGKDVTQRN KEEGYTHIVE  60
VTFESVETIQ GYIIHPAHVG FGDVYRSFWE ELLIFDYTPR K                     101

SEQ ID NO: 225         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 225
atggccgtca agcatttaat cgtcgtcaaa tttaaggacg gtatcacaga agctcaaaag  60
gaggaattct tcaaaaccta tgtaaactta gtgaacataa ttcctgctat gaaagacgtt  120
tattggggta aggatgttac gcaaagaaat aaggaagaag gatacaccca cattgtagaa  180
gtcacttttg aatcagtgga aaccatacaa ggttatatcc agcaccctgc acatgttggg  240
ttcggtgatg tctacagatc attttgggaa gaattattga tctttgatta cactccaagg  300
aag                                                               303

SEQ ID NO: 226         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 226
MAVKHLIVVK FKDGITEAQK EEFFKTYVNL VNIIPAMKDV YWGKDVTQRN KEEGYTHIVE  60
VTFESVETIQ GYIQHPAHVG FGDVYRSFWE ELLIFDYTPR K                     101

SEQ ID NO: 227         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 227
atggccgtca agcatttaat cgtcgtcaaa tttaaggacg gtatcacaga agctcaaaag  60
gaggaattct tcaaaaccta tgtaaactta gtgaacataa ttcctgctat gaaagacgtt  120
tattggggta aggatgtttc tcaaagaaat aaggaagaag gatacaccca cattgtagaa  180
gtcacttttg aatcagtgga aaccatacaa ggttatatca ttcaccctgc acatgttggg  240
ttcggtgatg tctacagatc attttgggaa gaattattga tctttgatta cactccaagg  300
aag                                                               303

SEQ ID NO: 228         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 228
MAVKHLIVVK FKDGITEAQK EEFFKTYVNL VNIIPAMKDV YWGKDVSQRN KEEGYTHIVE  60
VTFESVETIQ GYIIHPAHVG FGDVYRSFWE ELLIFDYTPR K                     101

SEQ ID NO: 229         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 229
atggccgtca agcatttaat cgtcgtcaaa tttaaggacg gtatcacaga agctcaaaag  60
gaggaattct tcaaaaccta tgtaaactta gtgaacataa ttcctgctat gaaagacgtt  120
tattggggta aggatgttac gcaaagaaat aaggaagaag gatacaccca cattgtagaa  180
gtcacttttg aatcagtgga aaccatacaa ggttatatca atcaccctgc acatgttggg  240
ttcggtgatg tctacagatc attttgggaa gaattattga tctttgatta cactccaagg  300
aag                                                               303

SEQ ID NO: 230         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 230
```

-continued

```
MAVKHLIVVK FKDGITEAQK EEFFKTYVNL VNIIPAMKDV YWGKDVTQRN KEEGYTHIVE  60
VTFESVETIQ GYINHPAHVG FGDVYRSFWE ELLIFDYTPR K                      101

SEQ ID NO: 231          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 231
atggccgtca agcatttaat cgtcgtcaaa tttaaggacg gtatcacaga agctcaaaag  60
gaggaattct tcaaaaccta tgtaaactta gtgaacataa ttcctgctat gaaagacgtt  120
tattggggta aggatttgac gcaaagaaat aaggaatcgg gatacaccca cattgtagaa  180
gtcacttttg aatcagtgga aaccatacaa ggttatatca tacaccctgc acatgttggg  240
ttcggtgatg tctacagatc attttgggaa gaattattga tctttgatta cactccaagg  300
aag                                                                303

SEQ ID NO: 232          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 232
MAVKHLIVVK FKDGITEAQK EEFFKTYVNL VNIIPAMKDV YWGKDLTQRN KESGYTHIVE  60
VTFESVETIQ GYIIHPAHVG FGDVYRSFWE ELLIFDYTPR K                      101

SEQ ID NO: 233          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 233
atgggtgtca agcaccttat cgtaattaaa ttcaaggacg aaattacaga agcccagaaa  60
gaagaatttt tcagaaccta tgtaaacctg gtgaatatca tccctgcgat gaaagatgtt  120
tattggggca aagacgtcac ccaaaaaaac aaagaagaag gttacactca catcgtcgaa  180
gtcactttcg agtcagtaga gacgatccaa gattacataa tacacccggc ccatgtggga  240
ttcggagacg tttaccgtag cttctgggaa aaacttttga ttttcgacta taccccgaga  300
aaa                                                                303

SEQ ID NO: 234          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 234
MGVKHLIVIK FKDEITEAQK EEFFRTYVNL VNIIPAMKDV YWGKDVTQKN KEEGYTHIVE  60
VTFESVETIQ DYIIHPAHVG FGDVYRSFWE KLLIFDYTPR K                      101

SEQ ID NO: 235          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 235
atggctgtca agcaccttat cgtaattaaa ttcaaggacg aaattacaga agcccagaaa  60
gaagaatttt tcaagaccta tgtaaacctg gtgaatatca tccctgcgat gaaagatgtt  120
tattggggca aagacgtcac ccaaaaaaac aaagaatctg gttacactca catcgtcgaa  180
gtcactttcg agtcagtaga gacgatccaa gattacataa tacacccggc ccatgtggga  240
ttcggagacg tttaccgtag cttctgggaa aaacttttga aattcgacta taccccgaga  300
aaa                                                                303

SEQ ID NO: 236          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 236
MAVKHLIVIK FKDEITEAQK EEFFKTYVNL VNIIPAMKDV YWGKDVTQKN KESGYTHIVE  60
```

```
VTFESVETIQ DYIIHPAHVG FGDVYRSFWE KLLKFDYTPR K                 101

SEQ ID NO: 237         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 237
atggctgtca agcaccttat cgtactgaaa ttcaaggacg aaattacaga agcccagaaa  60
gaagaatttt tcaagaccta tgtaaacctg gtgaatatca tccctgaaat gaaagatgtt  120
tattggggca aagacgtcac ccaaaaaaac aaagaagaag gttacactca catcgtcgaa  180
gtcactttcg agtcagtaga gacgatccaa gattacataa tacacccggc ccatgtggga  240
ttcggagacg tttaccgtag cttctgggaa aaacttttga ttttcgacta taccccgaga  300
aaa                                                                303

SEQ ID NO: 238         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 238
MAVKHLIVLK FKDEITEAQK EEFFKTYVNL VNIIPEMKDV YWGKDVTQKN KEEGYTHIVE  60
VTFESVETIQ DYIIHPAHVG FGDVYRSFWE KLLIFDYTPR K                 101

SEQ ID NO: 239         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 239
atggctgtca agcaccttat cgtactgaaa ttcaaggacg aaattacaga agcccagaaa  60
gaagaatttt tcaagaccta tgtaaacctg gtgaatatca tccctgcgat gaaagatgtt  120
tattggggca aagacgtcac ccaaaaaaac aaagaacatg gttacactca catcgtcgaa  180
gtcactttcg attcagtaga gacgatccaa gattacataa tacacccggc ccatgtggga  240
ttcggagacg tttaccgtag cttctgggaa aaacttttga ttttcgacta taccccgaga  300
aaa                                                                303

SEQ ID NO: 240         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 240
MAVKHLIVLK FKDEITEAQK EEFFKTYVNL VNIIPAMKDV YWGKDVTQKN KEHGYTHIVE  60
VTFDSVETIQ DYIIHPAHVG FGDVYRSFWE KLLIFDYTPR K                 101

SEQ ID NO: 241         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 241
atggctgtca agcaccttat cgtaattaaa ttcaaggacg aaattacaga agcccagaaa  60
gaagaatttt tcagaaccta tgtaaacctg gtgaatatca tccctgaaat gaaagatgtt  120
tattggggca aagacgtcac ccaaaaaaac aaagaacatg gttacactca catcgtcgaa  180
gtcactttcg agtcagtaga gacgatccaa gattacataa tacacccggc ccatgtggga  240
ttcggagacg tttaccgtag cttctgggaa aaacttttga aattcgacta taccccgaga  300
aaa                                                                303

SEQ ID NO: 242         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 242
MAVKHLIVIK FKDEITEAQK EEFFRTYVNL VNIIPEMKDV YWGKDVTQKN KEHGYTHIVE  60
VTFESVETIQ DYIIHPAHVG FGDVYRSFWE KLLKFDYTPR K                 101
```

```
SEQ ID NO: 243         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 243
atgggtgtca agcaccttat cgtaattaaa ttcaaggacg aaattacaga agcccagaaa  60
gaagaatttt tcagaaccta tgtaaacctg gtgaatatca tccctgcgat gaaagatgtt  120
tattggggca aagacgtcac ccaaaaaaac aaagaatctg gttacactca catcgtcgaa  180
gtcactttcg attcagtaga gacgatccaa gattacataa tacacccggc ccatgtggga  240
ttcggagacg tttaccgtag cttctgggaa aaacttttga aattcgacta taccccgaga  300
aaa                                                                303

SEQ ID NO: 244         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 244
MGVKHLIVIK FKDEITEAQK EEFFRTYVNL VNIIPAMKDV YWGKDVTQKN KESGYTHIVE  60
VTFDSVETIQ DYIIHPAHVG FGDVYRSFWE KLLKFDYTPR K                     101

SEQ ID NO: 245         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 245
atggctgtca agcaccttat cgtactgaaa ttcaaggacg aaattacaga agcccagaaa  60
gaagaatttt tctctaccta tgtaaacctg gtgaatatca tccctgaaat gaaagatgtt  120
tattggggca aagacgtcac ccaaaaaaac aaagaagaag gttacactca catcgtcgaa  180
gtcactttcg agtcagtaga gacgatccaa gattacataa tacacccggc ccatgtggga  240
ttcggagacg tttaccgtag cttctgggaa aaacttttga ttttcgacta taccccgaga  300
aaa                                                                303

SEQ ID NO: 246         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 246
MAVKHLIVLK FKDEITEAQK EEFFSTYVNL VNIIPEMKDV YWGKDVTQKN KEEGYTHIVE  60
VTFESVETIQ DYIIHPAHVG FGDVYRSFWE KLLIFDYTPR K                     101

SEQ ID NO: 247         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 247
atggctgtca agcaccttat cgtaattaaa ttcaaggacg aaattcaaga agcccagaaa  60
gaagaatttt tcagaaccta tgtaaacctg gtgaatatca tccctgcgat gaaagatgtt  120
tattggggca aagacgtcac ccaaaaaaac aaagaatctg gttacactca catcgtcgaa  180
gtcactttcg attcagtaga gacgatccaa gattacataa tacacccggc ccatgtggga  240
ttcggagacg tttaccgtag cttctgggaa aaacttttga ttttcgacta taccccgaga  300
aaa                                                                303

SEQ ID NO: 248         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 248
MAVKHLIVIK FKDEIQEAQK EEFFRTYVNL VNIIPAMKDV YWGKDVTQKN KESGYTHIVE  60
VTFDSVETIQ DYIIHPAHVG FGDVYRSFWE KLLIFDYTPR K                     101
```

```
SEQ ID NO: 249         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 249
atggctgtca agcaccttat cgtactgaaa ttcaaggacg aaattacaga agcccagaaa  60
gaagaatttt tctctaccta tgtaaacctg gtgaatatca tccctgcgat gaaagatgtt  120
tattggggca aagacgtcac ccaaaaaaac aaagaagaag gttacactca catcgtcgaa  180
gtcactttcg agtcagtaga gacgatccaa gattacataa tacacccggc ccatgtggga  240
ttcggagacg tttaccgtag cttctgggaa aaacttttga aattcgacta taccccgaga  300
aaa                                                               303

SEQ ID NO: 250         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 250
MAVKHLIVLK FKDEITEAQK EEFFSTYVNL VNIIPAMKDV YWGKDVTQKN KEEGYTHIVE  60
VTFESVETIQ DYIIHPAHVG FGDVYRSFWE KLLKFDYTPR K                     101

SEQ ID NO: 251         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 251
atgggtgtca agcaccttat cgtaattaaa ttcaaggacg aaattacaga agcccagaaa  60
gaagaatttt tcggtaccta tgtaaacctg gtgaatatca tccctgcgat gaaagatgtt  120
tattggggca aagacgtcac ccaaaaaaac aaagaagaag gttacactca catcgtcgaa  180
gtcactttcg agtcagtaga gacgatccaa gattacataa tacacccggc ccatgtggga  240
ttcggagacg tttaccgtag cttctgggaa aaacttttga ttttcgacta taccccgaga  300
aaa                                                               303

SEQ ID NO: 252         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 252
MGVKHLIVIK FKDEITEAQK EEFFGTYVNL VNIIPAMKDV YWGKDVTQKN KEEGYTHIVE  60
VTFESVETIQ DYIIHPAHVG FGDVYRSFWE KLLIFDYTPR K                     101

SEQ ID NO: 253         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 253
atggctgtca agcaccttat cgtactgaaa ttcaaggacg aaattacaga agcccagaaa  60
gaagaatttt tcaagaccta tgtaaacctg gtgaatatca tccctgcgat gaaagatgtt  120
tattggggca aagacgtcac ccaaaaaaac aaagaagctg gttacactca catcgtcgaa  180
gtcactttcg agtcagtaga gacgatccaa gattacataa tacacccggc ccatgtggga  240
ttcggagacg tttaccgtag cttctgggaa aaacttttga ttttcgacta taccccgaga  300
aaa                                                               303

SEQ ID NO: 254         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 254
MAVKHLIVLK FKDEITEAQK EEFFKTYVNL VNIIPAMKDV YWGKDVTQKN KEAGYTHIVE  60
VTFESVETIQ DYIIHPAHVG FGDVYRSFWE KLLIFDYTPR K                     101

SEQ ID NO: 255         moltype = DNA  length = 303
```

-continued

```
FEATURE                 Location/Qualifiers
misc_feature            1..303
                        note = Synthetic biopolymer
source                  1..303
                        mol_type = other DNA
                        organism = synthetic construct
SEQUENCE: 255
atgggtgtca agcaccttat cgtagttaaa ttcaaggacg aaattccaga agcccagaaa  60
gaagaatttt tcaagaccta tgtaaacctg gtgaatatca tccctgcgat gaaagatgtt  120
tattggggca aagacgtcac ccaaaaaaac aaagaagaag gttacactca catcgtcgaa  180
gtcactttcg agtcagtaga gacgatccaa gattacataa tacacccggc ccatgtggga  240
ttcggagacg tttaccgtag cttctgggaa aaacttttga ttttcgacta taccccgaga  300
aaa                                                                303

SEQ ID NO: 256          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 256
MGVKHLIVVK FKDEIPEAQK EEFFKTYVNL VNIIPAMKDV YWGKDVTQKN KEEGYTHIVE  60
VTFESVETIQ DYIIHPAHVG FGDVYRSFWE KLLIFDYTPR K                      101

SEQ ID NO: 257          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 257
atggctgtca agcaccttat cgtactgaaa ttcaaggacg aaattacaga agcccagaaa  60
gaagaatttt tcaagaccta tgtaaacctg gtgaatatca tccctgcgat gaaagatgtt  120
tattggggca aagacgtcac ccaaaaaaac aaagaagctg gttacactca catcgtcgaa  180
gtcactttcg attcagtaga gacgatccaa gattacataa tacacccggc ccatgtggga  240
ttcggagacg tttaccgtag cttctgggaa aaacttttga aattcgacta taccccgaga  300
aaa                                                                303

SEQ ID NO: 258          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 258
MAVKHLIVLK FKDEITEAQK EEFFKTYVNL VNIIPAMKDV YWGKDVTQKN KEAGYTHIVE  60
VTFDSVETIQ DYIIHPAHVG FGDVYRSFWE KLLKFDYTPR K                      101

SEQ ID NO: 259          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 259
atggctgtca agcaccttat cgtaattaaa ttcaaggacg aaattacaga agcccagaaa  60
gaagaatttt tctctaccta tgtaaacctg gtgaatatca tccctgaaat gaaagatgtt  120
tattggggca aagacgtcac ccaaaaaaac aaagaagaag gttacactca catcgtcgaa  180
gtcactttcg attcagtaga gacgatccaa gattacataa tacacccggc ccatgtggga  240
ttcggagacg tttaccgtag cttctgggaa aaacttttga aattcgacta taccccgaga  300
aaa                                                                303

SEQ ID NO: 260          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 260
MAVKHLIVIK FKDEITEAQK EEFFSTYVNL VNIIPEMKDV YWGKDVTQKN KEEGYTHIVE  60
VTFDSVETIQ DYIIHPAHVG FGDVYRSFWE KLLKFDYTPR K                      101

SEQ ID NO: 261          moltype = DNA  length = 303
FEATURE                 Location/Qualifiers
```

-continued

```
misc_feature            1..303
                        note = Synthetic biopolymer
source                  1..303
                        mol_type = other DNA
                        organism = synthetic construct
SEQUENCE: 261
atggctgtca agcaccttat cgtaattaaa ttcaaggacg aaattacaga agcccagaaa  60
gaagaatttt tctctaccta tgtaaacctg gtgaatatca tccctgaaat gaaagatgtt  120
tattggggca aagacgtcac ccaaaaaaac aaagaaagag gttacactca catcgtcgaa  180
gtcactttcg agtcagtaga gacgatccaa gattacataa tacacccggc ccatgtggga  240
ttcggagacg tttaccgtag cttctgggaa aaacttttga aattcgacta taccccgaga  300
aaa                                                               303

SEQ ID NO: 262          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 262
MAVKHLIVIK FKDEITEAQK EEFFSTYVNL VNIIPEMKDV YWGKDVTQKN KERGYTHIVE  60
VTFESVETIQ DYIIHPAHVG FGDVYRSFWE KLLKFDYTPR K                     101

SEQ ID NO: 263          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 263
atggctgtca agcaccttat cgtactgaaa ttcaaggacg aaattacaga agcccagaaa  60
gaagaatttt tcgagaccta tgtaaacctg gtgaatatca tccctgaaat gaaagatgtt  120
tattggggca aagacgtcac ccaaaaaaac aaagaagaag gttacactca catcgtcgaa  180
gtcactttcg attcagtaga gacgatccaa gattacataa tacacccggc ccatgtggga  240
ttcggagacg tttaccgtag cttctgggaa aaacttttga aattcgacta taccccgaga  300
aaa                                                               303

SEQ ID NO: 264          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 264
MAVKHLIVLK FKDEITEAQK EEFFETYVNL VNIIPEMKDV YWGKDVTQKN KEEGYTHIVE  60
VTFDSVETIQ DYIIHPAHVG FGDVYRSFWE KLLKFDYTPR K                     101

SEQ ID NO: 265          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 265
atggctgtca agcaccttat cgtactgaaa ttcaaggacg aaattacaga agcccagaaa  60
gaagaatttt tcagaaccta tgtaaacctg gtgaatatca tccctgcgat gaaagatgtt  120
tattggggca aagacgtcac ccaaaaaaac aaagaagaag gttacactca catcgtcgaa  180
gtcactttcg attcagtaga gacgatccaa gattacataa tacacccggc ccatgtggga  240
ttcggagacg tttaccgtag cttctgggaa aaacttttga ttttcgacta taccccgaga  300
aaa                                                               303

SEQ ID NO: 266          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 266
MAVKHLIVLK FKDEITEAQK EEFFRTYVNL VNIIPAMKDV YWGKDVTQKN KEEGYTHIVE  60
VTFDSVETIQ DYIIHPAHVG FGDVYRSFWE KLLIFDYTPR K                     101

SEQ ID NO: 267          moltype = DNA  length = 303
FEATURE                 Location/Qualifiers
misc_feature            1..303
```

```
                        note = Synthetic biopolymer
source                  1..303
                        mol_type = other DNA
                        organism = synthetic construct
SEQUENCE: 267
atggctgtca agcaccttat cgtactgaaa ttcaaggacg aaattacaga agcccagaaa  60
gaagaatttt tcagaaccta tgtaaacctg gtgaatatca tccctgaaat gaaagatgtt  120
tattggggca aagacgtcac ccaaaaaaac aaagaatctg gttacactca catcgtcgaa  180
gtcactttcg attcagtaga gacgatccaa gattacataa tacacccggc ccatgtggga  240
ttcggagacg tttaccgtag cttctgggaa aaacttttga aattcgacta taccccgaga  300
aaa                                                                303

SEQ ID NO: 268          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 268
MAVKHLIVLK FKDEITEAQK EEFFRTYVNL VNIIPEMKDV YWGKDVTQKN KESGYTHIVE  60
VTFDSVETIQ DYIIHPAHVG FGDVYRSFWE KLLKFDYTPR K                      101

SEQ ID NO: 269          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 269
atgggtgtca agcaccttat cgtaattaaa ttcaaggacg aaattacaga agcccagaaa  60
gaagaatttt tcaagaccta tgtaaacctg gtgaatatca tccctgaaat gaaagatgtt  120
tattggggca aagacgtcac ccaaaaaaac aaagaatctg gttacactca catcgtcgaa  180
gtcactttcg attcagtaga gacgatccaa gattacataa tacacccggc ccatgtggga  240
ttcggagacg tttaccgtag cttctgggaa aaacttttga aattcgacta taccccgaga  300
aaa                                                                303

SEQ ID NO: 270          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 270
MGVKHLIVIK FKDEITEAQK EEFFKTYVNL VNIIPEMKDV YWGKDVTQKN KESGYTHIVE  60
VTFDSVETIQ DYIIHPAHVG FGDVYRSFWE KLLKFDYTPR K                      101

SEQ ID NO: 271          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 271
atgggtgtca agcaccttat cgtagttaaa ttcaaggacg aaattacaga agcccagaaa  60
gaagaatttt tcaagacctt tgtaaacctg gtgaatatca tccctgcgat gaaagatgtt  120
tattggggca aagacgtcac ccaaaaaaac aaaagagaag gttacactca catcgtcgaa  180
gtcactttcg agtcattgga gacgatccaa gattacataa tacacccggc ccatgtggga  240
ttcggagaca tgtaccgtag cttctgggaa aaacttttga ttttcgacta taccccgaga  300
aaa                                                                303

SEQ ID NO: 272          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 272
MGVKHLIVVK FKDEITEAQK EEFFKTFVNL VNIIPAMKDV YWGKDVTQKN KREGYTHIVE  60
VTFESLETIQ DYIIHPAHVG FGDMYRSFWE KLLIFDYTPR K                      101

SEQ ID NO: 273          moltype = DNA  length = 303
FEATURE                 Location/Qualifiers
misc_feature            1..303
                        note = Synthetic biopolymer
```

```
source                 1..303
                       mol_type = other DNA
                       organism = synthetic construct
SEQUENCE: 273
atggctgtca agcaccttat cgtagttaaa ttcaaggacg aaattacaga agcccagaaa  60
gaagaatttt tcaagaccta tgtaaacctg gtgaatatca tccctgcgat gaaagatgtt  120
tattggggca aagacgtcac ccaaaaaaac aaagaagaag gttacactca catcgtcgaa  180
gtcactttcg agtcattgga gacgatccaa gattacataa tacacccggc ccatgtggga  240
ttcggagacg tttaccgtag cttctgggaa aaacttttga ttttcgacta taccccgaga  300
aaa                                                                303

SEQ ID NO: 274         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 274
MAVKHLIVVK FKDEITEAQK EEFFKTYVNL VNIIPAMKDV YWGKDVTQKN KEEGYTHIVE  60
VTFESLETIQ DYIIHPAHVG FGDVYRSFWE KLLIFDYTPR K                     101

SEQ ID NO: 275         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 275
atggctgtca agcaccttat cgtagttaaa ttcaaggacg aaattacaga agcccagaaa  60
gaagaatttt tcaagacctt tgtaaacctg gtgaatatca tccctgcgat gaaagatgtt  120
tattggggca aagacgtcac ccaaaaaaac aaagaagaag gttacactca catcgtcgaa  180
gtcactttcg agtcagtaga gacgatccaa gattacataa tacacccggc ccatgtggga  240
ttcggagaca tgtaccgtag cttctgggaa aaacttttga ttttcgacta taccccgaga  300
aaa                                                                303

SEQ ID NO: 276         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 276
MAVKHLIVVK FKDEITEAQK EEFFKTFVNL VNIIPAMKDV YWGKDVTQKN KEEGYTHIVE  60
VTFESVETIQ DYIIHPAHVG FGDMYRSFWE KLLIFDYTPR K                     101

SEQ ID NO: 277         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 277
atgggtgtca agcaccttat cgtagttaaa ttcaaggacg aaattacaga agcccagaaa  60
gaagaatttt tcaagaccta tgtaaacctg gtgaatatca tccctgcgat gaaagatgtt  120
tattggggca aagacgtcac ccaaaaaaac aaagaagaag gttacactca catcgtcgaa  180
gtcactttcg agtcagtaga gacgatccaa gattacataa tacacccggc ccatgtggga  240
ttcggagacg tttaccgtag cttctgggaa aaacttttga ttttcgacta taccccgaga  300
aaa                                                                303

SEQ ID NO: 278         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 278
MGVKHLIVVK FKDEITEAQK EEFFKTYVNL VNIIPAMKDV YWGKDVTQKN KEEGYTHIVE  60
VTFESVETIQ DYIIHPAHVG FGDVYRSFWE KLLIFDYTPR K                     101

SEQ ID NO: 279         moltype = DNA  length = 303
FEATURE                Location/Qualifiers
misc_feature           1..303
                       note = Synthetic biopolymer
source                 1..303
```

```
                        mol_type = other DNA
                        organism = synthetic construct
SEQUENCE: 279
atggctgtca agcaccttat cgtaattaaa ttcaaggacg aaattacaga agcccagaaa  60
gaagaatttt tcaagacctt tgtaaacctg gtgaatatca tccctgcgat gaaagatgtt  120
tattggggca aagacgtcac ccaaaaaaac aaagaatcgg gatacactca catcgtcgaa  180
gtcactttcg agtcattgga gacgatccaa gattacataa tacacccggc ccatgtggga  240
ttcggagaca tgtaccgtag cttctgggaa aaacttttga ttttcgacta taccccgaga  300
aaa                                                                303

SEQ ID NO: 280          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 280
MAVKHLIVIK FKDEITEAQK EEFFKTFVNL VNIIPAMKDV YWGKDVTQKN KESGYTHIVE  60
VTFESLETIQ DYIIHPAHVG FGDMYRSFWE KLLIFDYTPR K                     101

SEQ ID NO: 281          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 281
atggctgtca agcaccttat cgtactgaaa ttcaaggacg aaattacaga agcccagaaa  60
gaagaatttt tcaagaccta tgtaaacctg gtgaatatca tccctgcgat gaaagatgtt  120
tattggggca aagacgtcac ccaaaaaaac aaagaagaag gttacactca catcgtcgaa  180
gtcactttcg agtcattgga gacgatccaa gattacataa tacacccggc ccatgtggga  240
ttcggagaca tgtaccgtag cttctgggaa aaacttttga ttttcgacta taccccgaga  300
aaa                                                                303

SEQ ID NO: 282          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 282
MAVKHLIVLK FKDEITEAQK EEFFKTYVNL VNIIPAMKDV YWGKDVTQKN KEEGYTHIVE  60
VTFESLETIQ DYIIHPAHVG FGDMYRSFWE KLLIFDYTPR K                     101

SEQ ID NO: 283          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 283
atggctgtca agcaccttat cgtagttaaa ttcaaggacg aaattacaga agcccagaaa  60
gaagaatttt tcaagaccta tgtaaacctg gtgaatatca tccctgcgat gaaagatgtt  120
tattggggca aagacgtcac ccaaaaaaac aaacaagaag gttacactca catcgtcgaa  180
gtcactttcg agtcattgga gacgatccaa gattacataa tacacgttgc ccatgtggga  240
ttcggagacg tttaccgtag cttctgggaa aaacttttga ttttcgacta taccccgaga  300
aaa                                                                303

SEQ ID NO: 284          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 284
MAVKHLIVVK FKDEITEAQK EEFFKTYVNL VNIIPAMKDV YWGKDVTQKN KQEGYTHIVE  60
VTFESLETIQ DYIIHVAHVG FGDVYRSFWE KLLIFDYTPR K                     101

SEQ ID NO: 285          moltype = DNA  length = 303
FEATURE                 Location/Qualifiers
misc_feature            1..303
                        note = Synthetic biopolymer
source                  1..303
                        mol_type = other DNA
```

```
                        organism = synthetic construct
SEQUENCE: 285
atggctgtca agcaccttat cgtaattaaa ttcaaggacg aaattacaga agcccagaaa  60
gaagaatttt tcaagacctt tgtaaacctg gtgaatatca tccctgcgat gaaagatgtt  120
tattggggca aagacgtcac ccaaaaaaac aaagaagaag gttacactca catcgtcgaa  180
gtcactttcg agtcattgga gacgatccaa gattacataa tacacccggc ccatgtggga  240
ttcggagaca tttaccgtag cttctgggaa aaacttttga ttttcgacta taccccgaga  300
aaa                                                                303

SEQ ID NO: 286          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 286
MAVKHLIVIK FKDEITEAQK EEFFKTFVNL VNIIPAMKDV YWGKDVTQKN KEEGYTHIVE  60
VTFESLETIQ DYIIHPAHVG FGDIYRSFWE KLLIFDYTPR K                      101

SEQ ID NO: 287          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 287
atgggtgtca agcaccttat cgtagttaaa ttcaaggacg aaattacaga agcccagaaa  60
gaagaatttt tcaagacctt tgtaaacctg gtgaatatca tccctgcgat gaaagatgtt  120
tattggggca aagacgtcac ccaaaaaaac aaagaagaag gttacactca catcgtcgaa  180
gtcactttcg agtcattgga gacgatccaa gattacataa tacacccggc ccatgtggga  240
ttcggagacg tttaccgtag cttctgggaa aaacttttga ttttcgacta taccccgaga  300
aaa                                                                303

SEQ ID NO: 288          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 288
MGVKHLIVVK FKDEITEAQK EEFFKTFVNL VNIIPAMKDV YWGKDVTQKN KEEGYTHIVE  60
VTFESLETIQ DYIIHPAHVG FGDVYRSFWE KLLIFDYTPR K                      101

SEQ ID NO: 289          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 289
atggctgtca agcaccttat cgtactgaaa ttcaaggacg aaattacaga agcccagaaa  60
gaagaatttt tcaagacctt tgtaaacctg gtgaatatca tccctgcgat gaaagatgtt  120
tattggggca aagacgtcac ccaaaaaaac aaagaagaag gttacactca catcgtcgaa  180
gtcactttcg agtcagtaga gacgatccaa gattacataa tacacccggc ccatgtggga  240
ttcggagacg tttaccgtag cttctgggaa aaacttttga ttttcgacta taccccgaga  300
aaa                                                                303

SEQ ID NO: 290          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 290
MAVKHLIVLK FKDEITEAQK EEFFKTFVNL VNIIPAMKDV YWGKDVTQKN KEEGYTHIVE  60
VTFESVETIQ DYIIHPAHVG FGDVYRSFWE KLLIFDYTPR K                      101

SEQ ID NO: 291          moltype = DNA  length = 303
FEATURE                 Location/Qualifiers
misc_feature            1..303
                        note = Synthetic biopolymer
source                  1..303
                        mol_type = other DNA
                        organism = synthetic construct
```

```
SEQUENCE: 291
atgggtgtca agcaccttat cgtagttaaa ttcaaggacg aaattacaga agcccagaaa  60
gaagaatttt tcaagaccta tgtaaacctg gtgaatatca tccctgcgat gaaagatgtt  120
tattggggca aagacgtcac ccaaaaaaac aaagaagaag gttacactca catcgtcgaa  180
gtcactttcg agtcattgga gacgatccaa gattacataa tacacccggc ccatgtggga  240
ttcggagaca tgtaccgtag cttctgggaa aaacttttga ttttcgacta taccccgaga  300
aaa                                                                303

SEQ ID NO: 292         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 292
MGVKHLIVVK FKDEITEAQK EEFFKTYVNL VNIIPAMKDV YWGKDVTQKN KEEGYTHIVE  60
VTFESLETIQ DYIIHPAHVG FGDMYRSFWE KLLIFDYTPR K                      101

SEQ ID NO: 293         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 293
atggctgtca agcaccttat cgtagttaaa ttcaaggacg aaattacaga agcccagaaa  60
gaagaatttt tcaaggccta tgtaaacctg gtgaatatca tccctgcgat gaaagatgtt  120
tattggggca aagacgtcac ccaaaaaaac aaacaagaag gttacactca catcgtcgaa  180
gtcactttcg agtcagtaga gacgatccaa gattacataa tacacgttgc ccatgtggga  240
ttcggagacg tttaccgtag cttctgggaa aaacttttga ttttcgacta taccccgaga  300
aaa                                                                303

SEQ ID NO: 294         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 294
MAVKHLIVVK FKDEITEAQK EEFFKAYVNL VNIIPAMKDV YWGKDVTQKN KQEGYTHIVE  60
VTFESVETIQ DYIIHVAHVG FGDVYRSFWE KLLIFDYTPR K                      101

SEQ ID NO: 295         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 295
atggctgtca agcaccttat cgtagttaaa tttaaggacg aaattacaga agcccagaaa  60
gaagaatttt tcaagaccta tgtaaacctg gtgaatatca tccctgcgat gaaagatgtt  120
tattggggca aagacgtcac ccaaaaaaac aaaagagaag gttacactca catcgtcgaa  180
gtcactttcg agtcagtaga gacgatccaa gattacataa tacacccggc ccatgtggga  240
ttcggagaca tgtaccgtag cttctgggaa aaacttttga ttttcgacta taccccgaga  300
aaa                                                                303

SEQ ID NO: 296         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 296
MAVKHLIVVK FKDEITEAQK EEFFKTYVNL VNIIPAMKDV YWGKDVTQKN KREGYTHIVE  60
VTFESVETIQ DYIIHPAHVG FGDMYRSFWE KLLIFDYTPR K                      101

SEQ ID NO: 297         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 297
```

-continued

```
atggctgtca agcaccttat cgtagttaaa ttcaaggacg aaattacaga agcccagaaa  60
gaagaatttt tcaagacctt tgtaaacctg gtgaatatca tccctgcgat gaaagatgtt  120
tattggggca aagacgtcac ccaaaaaaac aaagaagaag gttacactca catcgtcgaa  180
gtcactttcg agtcattgga gacgatccaa gattacataa tacacccggc ccatgtggga  240
ttcggagaca tgtaccgtag cttctgggaa aaacttttga ttttcgacta taccccgaga  300
aaa                                                                 303

SEQ ID NO: 298         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 298
MAVKHLIVVK FKDEITEAQK EEFFKTFVNL VNIIPAMKDV YWGKDVTQKN KEEGYTHIVE  60
VTFESLETIQ DYIIHPAHVG FGDMYRSFWE KLLIFDYTPR K                       101

SEQ ID NO: 299         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 299
atggctgtca agcaccttat cgtaattaaa ttcaaggacg aaattacaga agcccagaaa  60
gaagaatttt tcaagaccta tgtaggtctg gtgaatatca tccctgcgat gaaagatgtt  120
tattggggca aagacgtcac ccaaaaaaac aaagaagaag gttacactca catcgtcgaa  180
gtcggtttcg agtcagtaga ggaaatccaa gattacataa tacacccggc ccatgtggga  240
ttcggagacg tttaccgtag cttctgggaa aaacttttga aattcgacta taccccgaga  300
aaa                                                                 303

SEQ ID NO: 300         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 300
MAVKHLIVIK FKDEITEAQK EEFFKTYVGL VNIIPAMKDV YWGKDVTQKN KEEGYTHIVE  60
VGFESVEEIQ DYIIHPAHVG FGDVYRSFWE KLLKFDYTPR K                       101

SEQ ID NO: 301         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 301
atggctgtca agcaccttat cgtaattaaa ttcaaggacg gtattacaga agcccagaaa  60
gaagaatttt tcaagaccta tgtaaacctg gtgaatatca tccctgcgat gaaagatgtt  120
tattggggcc cagacgtcac ccaaaaaaac aaagaagaag gttacactca catcgtcgaa  180
gtcactttcg agtcagtaga ggaaatccaa gattacataa tacacccggc ccatgtggga  240
ttcggagacg tttaccgtag cttctgggaa aaacttttga aattcgacta taccccgaga  300
aaa                                                                 303

SEQ ID NO: 302         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 302
MAVKHLIVIK FKDGITEAQK EEFFKTYVNL VNIIPAMKDV YWGPDVTQKN KEEGYTHIVE  60
VTFESVEEIQ DYIIHPAHVG FGDVYRSFWE KLLKFDYTPR K                       101

SEQ ID NO: 303         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 303
atggctgtca agcaccttat cgtactgaaa ttcaaggacg gtattacaga agcccagaaa  60
```

-continued

```
gaagaatttt tcaagaccta tgtaaacctg gtgaatatca tccctgcgat gaaagatgtt  120
tattggggca aagacgtcac ccaaaaaaac aaagaagaag gttacactca catcgtcgaa  180
gtcactttcg agtcagtaga gtctatccaa gattacataa tacacccggc ccatgtggga  240
ttcggagacg tttaccgtag cttctgggaa aaacttttga aattcgacta taccccgaga  300
aaa                                                                303

SEQ ID NO: 304         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 304
MAVKHLIVLK FKDGITEAQK EEFFKTYVNL VNIIPAMKDV YWGKDVTQKN KEEGYTHIVE  60
VTFESVESIQ DYIIHPAHVG FGDVYRSFWE KLLKFDYTPR K                      101

SEQ ID NO: 305         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 305
atggctgtca agcaccttat cgtactgaaa ttcaaggacg gtattacaga agcccagaaa  60
gaagaatttt tcaagaccta tgtaaacctg gtgaatatca tccctgcgat gaaagatgtt  120
tattggggca aagacgtcac ccaaaaaaac aaagaagaag gttacactca catcgtcgaa  180
gtcactttcg agtcagtaga ggctatccaa gattacataa tacacccggc ccatgtggga  240
ttcggagacg tttaccgtag cttctgggaa aaacttttga aattcgacta taccccgaga  300
aaa                                                                303

SEQ ID NO: 306         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 306
MAVKHLIVLK FKDGITEAQK EEFFKTYVNL VNIIPAMKDV YWGKDVTQKN KEEGYTHIVE  60
VTFESVEAIQ DYIIHPAHVG FGDVYRSFWE KLLKFDYTPR K                      101

SEQ ID NO: 307         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 307
atggctgtca agcaccttat cgtactgaaa ttcaaggacg aaattacaga agcccagaaa  60
gaagaatttt tcaagaccta tgtaaacctg gtgaatatca tccctgcgat gaaagatgtt  120
tattggggca aagacgtcac ccaaaaaaac aaagaagaag gttacactca catcgtcgaa  180
gtcggtttcg agtcagtaga gggtatccaa gattacataa tacacccggc ccatgtggga  240
ttcggagacg tttaccgtag cttctgggaa aaacttttga aattcgacta taccccgaga  300
aaa                                                                303

SEQ ID NO: 308         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 308
MAVKHLIVLK FKDEITEAQK EEFFKTYVNL VNIIPAMKDV YWGKDVTQKN KEEGYTHIVE  60
VGFESVEGIQ DYIIHPAHVG FGDVYRSFWE KLLKFDYTPR K                      101

SEQ ID NO: 309         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 309
atggccgtca agcatttaat cgtcgtcaaa tttaaggacg gtatcacaga agctcaaaag  60
gaggaattct tcaaaaccta tgtaaactta gtgaacataa ttcctgctat gaaagatgtt  120
```

-continued

```
tattggggca aagacgtcac ccaaaaaaac aaagaagaag gttacactca cattgtagaa  180
gtcactttcg agtcagtaga ggaaatccaa gattacataa tacacccggc ccatgtggga  240
ttcggagacg tttaccgtag cttctgggaa aaacttttga aattcgacta taccccgaga  300
aaa                                                                 303

SEQ ID NO: 310         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 310
MAVKHLIVVK FKDGITEAQK EEFFKTYVNL VNIIPAMKDV YWGKDVTQKN KEEGYTHIVE  60
VTFESVEEIQ DYIIHPAHVG FGDVYRSFWE KLLKFDYTPR K                       101

SEQ ID NO: 311         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 311
atggccgtca agcaccttat cgtagttaaa ttcaaggacg aaattacaga agcccagaaa  60
gaagaatttt tcaagaccta tgtaaacctg gtgaatatca tccctgcgat gaaagatgtt  120
tattggggca aagacgtcac ccaaaaaaac aaagaagaag gttacactca catcgtcgaa  180
gtcactttcg agtcagtaga gacgatccaa gattacataa tacacccggc ccatgtggga  240
ttcggagacg tttaccgtag cttctgggaa aaacttttga aattcgacta taccccgaga  300
aaa                                                                 303

SEQ ID NO: 312         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 312
MAVKHLIVVK FKDEITEAQK EEFFKTYVNL VNIIPAMKDV YWGKDVTQKN KEEGYTHIVE  60
VTFESVETIQ DYIIHPAHVG FGDVYRSFWE KLLKFDYTPR K                       101

SEQ ID NO: 313         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 313
atggctgtca agcaccttat cgtagttaaa ttcaaggacg aaattacaga agcccagaaa  60
gaagaatttt tcaagaccta tgtaggtctg gtgaatatca tccctgcgat gaaagatgtt  120
tattggggca aagacgtcac ccaaaaaaac aaagaagaag gttacactca catcgtcgaa  180
gtcactttcg agtcagtaga ggaaatccaa gattacataa tacacccggc ccatgtggga  240
ttcggagacg tttaccgtag cttctgggaa aaacttttga aattcgacta taccccgaga  300
aaa                                                                 303

SEQ ID NO: 314         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 314
MAVKHLIVVK FKDEITEAQK EEFFKTYVGL VNIIPAMKDV YWGKDVTQKN KEEGYTHIVE  60
VTFESVEEIQ DYIIHPAHVG FGDVYRSFWE KLLKFDYTPR K                       101

SEQ ID NO: 315         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 315
atgggtgtca agcaccttat cgtactgaaa ttcaaggacg aaattccaga agcccagaaa  60
gaagaatttt tcaagaccta tgtaaacctg atgaatatca tccctgcgat gaaagatgtt  120
tattggggca aagacgtcac ccaaagaaac aaagaagaag gttacactca catcgtcgaa  180
```

```
gtcactttcg agtcagtaga gacgatccaa gattacataa tacacccggc ccatgtggga  240
ttcggagacg tttaccgtaa attctgggaa aaacttttga ttttcgacta taccccgaga  300
aaa                                                                303

SEQ ID NO: 316         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 316
MGVKHLIVLK FKDEIPEAQK EEFFKTYVNL MNIIPAMKDV YWGKDVTQRN KEEGYTHIVE  60
VTFESVETIQ DYIIHPAHVG FGDVYRKFWE KLLIFDYTPR K                      101

SEQ ID NO: 317         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 317
atggctgtca agcaccttat cgtactgaaa ttcaaggacg aaattacaga agcccagaaa  60
gaagaatttt tcaagaccta tgtaaacctg gaaaatatca tccctgcgat gaaagatgtt  120
tattggggca aagacgtcac ccaaaaaaac aaagaagaag gttacactca catcgtcgaa  180
gtcactttgg agtcagtaga gacgatccaa gattacataa tccacccggc ccatgtggga  240
ttcggagacg tttaccgtaa attttgggaa aaacttttga ttttcgacta taccccgaga  300
aaa                                                                303

SEQ ID NO: 318         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 318
MAVKHLIVLK FKDEITEAQK EEFFKTYVNL ENIIPAMKDV YWGKDVTQKN KEEGYTHIVE  60
VTLESVETIQ DYIIHPAHVG FGDVYRKFWE KLLIFDYTPR K                      101

SEQ ID NO: 319         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 319
atgggtgtca agcaccttat cgtactgaaa ttcaaggacg aaattacaga agcccagaaa  60
gaagaatttt tcaagaccta tgtaaacctg gtgaatatca tccctgcgat gaaagatgtt  120
tattggggca aagacgtcac ccaaagaaac aaagaagaag gttacactca catcgtcgaa  180
gtcactttcg agtcagtaga gacgatccaa gattacataa tacacccggc ccatgtggga  240
ttcggagacg tttaccgtag cttctgggaa aaacttttga ttttcgacta taccccgaga  300
aaa                                                                303

SEQ ID NO: 320         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 320
MGVKHLIVLK FKDEITEAQK EEFFKTYVNL VNIIPAMKDV YWGKDVTQRN KEEGYTHIVE  60
VTFESVETIQ DYIIHPAHVG FGDVYRSFWE KLLIFDYTPR K                      101

SEQ ID NO: 321         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 321
atggctgtca agcaccttat cgtactgaaa ttcaaggacg aaattacaga agcccagaaa  60
gaagaatttt tcaagaccta tgtaaacctg atgaatatca tccctgcgat gaaagatgtt  120
tattggggca aagacgtcac ccaaagaaac aaagaagaag gttacactca catcgtcgaa  180
gtcactttcg agtcagtaga gacgatccaa gattacataa tacacccggc ccatgtggga  240
```

```
ttcggagacg tttaccgtaa attctgggaa aaacttttga ttttcgacta taccccgaga  300
aaa                                                                303

SEQ ID NO: 322         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 322
MAVKHLIVLK FKDEITEAQK EEFFKTYVNL MNIIPAMKDV YWGKDVTQRN KEEGYTHIVE  60
VTFESVETIQ DYIIHPAHVG FGDVYRKFWE KLLIFDYTPR K                      101

SEQ ID NO: 323         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 323
atgggtgtca agcaccttat cgtactgaaa ttcaaggacg aaattacaga agcccagaaa  60
gaagaatttt tcaagaccta tgtaaacctg tctaatatca tccctgcgat gaaagatgtt  120
tattggggca aagacgtcac ccaaagaaac aaagaagaag gttacactca catcgtcgaa  180
gtcactttcg agtcagtaga gacgatccaa gattacataa tacacccggc ccatgtggga  240
ttcggagacg tttaccgtag cttctgggaa gaacttttga ttttcgacta taccccgaga  300
aaa                                                                303

SEQ ID NO: 324         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 324
MGVKHLIVLK FKDEITEAQK EEFFKTYVNL SNIIPAMKDV YWGKDVTQRN KEEGYTHIVE  60
VTFESVETIQ DYIIHPAHVG FGDVYRSFWE ELLIFDYTPR K                      101

SEQ ID NO: 325         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 325
atggctgtca agcaccttat cgtactgaaa ttcaaggacg aaattacaga agcccagaaa  60
gaagaatttt tcaagaccta tgtaaacctg gaaaatatca tccctgcgat gaaagatgtt  120
tattggggca aagacgtcac ccaaagaaac aaagaagaag gttacactca catcgtcgaa  180
gtcactttcg agtcagtaga gacgatccaa gattacataa tacacccggc ccatgtggga  240
ttcggagacg tttaccgtaa attctgggaa aaacttttga ttttcgacta taccccgaga  300
aaa                                                                303

SEQ ID NO: 326         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 326
MAVKHLIVLK FKDEITEAQK EEFFKTYVNL ENIIPAMKDV YWGKDVTQRN KEEGYTHIVE  60
VTFESVETIQ DYIIHPAHVG FGDVYRKFWE KLLIFDYTPR K                      101

SEQ ID NO: 327         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 327
atggctgtca agcaccttat cgtactgaaa ttcaaggacg aaattccaga agcccagaaa  60
gaagaatttt tcaagaccta tgtaaacctg atgaatatca tccctgcgat gaaagatgtt  120
tattggggca aagacgtcac ccaaagaaac aaagaagaag gttacactca catcgtcgaa  180
gtcactttcg agtcagtaga gacgatccaa gattacataa tacacccggc ccatgtggga  240
ttcggagacg tttaccgtag cttctgggaa aaacttttga ttttcgacta taccccgaga  300
```

```
aaa                                                                303

SEQ ID NO: 328         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 328
MAVKHLIVLK FKDEIPEAQK EEFFKTYVNL MNIIPAMKDV YWGKDVTQRN KEEGYTHIVE  60
VTFESVETIQ DYIIHPAHVG FGDVYRSFWE KLLIFDYTPR K                      101

SEQ ID NO: 329         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 329
atggccgtca agcatttaat cgtcgtcaaa tttaaggacg gtatcacaga agctcaaaag  60
gaggaattct tcaagaccta tgtaaacctg tctaatatca tccctgcgat gaaagatgtt  120
tattggggca aagacgtcac ccaaagaaac aaagaagaag gttacactca catcgtcgaa  180
gtcactttcg agtcagtaga gacgatccaa gattacataa tacacccggc ccatgtggga  240
ttcggagacg tttaccgtag cttctgggaa gaacttttga ttttcgacta taccccgaga  300
aaa                                                                303

SEQ ID NO: 330         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 330
MAVKHLIVVK FKDGITEAQK EEFFKTYVNL SNIIPAMKDV YWGKDVTQRN KEEGYTHIVE  60
VTFESVETIQ DYIIHPAHVG FGDVYRSFWE ELLIFDYTPR K                      101

SEQ ID NO: 331         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 331
atggctgtca agcaccttat cgtactgaaa ttcttggacg aaattacaga agcccagaaa  60
gaagaatttt tcaagaccta tgtaaacctg atgaatatca tccctgcgat gaaagatgtt  120
tattggggca aagacgtcac ccaaagaaac aaagaagaag gttacactca catcgtcgaa  180
gtcactttcg agtcagtaga gacgatccaa gattacataa tacacccggc ccatgtggga  240
ttcggagacg tttaccgtag cttctgggaa aaacttttga ttttcgacta taccccgaga  300
aaa                                                                303

SEQ ID NO: 332         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 332
MAVKHLIVLK FLDEITEAQK EEFFKTYVNL MNIIPAMKDV YWGKDVTQRN KEEGYTHIVE  60
VTFESVETIQ DYIIHPAHVG FGDVYRSFWE KLLIFDYTPR K                      101

SEQ ID NO: 333         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 333
atggctgtca agcaccttat cgtagttaaa ttcaaggacg aaattacaga agcccagaaa  60
gaagaatttt tcaagaccta tgtaaacctg gtgaatatca tccctgcgat gaaagatgtt  120
tattggggca aagacgtcac ccaaaaaaac aaagaagaag gttacactca catcgtcgaa  180
gtcactttcg agtcagtaga gacgatccaa gattacataa tacacccggc ccatgtggga  240
ttcggagacg tttaccgtag cttctgggaa gaacttttga ttttcgacta taccccgaga  300
aaa                                                                303
```

```
SEQ ID NO: 334         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 334
MAVKHLIVVK FKDEITEAQK EEFFKTYVNL VNIIPAMKDV YWGKDVTQKN KEEGYTHIVE  60
VTFESVETIQ DYIIHPAHVG FGDVYRSFWE ELLIFDYTPR K                     101

SEQ ID NO: 335         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 335
atggctgtca agcaccttat cgtaattaaa ttcaaggacg gtattacaga agcccagaaa  60
gaagaatttt tcaagaccta tgtaaacctg gtgaatatca tccctgcgat gaaagatgct  120
tattggggca aagacgtcac ccaaagaaac aaagaagaag gttacactca catcgtcgaa  180
gtcactttcg agtcagtaga gacgatccaa gattacataa tacacccggc ccatgtggga  240
ttcggagacg tttaccgtag cttctgggaa aaacttttga ttttcgacta taccccgaga  300
aaa                                                               303

SEQ ID NO: 336         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 336
MAVKHLIVIK FKDGITEAQK EEFFKTYVNL VNIIPAMKDA YWGKDVTQRN KEEGYTHIVE  60
VTFESVETIQ DYIIHPAHVG FGDVYRSFWE KLLIFDYTPR K                     101

SEQ ID NO: 337         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 337
atggctgtca agcaccttat cgtagttaaa ttcaaggacg aaattacaga agcccagaaa  60
gaagaatttt tcaagaccta tgtaaacctg gtgaatatca tccctgcgat gaaagatgtt  120
tattggggca aagacgtcac ccaaagaaac aaagaagaag gttacactca catcgtcgaa  180
gtcactttcg agtcagtaga gacgatccaa ggttacataa tacacccggc ccatgtggga  240
ttcggagacg tttaccgtag cttctgggaa gaacttttga ttttcgacta taccccgaga  300
aaa                                                               303

SEQ ID NO: 338         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 338
MAVKHLIVVK FKDEITEAQK EEFFKTYVNL VNIIPAMKDV YWGKDVTQRN KEEGYTHIVE  60
VTFESVETIQ GYIIHPAHVG FGDVYRSFWE ELLIFDYTPR K                     101

SEQ ID NO: 339         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 339
atggctgtca agcaccttat cgtaattaaa ttcaaggacg gtattacaga agcccagaaa  60
gaagaatttt tcaagacctt tgtaaacctg gtgaatatca tccctgcgat gaaagatgtt  120
tattggggca aagacgtcac ccaaaaaaac aaagaagaag gttacactca catcgtcgaa  180
gtcactttcg agtcagtaga gacgatccaa ggttacataa tacacccggc ccatgtggga  240
ttcggagacg tttaccgtag cttctgggaa gaacttttga ttttcgacta taccccgaga  300
aaa                                                               303
```

-continued

```
SEQ ID NO: 340         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 340
MAVKHLIVIK FKDGITEAQK EEFFKTFVNL VNIIPAMKDV YWGKDVTQKN KEEGYTHIVE  60
VTFESVETIQ GYIIHPAHVG FGDVYRSFWE ELLIFDYTPR K                     101

SEQ ID NO: 341         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 341
atggctgtca agcaccttat cgtactgaaa ttcaaggacg gtattacaga agcccagaaa  60
gaagaatttt tcaagaccta tgtaaacctg gtgaatatca tccctgcgat gaaagatgtt  120
tattggggca aagacgtcac ccaaagaaac aaagaagaag gttacactca catcgtcgaa  180
gtcactttcg agtcagtaga gacgatccaa ggttacataa tacacccggc ccatgtggga  240
ttcggagacg tttaccgtag cttctgggaa gaacttttga ttttcgacta taccccgaga  300
aaa                                                               303

SEQ ID NO: 342         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 342
MAVKHLIVLK FKDGITEAQK EEFFKTYVNL VNIIPAMKDV YWGKDVTQRN KEEGYTHIVE  60
VTFESVETIQ GYIIHPAHVG FGDVYRSFWE ELLIFDYTPR K                     101

SEQ ID NO: 343         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 343
atggctgtca agcaccttat cgtaattaaa ttcaaggacg aaattacaga agcccagaaa  60
gaagaatttt tcaagacctt tgtaaacctg gtgaatatca tccctgcgat gaaagatgtt  120
tattggggca aagacgtcac ccaaaaaaac aaagaagaag gttacactca catcgtcgaa  180
gtcactttcg agtcagtaga gacgatccaa gattacataa tacacccggc ccatgtggga  240
ttcggagacg tttaccgtag cttctgggaa gaacttttga ttttcgacta taccccgaga  300
aaa                                                               303

SEQ ID NO: 344         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 344
MAVKHLIVIK FKDEITEAQK EEFFKTFVNL VNIIPAMKDV YWGKDVTQKN KEEGYTHIVE  60
VTFESVETIQ DYIIHPAHVG FGDVYRSFWE ELLIFDYTPR K                     101

SEQ ID NO: 345         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 345
atggctgtca agcaccttat cgtactgaaa ttcaaggacg aaattacaga agcccagaaa  60
gaagaatttt tcaagaccta tgtaaacctg gtgaatatca tccctgcgat gaaagatgtt  120
tattggggca aagacgtcac ccaaagaaac aaagaagaag gttacactca catcgtcgaa  180
gtcactttcg agtcagtaga gacgatccaa gattacataa tacacccggc ccatgtggga  240
ttcggagacg ttttccgtag cttctgggaa gaacttttga ttttcgacta taccccgaga  300
aaa                                                               303

SEQ ID NO: 346         moltype = AA  length = 101
```

```
FEATURE                Location/Qualifiers
REGION                 1..101
                       note = Synthetic biopolymer
source                 1..101
                       mol_type = protein
                       organism = synthetic construct
SEQUENCE: 346
MAVKHLIVLK FKDEITEAQK EEFFKTYVNL VNIIPAMKDV YWGKDVTQRN KEEGYTHIVE  60
VTFESVETIQ DYIIHPAHVG FGDVFRSFWE ELLIFDYTPR K                     101

SEQ ID NO: 347         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 347
atggctgtca agcaccttat cgtaattaaa ttcaaggacg gtattacaga agcccagaaa  60
gaagaatttt tcaagaccta tgtaaacctg gtgaatatca tccctgcgat gaaagatgtt  120
tattggggca aagacgtcac ccaaaaaaac aaagaagaag gttacactca catcgtcgaa  180
gtcactttcg agtcagtaga gacgatccaa ggttacataa tacacccggc ccatgtggga  240
ttcggagacg tttaccgtag cttctgggaa gaacttttga ttttcgacta taccccgaga  300
aaa                                                               303

SEQ ID NO: 348         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 348
MAVKHLIVIK FKDGITEAQK EEFFKTYVNL VNIIPAMKDV YWGKDVTQKN KEEGYTHIVE  60
VTFESVETIQ GYIIHPAHVG FGDVYRSFWE ELLIFDYTPR K                     101

SEQ ID NO: 349         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 349
atggctgtca agcaccttat cgtagttaaa ttcaaggacg aaattacaga agcccagaaa  60
gaagaatttt tcaagaccta tgtaaacctg gtgaatatca tccctgcgat gaaagatgtt  120
tattggggca aagacgtcac ccaaagaaac aaagaagaag gttacactca catcgtcgaa  180
gtcactttcg agtcagtaga gacgatccaa gattacataa tacacccggc ccatgtggga  240
ttcggagacg tttaccgtag cttctgggaa gaacttttga ttttcgacta taccccgaga  300
aaa                                                               303

SEQ ID NO: 350         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 350
MAVKHLIVVK FKDEITEAQK EEFFKTYVNL VNIIPAMKDV YWGKDVTQRN KEEGYTHIVE  60
VTFESVETIQ DYIIHPAHVG FGDVYRSFWE ELLIFDYTPR K                     101

SEQ ID NO: 351         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 351
atggctgtca agcaccttat cgtaattaaa ttcaaggacg gtattacaga agcccagaaa  60
gaagaatttt tcaagaccta tgtaaacctg gtgaatatca tccctgcgat gaaagatgtt  120
tattggggca aagacgtcac ccaaagaaac aaagaagaag gttacactca catcgtcgaa  180
gtcactttcg agtcagtaga gacgatccaa ggttacataa tacacccggc ccatgtggga  240
ttcggagacg tttaccgtag cttctgggaa aaacttttga ttttcgacta taccccgaga  300
aaa                                                               303

SEQ ID NO: 352         moltype = AA  length = 101
FEATURE                Location/Qualifiers
```

```
REGION                  1..101
                        note = Synthetic biopolymer
source                  1..101
                        mol_type = protein
                        organism = synthetic construct
SEQUENCE: 352
MAVKHLIVIK FKDGITEAQK EEFFKTYVNL VNIIPAMKDV YWGKDVTQRN KEEGYTHIVE  60
VTFESVETIQ GYIIHPAHVG FGDVYRSFWE KLLIFDYTPR K                     101

SEQ ID NO: 353          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 353
atggctgtca agcaccttat cgtactgaaa ttcaaggacg gtattacaga agcccagaaa  60
gaagaatttt tcaagacctt tgtaaacctg gtgaatatca tccctgcgat gaaagatgtt  120
tattggggca aagacgtcac ccaaagaaac aaagaagaag gttacactca catcgtcgaa  180
gtcactttcg agtcagtaga gacgatccaa gattacataa tacacccggc ccatgtggga  240
ttcggagacg tttaccgtag cttctgggaa aaacttttga ttttcgacta taccccgaga  300
aaa                                                               303

SEQ ID NO: 354          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 354
MAVKHLIVLK FKDGITEAQK EEFFKTFVNL VNIIPAMKDV YWGKDVTQRN KEEGYTHIVE  60
VTFESVETIQ DYIIHPAHVG FGDVYRSFWE KLLIFDYTPR K                     101

SEQ ID NO: 355          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 355
atggctgtca agcaccttat cgtagttaaa ttcaaggacg aaattcaaga agcccagaaa  60
gaagaatttt tcaagaccta tgtaaacctg gtgaatatca tccctgcgat gaaagatgtt  120
tattggggca aagacgtcac ccaaagaaac aaagaagaag gttacactca catcgtcgaa  180
gtcactttcg agtcagtaga gacgatccaa gattacataa tacacccggc ccatgtggga  240
ttcggagacg tttaccgtag cttctgggaa gaacttttga ttttcgacta taccccgaga  300
aaa                                                               303

SEQ ID NO: 356          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 356
MAVKHLIVVK FKDEIQEAQK EEFFKTYVNL VNIIPAMKDV YWGKDVTQRN KEEGYTHIVE  60
VTFESVETIQ DYIIHPAHVG FGDVYRSFWE ELLIFDYTPR K                     101

SEQ ID NO: 357          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 357
atggctgtca agcaccttat cgtaattaaa ttcaaggacg aaattacaga agcccagaaa  60
gaagaatttt tcaagaccta tgtaaacctg gtgaatatca tccctgcgat gaaagatgtt  120
tattggggca aagacgtcac ccaaagaaac aaagaagaag gttacactca catcgtcgaa  180
gtcactttcg agtcagtaga gacgatccaa gattacataa tacacccggc ccatgtggga  240
ttcggagacg tttaccgtag cttctgggaa gaacttttga ttttcgacta taccccgaga  300
aaa                                                               303

SEQ ID NO: 358          moltype = AA  length = 101
FEATURE                 Location/Qualifiers
REGION                  1..101
```

```
                        note = Synthetic biopolymer
source                  1..101
                        mol_type = protein
                        organism = synthetic construct
SEQUENCE: 358
MAVKHLIVIK FKDEITEAQK EEFFKTYVNL VNIIPAMKDV YWGKDVTQRN KEEGYTHIVE  60
VTFESVETIQ DYIIHPAHVG FGDVYRSFWE ELLIFDYTPR K                     101

SEQ ID NO: 359          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 359
atggctgtca agcaccttat cgtagttaaa ttcaaggacg gtattacaga agcccagaaa  60
gaagaatttt tcaagacctt tgtaaacctg gtgaatatca tccctgcgat gaaagatgtt  120
tattggggca aagacgtcac ccaaagaaac aaagaagaag gttacactca catcgtcgaa  180
gtcactttcg agtcagtaga gacgatccaa gattacataa tacacccggc ccatgtggga  240
ttcggagacg tttaccgtag cttctgggaa gaacttttga ttttcgacta taccccgaga  300
aaa                                                               303

SEQ ID NO: 360          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 360
MAVKHLIVVK FKDGITEAQK EEFFKTFVNL VNIIPAMKDV YWGKDVTQRN KEEGYTHIVE  60
VTFESVETIQ DYIIHPAHVG FGDVYRSFWE ELLIFDYTPR K                     101

SEQ ID NO: 361          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 361
atggctgtca agcaccttat cgtactgaaa ttcaaggacg aaattacaga agcccagaaa  60
gaagaatttt tcaagaccta tgtaaacctg gtgaatatca tccctgcgat gaaagatgtt  120
tattggggca aagacgtcac ccaaagaaac aaagaagaag gttacactca catcgtcgaa  180
gtcactttcg agtcagtaga gacgatccaa gattacataa tacacccggc ccatgtggga  240
ttcggagacg tttaccgtag cttctgggaa gaacttttga ttttcgacta taccccgaga  300
aaa                                                               303

SEQ ID NO: 362          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 362
MAVKHLIVLK FKDEITEAQK EEFFKTYVNL VNIIPAMKDV YWGKDVTQRN KEEGYTHIVE  60
VTFESVETIQ DYIIHPAHVG FGDVYRSFWE ELLIFDYTPR K                     101

SEQ ID NO: 363          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 363
atggctgtca agcaccttat cgtaattaaa ttcaaggacg gtattacaga agcccagaaa  60
gaagaatttt tcaagaccta tgtaaacctg gtgaatatca tccctgcgat gaaagatgtt  120
tattggggca aagacgtcac ccaaaaaaac aaagaagaag gttacactca catcgtcgaa  180
gtcactttcg agtcagtaga gacgatccaa ggttacataa tacacccggc ccatgtggga  240
ttcggagacg tttaccgtag cttctgggaa aaacttttga ttttcgacta taccccgaga  300
aaa                                                               303

SEQ ID NO: 364          moltype = AA  length = 101
FEATURE                 Location/Qualifiers
REGION                  1..101
                        note = Synthetic biopolymer
```

```
source                  1..101
                        mol_type = protein
                        organism = synthetic construct
SEQUENCE: 364
MAVKHLIVIK FKDGITEAQK EEFFKTYVNL VNIIPAMKDV YWGKDVTQKN KEEGYTHIVE  60
VTFESVETIQ GYIIHPAHVG FGDVYRSFWE KLLIFDYTPR K                     101

SEQ ID NO: 365          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 365
atggctgtca agcaccttat cgtactgaaa ttcaaggacg gtattacaga agcccagaaa  60
gaagaatttt tcaagaccta tgtaaacctg gtgaatatca tccctgcgat gaaagatgtt  120
tattggggca aagacgtcac ccaaagaaac aaagaagaag gttacactca catcgtcgaa  180
gtcactttcg agtcagtaga gacgatccaa gattacataa tacacccggc ccatgtggga  240
ttcggagacg tttaccgtag cttctgggaa gaacttttga ttttcgacta taccccgaga  300
aaa                                                               303

SEQ ID NO: 366          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 366
MAVKHLIVLK FKDGITEAQK EEFFKTYVNL VNIIPAMKDV YWGKDVTQRN KEEGYTHIVE  60
VTFESVETIQ DYIIHPAHVG FGDVYRSFWE ELLIFDYTPR K                     101

SEQ ID NO: 367          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 367
atggctgtca agcaccttat cgtactgaaa ttcaaggacg aaattacaga agcccagaaa  60
gaagaatttt tcaagaccta tgtaaacctg gtgaatatca tccctgcgat gaaagatgtt  120
tattggggca aagacgtcac ccaaagaaac aaagaagaag gttacactca catcgtcgaa  180
gtcactttcg attcagtaga gacgatccaa gattacataa ctcacccggc ccatgtggga  240
ttcggagacg tttaccgtag cttctgggaa aaacttttga ttttcgacta taccccgaga  300
aaa                                                               303

SEQ ID NO: 368          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 368
MAVKHLIVLK FKDEITEAQK EEFFKTYVNL VNIIPAMKDV YWGKDVTQRN KEEGYTHIVE  60
VTFDSVETIQ DYITHPAHVG FGDVYRSFWE KLLIFDYTPR K                     101

SEQ ID NO: 369          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 369
atggctgtca agcaccttat cgtactgaaa ttcttggacg aaattacaga agcccagaaa  60
gaagaatttt tcaagacctt tgtaaacctg gtgaatatca tccctgcgat gaaagatgtt  120
tattggggca aagacgtcac ccaaagaaac aaagaagaag gttacactca catcgtcgaa  180
gtcactttcg agtcagtaga gacgatccaa gattacataa tgcacccggc ccatgtggga  240
ttcggagacg tttaccgtag cttctgggaa aaacttttga ttttcgacta taccccgaga  300
aaa                                                               303

SEQ ID NO: 370          moltype = AA  length = 101
FEATURE                 Location/Qualifiers
REGION                  1..101
                        note = Synthetic biopolymer
source                  1..101
```

```
                         mol_type = protein
                         organism = synthetic construct
SEQUENCE: 370
MAVKHLIVLK FLDEITEAQK EEFFKTFVNL VNIIPAMKDV YWGKDVTQRN KEEGYTHIVE  60
VTFESVETIQ DYIMHPAHVG FGDVYRSFWE KLLIFDYTPR K                     101

SEQ ID NO: 371           moltype = DNA  length = 303
FEATURE                  Location/Qualifiers
misc_feature             1..303
                         note = Synthetic biopolymer
source                   1..303
                         mol_type = other DNA
                         organism = synthetic construct
SEQUENCE: 371
atgggtgtca agcaccttat cgtactgaaa ttcaaggacg aaattacaga agcccagaaa  60
gaagaatttt tcaagacctt tgtaaacctg gtgaatatca tccctgcgat gaaagatgtt  120
tattggggca aagacgtcac ccaaaaaaac aaagaagaag gttacactca catcgtcgaa  180
gtcactttca aatcagtaga gacgatccaa gattacatag ttcacccggc ccatgtggga  240
ttcggagacg tttaccgtag cttctgggaa aaacttttga ttttcgacta taccccgaga  300
aaa                                                               303

SEQ ID NO: 372           moltype = AA  length = 101
FEATURE                  Location/Qualifiers
REGION                   1..101
                         note = Synthetic biopolymer
source                   1..101
                         mol_type = protein
                         organism = synthetic construct
SEQUENCE: 372
MGVKHLIVLK FKDEITEAQK EEFFKTFVNL VNIIPAMKDV YWGKDVTQKN KEEGYTHIVE  60
VTFKSVETIQ DYIVHPAHVG FGDVYRSFWE KLLIFDYTPR K                     101

SEQ ID NO: 373           moltype = DNA  length = 303
FEATURE                  Location/Qualifiers
misc_feature             1..303
                         note = Synthetic biopolymer
source                   1..303
                         mol_type = other DNA
                         organism = synthetic construct
SEQUENCE: 373
atggctgtca agcaccttat cgtactgaaa ttcaaggacg aaattacaga agcccagaaa  60
gaagaatttt tcaagacctt tgtaaacctg gtgaatatca tccctgcgat gaaagatgtt  120
tattggggca aagacgtcac ccaaagaaac aaagaagaag gttacactca catcgtcgaa  180
gtcactttcg attcagtaga gacgatccaa gattacatag ttcacccggc ccatgtggga  240
ttcggagacg tttaccgtag cttctgggaa aaacttttga ttttcgacta taccccgaga  300
aaa                                                               303

SEQ ID NO: 374           moltype = AA  length = 101
FEATURE                  Location/Qualifiers
REGION                   1..101
                         note = Synthetic biopolymer
source                   1..101
                         mol_type = protein
                         organism = synthetic construct
SEQUENCE: 374
MAVKHLIVLK FKDEITEAQK EEFFKTFVNL VNIIPAMKDV YWGKDVTQRN KEEGYTHIVE  60
VTFDSVETIQ DYIVHPAHVG FGDVYRSFWE KLLIFDYTPR K                     101

SEQ ID NO: 375           moltype = DNA  length = 303
FEATURE                  Location/Qualifiers
misc_feature             1..303
                         note = Synthetic biopolymer
source                   1..303
                         mol_type = other DNA
                         organism = synthetic construct
SEQUENCE: 375
atggctgtca agcaccttat cgtactgaaa ttcaaggacg aaattacaga agcccagaaa  60
gaagaatttt tcaagacctt tgtaaacctg gtgaatatca tccctgcgat gaaagatgtt  120
tattggggca aagacgtcac ccaaagaaac aaagaagaag gttacactca catcgtcgaa  180
gtcactttcg attcagtaga gacgatccaa gattacataa ctcacccggc ccatgtggga  240
ttcggagacg tttaccgtag cttctgggaa aaacttttga ttttcgacta taccccgaga  300
aaa                                                               303

SEQ ID NO: 376           moltype = AA  length = 101
FEATURE                  Location/Qualifiers
REGION                   1..101
                         note = Synthetic biopolymer
source                   1..101
                         mol_type = protein
```

```
                         organism = synthetic construct
SEQUENCE: 376
MAVKHLIVLK FKDEITEAQK EEFFKTFVNL VNIIPAMKDV YWGKDVTQRN KEEGYTHIVE  60
VTFDSVETIQ DYITHPAHVG FGDVYRSFWE KLLIFDYTPR K                      101

SEQ ID NO: 377           moltype = DNA  length = 303
FEATURE                  Location/Qualifiers
misc_feature             1..303
                         note = Synthetic biopolymer
source                   1..303
                         mol_type = other DNA
                         organism = synthetic construct
SEQUENCE: 377
atgggtgtca agcaccttat cgtactgaaa ttcaaggacg aaattacaga agcccagaaa  60
gaagaatttt tcaagaccta tgtaaacctg gtgaatatca tccctgcgat gaaagatgtt  120
tattggggca aagacgtcac ccaaagaaac aaagaagaag gttacactca catcgtcgaa  180
gtcactttcg attcagtaga gacgatccaa gattacataa tgcacccggc ccatgtggga  240
ttcggagacg tttaccgtag cttctgggaa aaacttttga ttttcgacta taccccgaga  300
aaa                                                                303

SEQ ID NO: 378           moltype = AA  length = 101
FEATURE                  Location/Qualifiers
REGION                   1..101
                         note = Synthetic biopolymer
source                   1..101
                         mol_type = protein
                         organism = synthetic construct
SEQUENCE: 378
MGVKHLIVLK FKDEITEAQK EEFFKTYVNL VNIIPAMKDV YWGKDVTQRN KEEGYTHIVE  60
VTFDSVETIQ DYIMHPAHVG FGDVYRSFWE KLLIFDYTPR K                      101

SEQ ID NO: 379           moltype = DNA  length = 303
FEATURE                  Location/Qualifiers
misc_feature             1..303
                         note = Synthetic biopolymer
source                   1..303
                         mol_type = other DNA
                         organism = synthetic construct
SEQUENCE: 379
atgggtgtca agcaccttat cgtactgaaa ttcaaggacg aaattacaga agcccagaaa  60
gaagaatttt tcaagaccta tgtaaacctg gtgaatatca tccctgcgat gaaagatgtt  120
tattggggca aagacgtcac ccaaagaaac aaagaagaag gttacactca catcgtcgaa  180
gtcactttcg attcagtaga gacgatccaa gattacataa atcacccggc ccatgtggga  240
ttcggagacg tttaccgtag cttctgggaa aaacttttga ttttcgacta taccccgaga  300
aaa                                                                303

SEQ ID NO: 380           moltype = AA  length = 101
FEATURE                  Location/Qualifiers
REGION                   1..101
                         note = Synthetic biopolymer
source                   1..101
                         mol_type = protein
                         organism = synthetic construct
SEQUENCE: 380
MGVKHLIVLK FKDEITEAQK EEFFKTYVNL VNIIPAMKDV YWGKDVTQRN KEEGYTHIVE  60
VTFDSVETIQ DYINHPAHVG FGDVYRSFWE KLLIFDYTPR K                      101

SEQ ID NO: 381           moltype = DNA  length = 303
FEATURE                  Location/Qualifiers
misc_feature             1..303
                         note = Synthetic biopolymer
source                   1..303
                         mol_type = other DNA
                         organism = synthetic construct
SEQUENCE: 381
atggctgtca agcaccttat cgtactgaaa ttcaaggacg aaattacaga agcccagaaa  60
gaagaatttt tcaagaccta tgtaaacctg gtgaatatca tccctgcgat gaaagatgtt  120
tattggggca aagacgtcac ccaaagaaac aaagaagaag gttacactca catcgtcgaa  180
gtcactttca aatcagtaga gacgatccaa gattacataa atcacccggc ccatgtggga  240
ttcggagacg tttaccgtag cttctgggaa aaacttttga ttttcgacta taccccgaga  300
aaa                                                                303

SEQ ID NO: 382           moltype = AA  length = 101
FEATURE                  Location/Qualifiers
REGION                   1..101
                         note = Synthetic biopolymer
source                   1..101
                         mol_type = protein
                         organism = synthetic construct
```

```
SEQUENCE: 382
MAVKHLIVLK FKDEITEAQK EEFFKTYVNL VNIIPAMKDV YWGKDVTQRN KEEGYTHIVE  60
VTFKSVETIQ DYINHPAHVG FGDVYRSFWE KLLIFDYTPR K                      101

SEQ ID NO: 383         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 383
atggccgtca agcatttaat cgtcgtcaaa tttaaggacg gtatcacaga agctcaaaag  60
gaggaattct tcgcgaccta tgtaaactta gtgaatatca tccctgcgat gaaagatgtt  120
tattggggca aagacgtcac cccaaaaaac aaagaagaag gttacactca catcgtcgaa  180
gtcactttcg agtcagtaga gacgatccaa gattacataa atcacccggc ccatgtggga  240
ttcggagacg tttaccgtag cttctgggaa aaacttttga ttttcgacta taccccgaga  300
aaa                                                                303

SEQ ID NO: 384         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 384
MAVKHLIVVK FKDGITEAQK EEFFATYVNL VNIIPAMKDV YWGKDVTPKN KEEGYTHIVE  60
VTFESVETIQ DYINHPAHVG FGDVYRSFWE KLLIFDYTPR K                      101

SEQ ID NO: 385         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 385
atggctgtca agcaccttat cgtactgaaa ttcttggacg aaattacaga agcccagaaa  60
gaagaatttt tcaagaccta tgtaaacctg gtgaatatca tccctgcgat gaaagatgtt  120
tattggggca aagacgtcac ccaaagaaac aaagaagaag gttacactca catcgtcgaa  180
gtcactttcg agtcagtaga gacgatccaa gattacatag ttcacccggc ccatgtggga  240
ttcggagacg tttaccgtag cttctgggaa aaacttttga ttttcgacta taccccgaga  300
aaa                                                                303

SEQ ID NO: 386         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 386
MAVKHLIVLK FLDEITEAQK EEFFKTYVNL VNIIPAMKDV YWGKDVTQRN KEEGYTHIVE  60
VTFESVETIQ DYIVHPAHVG FGDVYRSFWE KLLIFDYTPR K                      101

SEQ ID NO: 387         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 387
atggctgtca agcaccttat cgtactgaaa ttcaaggacg aaattacaga agcccagaaa  60
gaagaatttt tcaagacctt tgtaaacctg gtgaatatca tccctgcgat gaaagatgtt  120
tattggggca aagacgtcac ccaaagaaac aaagaagaag gttacactca catcgtcgaa  180
gtcactttcg agtcagtaga gacgatccaa gattacatag ttcacccggc ccatgtggga  240
ttcggagacg tttaccgtag cttctgggaa aaacttttga ttttcgacta taccccgaga  300
aaa                                                                303

SEQ ID NO: 388         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 388
```

-continued

```
MAVKHLIVLK FKDEITEAQK EEFFKTFVNL VNIIPAMKDV YWGKDVTQRN KEEGYTHIVE  60
VTFESVETIQ DYIVHPAHVG FGDVYRSFWE KLLIFDYTPR K                      101

SEQ ID NO: 389         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 389
atggctgtca agcaccttat cgtactgaaa ttcaaggacg aaattacaga agcccagaaa  60
gaagaatttt tcaagaccta tgtaaacctg gtgaatatca tccctgcgat gaaagatgtt  120
tattggggca aagacgtcac ccaaagaaac aaagaagaag gttacactca catcgtcgaa  180
gtcactttcg agtcagtaga gacgatccaa gattacatat ctcacccggc ccatgtggga  240
ttcggagacg tttaccgtag cttctgggaa aaacttttga ttttcgacta taccccgaga  300
aaa                                                                303

SEQ ID NO: 390         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 390
MAVKHLIVLK FKDEITEAQK EEFFKTYVNL VNIIPAMKDV YWGKDVTQRN KEEGYTHIVE  60
VTFESVETIQ DYISHPAHVG FGDVYRSFWE KLLIFDYTPR K                      101

SEQ ID NO: 391         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 391
atgggtgtca agcaccttat cgtactgaaa ttcttggacg aaattacaga agcccagaaa  60
gaagaatttt tcaagaccta tgtaaacctg gtgaatatca tccctgcgat gaaagatgtt  120
tattggggca aagacgtcac ccaaagaaac aaagaagaag gttacactca catcgtcgaa  180
gtcactttcg agtcagtaga gacgatccaa gattacataa atcacccggc ccatgtggga  240
ttcggagacg tttaccgtag cttctgggaa aaacttttga ttttcgacta taccccgaga  300
aaa                                                                303

SEQ ID NO: 392         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 392
MGVKHLIVLK FLDEITEAQK EEFFKTYVNL VNIIPAMKDV YWGKDVTQRN KEEGYTHIVE  60
VTFESVETIQ DYINHPAHVG FGDVYRSFWE KLLIFDYTPR K                      101

SEQ ID NO: 393         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 393
atggccgtca agcatttaat cgtcgtcaaa tttaaggacg gtatcacaga agctcaaaag  60
gaggaattct tcaaaaccta tgtaaactta gtgaacataa ttcctgctat gaaagatgtt  120
tattggggca aagacgtcgc ccaaaaaaac aaagaagaag gttacactca catcgtcgaa  180
gtcactttcg attcagtaga gacgatccaa gattacatag ttcacccggc ccatgtggga  240
ttcggagacg tttaccgtag cttctgggaa aaacttttga ttttcgacta taccccgaga  300
aaa                                                                303

SEQ ID NO: 394         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 394
MAVKHLIVVK FKDGITEAQK EEFFKTYVNL VNIIPAMKDV YWGKDVAQKN KEEGYTHIVE  60
```

```
VTFDSVETIQ DYIVHPAHVG FGDVYRSFWE KLLIFDYTPR K                  101

SEQ ID NO: 395          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 395
atggctgtca agcaccttat cgtactgaaa ttcttggacg aaattacaga agcccagaaa  60
gaagaatttt tcaagaccta tgtaaacctg gtgaatatca tccctgcgat gaaagatgtt  120
tattggggca aagacgtcac ccaaagaaac aaagaagaag gttacactca catcgtcgaa  180
gtcactttcg attcagtaga gacgatccaa gattacatat ctcacccggc ccatgtggga  240
ttcggagacg tttaccgtag cttctgggaa aaacttttga ttttcgacta taccccgaga  300
aaa                                                                303

SEQ ID NO: 396          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 396
MAVKHLIVLK FLDEITEAQK EEFFKTYVNL VNIIPAMKDV YWGKDVTQRN KEEGYTHIVE  60
VTFDSVETIQ DYISHPAHVG FGDVYRSFWE KLLIFDYTPR K                  101

SEQ ID NO: 397          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 397
atggctgtca agcaccttat cgtactgaaa ttcaaggacg aaattacaga agcccagaaa  60
gaagaatttt tcaagacctt tgtaaacctg gtgaatatca tccctgcgat gaaagatgtt  120
tattggggca aagacgtcac ccaaagaaac aaagaagaag gttacactca catcgtcgaa  180
gtcactttcg agtcagtaga gacgatccaa gattacataa atcacccggc ccatgtggga  240
ttcggagacg tttaccgtag cttctgggaa aaacttttga ttttcgacta taccccgaga  300
aaa                                                                303

SEQ ID NO: 398          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 398
MAVKHLIVLK FKDEITEAQK EEFFKTFVNL VNIIPAMKDV YWGKDVTQRN KEEGYTHIVE  60
VTFESVETIQ DYINHPAHVG FGDVYRSFWE KLLIFDYTPR K                  101

SEQ ID NO: 399          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 399
atgggtgtca agcaccttat cgtactgaaa ttcaaggacg aaattacaga agcccagaaa  60
gaagaatttt tcaagaccta tgtaaacctg gtgaatatca tccctgcgat gaaagatgtt  120
tattggggca aagacgtcac ccaaaaaaac aaagaagaag gttacactca catcgtcgaa  180
gtcactttca aatcagtaga gacgatccaa gattacataa tgcacccggc ccatgtggga  240
ttcggagacg tttaccgtag cttctgggaa aaacttttga ttttcgacta taccccgaga  300
aaa                                                                303

SEQ ID NO: 400          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 400
MGVKHLIVLK FKDEITEAQK EEFFKTYVNL VNIIPAMKDV YWGKDVTQKN KEEGYTHIVE  60
VTFKSVETIQ DYIMHPAHVG FGDVYRSFWE KLLIFDYTPR K                  101
```

```
SEQ ID NO: 401          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 401
atggctgtaa agcaccttat catcatcaaa ttcaaggacg aaattacaga agcccagaaa  60
gaagaatttt tcaagaccta tgtaaacctg gtgaatgtca tccctgcgat gaaagatgtt  120
tattggggca aagacgtcac ccaacgtaac aaagaagaag gttactcaca catcgtcgaa  180
gtcactttcg agtcagtaga gacgatccaa acctacataa tacacccggc ccatgtggga  240
ttcggagacg tttaccgtag cttctgggaa aaacttttga ttttcgacta taccccgaga  300
aaa                                                                303

SEQ ID NO: 402          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 402
MAVKHLIIIK FKDEITEAQK EEFFKTYVNL VNVIPAMKDV YWGKDVTQRN KEEGYSHIVE  60
VTFESVETIQ TYIIHPAHVG FGDVYRSFWE KLLIFDYTPR K                      101

SEQ ID NO: 403          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 403
atggctgtca agcaccttat catcatcaaa ttcaaggacg aaattacaga agcccagaaa  60
gaagaatttt tcaagaccta tgtaaacctg gtgaatgaca tccctgcgat gaaagatgtt  120
tattggggca aagacgtcac ccaacgtaac aaagaagaag gttactcaca cgtcgtcgaa  180
gtcactttcg agtcagtaga gacgatccaa gattacataa tacacccggc ccatgtggga  240
ttcggagacg tttaccgtag cttctgggaa aaacttttga ttttcgacta taccccgaga  300
aaa                                                                303

SEQ ID NO: 404          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 404
MAVKHLIIIK FKDEITEAQK EEFFKTYVNL VNDIPAMKDV YWGKDVTQRN KEEGYSHVVE  60
VTFESVETIQ DYIIHPAHVG FGDVYRSFWE KLLIFDYTPR K                      101

SEQ ID NO: 405          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 405
atggctgtca agcaccttat catcatcaaa ttcaacgacg aaattacaga agcccagaaa  60
gaagaatttt tcaagaccta tgtaaacctg gtgaatatca tccctgcgat gaaagatgtt  120
tattggggca aagacgtcac ccaacgtaac aaagaagaag gttggtcaca catcgtcgaa  180
gtcactttcg agtcagtaga gacgatccaa gattacataa tacacccggc ccatgtggga  240
ttcggagacg tttaccgtag cttctgggaa aaacttttga ttttcgacta taccccgaga  300
aag                                                                303

SEQ ID NO: 406          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 406
MAVKHLIIIK FNDEITEAQK EEFFKTYVNL VNIIPAMKDV YWGKDVTQRN KEEGWSHIVE  60
VTFESVETIQ DYIIHPAHVG FGDVYRSFWE KLLIFDYTPR K                      101
```

-continued

```
SEQ ID NO: 407         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 407
atggctgtca agcaccttat catcatcaaa ttcgtcgacg aaattacaga agcccagaaa  60
gaagaatttt tcaagaccta tgtaaacctg gtgaatgtca tccctgcgat gaaagatgtt  120
tattggggca aagacgtcac ccaaaaaaac aaagaagaag gttactcaca catcgtcgaa  180
gtcactttcg actcagtaga gacgatccaa gattacataa tacacccggc ccatgtggga  240
ttcggagacg tttaccgtag cttctgggaa aaacttttga ttttcgacta taccccgaga  300
aaa                                                                303

SEQ ID NO: 408         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 408
MAVKHLIIIK FVDEITEAQK EEFFKTYVNL VNVIPAMKDV YWGKDVTQKN KEEGYSHIVE  60
VTFDSVETIQ DYIIHPAHVG FGDVYRSFWE KLLIFDYTPR K                      101

SEQ ID NO: 409         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 409
atggctgtaa agcaccttat cgtaatcaaa ttcgtcgacg aaattacaga agcccagaaa  60
gaagaatttt tcaagaccta tgtaaacctg gtgaatgtca tccctgcgat gaaagatgtt  120
tattggggca aagacgtcac ccaaaaaaac aaagaagaag gttactcaca cgtcgtcgaa  180
gtcactttcg actcagtaga gacgatccaa gattacataa tacacccggc tcatgtggga  240
ttcggagacg tttaccgtag cttctgggaa aaacttttga ttttcgacta taccccgaga  300
aaa                                                                303

SEQ ID NO: 410         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 410
MAVKHLIVIK FVDEITEAQK EEFFKTYVNL VNVIPAMKDV YWGKDVTQKN KEEGYSHVVE  60
VTFDSVETIQ DYIIHPAHVG FGDVYRSFWE KLLIFDYTPR K                      101

SEQ ID NO: 411         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 411
atgccggtca agcaccttat catcatcaaa ttcaaggacg aaattacaga agcccagaaa  60
gaagaatttt tcaagaccta tgtaaacctg gtgaatatca tccctgcgat gaaagatgtt  120
tattggggca aagacgtcac ccaaaaaaac aaagaagaag gttacactca catcgtcgaa  180
gtcactttcg actcagtaga gtcaatccaa gattacataa tacacccggc ccatgtggga  240
ttcggagacg tttaccgtag cttctgggaa aaacttttga ttttcgacta taccccggga  300
aaa                                                                303

SEQ ID NO: 412         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 412
MPVKHLIIIK FKDEITEAQK EEFFKTYVNL VNIIPAMKDV YWGKDVTQKN KEEGYTHIVE  60
VTFDSVESIQ DYIIHPAHVG FGDVYRSFWE KLLIFDYTPG K                      101

SEQ ID NO: 413         moltype = DNA  length = 303
```

```
FEATURE                Location/Qualifiers
misc_feature           1..303
                       note = Synthetic biopolymer
source                 1..303
                       mol_type = other DNA
                       organism = synthetic construct
SEQUENCE: 413
atggctgtca agcaccttat catcctgaaa ttcgtcgacg aaattacaga agcccagaaa  60
gaagaatttt tcaagaccta tgtaaacctg gtgaatatca tccctgcgat gaaagatgtt  120
tattggggca aagacgtcac ccaaaaaaac aaagaagaag gttactcaca cgtcgtcgaa  180
gtcactttcg actcagtaga gacgatccaa gattacataa tacacccggc ccatgtggga  240
ttcggagacg tttaccgtag cttctgggaa aaactttga ttttcgactt caccccgaga  300
aaa                                                                303

SEQ ID NO: 414         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 414
MAVKHLIILK FVDEITEAQK EEFFKTYVNL VNIIPAMKDV YWGKDVTQKN KEEGYSHVVE  60
VTFDSVETIQ DYIIHPAHVG FGDVYRSFWE KLLIFDFTPR K                     101

SEQ ID NO: 415         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 415
atggctgtca agcaccttat cgtactgaaa ttcaaggacg aaattacaga agcccagaaa  60
gaagaatttt tcaagaccta tgtaaacctg atgaatatca tccctgcgat gaaagatgtt  120
tattggggca aagacgtcac ccaacgtaac aaagaagaag gttacactca cgtcgtcgaa  180
gtctgtttcg actcagtaga ggccatccaa gattacataa tacacccggc ccatgtggga  240
ttcggagacg tttaccgtag cttctgggaa aaacttttga ttttcgacta taccccgaga  300
aaa                                                                303

SEQ ID NO: 416         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 416
MAVKHLIVLK FKDEITEAQK EEFFKTYVNL MNIIPAMKDV YWGKDVTQRN KEEGYTHVVE  60
VCFDSVEAIQ DYIIHPAHVG FGDVYRSFWE KLLIFDYTPR K                     101

SEQ ID NO: 417         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 417
atggctgtca agcaccttat catcctgaaa ttcaaggacg aaattacaga agcccagaaa  60
gaagaatttt tcaagaccta tgtaaacctg gtgaatatca tccctgcgat gaaagatgtt  120
tattggggca aagacgtcac ccaacgtaac aaagaagaag gttacactca cgtcgtcgaa  180
gtcactttcg actcagtaga gatgatccaa gattacataa tgcacccggc ccatgtggga  240
ttcggagacg tttaccgtag cttctgggaa aaacttttga ttttcgacta taccccgaga  300
aaa                                                                303

SEQ ID NO: 418         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 418
MAVKHLIILK FKDEITEAQK EEFFKTYVNL VNIIPAMKDV YWGKDVTQRN KEEGYTHVVE  60
VTFDSVEMIQ DYIMHPAHVG FGDVYRSFWE KLLIFDYTPR K                     101

SEQ ID NO: 419         moltype = DNA  length = 303
FEATURE                Location/Qualifiers
```

```
misc_feature           1..303
                       note = Synthetic biopolymer
source                 1..303
                       mol_type = other DNA
                       organism = synthetic construct
SEQUENCE: 419
atggctgtaa agcaccttat cgtactgaaa ttcaaggacg aaattacaga agcccagaaa  60
gaagaatttt tcaagaccta tgtaaacctg gtgaatatca tccctccgat gaaagatgtt  120
tattggggca aagacgtcac ccaaaaaaac aaagaagaag gttacactca cgtcgtcgaa  180
gtcactttcg actcagtaga gggaatcaaa gattacataa tgcacccggc ccatgtggga  240
ttcggagacg tttaccgtag cttctgggaa aaacttttga ttttcgacta taccccgaga  300
aaa                                                                303

SEQ ID NO: 420         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 420
MAVKHLIVLK FKDEITEAQK EEFFKTYVNL VNIIPPMKDV YWGKDVTQKN KEEGYTHVVE  60
VTFDSVEGIK DYIMHPAHVG FGDVYRSFWE KLLIFDYTPR K                      101

SEQ ID NO: 421         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 421
atggctgtaa agcaccttat cgtactgaaa ttcaaggacg gaattacaga agcccagaaa  60
gaagaatttt tcaagaccta tgtaaacctg gtgaatatca tccctcaaat gaaagatgtt  120
tattggggca aagacgtcac ccaacgtaac aaagaagaag gttacactca cgtcgtcgaa  180
gtcactttcg actcagtaga gacgatcaaa gattacataa tacacccggc ccatgtggga  240
ttcggagacg tttaccgtag cttctgggaa aaacttttga ttttcgacta taccccgaga  300
aaa                                                                303

SEQ ID NO: 422         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 422
MAVKHLIVLK FKDGITEAQK EEFFKTYVNL VNIIPQMKDV YWGKDVTQRN KEEGYTHVVE  60
VTFDSVETIK DYIIHPAHVG FGDVYRSFWE KLLIFDYTPR K                      101

SEQ ID NO: 423         moltype = DNA  length = 25
FEATURE                Location/Qualifiers
misc_feature           1..25
                       note = Synthetic biopolymer
source                 1..25
                       mol_type = other DNA
                       organism = synthetic construct
SEQUENCE: 423
ctaagtctag ccacgaaaac tgcaa                                        25

SEQ ID NO: 424         moltype = DNA  length = 30
FEATURE                Location/Qualifiers
misc_feature           1..30
                       note = Synthetic biopolymer
source                 1..30
                       mol_type = other DNA
                       organism = synthetic construct
SEQUENCE: 424
ggttatgaag aggaaaaatt ggcagtaacc                                   30

SEQ ID NO: 425         moltype = DNA  length = 30
FEATURE                Location/Qualifiers
misc_feature           1..30
                       note = Synthetic biopolymer
source                 1..30
                       mol_type = other DNA
                       organism = synthetic construct
SEQUENCE: 425
gaacgaatca aattaacaac cataggatga                                   30
```

```
SEQ ID NO: 426          moltype = DNA  length = 28
FEATURE                 Location/Qualifiers
misc_feature            1..28
                        note = Synthetic biopolymer
source                  1..28
                        mol_type = other DNA
                        organism = synthetic construct
SEQUENCE: 426
gcaccaaaag taagaaacga caaagttt                                    28

SEQ ID NO: 427          moltype = DNA  length = 50
FEATURE                 Location/Qualifiers
misc_feature            1..50
                        note = Synthetic biopolymer
source                  1..50
                        mol_type = other DNA
                        organism = synthetic construct
SEQUENCE: 427
caaaaaattg ttaatatacc tctatacttt aacgtcaagg agaaaaaacc            50

SEQ ID NO: 428          moltype = DNA  length = 50
FEATURE                 Location/Qualifiers
misc_feature            1..50
                        note = Synthetic biopolymer
source                  1..50
                        mol_type = other DNA
                        organism = synthetic construct
SEQUENCE: 428
taaattgaat tgaattgaaa tcgatagatc aattttttc ttttctcttt             50

SEQ ID NO: 429          moltype = DNA  length = 667
FEATURE                 Location/Qualifiers
misc_feature            1..667
                        note = Synthetic biopolymer
source                  1..667
                        mol_type = other DNA
                        organism = synthetic construct
SEQUENCE: 429
ttttcaaaaa ttcttacttt ttttttggat ggacgcaaag aagtttaata atcatattac  60
atggcattac caccatatac atatccatat acatatccat atctaatctt acttatatgt  120
tgtggaaatg taaagagccc cattatctta gcctaaaaaa accttctctt tggaactttc  180
agtaatacgc ttaactgctc attgctatat tgaagtacgg attagaagcc gccgagcggg  240
tgacagccct ccgaaggaag actctcctcc gtgcgtcctc gtcttcaccg gtcgcgttcc  300
tgaaacgcag atgtgcctcg cgccgcactg ctccgaacaa taaagattct acaatactag  360
cttttatggt tatgaagagg aaaaattggc agtaacctgg ccccacaaac cttcaaatga  420
acgaatcaaa ttaacaacca taggatgata atgcgattag ttttttagcc ttatttctgg  480
ggtaattaat cagcgaagcg atgatttttg atctattaac agatatataa atgcaaaaac  540
tgcataacca ctttaactaa tactttcaac attttcggtt tgtattactt cttattcaaa  600
tgtaataaaa gtatcaacaa aaaattgtta atatacctct atactttaac gtcaaggaga  660
aaaaacc                                                            667

SEQ ID NO: 430          moltype = DNA  length = 225
FEATURE                 Location/Qualifiers
misc_feature            1..225
                        note = Synthetic biopolymer
source                  1..225
                        mol_type = other DNA
                        organism = synthetic construct
SEQUENCE: 430
attgaattga attgaaatcg atagatcaat ttttttcttt tctctttccc catcctttac  60
gctaaaataa tagtttattt tattttttga atattttttta tttatatacg tatatataga  120
ctattattta tcttttaatg attattaaga tttttattaa aaaaaaattc gctcctcttt  180
taatgccttt atgcagtttt tttttcccat tcgatatttc tatgt                   225

SEQ ID NO: 431          moltype = DNA  length = 42
FEATURE                 Location/Qualifiers
misc_feature            1..42
                        note = Synthetic biopolymer
source                  1..42
                        mol_type = other DNA
                        organism = synthetic construct
SEQUENCE: 431
tacgataagg tgcttgacac ccatggtttt ttctccttga cg                    42

SEQ ID NO: 432          moltype = DNA  length = 42
FEATURE                 Location/Qualifiers
misc_feature            1..42
                        note = Synthetic biopolymer
```

```
source                  1..42
                        mol_type = other DNA
                        organism = synthetic construct
SEQUENCE: 432
ttcttctttc tgggcttctt gaatttcgtc cttgaatttc ag                    42

SEQ ID NO: 433          moltype = DNA  length = 42
FEATURE                 Location/Qualifiers
misc_feature            1..42
                        note = Synthetic biopolymer
source                  1..42
                        mol_type = other DNA
                        organism = synthetic construct
SEQUENCE: 433
gacgatgtga gtgtaacctc tttctttgtt tttttgggtg ac                    42

SEQ ID NO: 434          moltype = DNA  length = 42
FEATURE                 Location/Qualifiers
misc_feature            1..42
                        note = Synthetic biopolymer
source                  1..42
                        mol_type = other DNA
                        organism = synthetic construct
SEQUENCE: 434
cgtctctact gactcgaaac cgacttcgac gatgtgagtg ta                    42

SEQ ID NO: 435          moltype = DNA  length = 42
FEATURE                 Location/Qualifiers
misc_feature            1..42
                        note = Synthetic biopolymer
source                  1..42
                        mol_type = other DNA
                        organism = synthetic construct
SEQUENCE: 435
tattatgtaa tcttggattt cctctactga ctcgaaagtg ac                    42

SEQ ID NO: 436          moltype = DNA  length = 42
FEATURE                 Location/Qualifiers
misc_feature            1..42
                        note = Synthetic biopolymer
source                  1..42
                        mol_type = other DNA
                        organism = synthetic construct
SEQUENCE: 436
tcccacatgg gccgggtgca ttatgtaatc ttggatcgtc tc                    42

SEQ ID NO: 437          moltype = DNA  length = 42
FEATURE                 Location/Qualifiers
misc_feature            1..42
                        note = Synthetic biopolymer
source                  1..42
                        mol_type = other DNA
                        organism = synthetic construct
SEQUENCE: 437
ttcccagaag ctacggtaaa tgtctccgaa tcccacatgg gc                    42

SEQ ID NO: 438          moltype = DNA  length = 42
FEATURE                 Location/Qualifiers
misc_feature            1..42
                        note = Synthetic biopolymer
source                  1..42
                        mol_type = other DNA
                        organism = synthetic construct
SEQUENCE: 438
ccaataaaca tctttcattt cagggatgat attcaccagg tt                    42

SEQ ID NO: 439          moltype = DNA  length = 42
FEATURE                 Location/Qualifiers
misc_feature            1..42
                        note = Synthetic biopolymer
source                  1..42
                        mol_type = other DNA
                        organism = synthetic construct
SEQUENCE: 439
gacgatgtga gtgtaaccaa attctttgtt tttttgggtg ac                    42

SEQ ID NO: 440          moltype = DNA  length = 42
FEATURE                 Location/Qualifiers
misc_feature            1..42
```

```
                         note = Synthetic biopolymer
source                   1..42
                         mol_type = other DNA
                         organism = synthetic construct
SEQUENCE: 440
ttggatcgtc tctactgatt tgaaagtgac ttcgacgatg tg                    42

SEQ ID NO: 441           moltype = DNA  length = 42
FEATURE                  Location/Qualifiers
misc_feature             1..42
                         note = Synthetic biopolymer
source                   1..42
                         mol_type = other DNA
                         organism = synthetic construct
SEQUENCE: 441
tattatgtaa tcttggatag actctactga ctcgaaagtg ac                    42

SEQ ID NO: 442           moltype = DNA  length = 42
FEATURE                  Location/Qualifiers
misc_feature             1..42
                         note = Synthetic biopolymer
source                   1..42
                         mol_type = other DNA
                         organism = synthetic construct
SEQUENCE: 442
tcccacatgg gccgggtgac ctatgtaatc ttggatcgtc tc                    42

SEQ ID NO: 443           moltype = DNA  length = 42
FEATURE                  Location/Qualifiers
misc_feature             1..42
                         note = Synthetic biopolymer
source                   1..42
                         mol_type = other DNA
                         organism = synthetic construct
SEQUENCE: 443
ttcccagaag ctacggtaca tgtctccgaa tcccacatgg gc                    42

SEQ ID NO: 444           moltype = DNA  length = 42
FEATURE                  Location/Qualifiers
misc_feature             1..42
                         note = Synthetic biopolymer
source                   1..42
                         mol_type = other DNA
                         organism = synthetic construct
SEQUENCE: 444
aatttcgtcc ttgaatttaa ctacgataag gtgcttgaca gc                    42

SEQ ID NO: 445           moltype = DNA  length = 42
FEATURE                  Location/Qualifiers
misc_feature             1..42
                         note = Synthetic biopolymer
source                   1..42
                         mol_type = other DNA
                         organism = synthetic construct
SEQUENCE: 445
agggatgata ttcaccagac ctacataggt cttgaaaaat tc                    42

SEQ ID NO: 446           moltype = DNA  length = 42
FEATURE                  Location/Qualifiers
misc_feature             1..42
                         note = Synthetic biopolymer
source                   1..42
                         mol_type = other DNA
                         organism = synthetic construct
SEQUENCE: 446
gacgatgtga gtgtaaccag attctttgtt tttttgggtg ac                    42

SEQ ID NO: 447           moltype = DNA  length = 42
FEATURE                  Location/Qualifiers
misc_feature             1..42
                         note = Synthetic biopolymer
source                   1..42
                         mol_type = other DNA
                         organism = synthetic construct
SEQUENCE: 447
ttggatcgtc tctactgaat cgaaagtgac ttcgacgatg tg                    42

SEQ ID NO: 448           moltype = DNA  length = 42
FEATURE                  Location/Qualifiers
```

```
misc_feature           1..42
                       note = Synthetic biopolymer
source                 1..42
                       mol_type = other DNA
                       organism = synthetic construct
SEQUENCE: 448
ggccgggtgt attatgtaac cttggatcgt ctctactgac tc                    42

SEQ ID NO: 449         moltype = DNA  length = 42
FEATURE                Location/Qualifiers
misc_feature           1..42
                       note = Synthetic biopolymer
source                 1..42
                       mol_type = other DNA
                       organism = synthetic construct
SEQUENCE: 449
caaaagtttt tcccagaatt tacggtaaac gtctccgaat cc                    42

SEQ ID NO: 450         moltype = DNA  length = 42
FEATURE                Location/Qualifiers
misc_feature           1..42
                       note = Synthetic biopolymer
source                 1..42
                       mol_type = other DNA
                       organism = synthetic construct
SEQUENCE: 450
aatttcgtcc ttgaatttaa ttacgataag gtgcttgaca gc                    42

SEQ ID NO: 451         moltype = DNA  length = 42
FEATURE                Location/Qualifiers
misc_feature           1..42
                       note = Synthetic biopolymer
source                 1..42
                       mol_type = other DNA
                       organism = synthetic construct
SEQUENCE: 451
catcgcaggg atgatattag acaggtttac ataggtcttg aa                    42

SEQ ID NO: 452         moltype = DNA  length = 42
FEATURE                Location/Qualifiers
misc_feature           1..42
                       note = Synthetic biopolymer
source                 1..42
                       mol_type = other DNA
                       organism = synthetic construct
SEQUENCE: 452
gtttttttgg gtgacgtctg ggccccaata aacatctttc at                    42

SEQ ID NO: 453         moltype = DNA  length = 42
FEATURE                Location/Qualifiers
misc_feature           1..42
                       note = Synthetic biopolymer
source                 1..42
                       mol_type = other DNA
                       organism = synthetic construct
SEQUENCE: 453
gacgatgtga gtgtaaccca attctttgtt tttttgggtg ac                    42

SEQ ID NO: 454         moltype = DNA  length = 42
FEATURE                Location/Qualifiers
misc_feature           1..42
                       note = Synthetic biopolymer
source                 1..42
                       mol_type = other DNA
                       organism = synthetic construct
SEQUENCE: 454
gtaatcttgg atcgtctcca atgactcgaa agtgacttcg ac                    42

SEQ ID NO: 455         moltype = DNA  length = 42
FEATURE                Location/Qualifiers
misc_feature           1..42
                       note = Synthetic biopolymer
source                 1..42
                       mol_type = other DNA
                       organism = synthetic construct
SEQUENCE: 455
tcccacatgg gccgggtgat ttatgtaatc ttggatcgtc tc                    42

SEQ ID NO: 456         moltype = DNA  length = 42
```

```
FEATURE                Location/Qualifiers
misc_feature           1..42
                       note = Synthetic biopolymer
source                 1..42
                       mol_type = other DNA
                       organism = synthetic construct
SEQUENCE: 456
atagtcgaaa atcaaaagtt cttcccagaa gctacggtaa ac                     42

SEQ ID NO: 457         moltype = DNA  length = 42
FEATURE                Location/Qualifiers
misc_feature           1..42
                       note = Synthetic biopolymer
source                 1..42
                       mol_type = other DNA
                       organism = synthetic construct
SEQUENCE: 457
caccaggttt acataggtag agaaaaattc ttctttctgg gc                     42

SEQ ID NO: 458         moltype = DNA  length = 42
FEATURE                Location/Qualifiers
misc_feature           1..42
                       note = Synthetic biopolymer
source                 1..42
                       mol_type = other DNA
                       organism = synthetic construct
SEQUENCE: 458
catcgcaggg atgatattca tcaggtttac ataggtcttg aa                     42

SEQ ID NO: 459         moltype = DNA  length = 42
FEATURE                Location/Qualifiers
misc_feature           1..42
                       note = Synthetic biopolymer
source                 1..42
                       mol_type = other DNA
                       organism = synthetic construct
SEQUENCE: 459
gacgatgtga gtgtaaccat gttctttgtt tttttgggtg ac                     42

SEQ ID NO: 460         moltype = DNA  length = 42
FEATURE                Location/Qualifiers
misc_feature           1..42
                       note = Synthetic biopolymer
source                 1..42
                       mol_type = other DNA
                       organism = synthetic construct
SEQUENCE: 460
tattatgtaa tcttggattt gctctactga ctcgaaagtg ac                     42

SEQ ID NO: 461         moltype = DNA  length = 42
FEATURE                Location/Qualifiers
misc_feature           1..42
                       note = Synthetic biopolymer
source                 1..42
                       mol_type = other DNA
                       organism = synthetic construct
SEQUENCE: 461
tcccacatgg gccgggtgaa ctatgtaatc ttggatcgtc tc                     42

SEQ ID NO: 462         moltype = DNA  length = 42
FEATURE                Location/Qualifiers
misc_feature           1..42
                       note = Synthetic biopolymer
source                 1..42
                       mol_type = other DNA
                       organism = synthetic construct
SEQUENCE: 462
tctcggggta tagtcgaatt tcaaaagttt ttcccagaag ct                     42

SEQ ID NO: 463         moltype = DNA  length = 42
FEATURE                Location/Qualifiers
misc_feature           1..42
                       note = Synthetic biopolymer
source                 1..42
                       mol_type = other DNA
                       organism = synthetic construct
SEQUENCE: 463
ggcttctgta atttcgtcca agaatttcag tacgataagg tg                     42
```

```
SEQ ID NO: 464         moltype = DNA  length = 42
FEATURE                Location/Qualifiers
misc_feature           1..42
                       note = Synthetic biopolymer
source                 1..42
                       mol_type = other DNA
                       organism = synthetic construct
SEQUENCE: 464
caccaggttt acataggtac cgaaaaattc ttctttctgg gc                    42

SEQ ID NO: 465         moltype = DNA  length = 42
FEATURE                Location/Qualifiers
misc_feature           1..42
                       note = Synthetic biopolymer
source                 1..42
                       mol_type = other DNA
                       organism = synthetic construct
SEQUENCE: 465
catcgcaggg atgatatttt ccaggtttac ataggtcttg aa                    42

SEQ ID NO: 466         moltype = DNA  length = 42
FEATURE                Location/Qualifiers
misc_feature           1..42
                       note = Synthetic biopolymer
source                 1..42
                       mol_type = other DNA
                       organism = synthetic construct
SEQUENCE: 466
gtaaccttct tctttgtttc tttgggtgac gtctttgccc ca                    42

SEQ ID NO: 467         moltype = DNA  length = 42
FEATURE                Location/Qualifiers
misc_feature           1..42
                       note = Synthetic biopolymer
source                 1..42
                       mol_type = other DNA
                       organism = synthetic construct
SEQUENCE: 467
gacgatgtga gtgtaaccag cttctttgtt tttttgggtg ac                    42

SEQ ID NO: 468         moltype = DNA  length = 42
FEATURE                Location/Qualifiers
misc_feature           1..42
                       note = Synthetic biopolymer
source                 1..42
                       mol_type = other DNA
                       organism = synthetic construct
SEQUENCE: 468
tattatgtaa tcttggatag cctctactga ctcgaaagtg ac                    42

SEQ ID NO: 469         moltype = DNA  length = 42
FEATURE                Location/Qualifiers
misc_feature           1..42
                       note = Synthetic biopolymer
source                 1..42
                       mol_type = other DNA
                       organism = synthetic construct
SEQUENCE: 469
tcccacatgg gccgggtgag ttatgtaatc ttggatcgtc tc                    42

SEQ ID NO: 470         moltype = DNA  length = 42
FEATURE                Location/Qualifiers
misc_feature           1..42
                       note = Synthetic biopolymer
source                 1..42
                       mol_type = other DNA
                       organism = synthetic construct
SEQUENCE: 470
tttctgggct tctgtaatac cgtccttgaa tttcagtacg at                    42

SEQ ID NO: 471         moltype = DNA  length = 42
FEATURE                Location/Qualifiers
misc_feature           1..42
                       note = Synthetic biopolymer
source                 1..42
                       mol_type = other DNA
                       organism = synthetic construct
SEQUENCE: 471
caccaggttt acataggttc tgaaaaattc ttctttctgg gc                    42
```

```
SEQ ID NO: 472          moltype = DNA  length = 42
FEATURE                 Location/Qualifiers
misc_feature            1..42
                        note = Synthetic biopolymer
source                  1..42
                        mol_type = other DNA
                        organism = synthetic construct
SEQUENCE: 472
gatgtgagtg taaccttctt gtttgttttt ttgggtgacg tc                     42

SEQ ID NO: 473          moltype = DNA  length = 42
FEATURE                 Location/Qualifiers
misc_feature            1..42
                        note = Synthetic biopolymer
source                  1..42
                        mol_type = other DNA
                        organism = synthetic construct
SEQUENCE: 473
tattatgtaa tcttggatac cctctactga ctcgaaagtg ac                     42

SEQ ID NO: 474          moltype = DNA  length = 42
FEATURE                 Location/Qualifiers
misc_feature            1..42
                        note = Synthetic biopolymer
source                  1..42
                        mol_type = other DNA
                        organism = synthetic construct
SEQUENCE: 474
tcccacatgg gccgggtgag atatgtaatc ttggatcgtc tc                     42

SEQ ID NO: 475          moltype = DNA  length = 42
FEATURE                 Location/Qualifiers
misc_feature            1..42
                        note = Synthetic biopolymer
source                  1..42
                        mol_type = other DNA
                        organism = synthetic construct
SEQUENCE: 475
ttcttctttc tgggcttctg gaatttcgtc cttgaatttc ag                     42

SEQ ID NO: 476          moltype = DNA  length = 42
FEATURE                 Location/Qualifiers
misc_feature            1..42
                        note = Synthetic biopolymer
source                  1..42
                        mol_type = other DNA
                        organism = synthetic construct
SEQUENCE: 476
gatgtgagtg taaccttctc ttttgttttt ttgggtgacg tc                     42

SEQ ID NO: 477          moltype = DNA  length = 42
FEATURE                 Location/Qualifiers
misc_feature            1..42
                        note = Synthetic biopolymer
source                  1..42
                        mol_type = other DNA
                        organism = synthetic construct
SEQUENCE: 477
gaaagtgact tcgacgatac cagtgtaacc ttcttctttg tt                     42

SEQ ID NO: 478          moltype = DNA  length = 42
FEATURE                 Location/Qualifiers
misc_feature            1..42
                        note = Synthetic biopolymer
source                  1..42
                        mol_type = other DNA
                        organism = synthetic construct
SEQUENCE: 478
tattatgtaa tcttggatca tctctactga ctcgaaagtg ac                     42

SEQ ID NO: 479          moltype = DNA  length = 42
FEATURE                 Location/Qualifiers
misc_feature            1..42
                        note = Synthetic biopolymer
source                  1..42
                        mol_type = other DNA
                        organism = synthetic construct
SEQUENCE: 479
```

```
tacgataagg tgcttgacac ccatggtttt ttctccttga cg                    42

SEQ ID NO: 480          moltype = DNA  length = 30
FEATURE                 Location/Qualifiers
misc_feature            1..30
                        note = Synthetic biopolymer
source                  1..30
                        mol_type = other DNA
                        organism = synthetic construct
SEQUENCE: 480
ggttatgaag aggaaaaatt ggcagtaacc                                  30

SEQ ID NO: 481          moltype = DNA  length = 60
FEATURE                 Location/Qualifiers
misc_feature            1..60
                        note = Synthetic biopolymer
source                  1..60
                        mol_type = other DNA
                        organism = synthetic construct
SEQUENCE: 481
ctttaacact atcaagtgct ttacagccat ggtttttct ccttgacgtt aaagtataga  60

SEQ ID NO: 482          moltype = DNA  length = 32
FEATURE                 Location/Qualifiers
misc_feature            1..32
                        note = Synthetic biopolymer
source                  1..32
                        mol_type = other DNA
                        organism = synthetic construct
SEQUENCE: 482
ggaaacctct acacatagaa atatcgaatg gg                               32

SEQ ID NO: 483          moltype = DNA  length = 60
FEATURE                 Location/Qualifiers
misc_feature            1..60
                        note = Synthetic biopolymer
source                  1..60
                        mol_type = other DNA
                        organism = synthetic construct
SEQUENCE: 483
ttgttaattt ttgattacac tccaaggaag taaattgaat tgaattgaaa tcgatagatc  60

SEQ ID NO: 484          moltype = DNA  length = 30
FEATURE                 Location/Qualifiers
misc_feature            1..30
                        note = Synthetic biopolymer
source                  1..30
                        mol_type = other DNA
                        organism = synthetic construct
SEQUENCE: 484
gaggagcgaa ttttttttta ataaaaatct                                  30

SEQ ID NO: 485          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 485
atgccggtca agcaccttat catcatcaaa ttcaaggacg aaattacaga agcccagaaa  60
gaagaatttt tcaagaccta tgtaaacctg gtgaatgtca tccctgcgat gaaagatgtt  120
tattggggca aagacgtcac ccaaaaaaac aaagaagaag gttacactca catcgtcgaa  180
gtcactttcg actcagtaga gacgatccaa gattacataa tacacccggc ccatgtggga  240
ttcggagacg tttaccgtag cttctgggaa aaacttttga aattcgacta taccccgaga  300
aaa                                                               303

SEQ ID NO: 486          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 486
MPVKHLIIIK FKDEITEAQK EEFFKTYVNL VNVIPAMKDV YWGKDVTQKN KEEGYTHIVE  60
VTFDSVETIQ DYIIHPAHVG FGDVYRSFWE KLLKFDYTPR K                     101

SEQ ID NO: 487          moltype = DNA  length = 303
```

```
FEATURE                Location/Qualifiers
misc_feature           1..303
                       note = Synthetic biopolymer
source                 1..303
                       mol_type = other DNA
                       organism = synthetic construct
SEQUENCE: 487
atggctgtca agcaccttat catcatcaaa ttcaaggacg aaattacaga agcccagaaa  60
gaagaatttt tcaagaccta tgtaaacctg gtgaatatca tcccttcaat gaaagatgtt  120
tattggggca aagacgtcac ccaaaaaaac aaagaagaag gttggactca catcgtcgaa  180
gtcactttcg actcagtaga gacgatccaa gattacataa tacacccggc ccatgtggga  240
ttcggagacg tttaccgtag cttctgggaa aaacttttga aattcgacta taccccgaga  300
aaa                                                                303

SEQ ID NO: 488         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 488
MAVKHLIIIK FKDEITEAQK EEFFKTYVNL VNIIPSMKDV YWGKDVTQKN KEEGWTHIVE  60
VTFDSVETIQ DYIIHPAHVG FGDVYRSFWE KLLKFDYTPR K                     101

SEQ ID NO: 489         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 489
atggctgtca agcaccttat catcatcaaa ttcaaggacg aaattacaga agcccagaaa  60
gaagaatttt tcaagaccta tgtaaacctg gtgaatgtca tccctgcgat gaaagatgtt  120
tattggggca aagacgtcac ccaacgtaac aaagaagaag gttacactca cgtcgtcgaa  180
gtctgtttcg agtcagtaga gacgatccaa gattacataa tacacccggc ccatgtggga  240
ttcggagacg tttaccgtag cttctgggaa aaacttttga ttttcgacta taccccgaga  300
aaa                                                                303

SEQ ID NO: 490         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 490
MAVKHLIIIK FKDEITEAQK EEFFKTYVNL VNVIPAMKDV YWGKDVTQRN KEEGYTHVVE  60
VCFESVETIQ DYIIHPAHVG FGDVYRSFWE KLLIFDYTPR K                     101

SEQ ID NO: 491         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 491
atggctgtca agcaccttat catcatcaaa ttcaaggacg aaattacaga agcccagaaa  60
gaagaatttt tcaagaccta tgtaaacctg gtgaatgtca tccctgcgat gaaagatgtt  120
tattggggca aagacgtcac ccaacgtaac aaagaagaag gttacactca cgtcgtcgaa  180
gtctgtttcg agtcagtaga gacgatccaa gattacataa tacacccggc ccatgtggga  240
ttcggagacg tttaccgtag cttctgggaa aaacttttga ttttcgacta taccccgaga  300
aaa                                                                303

SEQ ID NO: 492         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 492
MAVKHLIIIK FKDEITEAQK EEFFKTYVNL VNVIPAMKDV YWGKDVTQRN KEEGYTHVVE  60
VCFESVETIQ DYIIHPAHVG FGDVYRSFWE KLLIFDYTPR K                     101

SEQ ID NO: 493         moltype = DNA  length = 303
FEATURE                Location/Qualifiers
```

```
misc_feature           1..303
                       note = Synthetic biopolymer
source                 1..303
                       mol_type = other DNA
                       organism = synthetic construct
SEQUENCE: 493
atggctgtca agcaccttat catcatcaaa ttcaaggacg aaattacaga agcccagaaa  60
gaagaatttt tcaagaccta tgtaaacctg gtgaatgaca tccctgcgat gaaagatgtt  120
tattggggca aagacgtcac ccaacgtaac aaagaagaag gttactcaca catcgtcgaa  180
gtcactttcg agtcagtaga gacgatccaa acctacataa tacacccggc ccatgtggga  240
ttcggagacg tttaccgtag cttctgggaa aaacttttga tttttgatta cactccaagg  300
aag                                                                303

SEQ ID NO: 494         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 494
MAVKHLIIIK FKDEITEAQK EEFFKTYVNL VNDIPAMKDV YWGKDVTQRN KEEGYSHIVE  60
VTFESVETIQ TYIIHPAHVG FGDVYRSFWE KLLIFDYTPR K                      101

SEQ ID NO: 495         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 495
atggctgtca agcaccttat catcatcaaa ttcaacgacg aaattacaga agcccagaaa  60
gaagaatttt tcaagaccta tgtaaacctg gtgaatgtca tccctgcgat gaaagatgtt  120
tattggggca aagacgtcac ccaacgtaac aaagaagaag gttacactca catcgtcgaa  180
gtcactttcg agtcagtaga gacgatccaa acctacataa tacacccggc ccatgtggga  240
ttcggagacg tttaccgtag cttctgggaa aaacttttga ttttcgacta taccccgaga  300
aaa                                                                303

SEQ ID NO: 496         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 496
MAVKHLIIIK FNDEITEAQK EEFFKTYVNL VNVIPAMKDV YWGKDVTQRN KEEGYTHIVE  60
VTFESVETIQ TYIIHPAHVG FGDVYRSFWE KLLIFDYTPR K                      101

SEQ ID NO: 497         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 497
atggctgtaa agcaccttat catcatcaaa ttcaaggacg aaattacaga agcccagaaa  60
gaagaatttt tcaagaccta tgtaaacctg gtgaatgtca tccctgcgat gaaagatgtt  120
tattggggca aagacgtcac ccaacgtaac aaagaagaag gttacactca cgtcgtcgaa  180
gtcactttcg agtcagtaga gacgatccaa gattacataa tacacccggc ccatgtggga  240
ttcggagacg tttaccgtag cttctgggaa aaacttttga ttttcgacta taccccggga  300
aaa                                                                303

SEQ ID NO: 498         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 498
MAVKHLIIIK FKDEITEAQK EEFFKTYVNL VNVIPAMKDV YWGKDVTQRN KEEGYTHVVE  60
VTFESVETIQ DYIIHPAHVG FGDVYRSFWE KLLIFDYTPG K                      101

SEQ ID NO: 499         moltype = DNA  length = 303
FEATURE                Location/Qualifiers
misc_feature           1..303
```

```
                        note = Synthetic biopolymer
source                  1..303
                        mol_type = other DNA
                        organism = synthetic construct
SEQUENCE: 499
atggctgtaa agcaccttat catcatcaaa ttcaacgacg aaattacaga agcccagaaa  60
gaagaatttt tcaagaccta tgtaaacctg gtgaatgtca tccctgcgat gaaagatgtt  120
tattggggca aagacgtcac ccaacgtaac aaagaagaag gttacactca catcgtcgaa  180
gtcactttcg agtcagtaga gacgatccaa acctacataa tacacccggc ccatgtggga  240
ttcggagacg tttaccgtag cttctgggaa aaacttttga tttttgatta cactccaagg  300
aag                                                               303

SEQ ID NO: 500          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 500
MAVKHLIIIK FNDEITEAQK EEFFKTYVNL VNVIPAMKDV YWGKDVTQRN KEEGYTHIVE  60
VTFESVETIQ TYIIHPAHVG FGDVYRSFWE KLLIFDYTPR K                     101

SEQ ID NO: 501          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 501
atggctgtca agcaccttat catcatcaaa ttcaaggacg aaattacaga agcccagaaa  60
gaagaatttt tcaagaccta tgtaaacctg gtgaatatca tccctgcgat gaaagatgtt  120
tattggggca aagacgtcac ccaacgtaac aaagaagaag gttggactca cgtcgtcgaa  180
gtcactttcg agtcagtaga gacgatccaa gattacataa tacacccggc ccatgtggga  240
ttcggagacg tttaccgtag cttctgggaa aaacttttga ttttcgacta taccccggga  300
aaa                                                               303

SEQ ID NO: 502          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 502
MAVKHLIIIK FKDEITEAQK EEFFKTYVNL VNIIPAMKDV YWGKDVTQRN KEEGWTHVVE  60
VTFESVETIQ DYIIHPAHVG FGDVYRSFWE KLLIFDYTPG K                     101

SEQ ID NO: 503          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 503
atggctgtca agcaccttat catcatcaaa ttcaaggacg aaattacaga agcccagaaa  60
gaagaatttt tcaagaccta tgtaaacctg gtgaatgtca tccctgcgat gaaagatgtt  120
tattggggca aagacgtcac ccaacgtaac aaagaagaag gttactcaca catcgtcgaa  180
gtcactttcg agtcagtaga gacgatccaa gattacataa tacacccggc ccatgtggga  240
ttcggagacg tttaccgtag cttctgggaa aaacttttga ttttcgacta taccccggga  300
aaa                                                               303

SEQ ID NO: 504          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 504
MAVKHLIIIK FKDEITEAQK EEFFKTYVNL VNVIPAMKDV YWGKDVTQRN KEEGYSHIVE  60
VTFESVETIQ DYIIHPAHVG FGDVYRSFWE KLLIFDYTPG K                     101

SEQ ID NO: 505          moltype = DNA  length = 303
FEATURE                 Location/Qualifiers
misc_feature            1..303
                        note = Synthetic biopolymer
```

```
source                  1..303
                        mol_type = other DNA
                        organism = synthetic construct
SEQUENCE: 505
atggctgtca agcaccttat catcatcaaa ttcaaggacg aaattacaga agcccagaaa  60
gaagaatttt tcaagaccta tgtaaacctg gtgaatgtca tccctttaat gaaagatgtt  120
tattggggca aagacgtcac ccaacgtaac aaagaagaag gttacactca cgtcgtcgaa  180
gtcactttcg agtcagtaga gacgatccaa gattacataa tacacccggc ccatgtggga  240
ttcggagacg tttaccgtag cttctgggaa aaacttttga ttttcgacta taccccgaga  300
aaa                                                                303

SEQ ID NO: 506          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 506
MAVKHLIIIK FKDEITEAQK EEFFKTYVNL VNVIPLMKDV YWGKDVTQRN KEEGYTHVVE  60
VTFESVETIQ DYIIHPAHVG FGDVYRSFWE KLLIFDYTPR K                      101

SEQ ID NO: 507          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 507
atggctgtaa agcaccttat cgtaatcaaa ttcaaggacg aaattacaga agcccagaaa  60
gaagaatttt tcaagaccta tgtaaacctg gtgaatgtca tccctcaaat gaaagatgtt  120
tattggggca aagacgtcac ccaaaaaaac aaagaagaag gttacactca cgtcgtcgaa  180
gtcactttcg actcagtaga gacgatccaa gattacataa tacacccggc ccatgtggga  240
ttcggagacg tttaccgtag cttctgggaa aaacttttga aattcgacta taccccgaga  300
aaa                                                                303

SEQ ID NO: 508          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 508
MAVKHLIVIK FKDEITEAQK EEFFKTYVNL VNVIPQMKDV YWGKDVTQKN KEEGYTHVVE  60
VTFDSVETIQ DYIIHPAHVG FGDVYRSFWE KLLKFDYTPR K                      101

SEQ ID NO: 509          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 509
atggctgtca agcaccttat catcatcgcc ttcaaggacg aaattacaga agcccagaaa  60
gaagaatttt tcaagaccta tgtaaacctg gtgaatgtca tccctgcgat gaaagatgtt  120
tattggggca aagacgtcac ccaaaaaaac aaagaagaag gttactcaca cgtcgtcgaa  180
gtcactttcg agtcagtaga gacgatccaa gattacataa tacacccggc ccatgtggga  240
ttcggagacg tttaccgtag cttctgggaa aaacttttga ttttcgacta taccccgaga  300
aaa                                                                303

SEQ ID NO: 510          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 510
MAVKHLIIIA FKDEITEAQK EEFFKTYVNL VNVIPAMKDV YWGKDVTQKN KEEGYSHVVE  60
VTFESVETIQ DYIIHPAHVG FGDVYRSFWE KLLIFDYTPR K                      101

SEQ ID NO: 511          moltype = DNA  length = 303
FEATURE                 Location/Qualifiers
misc_feature            1..303
                        note = Synthetic biopolymer
source                  1..303
```

```
                        mol_type = other DNA
                        organism = synthetic construct
SEQUENCE: 511
atggctgtca agcaccttat cgtaatcaaa ttcaaggacg aaattacaga agcccagaaa  60
gaagaatttt tcaagaccta tgtaaacctg gtgaatgtca tccctgcgat gaaagatgtt  120
tattggggca aagacgtcac ccaacgtaac aaagaagaag gttactcaca cgtcgtcgaa  180
gtcactttcg agtcagtaga gacgatccaa gattacataa tacacccggc ccatgtggga  240
ttcggagacg tttaccgtag cttctgggaa aaacttttga ttttcgacta taccccggga  300
aaa                                                                303

SEQ ID NO: 512          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 512
MAVKHLIVIK FKDEITEAQK EEFFKTYVNL VNVIPAMKDV YWGKDVTQRN KEEGYSHVVE  60
VTFESVETIQ DYIIHPAHVG FGDVYRSFWE KLLIFDYTPG K                      101

SEQ ID NO: 513          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 513
atggctgtaa agcaccttat catcatcaaa ttcaacgacg aaattacaga agcccagaaa  60
gaagaatttt tcaagaccta tgtaaacctg gtgaatgtca tccctgcgat gaaagatgtt  120
tattggggca aagacgtcac ccaacgtaac aaagaagaag gttacactca catcgtcgaa  180
gtcactttcg agtcagtaga gacgatccaa acctacataa tacacccggc ccatgtggga  240
ttcggagacg tttaccgtag cttctgggaa aaacttttga ttttcgacta taccccgaga  300
aaa                                                                303

SEQ ID NO: 514          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 514
MAVKHLIIIK FNDEITEAQK EEFFKTYVNL VNVIPAMKDV YWGKDVTQRN KEEGYTHIVE  60
VTFESVETIQ TYIIHPAHVG FGDVYRSFWE KLLIFDYTPR K                      101

SEQ ID NO: 515          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 515
atggctgtaa agcaccttat cgtaatcaaa ttcaaggacg aaattacaga agcccagaaa  60
gaagaatttt tcaagaccta tgtaaacctg gtgaatgtca tccctcaaat gaaagatgtt  120
tattggggca aagacgtcac ccaaaaaaac aaagaagaag gttacactca cgtcgtcgaa  180
gtcactttcg actcagtaga gacgatccaa gattacataa tacacccggc ccatgtggga  240
ttcggagacg tttaccgtag cttctgggaa aaacttttga aattcgacta taccccgaga  300
aaa                                                                303

SEQ ID NO: 516          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 516
MAVKHLIVIK FKDEITEAQK EEFFKTYVNL VNVIPQMKDV YWGKDVTQKN KEEGYTHVVE  60
VTFDSVETIQ DYIIHPAHVG FGDVYRSFWE KLLKFDYTPR K                      101

SEQ ID NO: 517          moltype = DNA  length = 303
FEATURE                 Location/Qualifiers
misc_feature            1..303
                        note = Synthetic biopolymer
source                  1..303
                        mol_type = other DNA
```

```
                         organism = synthetic construct
SEQUENCE: 517
atggctgtca agcaccttat catcatcgcc ttcaaggacg aaattacaga agcccagaaa  60
gaagaatttt tcaagaccta tgtagacctg gtgaatgtca tccctgcgat gaaagatgtt  120
tattggggca aagacgtcac ccaaaaaaac aaagaagaag gttacactca cgtcgtcgaa  180
gtcactttcg agtcagtaga gacgatccaa gattacataa tacacccggc ccatgtggga  240
ttcggagacg tttaccgtag cttctgggaa aaacttttga ttttcgacta taccccgaga  300
aaa                                                                 303

SEQ ID NO: 518           moltype = AA  length = 101
FEATURE                  Location/Qualifiers
REGION                   1..101
                         note = Synthetic biopolymer
source                   1..101
                         mol_type = protein
                         organism = synthetic construct
SEQUENCE: 518
MAVKHLIIIA FKDEITEAQK EEFFKTYVDL VNVIPAMKDV YWGKDVTQKN KEEGYTHVVE  60
VTFESVETIQ DYIIHPAHVG FGDVYRSFWE KLLIFDYTPR K                     101

SEQ ID NO: 519           moltype = DNA  length = 303
FEATURE                  Location/Qualifiers
misc_feature             1..303
                         note = Synthetic biopolymer
source                   1..303
                         mol_type = other DNA
                         organism = synthetic construct
SEQUENCE: 519
atggctgtaa agcaccttat cgtaatcaaa ttcaaggacg aaattacaga agcccagaaa  60
gaagaatttt tcaagaccta tgtaaacctg gtgaatgtca tccctgcgat gaaagatgtt  120
tattggggca aagacgtcac ccaacgtaac aaagaagaag gttactcaca cgtcgtcgaa  180
gtcactttcg agtcagtaga gacgatccaa gattacataa tacacccggc ccatgtggga  240
ttcggagacg tttaccgtag cttctgggaa aaacttttga ttttcgacta taccccggga  300
aaa                                                                 303

SEQ ID NO: 520           moltype = AA  length = 101
FEATURE                  Location/Qualifiers
REGION                   1..101
                         note = Synthetic biopolymer
source                   1..101
                         mol_type = protein
                         organism = synthetic construct
SEQUENCE: 520
MAVKHLIVIK FKDEITEAQK EEFFKTYVNL VNVIPAMKDV YWGKDVTQRN KEEGYSHVVE  60
VTFESVETIQ DYIIHPAHVG FGDVYRSFWE KLLIFDYTPG K                     101

SEQ ID NO: 521           moltype = DNA  length = 303
FEATURE                  Location/Qualifiers
misc_feature             1..303
                         note = Synthetic biopolymer
source                   1..303
                         mol_type = other DNA
                         organism = synthetic construct
SEQUENCE: 521
atggctgtca agcaccttat catcatcaaa ttcaaggacg aaattacaga agcccagaaa  60
gaagaatttt tcaagaccta tgtaaacctg gtgaatgaca tccctgcgat gaaagatgtt  120
tattggggca aagacgtcac ccaaaaaaac aaagaagaag gttactcaca cgtcgtcgaa  180
gtcactttcg actcagtaga gacgatccaa gattacataa tacacccggc ccatgtggga  240
ttcggagacg tttaccgtag cttctgggaa aaacttttga ttttcgacta taccccgaga  300
aaa                                                                 303

SEQ ID NO: 522           moltype = AA  length = 101
FEATURE                  Location/Qualifiers
REGION                   1..101
                         note = Synthetic biopolymer
source                   1..101
                         mol_type = protein
                         organism = synthetic construct
SEQUENCE: 522
MAVKHLIIIK FKDEITEAQK EEFFKTYVNL VNDIPAMKDV YWGKDVTQKN KEEGYSHVVE  60
VTFDSVETIQ DYIIHPAHVG FGDVYRSFWE KLLIFDYTPR K                     101

SEQ ID NO: 523           moltype = DNA  length = 303
FEATURE                  Location/Qualifiers
misc_feature             1..303
                         note = Synthetic biopolymer
source                   1..303
                         mol_type = other DNA
                         organism = synthetic construct
```

-continued

SEQUENCE: 523
atggctgtca agcaccttat catcatcaaa ttcaaggacg aaattacaga agcccagaaa 60
gaagaatttt tcaagaccta tgtaaacctg gtgaatgaca tccctgcgat gaaagatgtt 120
tattggggca aagacgtcac ccaacgtaac aaagaagaag gttactcaca catcgtcgaa 180
gtcactttcg agtcagtaga gacgatccaa acctacataa tacacccggc ccatgtggga 240
ttcggagacg tttaccgtag cttctgggaa aaacttttga ttttcgacta taccccgaga 300
aaa 303

SEQ ID NO: 524 moltype = AA length = 101
FEATURE Location/Qualifiers
REGION 1..101
note = Synthetic biopolymer
source 1..101
mol_type = protein
organism = synthetic construct
SEQUENCE: 524
MAVKHLIIIK FKDEITEAQK EEFFKTYVNL VNDIPAMKDV YWGKDVTQRN KEEGYSHIVE 60
VTFESVETIQ TYIIHPAHVG FGDVYRSFWE KLLIFDYTPR K 101

SEQ ID NO: 525 moltype = DNA length = 303
FEATURE Location/Qualifiers
misc_feature 1..303
note = Synthetic biopolymer
source 1..303
mol_type = other DNA
organism = synthetic construct
SEQUENCE: 525
atggctgtca agcaccttat catcatcaaa ttcaaggacg aaattacaga agcccagaaa 60
gaagaatttt tcaagaccta tgtaaacctg gtgaatgaca tccctgcgat gaaagatgtt 120
tattggggca aagacgtcac ccaacgtaac aaagaagaag gttactcaca catcgtcgaa 180
gtcactttcg agtcagtaga gacgatccaa acctacataa tacacccggc ccatgtggga 240
ttcggagacg tttaccgtag cttctgggaa aaacttttga ttttcgacta taccccgaga 300
aaa 303

SEQ ID NO: 526 moltype = AA length = 101
FEATURE Location/Qualifiers
REGION 1..101
note = Synthetic biopolymer
source 1..101
mol_type = protein
organism = synthetic construct
SEQUENCE: 526
MAVKHLIIIK FKDEITEAQK EEFFKTYVNL VNDIPAMKDV YWGKDVTQRN KEEGYSHIVE 60
VTFESVETIQ TYIIHPAHVG FGDVYRSFWE KLLIFDYTPR K 101

SEQ ID NO: 527 moltype = DNA length = 303
FEATURE Location/Qualifiers
misc_feature 1..303
note = Synthetic biopolymer
source 1..303
mol_type = other DNA
organism = synthetic construct
SEQUENCE: 527
atggctgtca agcaccttat cgtaatcaaa ttcaaggacg aaattacaga agcccagaaa 60
gaagaatttt tcaagaccta tgtaaacctg gtgaatatca tccctcaaat gaaagatgtt 120
tattggggca aagacgtcac ccaaaaaaac aaagaagaag gttggactca cgtcgtcgaa 180
gtcactttcg actcagtaga gacgatccaa gattacataa tacacccggc ccatgtggga 240
ttcggagacg tttaccgtag cttctgggaa aaacttttga aattcgacta taccccgaga 300
aaa 303

SEQ ID NO: 528 moltype = AA length = 101
FEATURE Location/Qualifiers
REGION 1..101
note = Synthetic biopolymer
source 1..101
mol_type = protein
organism = synthetic construct
SEQUENCE: 528
MAVKHLIVIK FKDEITEAQK EEFFKTYVNL VNIIPQMKDV YWGKDVTQKN KEEGWTHVVE 60
VTFDSVETIQ DYIIHPAHVG FGDVYRSFWE KLLKFDYTPR K 101

SEQ ID NO: 529 moltype = DNA length = 303
FEATURE Location/Qualifiers
misc_feature 1..303
note = Synthetic biopolymer
source 1..303
mol_type = other DNA
organism = synthetic construct
SEQUENCE: 529

```
atggctgtca agcaccttat catcatcaaa ttcaaggacg aaattacaga agcccagaaa  60
gaagaatttt tcaagaccta tgtaaacctg gtgaatgtca tccctgcgat gaaagatgtt  120
tattggggca aagacgtcac ccaaaaaaac aaagaagaag gttactcaca cgtcgtcgaa  180
gtcactttcg agtcagtaga gacgatcaaa gattacataa tacacccggc ccatgtggga  240
ttcggagacg tttaccgtag cttctgggaa aaacttttga ttttcgacta taccccgaga  300
aaa                                                                303

SEQ ID NO: 530         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 530
MAVKHLIIIK FKDEITEAQK EEFFKTYVNL VNVIPAMKDV YWGKDVTQKN KEEGYSHVVE  60
VTFESVETIK DYIIHPAHVG FGDVYRSFWE KLLIFDYTPR K                     101

SEQ ID NO: 531         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 531
atggctgtca agcaccttat catcatcaaa ttcaaggacg aaattacaga agcccagaaa  60
gaagaatttt tcaagaccta tgtaaacctg gtgaatatca tccctgcgat gaaagatgtt  120
tattggggca aagacgtcac ccaacgtaac aaagaagaag gttggtcaca catcgtcgaa  180
gtcactttcg agtcagtaga gacgatccaa gattacataa tacacccggc ccatgtggga  240
ttcggagacg tttaccgtag cttctgggaa aaacttttga ttttcgacta taccccggga  300
aaa                                                                303

SEQ ID NO: 532         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 532
MAVKHLIIIK FKDEITEAQK EEFFKTYVNL VNIIPAMKDV YWGKDVTQRN KEEGWSHIVE  60
VTFESVETIQ DYIIHPAHVG FGDVYRSFWE KLLIFDYTPG K                     101

SEQ ID NO: 533         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 533
atggctgtca agcaccttat catcatcaaa ttcaaggacg aaattacaga agcccagaaa  60
gaagaatttt tcaagaccta tgtaaacctg gtgaatgaca tccctgcgat gaaagatgtt  120
tattggggca aagacgtcac ccaacgtaac aaagaagaag gttactcaca catcgtcgaa  180
gtcactttcg agtcagtaga gacgatccaa acctacataa tacacccggc ccatgtggga  240
ttcggagacg tttaccgtag cttctgggaa aaacttttga ttttcgacta taccccgaga  300
aaa                                                                303

SEQ ID NO: 534         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 534
MAVKHLIIIK FKDEITEAQK EEFFKTYVNL VNDIPAMKDV YWGKDVTQRN KEEGYSHIVE  60
VTFESVETIQ TYIIHPAHVG FGDVYRSFWE KLLIFDYTPR K                     101

SEQ ID NO: 535         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 535
atggctgtca agcaccttat catcatcgcc ttcaaggacg aaattacaga agcccagaaa  60
```

```
gaagaatttt tcaagaccta tgtagacctg gtgaatgtca tccctgcgat gaaagatgtt  120
tattggggca aagacgtcac ccaaaaaaac aaagaagaag gttactcaca catcgtcgaa  180
gtcactttcg agtcagtaga gacgatccaa gattacataa tacacccggc ccatgtggga  240
ttcggagacg tttaccgtag cttctgggaa aaacttttga ttttcgacta taccccgaga  300
aaa                                                                303

SEQ ID NO: 536         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 536
MAVKHLIIIA FKDEITEAQK EEFFKTYVDL VNVIPAMKDV YWGKDVTQKN KEEGYSHIVE  60
VTFESVETIQ DYIIHPAHVG FGDVYRSFWE KLLIFDYTPR K                      101

SEQ ID NO: 537         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 537
atggctgtca agcaccttat catcatcgcc ttcaaggacg aaattacaga agcccagaaa  60
gaagaatttt tcaagaccta tgtagacctg gtgaatgtca tccctgcgat gaaagatgtt  120
tattggggca aagacgtcac ccaaaaaaac aaagaagaag gttactcaca catcgtcgaa  180
gtcactttcg agtcagtaga gacgatccaa gattacataa tacacccggc ccatgtggga  240
ttcggagacg tttaccgtag cttctgggaa aaacttttga ttttcgacta taccccgaga  300
aaa                                                                303

SEQ ID NO: 538         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 538
MAVKHLIIIA FKDEITEAQK EEFFKTYVDL VNVIPAMKDV YWGKDVTQKN KEEGYSHIVE  60
VTFESVETIQ DYIIHPAHVG FGDVYRSFWE KLLIFDYTPR K                      101

SEQ ID NO: 539         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 539
atgccggtca agcaccttat catcatcaaa ttcaaggacg aaattacaga agcccagaaa  60
gaagaatttt tcaagaccta tgtaaacctg gtgaatatca tccctgcgat gaaagatgtt  120
tattggggca aagacgtcac ccaaaaaaac aaagaagaag gttggactca catcgtcgaa  180
gtcactttcg actcagtaga gacgatccaa gattacataa tacacccggc ccatgtggga  240
ttcggagacg tttaccgtag cttctgggaa aaacttttga aattcgacta taccccgaga  300
aaa                                                                303

SEQ ID NO: 540         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 540
MPVKHLIIIK FKDEITEAQK EEFFKTYVNL VNIIPAMKDV YWGKDVTQKN KEEGWTHIVE  60
VTFDSVETIQ DYIIHPAHVG FGDVYRSFWE KLLKFDYTPR K                      101

SEQ ID NO: 541         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 541
atggctgtaa agcaccttat cgtaatcaaa ttcaaggacg aaattacaga agcccagaaa  60
gaagaatttt tcaagaccta tgtaaacctg gtgaatatca tccctcaaat gaaagatgtt  120
```

```
tattggggca aagacgtcac ccaaaaaaac aaagaagaag gttggactca cgtcgtcgaa  180
gtcactttcg actcagtaga gacgatccaa gattacataa tacacccggc ccatgtggga  240
ttcggagacg tttaccgtag cttctgggaa aaacttttga aattcgacta taccccgaga  300
aaa                                                                303

SEQ ID NO: 542         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 542
MAVKHLIVIK FKDEITEAQK EEFFKTYVNL VNIIPQMKDV YWGKDVTQKN KEEGWTHVVE  60
VTFDSVETIQ DYIIHPAHVG FGDVYRSFWE KLLKFDYTPR K                     101

SEQ ID NO: 543         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 543
atggctgtaa agcaccttat catcatcaaa ttcaaggacg aaattacaga agcccagaaa  60
gaagaatttt tcaagaccta tgtaaacctg gtgaatgtca tccctgcgat gaaagatgtt  120
tattggggca aagacgtcac ccaaaaaaac aaagaagaag gttactcaca cgtcgtcgaa  180
gtcactttcg agtcagtaga gacgatccaa gattacataa tacacccggc ccatgtggga  240
ttcggagacg tttaccgtag cttctgggaa aaacttttga ttttcgacta taccccggga  300
aaa                                                                303

SEQ ID NO: 544         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 544
MAVKHLIIIK FKDEITEAQK EEFFKTYVNL VNVIPAMKDV YWGKDVTQKN KEEGYSHVVE  60
VTFESVETIQ DYIIHPAHVG FGDVYRSFWE KLLIFDYTPG K                     101

SEQ ID NO: 545         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 545
atggctgtca agcaccttat catcatcaaa ttcaaggacg aaattacaga agcccagaaa  60
gaagaatttt tcaagaccta tgtaaacctg gtgaatatca tccctgcgat gaaagatgtt  120
tattggggca aagacgtcac ccaaaaaaac aaagaagaag gttggtcaca cgtcgtcgaa  180
gtcactttcg agtcagtaga gacgatccaa gattacataa tacacccggc ccatgtggga  240
ttcggagacg tttaccgtag cttctgggaa aaacttttga ttttcgacta taccccggga  300
aaa                                                                303

SEQ ID NO: 546         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 546
MAVKHLIIIK FKDEITEAQK EEFFKTYVNL VNIIPAMKDV YWGKDVTQKN KEEGWSHVVE  60
VTFESVETIQ DYIIHPAHVG FGDVYRSFWE KLLIFDYTPG K                     101

SEQ ID NO: 547         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 547
atggctgtca agcaccttat cgtaatcaaa ttcaaggacg aaattacaga agcccagaaa  60
gaagaatttt tcaagaccta tgtaaacctg gtgaatatca tccctcaaat gaaagatgtt  120
tattggggca aagacgtcac ccaaaaaaac aaagaagaag gttggactca cgtcgtcgaa  180
```

-continued

```
gtcactttcg actcagtaga gacgatccaa gattacataa tacacccggc ccatgtggga  240
ttcggagacg tttaccgtag cttctgggaa aaacttttga aattcgacta taccccgaga  300
aaa                                                                303

SEQ ID NO: 548         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 548
MAVKHLIVIK FKDEITEAQK EEFFKTYVNL VNIIPQMKDV YWGKDVTQKN KEEGWTHVVE  60
VTFDSVETIQ DYIIHPAHVG FGDVYRSFWE KLLKFDYTPR K                      101

SEQ ID NO: 549         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 549
atggctgtca agcaccttat catcatcaaa ttcaacgacg aaattcaaga agcccagaaa  60
gaagaatttt tcaagaccta tgtaaacctg gtgaatatca tccctgcgat gaaagatgtt  120
tattggggca aagacgtcac ccaacgtaac aaagaagaag gttactcaca catcgtcgaa  180
gtcactttcg agtcagtaga gacgatccaa gattacataa tacacccggc ccatgtggga  240
ttcggagacg tttaccgtag cttctgggaa aaacttttga ttttcgacta taccccgaga  300
aaa                                                                303

SEQ ID NO: 550         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 550
MAVKHLIIIK FNDEIQEAQK EEFFKTYVNL VNIIPAMKDV YWGKDVTQRN KEEGYSHIVE  60
VTFESVETIQ DYIIHPAHVG FGDVYRSFWE KLLIFDYTPR K                      101

SEQ ID NO: 551         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 551
atggctgtca agcaccttat catcatcaaa ttcaaggacg aaattacaga agcccagaaa  60
gaagaatttt tcaagaccta tgtaaacctg gtgaatatca tccctgcgat gaaagatgtt  120
tattggggca aagacgtcac ccaacgtaac aaagaagaag gttggactca cgtcgtcgaa  180
gtctgtttcg agtcagtaga gacgatccaa gattacataa tacacccggc ccatgtggga  240
ttcggagacg tttaccgtag cttctgggaa aaacttttga ttttcgacta taccccgaga  300
aaa                                                                303

SEQ ID NO: 552         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 552
MAVKHLIIIK FKDEITEAQK EEFFKTYVNL VNIIPAMKDV YWGKDVTQRN KEEGWTHVVE  60
VCFESVETIQ DYIIHPAHVG FGDVYRSFWE KLLIFDYTPR K                      101

SEQ ID NO: 553         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 553
atgccggtca agcaccttat catcatcaaa ttcaaggacg aaattcaaga agcccagaaa  60
gaagaatttt tcaagaccta tgtaaacctg gtgaatatca tccctgcgat gaaagatgtt  120
tattggggca aagacgtcac ccaaaaaaac aaagaagaag gttacactca catcgtcgaa  180
gtcactttcg actcagtaga gacgatccaa gattacataa tacacccggc ccatgtggga  240
```

```
ttcggagacg tttaccgtag cttctgggaa aaacttttga aattcgacta taccccgaga  300
aaa                                                                303

SEQ ID NO: 554          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 554
MPVKHLIIIK FKDEIQEAQK EEFFKTYVNL VNIIPAMKDV YWGKDVTQKN KEEGYTHIVE  60
VTFDSVETIQ DYIIHPAHVG FGDVYRSFWE KLLKFDYTPR K                      101

SEQ ID NO: 555          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 555
atggctgtca agcaccttat catcatcaaa ttcaaggacg aaattacaga agcccagaaa  60
gaagaatttt tcaagaccta tgtaaacctg gtgaatgaca tccctgcgat gaaagatgtt  120
tattggggca aagacgtcac ccaaaaaaac aaagaagaag gttactcaca cgtcgtcgaa  180
gtcactttcg actcagtaga gacgatccaa gattacataa tacacccggc ccatgtggga  240
ttcggagacg tttaccgtag cttctgggaa aaacttttga ttttcgacta taccccgaga  300
aaa                                                                303

SEQ ID NO: 556          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 556
MAVKHLIIIK FKDEITEAQK EEFFKTYVNL VNDIPAMKDV YWGKDVTQKN KEEGYSHVVE  60
VTFDSVETIQ DYIIHPAHVG FGDVYRSFWE KLLIFDYTPR K                      101

SEQ ID NO: 557          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 557
atggctgtca agcaccttat catcatcaaa ttcaaggacg aaattcaaga agcccagaaa  60
gaagaatttt tcaagaccta tgtaaacctg gtgaatatca tccctttcat gaaagatgtt  120
tattggggca aagacgtcac ccaacgtaac aaagaagaag gttacactca cgtcgtcgaa  180
gtcactttcg agtcagtaga gacgatccaa gattacataa tacacccggc ccatgtggga  240
ttcggagacg tttaccgtag cttctgggaa aaacttttga ttttcgacta taccccgaga  300
aaa                                                                303

SEQ ID NO: 558          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 558
MAVKHLIIIK FKDEIQEAQK EEFFKTYVNL VNIIPFMKDV YWGKDVTQRN KEEGYTHVVE  60
VTFESVETIQ DYIIHPAHVG FGDVYRSFWE KLLIFDYTPR K                      101

SEQ ID NO: 559          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 559
atggctgtca agcaccttat catcctgaaa ttcaaggacg aaattacaga agcccagaaa  60
gaagaatttt tcaagaccta tgtaaacctg gtgaatgtca tccctgcgat gaaagatgtt  120
tattggggca aagacgtcac ccaacgtaac aaagaagaag gttactcaca cgtcgtcgaa  180
gtcactttcg agtcagtaga gacgatccaa gattacataa tacacccggc ccatgtggga  240
ttcggagacg tttaccgtag cttctgggaa aaacttttga ttttcgacta taccccggga  300
```

```
aaa                                                                 303

SEQ ID NO: 560          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 560
MAVKHLIILK FKDEITEAQK EEFFKTYVNL VNVIPAMKDV YWGKDVTQRN KEEGYSHVVE  60
VTFESVETIQ DYIIHPAHVG FGDVYRSFWE KLLIFDYTPG K                      101

SEQ ID NO: 561          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 561
atggctgtca agcaccttat catcatcaaa ttcaaggacg aaattcaaga agcccagaaa  60
gaagaatttt tcaagaccta tgtaaacctg gtgaatatca tccctgcgat gaaagatgtt  120
tattggggca aagacgtcac ccaaaaaaac aaagaagaag gttactcaca cgtcgtcgaa  180
gtcactttcg agtcagtaga gacgatcaaa gattacataa tacacccggc ccatgtggga  240
ttcggagacg tttaccgtag cttctgggaa aaacttttga ttttcgacta taccccgaga  300
aaa                                                                 303

SEQ ID NO: 562          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 562
MAVKHLIIIK FKDEIQEAQK EEFFKTYVNL VNIIPAMKDV YWGKDVTQKN KEEGYSHVVE  60
VTFESVETIK DYIIHPAHVG FGDVYRSFWE KLLIFDYTPR K                      101

SEQ ID NO: 563          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 563
atggctgtca agcaccttat catcatcaaa ttcaaggacg aaattcaaga agcccagaaa  60
gaagaatttt tcaagaccta tgtaaacctg gtgaatatca tccctgcgat gaaagatgtt  120
tattggggca aagacgtcac ccaaaaaaac aaagaagaag gttactcaca cgtcgtcgaa  180
gtcactttcg agtcagtaga gacgatccaa gattacataa tacacccggc ccatgtggga  240
ttcggagacg tttaccgtag cttctgggaa aaacttttga ttttcgacta taccccggga  300
aaa                                                                 303

SEQ ID NO: 564          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 564
MAVKHLIIIK FKDEIQEAQK EEFFKTYVNL VNIIPAMKDV YWGKDVTQKN KEEGYSHVVE  60
VTFESVETIQ DYIIHPAHVG FGDVYRSFWE KLLIFDYTPG K                      101

SEQ ID NO: 565          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 565
atggctgtca agcaccttat catcatcgcc ttcaaggacg aaattacaga agcccagaaa  60
gaagaatttt tcaagaccta tgtagacctg gtgaatgtca tccctgcgat gaaagatgtt  120
tattggggca aagacgtcac ccaaaaaaac aaagaagaag gttactcaca catcgtcgaa  180
gtcactttcg agtcagtaga gacgatccaa gattacataa tacacccggc ccatgtggga  240
ttcggagacg tttaccgtag cttctgggaa aaacttttga ttttcgacta taccccgaga  300
aaa                                                                 303
```

```
SEQ ID NO: 566          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 566
MAVKHLIIIA FKDEITEAQK EEFFKTYVDL VNVIPAMKDV YWGKDVTQKN KEEGYSHIVE  60
VTFESVETIQ DYIIHPAHVG FGDVYRSFWE KLLIFDYTPR K                     101

SEQ ID NO: 567          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 567
atggctgtaa agcaccttat catcatcgcc ttcaaggacg aaattacaga agcccagaaa  60
gaagaatttt tcaagaccta tgtagacctg gtgaatgtca tccctgcgat gaaagatgtt  120
tattggggca aagacgtcac ccaaaaaaac aaagaagaag gttactcaca catcgtcgaa  180
gtcactttcg agtcagtaga gacgatccaa gattacataa tacacccggc ccatgtggga  240
ttcggagacg tttaccgtag cttctgggaa aaacttttga ttttcgacta taccccgaga  300
aaa                                                               303

SEQ ID NO: 568          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 568
MAVKHLIIIA FKDEITEAQK EEFFKTYVDL VNVIPAMKDV YWGKDVTQKN KEEGYSHIVE  60
VTFESVETIQ DYIIHPAHVG FGDVYRSFWE KLLIFDYTPR K                     101

SEQ ID NO: 569          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 569
atggctgtca agcaccttat cgtaatcaaa ttcaaggacg aaattacaga agcccagaaa  60
gaagaatttt tcaagaccta tgtaaacctg gtgaatgtca tccctgcgat gaaagatgtt  120
tattggggca aagacgtcac ccaacgtaac aaagaagaag gttactcaca cgtcgtcgaa  180
gtcactttcg agtcagtaga gacgatccaa gattacataa tacacccggc ccatgtggga  240
ttcggagacg tttaccgtag cttctgggaa aaacttttga ttttcgacta taccccggga  300
aaa                                                               303

SEQ ID NO: 570          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 570
MAVKHLIVIK FKDEITEAQK EEFFKTYVNL VNVIPAMKDV YWGKDVTQRN KEEGYSHVVE  60
VTFESVETIQ DYIIHPAHVG FGDVYRSFWE KLLIFDYTPG K                     101

SEQ ID NO: 571          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 571
atggctgtaa agcaccttat catcatcaaa ttcaaggacg aaattacaga agcccagaaa  60
gaagaatttt tcaagaccta tgtaaacctg gtgaatatca tccctgcgat gaaagatgtt  120
tattggggca aagacgtcac ccaaaaaaac aaagaagaag gttggtcaca cgtcgtcgaa  180
gtcactttcg agtcagtaga gacgatccaa gattacataa tacacccggc ccatgtggga  240
ttcggagacg tttaccgtag cttctgggaa aaacttttga ttttcgacta taccccggga  300
aaa                                                               303
```

```
SEQ ID NO: 572          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 572
MAVKHLIIIK FKDEITEAQK EEFFKTYVNL VNIIPAMKDV YWGKDVTQKN KEEGWSHVVE  60
VTFESVETIQ DYIIHPAHVG FGDVYRSFWE KLLIFDYTPG K                     101

SEQ ID NO: 573          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 573
atggctgtaa agcaccttat cgtaatcaaa ttcaaggacg aaattacaga agcccagaaa  60
gaagaatttt tcaagaccta tgtaaacctg gtgaatatca tccctcaaat gaaagatgtt  120
tattggggca aagacgtcac ccaaaaaaac aaagaagaag gttggactca cgtcgtcgaa  180
gtcactttcg actcagtaga gacgatccaa gattacataa tacacccggc ccatgtggga  240
ttcggagacg tttaccgtag cttctgggaa aaacttttga aattcgacta taccccgaga  300
aaa                                                               303

SEQ ID NO: 574          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 574
MAVKHLIVIK FKDEITEAQK EEFFKTYVNL VNIIPQMKDV YWGKDVTQKN KEEGWTHVVE  60
VTFDSVETIQ DYIIHPAHVG FGDVYRSFWE KLLKFDYTPR K                     101

SEQ ID NO: 575          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 575
atggctgtaa agcaccttat catcatcaaa ttcgtcgacg aaattacaga agcccagaaa  60
gaagaatttt tcaagaccta tgtaaacctg gtgaatgtca tccctgcgat gaaagatgtt  120
tattggggca aagacgtcac ccaaaaaaac aaagaagaag gttactcaca cgtcgtcgaa  180
gtcactttcg agtcagtaga gacgatccaa gattacataa tacacccggc ccatgtggga  240
ttcggagacg tttaccgtag cttctgggaa aaacttttga ttttcgacta taccccgaga  300
aaa                                                               303

SEQ ID NO: 576          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 576
MAVKHLIIIK FVDEITEAQK EEFFKTYVNL VNVIPAMKDV YWGKDVTQKN KEEGYSHVVE  60
VTFESVETIQ DYIIHPAHVG FGDVYRSFWE KLLIFDYTPR K                     101

SEQ ID NO: 577          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 577
atggctgtaa agcaccttat catcatcaaa ttcaaggacg aaattcaaga agcccagaaa  60
gaagaatttt tcaagaccta tgtaaacctg gtgaatatca tccctttcat gaaagatgtt  120
tattggggca aagacgtcac ccaacgtaac aaagaagaag gttacactca cgtcgtcgaa  180
gtcactttcg agtcagtaga gacgatccaa gattacataa tacacccggc ccatgtggga  240
ttcggagacg tttaccgtag cttctgggaa aaacttttga ttttcgacta taccccgaga  300
aaa                                                               303

SEQ ID NO: 578          moltype = AA  length = 101
```

```
FEATURE                 Location/Qualifiers
REGION                  1..101
                        note = Synthetic biopolymer
source                  1..101
                        mol_type = protein
                        organism = synthetic construct
SEQUENCE: 578
MAVKHLIIIK FKDEIQEAQK EEFFKTYVNL VNIIPFMKDV YWGKDVTQRN KEEGYTHVVE  60
VTFESVETIQ DYIIHPAHVG FGDVYRSFWE KLLIFDYTPR K                     101

SEQ ID NO: 579          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 579
atggctgtca agcaccttat catcatcaaa ttcaacgacg aaattacaga agcccagaaa  60
gaagaatttt tcaagaccta tgtaaacctg gtgaatgtca tccctgcgat gaaagatgtt  120
tattggggca aagacgtcac ccaaaaaaac aaagaagaag gttactcaca catcgtcgaa  180
gtcactttcg agtcagtaga gacgatccaa acctacataa tacacccggc ccatgtggga  240
ttcggagacg tttaccgtag cttctgggaa aaacttttga ttttcgacta taccccgaga  300
aaa                                                                303

SEQ ID NO: 580          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 580
MAVKHLIIIK FNDEITEAQK EEFFKTYVNL VNVIPAMKDV YWGKDVTQKN KEEGYSHIVE  60
VTFESVETIQ TYIIHPAHVG FGDVYRSFWE KLLIFDYTPR K                     101

SEQ ID NO: 581          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 581
atggctgtca agcaccttat catcatcaaa ttcaaggacg aaattacaga agcccagaaa  60
gaagaatttt tcaagaccta tgtaaacctg gtgaatatca tccctgcgat gaaagatgtt  120
tattggggca aagacgtcac ccaacgtaac aaagaagaag gttggtcaca catcgtcgaa  180
gtcactttcg agtcagtaga gacgatccaa gattacataa tacacccggc ccatgtggga  240
ttcggagacg tttaccgtag cttctgggaa aaacttttga ttttcgacta taccccggga  300
aaa                                                                303

SEQ ID NO: 582          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 582
MAVKHLIIIK FKDEITEAQK EEFFKTYVNL VNIIPAMKDV YWGKDVTQRN KEEGWSHIVE  60
VTFESVETIQ DYIIHPAHVG FGDVYRSFWE KLLIFDYTPG K                     101

SEQ ID NO: 583          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 583
atggctgtca agcaccttat catcatcaaa ttcaaggacg aaattacaga agcccagaaa  60
gaagaatttt tcaagaccta tgtaaacctg gtgaatgtca tcccttcaat gaaagatgtt  120
tattggggca aagacgtcac ccaaaaaaac aaagaagaag gttacactca catcgtcgaa  180
gtctgtttcg actcagtaga gacgatccaa gattacataa tacacccggc ccatgtggga  240
ttcggagacg tttaccgtag cttctgggaa aaacttttga ttttcgacta taccccgaga  300
aaa                                                                303

SEQ ID NO: 584          moltype = AA  length = 101
FEATURE                 Location/Qualifiers
```

```
REGION                  1..101
                        note = Synthetic biopolymer
source                  1..101
                        mol_type = protein
                        organism = synthetic construct
SEQUENCE: 584
MAVKHLIIIK FKDEITEAQK EEFFKTYVNL VNVIPSMKDV YWGKDVTQKN KEEGYTHIVE  60
VCFDSVETIQ DYIIHPAHVG FGDVYRSFWE KLLIFDYTPR K                     101

SEQ ID NO: 585          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 585
atggctgtaa agcaccttat catcctgaaa ttcaaggacg aaattacaga agcccagaaa  60
gaagaatttt tcaagaccta tgtaaacctg gtgaatatca tccctgcgat gaaagatgtt  120
tattggggca aagacgtcac ccaacgtaac aaagaagaag gttggtcaca cgtcgtcgaa  180
gtcactttcg agtcagtaga gacgatccaa gattacataa tacacccggc ccatgtggga  240
ttcggagacg tttaccgtag cttctgggaa aaacttttga ttttcgacta taccccggga  300
aaa                                                               303

SEQ ID NO: 586          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 586
MAVKHLIILK FKDEITEAQK EEFFKTYVNL VNIIPAMKDV YWGKDVTQRN KEEGWSHVVE  60
VTFESVETIQ DYIIHPAHVG FGDVYRSFWE KLLIFDYTPG K                     101

SEQ ID NO: 587          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 587
atggctgtca agcaccttat cgtaatcaaa ttcaaggacg aaattacaga agcccagaaa  60
gaagaatttt tcaagaccta tgtaaacctg gtgaatatca tccctcaaat gaaagatgtt  120
tattggggca aagacgtcac ccaaaaaaac aaagaagaag gttacactca cgtcgtcgaa  180
gtcactttcg actcagtaga gtcaatccaa gattacataa tacacccggc ccatgtggga  240
ttcggagacg tttaccgtag cttctgggaa aaacttttga aattcgacta taccccgaga  300
aaa                                                               303

SEQ ID NO: 588          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 588
MAVKHLIVIK FKDEITEAQK EEFFKTYVNL VNIIPQMKDV YWGKDVTQKN KEEGYTHVVE  60
VTFDSVESIQ DYIIHPAHVG FGDVYRSFWE KLLKFDYTPR K                     101

SEQ ID NO: 589          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 589
atggctgtca agcaccttat catcatcaaa ttcaaggacg aaattacaga agcccagaaa  60
gaagaatttt tcaagaccta tgtaaacctg gtgaatatca tccctgcgat gaaagatgtt  120
tattggggca aagacgtcac ccaaaaaaac aaagaagaag gttactcaca cgtcgtcgaa  180
gtcactttcg agtcagtaga gtcaatccaa gattacataa tacacccggc ccatgtggga  240
ttcggagacg tttaccgtag cttctgggaa aaacttttga ttttcgacta taccccggga  300
aaa                                                               303

SEQ ID NO: 590          moltype = AA  length = 101
FEATURE                 Location/Qualifiers
REGION                  1..101
```

-continued

```
                        note = Synthetic biopolymer
source                  1..101
                        mol_type = protein
                        organism = synthetic construct
SEQUENCE: 590
MAVKHLIIIK FKDEITEAQK EEFFKTYVNL VNIIPAMKDV YWGKDVTQKN KEEGYSHVVE  60
VTFESVESIQ DYIIHPAHVG FGDVYRSFWE KLLIFDYTPG K                     101

SEQ ID NO: 591          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 591
atggctgtca agcaccttat catcatcaaa ttcgtcgacg aaattacaga agcccagaaa  60
gaagaatttt tcaagaccta tgtaaacctg gtgaatatca tccctgcgat gaaagatgtt  120
tattggggca aagacgtcac ccaaaaaaac aaagaagaag gttactcaca catcgtcgaa  180
gtcactttcg actcagtaga gtcaatccaa gattacataa tacacccggc ccatgtggga  240
ttcggagacg tttaccgtag cttctgggaa aaacttttga ttttcgacta taccccgaga  300
aaa                                                               303

SEQ ID NO: 592          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 592
MAVKHLIIIK FVDEITEAQK EEFFKTYVNL VNIIPAMKDV YWGKDVTQKN KEEGYSHIVE  60
VTFDSVESIQ DYIIHPAHVG FGDVYRSFWE KLLIFDYTPR K                     101

SEQ ID NO: 593          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 593
atggctgtca agcaccttat cgtaatcaaa ttcaaggacg aaattacaga agcccagaaa  60
gaagaatttt tcaagaccta tgtaaacctg gtgaatatca tccctcaaat gaaagatgtt  120
tattggggca aagacgtcac ccaaaaaaac aaagaagaag gttacactca cgtcgtcgaa  180
gtcactttcg actcagtaga gacgatccaa gattacataa tacacccggc ccatgtggga  240
ttcggagacg tttaccgtag cttctgggaa aaacttttga aattcgactt caccccgaga  300
aaa                                                               303

SEQ ID NO: 594          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 594
MAVKHLIVIK FKDEITEAQK EEFFKTYVNL VNIIPQMKDV YWGKDVTQKN KEEGYTHVVE  60
VTFDSVETIQ DYIIHPAHVG FGDVYRSFWE KLLKFDFTPR K                     101

SEQ ID NO: 595          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 595
atggctgtca agcaccttat catcatcaaa ttcaaggacg aaattacaga agcccagaaa  60
gaagaatttt tcaagaccta ttgtaacctg gtgaatatca tccctgcgat gaaagatgtt  120
tattggggca aagacgtcac ccaacgtaac aaagaagaag gttactcaca cgtcgtcgaa  180
gtcactttcg agtcagtaga gacgatccaa gattacataa tacacccggc ccatgtggga  240
ttcggagacg tttaccgtag cttctgggaa aaacttttga tttttgatta cactccaagg  300
aag                                                               303

SEQ ID NO: 596          moltype = AA  length = 101
FEATURE                 Location/Qualifiers
REGION                  1..101
                        note = Synthetic biopolymer
```

```
source                  1..101
                        mol_type = protein
                        organism = synthetic construct
SEQUENCE: 596
MAVKHLIIIK FKDEITEAQK EEFFKTYCNL VNIIPAMKDV YWGKDVTQRN KEEGYSHVVE  60
VTFESVETIQ DYIIHPAHVG FGDVYRSFWE KLLIFDYTPR K                     101

SEQ ID NO: 597          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 597
atggctgtca agcaccttat catcatcaaa ttcgtcgacg aaattacaga agcccagaaa  60
gaagaatttt tcaagaccta tgtaaacctg gtgaatatca tccctgcgat gaaagatgtt  120
tattggggca aagacgtcac ccaaaaaaac aaagaagaag gttacactca cgtcgtcgaa  180
gtcactttcg actcagtaga gggaatccaa gattacataa tacacccggc ccatgtggga  240
ttcggagacg tttaccgtag cttctgggaa aaacttttga ttttcgacta taccccgaga  300
aaa                                                               303

SEQ ID NO: 598          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 598
MAVKHLIIIK FVDEITEAQK EEFFKTYVNL VNIIPAMKDV YWGKDVTQKN KEEGYTHVVE  60
VTFDSVEGIQ DYIIHPAHVG FGDVYRSFWE KLLIFDYTPR K                     101

SEQ ID NO: 599          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 599
atggctgtaa agcaccttat catcatcaaa ttcaaggacg aaattacaga agcccagaaa  60
gaagaatttt tcaagaccta tgtaaacctg gtgaatatca tcccttcaat gaaagatgtt  120
tattggggca aagacgtcac ccaaaaaaac aaagaagaag gttacactca catcgtcgaa  180
gtcactttcg actcagtaga gacgatccaa gattacataa tacacccggc ccatgtggga  240
ttcggagacg tttaccgtag cttctgggaa aaacttttga aattcgactt caccccgaga  300
aaa                                                               303

SEQ ID NO: 600          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 600
MAVKHLIIIK FKDEITEAQK EEFFKTYVNL VNIIPSMKDV YWGKDVTQKN KEEGYTHIVE  60
VTFDSVETIQ DYIIHPAHVG FGDVYRSFWE KLLKFDFTPR K                     101

SEQ ID NO: 601          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 601
atggctgtca agcaccttat catcatcaaa ttcaacgacg aaattacaga agcccagaaa  60
gaagaatttt tcaagaccta tgtaaacctg gtgaatatca tccctgcgat gaaagatgtt  120
tattggggca aagacgtcac ccaacgtaac aaagaagaag gttacactca catcgtcgaa  180
gtcactttcg agtcagtaga gggaatccaa acctacataa tacacccggc ccatgtggga  240
ttcggagacg tttaccgtag cttctgggaa aaacttttga ttttcgacta taccccgaga  300
aaa                                                               303

SEQ ID NO: 602          moltype = AA  length = 101
FEATURE                 Location/Qualifiers
REGION                  1..101
                        note = Synthetic biopolymer
source                  1..101
```

```
                        mol_type = protein
                        organism = synthetic construct
SEQUENCE: 602
MAVKHLIIIK FNDEITEAQK EEFFKTYVNL VNIIPAMKDV YWGKDVTQRN KEEGYTHIVE  60
VTFESVEGIQ TYIIHPAHVG FGDVYRSFWE KLLIFDYTPR K                     101

SEQ ID NO: 603          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 603
atggctgtca agcaccttat catcatcaaa ttcaaggacg aaattacaga agcccagaaa  60
gaagaatttt tcaagaccta tgtaaacctg gtgaatatca tccctgcgat gaaagatgtt  120
tattggggca aagacgtcac ccaacgtaac aaagaagaag gttacactca cgtcgtcgaa  180
gtctgtttcg agtcagtaga gacgatccaa gattacataa tacacccggc ccatgtggga  240
ttcggagacg tttaccgtag cttctgggaa aaacttttga ttttcgactt caccccgaga  300
aaa                                                               303

SEQ ID NO: 604          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 604
MAVKHLIIIK FKDEITEAQK EEFFKTYVNL VNIIPAMKDV YWGKDVTQRN KEEGYTHVVE  60
VCFESVETIQ DYIIHPAHVG FGDVYRSFWE KLLIFDFTPR K                     101

SEQ ID NO: 605          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 605
atggctgtca agcaccttat catcatcaaa ttcaaggacg aaattacaga agcccagaaa  60
gaagaatttt tcaagaccta ttgtaacctg gtgaatatca tccctgcgat gaaagatgtt  120
tattggggca aagacgtcac ccaacgtaac aaagaagaag gttactcaca catcgtcgaa  180
gtcactttcg agtcagtaga gacgatccaa acctacataa tacacccggc ccatgtggga  240
ttcggagacg tttaccgtag cttctgggaa aaacttttga ttttcgacta taccccgaga  300
aaa                                                               303

SEQ ID NO: 606          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 606
MAVKHLIIIK FKDEITEAQK EEFFKTYCNL VNIIPAMKDV YWGKDVTQRN KEEGYSHIVE  60
VTFESVETIQ TYIIHPAHVG FGDVYRSFWE KLLIFDYTPR K                     101

SEQ ID NO: 607          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 607
atggctgtca agcaccttat catcatcaaa ttcaaggacg aaattacaga agcccagaaa  60
gaagaatttt tcaagaccta tgtaaacctg gtgaatatca tccctgcgat gaaagatgtt  120
tattggggca aagacgtcac ccaacgtaac aaagaagaag gttacactca cgtcgtcgaa  180
gtctgtttcg agtcagtaga gacgatccaa gattacataa tacacccggc ccatgtggga  240
ttcggagacg tttaccgtag cttctgggaa aaacttttga ttttcgactt caccccgaga  300
aaa                                                               303

SEQ ID NO: 608          moltype = AA  length = 101
FEATURE                 Location/Qualifiers
REGION                  1..101
                        note = Synthetic biopolymer
source                  1..101
                        mol_type = protein
```

```
                        organism = synthetic construct
SEQUENCE: 608
MAVKHLIIIK FKDEITEAQK EEFFKTYVNL VNIIPAMKDV YWGKDVTQRN KEEGYTHVVE  60
VCFESVETIQ DYIIHPAHVG FGDVYRSFWE KLLIFDFTPR K                      101

SEQ ID NO: 609          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 609
atggctgtaa agcaccttat catcatcgcc ttcaaggacg aaattacaga agcccagaaa  60
gaagaatttt tcaagaccta tgtagacctg gtgaatatca tccctgcgat gaaagatgtt  120
tattggggca aagacgtcac ccaaaaaaac aaagaagaag gttacactca cgtcgtcgaa  180
gtcactttcg agtcagtaga gggaatccaa gattacataa tacacccggc ccatgtggga  240
ttcggagacg tttaccgtag cttctgggaa aaacttttga ttttcgacta taccccgaga  300
aaa                                                                303

SEQ ID NO: 610          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 610
MAVKHLIIIA FKDEITEAQK EEFFKTYVDL VNIIPAMKDV YWGKDVTQKN KEEGYTHVVE  60
VTFESVEGIQ DYIIHPAHVG FGDVYRSFWE KLLIFDYTPR K                      101

SEQ ID NO: 611          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 611
atggctgtca agcaccttat catcatcaaa ttcaaggacg aaattacaga agcccagaaa  60
gaagaatttt tcaagaccta tgtaaacctg gtgaatatca tccctgcgat gaaagatgtt  120
tattggggca aagacgtcac ccaacgtaac aaagaagaag gttacactca cgtcgtcgaa  180
gtcactttcg agtcagtaga gtcaatccaa gattacataa tacacccggc ccatgtggga  240
ttcggagacg tttaccgtag cttctgggaa aaacttttga ttttcgacta taccccggga  300
aaa                                                                303

SEQ ID NO: 612          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 612
MAVKHLIIIK FKDEITEAQK EEFFKTYVNL VNIIPAMKDV YWGKDVTQRN KEEGYTHVVE  60
VTFESVESIQ DYIIHPAHVG FGDVYRSFWE KLLIFDYTPG K                      101

SEQ ID NO: 613          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 613
atggctgtca agcaccttat cgtaatcaaa ttcaaggacg aaattacaga agcccagaaa  60
gaagaatttt tcaagaccta tgtaaacctg gtgaatatca tccctgcgat gaaagatgtt  120
tattggggca aagacgtcac ccaacgtaac aaagaagaag gttactcaca cgtcgtcgaa  180
gtcactttcg agtcagtaga gggaatccaa gattacataa tacacccggc ccatgtggga  240
ttcggagacg tttaccgtag cttctgggaa aaacttttga ttttcgacta taccccggga  300
aaa                                                                303

SEQ ID NO: 614          moltype = AA  length = 101
FEATURE                 Location/Qualifiers
REGION                  1..101
                        note = Synthetic biopolymer
source                  1..101
                        mol_type = protein
                        organism = synthetic construct
```

```
SEQUENCE: 614
MAVKHLIVIK FKDEITEAQK EEFFKTYVNL VNIIPAMKDV YWGKDVTQRN KEEGYSHVVE  60
VTFESVEGIQ DYIIHPAHVG FGDVYRSFWE KLLIFDYTPG K                     101

SEQ ID NO: 615         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 615
atggctgtca agcaccttat catcatcaaa ttcgtcgacg aaattacaga agcccagaaa  60
gaagaatttt tcaagaccta tgtaaacctg gtgaatatca tccctgcgat gaaagatgtt  120
tattggggca aagacgtcac ccaaaaaaac aaagaagaag gttactcaca catcgtcgaa  180
gtcactttcg actcagtaga gtcaatccaa gattacataa tacacccggc ccatgtggga  240
ttcggagacg tttaccgtag cttctgggaa aaactttga ttttcgacta taccccgaga  300
aaa                                                               303

SEQ ID NO: 616         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 616
MAVKHLIIIK FVDEITEAQK EEFFKTYVNL VNIIPAMKDV YWGKDVTQKN KEEGYSHIVE  60
VTFDSVESIQ DYIIHPAHVG FGDVYRSFWE KLLIFDYTPR K                     101

SEQ ID NO: 617         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 617
atggctgtca agcaccttat catcatcgcc ttcaaggacg aaattacaga agcccagaaa  60
gaagaatttt tcaagaccta tgtagacctg gtgaatatca tccctgcgat gaaagatgtt  120
tattggggca aagacgtcac ccaaaaaaac aaagaagaag gttacactca cgtcgtcgaa  180
gtcactttcg agtcagtaga gggaatccaa gattacataa tacacccggc ccatgtggga  240
ttcggagacg tttaccgtag cttctgggaa aaacttttga ttttcgacta taccccgaga  300
aaa                                                               303

SEQ ID NO: 618         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 618
MAVKHLIIIA FKDEITEAQK EEFFKTYVDL VNIIPAMKDV YWGKDVTQKN KEEGYTHVVE  60
VTFESVEGIQ DYIIHPAHVG FGDVYRSFWE KLLIFDYTPR K                     101

SEQ ID NO: 619         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 619
atggctgtca agcaccttat catcatcaaa ttcaaggacg aaattacaga agcccagaaa  60
gaagaatttt tcaagaccta tgtaaacctg gtgaatatca tcccttcaat gaaagatgtt  120
tattggggca aagacgtcac ccaaaaaaac aaagaagaag gttacactca catcgtcgaa  180
gtcactttcg actcagtaga gacgatccaa gattacataa tacacccggc ccatgtggga  240
ttcggagacg tttaccgtag cttctgggaa aaacttttga aattcgactt caccccgaga  300
aaa                                                               303

SEQ ID NO: 620         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 620
```

```
MAVKHLIIIK FKDEITEAQK EEFFKTYVNL VNIIPSMKDV YWGKDVTQKN KEEGYTHIVE  60
VTFDSVETIQ DYIIHPAHVG FGDVYRSFWE KLLKFDFTPR K                      101

SEQ ID NO: 621          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 621
atggctgtca agcaccttat catcatcaaa ttcaacgacg aaattacaga agcccagaaa  60
gaagaatttt tcaagaccta tgtaaacctg gtgaatatca tccctgcgat gaaagatgtt  120
tattggggca aagacgtcac ccaacgtaac aaagaagaag gttactcaca catcgtcgaa  180
gtcactttcg agtcagtaga gacgatccaa gattacataa tacacccggc ccatgtggga  240
ttcggagacg tttaccgtag cttctgggaa aaacttttga ttttcgactt cacccccgaga  300
aaa                                                                303

SEQ ID NO: 622          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 622
MAVKHLIIIK FNDEITEAQK EEFFKTYVNL VNIIPAMKDV YWGKDVTQRN KEEGYSHIVE  60
VTFESVETIQ DYIIHPAHVG FGDVYRSFWE KLLIFDFTPR K                      101

SEQ ID NO: 623          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 623
atggctgtaa agcaccttat catcatcaaa ttcgtcgacg aaattacaga agcccagaaa  60
gaagaatttt tcaagaccta tgtaaacctg gtgaatatca tccctgcgat gaaagatgtt  120
tattggggca aagacgtcac ccaaaaaaac aaagaagaag gttacactca cgtcgtcgaa  180
gtcactttcg actcagtaga gggaatccaa gattacataa tacacccggc ccatgtggga  240
ttcggagacg tttaccgtag cttctgggaa aaacttttga ttttcgacta taccccgaga  300
aaa                                                                303

SEQ ID NO: 624          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 624
MAVKHLIIIK FVDEITEAQK EEFFKTYVNL VNIIPAMKDV YWGKDVTQKN KEEGYTHVVE  60
VTFDSVEGIQ DYIIHPAHVG FGDVYRSFWE KLLIFDYTPR K                      101

SEQ ID NO: 625          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 625
atggctgtca agcaccttat catcatcaaa ttcgtcgacg aaattacaga agcccagaaa  60
gaagaatttt tcaagaccta tgtaaacctg gtgaatatca tccctgcgat gaaagatgtt  120
tattggggca aagacgtcac ccaaaaaaac aaagaagaag gttacactca cgtcgtcgaa  180
gtcactttcg actcagtaga gacgatccaa gattacataa tacacccggc ccatgtggga  240
ttcggagacg tttaccgtag cttctgggaa aaacttttga ttttcgactt cacccccgaga  300
aaa                                                                303

SEQ ID NO: 626          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 626
MAVKHLIIIK FVDEITEAQK EEFFKTYVNL VNIIPAMKDV YWGKDVTQKN KEEGYTHVVE  60
```

```
VTFDSVETIQ DYIIHPAHVG FGDVYRSFWE KLLIFDFTPR K                 101

SEQ ID NO: 627         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 627
atggctgtca agcaccttat catcatcaaa ttcaaggacg aaattacaga agcccagaaa  60
gaagaatttt tcaagaccta tgtaaacctg gtgaatatca tccctgcgat gaaagatgtt  120
tattggggca aagacgtcac ccaaaaaaac aaagaagaag gttactcaca cgtcgtcgaa  180
gtcactttcg agtcagtaga gtcaatccaa gattacataa tacacccggc ccatgtggga  240
ttcggagacg tttaccgtag cttctgggaa aaacttttga ttttcgacta taccccggga  300
aaa                                                                303

SEQ ID NO: 628         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 628
MAVKHLIIIK FKDEITEAQK EEFFKTYVNL VNIIPAMKDV YWGKDVTQKN KEEGYSHVVE  60
VTFESVESIQ DYIIHPAHVG FGDVYRSFWE KLLIFDYTPG K                 101

SEQ ID NO: 629         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 629
atggctgtaa agcaccttat catcatcaaa ttcaaggacg aaattacaga agcccagaaa  60
gaagaatttt tcaagaccta tgtaaacctg gtgaatatca tccctgcgat gaaagatgtt  120
tattggggca aagacgtcac ccaacgtaac aaagaagaag gttacactca cgtcgtcgaa  180
gtctgtttcg agtcagtaga gggaatccaa gattacataa tacacccggc ccatgtggga  240
ttcggagacg tttaccgtag cttctgggaa aaacttttga tttttgatta cactccaagg  300
aag                                                                303

SEQ ID NO: 630         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 630
MAVKHLIIIK FKDEITEAQK EEFFKTYVNL VNIIPAMKDV YWGKDVTQRN KEEGYTHVVE  60
VCFESVEGIQ DYIIHPAHVG FGDVYRSFWE KLLIFDYTPR K                 101

SEQ ID NO: 631         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 631
atggctgtca agcaccttat catcatcaaa ttcgtcgacg aaattacaga agcccagaaa  60
gaagaatttt tcaagaccta tgtaaacctg gtgaatatca tccctgcgat gaaagatgtt  120
tattggggca aagacgtcac ccaaaaaaac aaagaagaag gttactcaca catcgtcgaa  180
gtcactttcg actcagtaga gtcaatccaa gattacataa tacacccggc ccatgtggga  240
ttcggagacg tttaccgtag cttctgggaa aaacttttga ttttcgacta taccccgaga  300
aaa                                                                303

SEQ ID NO: 632         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 632
MAVKHLIIIK FVDEITEAQK EEFFKTYVNL VNIIPAMKDV YWGKDVTQKN KEEGYSHIVE  60
VTFDSVESIQ DYIIHPAHVG FGDVYRSFWE KLLIFDYTPR K                 101
```

```
SEQ ID NO: 633          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 633
atggctgtaa agcaccttat catcctgaaa ttcaaggacg aaattacaga agcccagaaa  60
gaagaatttt tcaagaccta tgtaaacctg gtgaatatca tccctgcgat gaaagatgtt  120
tattggggca aagacgtcac ccaacgtaac aaagaagaag gttactcaca cgtcgtcgaa  180
gtcactttcg agtcagtaga gtcaatccaa gattacataa tacacccggc ccatgtggga  240
ttcggagacg tttaccgtag cttctgggaa aaacttttga ttttcgacta taccccggga  300
aaa                                                                303

SEQ ID NO: 634          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 634
MAVKHLIILK FKDEITEAQK EEFFKTYVNL VNIIPAMKDV YWGKDVTQRN KEEGYSHVVE  60
VTFESVESIQ DYIIHPAHVG FGDVYRSFWE KLLIFDYTPG K                      101

SEQ ID NO: 635          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 635
atggctgtca agcaccttat catcatcaaa ttcaaggacg aaattacaga agcccagaaa  60
gaagaatttt tcaagaccta tgtaaacctg gtgaatatca tccctgcgat gaaagatgtt  120
tattggggca aagacgtcac ccaaaaaaac aaagaagaag gttactcaca cgtcgtcgaa  180
gtcactttcg agtcagtaga gggaatcaaa gattacataa tacacccggc ccatgtggga  240
ttcggagacg tttaccgtag cttctgggaa aaacttttga ttttcgacta taccccgaga  300
aaa                                                                303

SEQ ID NO: 636          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 636
MAVKHLIIIK FKDEITEAQK EEFFKTYVNL VNIIPAMKDV YWGKDVTQKN KEEGYSHVVE  60
VTFESVEGIK DYIIHPAHVG FGDVYRSFWE KLLIFDYTPR K                      101

SEQ ID NO: 637          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 637
atggctgtaa agcaccttat catcatcaaa ttcaaggacg aaattacaga agcccagaaa  60
gaagaatttt tcaagaccta tgtaaacctg gtgaatatca tccctgcgat gaaagatgtt  120
tattggggca aagacgtcac ccaacgtaac aaagaagaag gttacactca cgtcgtcgaa  180
gtctgtttcg agtcagtaga gggaatccaa gattacataa tacacccggc ccatgtggga  240
ttcggagacg tttaccgtag cttctgggaa aaacttttga tttttgatta cactccaagg  300
aag                                                                303

SEQ ID NO: 638          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 638
MAVKHLIIIK FKDEITEAQK EEFFKTYVNL VNIIPAMKDV YWGKDVTQRN KEEGYTHVVE  60
VCFESVEGIQ DYIIHPAHVG FGDVYRSFWE KLLIFDYTPR K                      101
```

```
SEQ ID NO: 639          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 639
atggctgtca agcaccttat catcatcaaa ttcgtcgacg aaattacaga agcccagaaa  60
gaagaatttt tcaagaccta tgtaaacctg gtgaatatca tccctgcgat gaaagatgtt  120
tattggggca aagacgtcac ccaaaaaaac aaagaagaag gttactcaca cgtcgtcgaa  180
gtcactttcg agtcagtaga gggaatccaa gattacataa tacacccggc ccatgtggga  240
ttcggagacg tttaccgtag cttctgggaa aaacttttga ttttcgacta taccccgaga  300
aaa                                                                303

SEQ ID NO: 640          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 640
MAVKHLIIIK FVDEITEAQK EEFFKTYVNL VNIIPAMKDV YWGKDVTQKN KEEGYSHVVE  60
VTFESVEGIQ DYIIHPAHVG FGDVYRSFWE KLLIFDYTPR K                    101

SEQ ID NO: 641          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 641
atggctgtca agcaccttat catcatcaaa ttcgtcgacg aaattacaga agcccagaaa  60
gaagaatttt tcaagaccta tgtaaacctg gtgaatatca tccctgcgat gaaagatgtt  120
tattggggca aagacgtcac ccaaaaaaac aaagaagaag gttactcaca cgtcgtcgaa  180
gtcactttcg agtcagtaga gtcaatccaa gattacataa tacacccggc ccatgtggga  240
ttcggagacg tttaccgtag cttctgggaa aaacttttga ttttcgacta taccccgaga  300
aaa                                                                303

SEQ ID NO: 642          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 642
MAVKHLIIIK FVDEITEAQK EEFFKTYVNL VNIIPAMKDV YWGKDVTQKN KEEGYSHVVE  60
VTFESVESIQ DYIIHPAHVG FGDVYRSFWE KLLIFDYTPR K                    101

SEQ ID NO: 643          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 643
atggctgtaa agcaccttat catcatcaaa ttcaaggacg aaattacaga agcccagaaa  60
gaagaatttt tcaagaccta tgtaaacctg gtgaatatca tccctttcat gaaagatgtt  120
tattggggca aagacgtcac ccaacgtaac aaagaagaag gttacactca cgtcgtcgaa  180
gtcactttcg agtcagtaga gtcaatccaa gattacataa tacacccggc ccatgtggga  240
ttcggagacg tttaccgtag cttctgggaa aaacttttga ttttcgacta taccccgaga  300
aaa                                                                303

SEQ ID NO: 644          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 644
MAVKHLIIIK FKDEITEAQK EEFFKTYVNL VNIIPFMKDV YWGKDVTQRN KEEGYTHVVE  60
VTFESVESIQ DYIIHPAHVG FGDVYRSFWE KLLIFDYTPR K                    101

SEQ ID NO: 645          moltype = DNA  length = 303
```

```
FEATURE                Location/Qualifiers
misc_feature           1..303
                       note = Synthetic biopolymer
source                 1..303
                       mol_type = other DNA
                       organism = synthetic construct
SEQUENCE: 645
atggctgtca agcaccttat catcatcaaa ttcaaggacg aaattacaga agcccagaaa  60
gaagaatttt tcaagaccta tgtaaacctg gtgaatatca tccctgcgat gaaagatgtt  120
tattggggca aagacgtcac ccaacgtaac aaagaagaag gttacactca cgtcgtcgaa  180
gtctgtttcg agtcagtaga gacgatccaa gattacataa tacacccggc ccatgtggga  240
ttcggagacg tttaccgtag cttctgggaa aaacttttga ttttcgactt caccccgaga  300
aaa                                                                303

SEQ ID NO: 646         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 646
MAVKHLIIIK FKDEITEAQK EEFFKTYVNL VNIIPAMKDV YWGKDVTQRN KEEGYTHVVE  60
VCFESVETIQ DYIIHPAHVG FGDVYRSFWE KLLIFDFTPR K                     101

SEQ ID NO: 647         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 647
atggctgtaa agcaccttat catcatcaaa ttcaaggacg aaattacaga agcccagaaa  60
gaagaatttt tcaagaccta tgtaaacctg gtgaatatca tccctttcat gaaagatgtt  120
tattggggca aagacgtcac ccaacgtaac aaagaagaag gttacactca cgtcgtcgaa  180
gtcactttcg agtcagtaga gacgatccaa gattacataa tacacccggc ccatgtggga  240
ttcggagacg tttaccgtag cttctgggaa aaacttttga ttttcgactt caccccgaga  300
aaa                                                                303

SEQ ID NO: 648         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 648
MAVKHLIIIK FKDEITEAQK EEFFKTYVNL VNIIPFMKDV YWGKDVTQRN KEEGYTHVVE  60
VTFESVETIQ DYIIHPAHVG FGDVYRSFWE KLLIFDFTPR K                     101

SEQ ID NO: 649         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 649
atggctgtca agcaccttat catcatcaaa ttcaacgacg aaattacaga agcccagaaa  60
gaagaatttt tcaagaccta tgtaaacctg gtgaatatca tccctgcgat gaaagatgtt  120
tattggggca aagacgtcac ccaacgtaac aaagaagaag gttacactca catcgtcgaa  180
gtcactttcg agtcagtaga gggaatccaa acctacataa tacacccggc ccatgtggga  240
ttcggagacg tttaccgtag cttctgggaa aaacttttga ttttcgacta taccccgaga  300
aaa                                                                303

SEQ ID NO: 650         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 650
MAVKHLIIIK FNDEITEAQK EEFFKTYVNL VNIIPAMKDV YWGKDVTQRN KEEGYTHIVE  60
VTFESVEGIQ TYIIHPAHVG FGDVYRSFWE KLLIFDYTPR K                     101

SEQ ID NO: 651         moltype = DNA  length = 303
FEATURE                Location/Qualifiers
```

```
misc_feature           1..303
                       note = Synthetic biopolymer
source                 1..303
                       mol_type = other DNA
                       organism = synthetic construct
SEQUENCE: 651
atggctgtca agcaccttat catcatcaaa ttcgtcgacg aaattacaga agcccagaaa  60
gaagaatttt tcaagaccta tgtaaacctg gtgaatatca tccctgcgat gaaagatgtt  120
tattggggca aagacgtcac ccaaaaaaac aaagaagaag gttactcaca catcgtcgaa  180
gtcactttcg actcagtaga gtcaatccaa gattacataa tacacccggc ccatgtggga  240
ttcggagacg tttaccgtag cttctgggaa aaacttttga ttttcgacta taccccgaga  300
aaa                                                                303

SEQ ID NO: 652         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 652
MAVKHLIIIK FVDEITEAQK EEFFKTYVNL VNIIPAMKDV YWGKDVTQKN KEEGYSHIVE  60
VTFDSVESIQ DYIIHPAHVG FGDVYRSFWE KLLIFDYTPR K                      101

SEQ ID NO: 653         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 653
atggctgtca agcaccttat catcatcaaa ttcaaggacg aaattacaga agcccagaaa  60
gaagaatttt tcaagaccta tgtaaacctg gtgaatatca tccctgcgat gaaagatgtt  120
tattggggca aagacgtcac ccaacgtaac aaagaagaag gttacactca cgtcgtcgaa  180
gtcactttcg agtcagtaga gacgatccaa gattacataa tacacccggc ccatgtggga  240
ttcggagacg tttaccgtag cttctgggaa aaacttttga ttttcgactt caccccggga  300
aaa                                                                303

SEQ ID NO: 654         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 654
MAVKHLIIIK FKDEITEAQK EEFFKTYVNL VNIIPAMKDV YWGKDVTQRN KEEGYTHVVE  60
VTFESVETIQ DYIIHPAHVG FGDVYRSFWE KLLIFDFTPG K                      101

SEQ ID NO: 655         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 655
atggctgtca agcaccttat catcatcaaa ttcaaggacg aaattacaga agcccagaaa  60
gaagaatttt tcaagaccta tgtaaacctg gtgaatatca tccctttcat gaaagatgtt  120
tattggggca aagacgtcac ccaacgtaac aaagaagaag gttacactca cgtcgtcgaa  180
gtcactttcg agtcagtaga gacgatccaa gattacataa tacacccggc ccatgtggga  240
ttcggagacg tttaccgtag cttctgggaa aaacttttga ttttcgactt caccccgaga  300
aaa                                                                303

SEQ ID NO: 656         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 656
MAVKHLIIIK FKDEITEAQK EEFFKTYVNL VNIIPFMKDV YWGKDVTQRN KEEGYTHVVE  60
VTFESVETIQ DYIIHPAHVG FGDVYRSFWE KLLIFDFTPR K                      101

SEQ ID NO: 657         moltype = DNA  length = 303
FEATURE                Location/Qualifiers
misc_feature           1..303
```

```
                         note = Synthetic biopolymer
source                   1..303
                         mol_type = other DNA
                         organism = synthetic construct
SEQUENCE: 657
atggctgtca agcaccttat catcatcaaa ttcgtcgacg aaattacaga agcccagaaa  60
gaagaatttt tcaagaccta tgtaaacctg gtgaatatca tccctgcgat gaaagatgtt  120
tattggggca aagacgtcac ccaaaaaaac aaagaagaag gttactcaca catcgtcgaa  180
gtcactttcg actcagtaga gtcaatccaa gattacataa tacacccggc ccatgtggga  240
ttcggagacg tttaccgtag cttctgggaa aaacttttga ttttcgacta taccccgaga  300
aaa                                                                303

SEQ ID NO: 658           moltype = AA  length = 101
FEATURE                  Location/Qualifiers
REGION                   1..101
                         note = Synthetic biopolymer
source                   1..101
                         mol_type = protein
                         organism = synthetic construct
SEQUENCE: 658
MAVKHLIIIK FVDEITEAQK EEFFKTYVNL VNIIPAMKDV YWGKDVTQKN KEEGYSHIVE  60
VTFDSVESIQ DYIIHPAHVG FGDVYRSFWE KLLIFDYTPR K                      101

SEQ ID NO: 659           moltype = DNA  length = 303
FEATURE                  Location/Qualifiers
misc_feature             1..303
                         note = Synthetic biopolymer
source                   1..303
                         mol_type = other DNA
                         organism = synthetic construct
SEQUENCE: 659
atggctgtca agcaccttat catcatcgcc ttcaaggacg aaattacaga agcccagaaa  60
gaagaatttt tcaagaccta tgtagacctg gtgaatatca tccctgcgat gaaagatgtt  120
tattggggca aagacgtcac ccaaaaaaac aaagaagaag gttactcaca catcgtcgaa  180
gtcactttcg agtcagtaga gtcaatccaa gattacataa tacacccggc ccatgtggga  240
ttcggagacg tttaccgtag cttctgggaa aaacttttga ttttcgacta taccccgaga  300
aaa                                                                303

SEQ ID NO: 660           moltype = AA  length = 101
FEATURE                  Location/Qualifiers
REGION                   1..101
                         note = Synthetic biopolymer
source                   1..101
                         mol_type = protein
                         organism = synthetic construct
SEQUENCE: 660
MAVKHLIIIA FKDEITEAQK EEFFKTYVDL VNIIPAMKDV YWGKDVTQKN KEEGYSHIVE  60
VTFESVESIQ DYIIHPAHVG FGDVYRSFWE KLLIFDYTPR K                      101

SEQ ID NO: 661           moltype = DNA  length = 303
FEATURE                  Location/Qualifiers
misc_feature             1..303
                         note = Synthetic biopolymer
source                   1..303
                         mol_type = other DNA
                         organism = synthetic construct
SEQUENCE: 661
atggctgtaa agcaccttat catcatcaaa ttcaaggacg aaattacaga agcccagaaa  60
gaagaatttt tcaagaccta ttgtaacctg gtgaatatca tccctgcgat gaaagatgtt  120
tattggggca aagacgtcac ccaacgtaac aaagaagaag gttactcaca cgtcgtcgaa  180
gtcactttcg agtcagtaga gacgatccaa gattacataa tacacccggc ccatgtggga  240
ttcggagacg tttaccgtag cttctgggaa aaacttttga ttttcgacta taccccgaga  300
aaa                                                                303

SEQ ID NO: 662           moltype = AA  length = 101
FEATURE                  Location/Qualifiers
REGION                   1..101
                         note = Synthetic biopolymer
source                   1..101
                         mol_type = protein
                         organism = synthetic construct
SEQUENCE: 662
MAVKHLIIIK FKDEITEAQK EEFFKTYCNL VNIIPAMKDV YWGKDVTQRN KEEGYSHVVE  60
VTFESVETIQ DYIIHPAHVG FGDVYRSFWE KLLIFDYTPR K                      101

SEQ ID NO: 663           moltype = DNA  length = 303
FEATURE                  Location/Qualifiers
misc_feature             1..303
                         note = Synthetic biopolymer
```

```
source                  1..303
                        mol_type = other DNA
                        organism = synthetic construct
SEQUENCE: 663
atggctgtaa agcaccttat catcatcgcc ttcaaggacg aaattacaga agcccagaaa  60
gaagaatttt tcaagaccta tgtaaacctg gtgaatatca tccctgcgat gaaagatgtt  120
tattggggca aagacgtcac ccaaaaaaac aaagaagaag gttactcaca cgtcgtcgaa  180
gtcactttcg agtcagtaga gacgatccaa gattacataa tacacccggc ccatgtggga  240
ttcggagacg tttaccgtag cttctgggaa aaacttttga ttttcgactt caccccgaga  300
aaa                                                                303

SEQ ID NO: 664          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 664
MAVKHLIIIA FKDEITEAQK EEFFKTYVNL VNIIPAMKDV YWGKDVTQKN KEEGYSHVVE  60
VTFESVETIQ DYIIHPAHVG FGDVYRSFWE KLLIFDFTPR K                      101

SEQ ID NO: 665          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 665
atggctgtca agcaccttat catcatcaaa ttcgtcgacg gaattacaga agcccagaaa  60
gaagaatttt tcaagaccta tgtaaacctg gtgaatatca tccctgcgat gaaagatgtt  120
tattggggca aagacgtcac ccaacgtaac aaagaagaag gttacactca catcgtcgaa  180
gtcactttcg agtcagtatc aacgatccaa gattacataa tacacccggc ccatgtggga  240
ttcggagacg tttaccgtag cttctgggaa aaacttttga ttttcgacta taccccgaga  300
aaa                                                                303

SEQ ID NO: 666          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 666
MAVKHLIIIK FVDGITEAQK EEFFKTYVNL VNIIPAMKDV YWGKDVTQRN KEEGYTHIVE  60
VTFESVSTIQ DYIIHPAHVG FGDVYRSFWE KLLIFDYTPR K                      101

SEQ ID NO: 667          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 667
atggctgtca agcaccttat cgtaatcaaa ttcaaggacg aaattacaga agcccagaaa  60
gaagaatttt tcaagaccta tgtaaacctg gtgaatatca tcccttcaat gaaagatgtt  120
tattggggca aagacgtcac ccaacgtaac aaagaagaag gttacactca catcgtcgaa  180
gtcactttcg actcagtaga gatgatccaa gattacataa tgcacccggc ccatgtggga  240
ttcggagacg tttaccgtag cttctgggaa aaacttttga ttttcgacta taccccgaga  300
aaa                                                                303

SEQ ID NO: 668          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 668
MAVKHLIVIK FKDEITEAQK EEFFKTYVNL VNIIPSMKDV YWGKDVTQRN KEEGYTHIVE  60
VTFDSVEMIQ DYIMHPAHVG FGDVYRSFWE KLLIFDYTPR K                      101

SEQ ID NO: 669          moltype = DNA  length = 303
FEATURE                 Location/Qualifiers
misc_feature            1..303
                        note = Synthetic biopolymer
source                  1..303
```

```
                        mol_type = other DNA
                        organism = synthetic construct
SEQUENCE: 669
atggctgtca agcaccttat cgtaatcaaa ttcaaggacg aaattacaga agcccagaaa  60
gaagaatttt tcaagaccta tgtaaacctg gtgaatatca tccctgcgat gaaagatgtt  120
gaatggggca aagacgtcac ccaacgtaac aaagaagaag gttacactca cgtcgtcgaa  180
gtcactttcg agtcaatcga ggaaatccaa gattacataa tacacccggc ccatgtggga  240
ttcggagacg tttaccgtag cttctgggaa aaacttttga ttttcgacta taccccgaga  300
aaa                                                                303

SEQ ID NO: 670          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 670
MAVKHLIVIK FKDEITEAQK EEFFKTYVNL VNIIPAMKDV EWGKDVTQRN KEEGYTHVVE  60
VTFESIEEIQ DYIIHPAHVG FGDVYRSFWE KLLIFDYTPR K                    101

SEQ ID NO: 671          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 671
atggctgtca agcaccttat catcatcaaa ttcgtcgacg gaattacaga agcccagaaa  60
gaagaatttt tcaagaccta tgtaaacctg gtgaatatca tccctgcgat gaaagatgtt  120
tattggggca aagacgtcac ccaacgtaac aaagaagaag gttacactca catcgtcgaa  180
gtcactttcg agtcagtatc aacgatccaa gattacataa tacacccggc ccatgtggga  240
ttcggagacg tttaccgtag cttctgggaa aaacttttga ttttcgacta taccccgaga  300
aaa                                                                303

SEQ ID NO: 672          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 672
MAVKHLIIIK FVDGITEAQK EEFFKTYVNL VNIIPAMKDV YWGKDVTQRN KEEGYTHIVE  60
VTFESVSTIQ DYIIHPAHVG FGDVYRSFWE KLLIFDYTPR K                    101

SEQ ID NO: 673          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 673
atggctgtca agcaccttat catcatcaaa ttcaacgacg aaattcaaga agcccagaaa  60
gaagaatttt tcaagaccta tgtaaacctg gtgaatatca tccctgcgat gaaagatgtt  120
tattggggca aagacgtcac ccaacgtaac aaagaagaag gttacactca cgtcgtcgaa  180
gtcactttcg agtcagtaga gacgatccaa gattacataa tacacccggc ccatgtggga  240
ttcggagacg tttaccgtag cttctgggaa aaacttttga ttttcgacta taccccgaga  300
aaa                                                                303

SEQ ID NO: 674          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 674
MAVKHLIIIK FNDEIQEAQK EEFFKTYVNL VNIIPAMKDV YWGKDVTQRN KEEGYTHVVE  60
VTFESVETIQ DYIIHPAHVG FGDVYRSFWE KLLIFDYTPR K                    101

SEQ ID NO: 675          moltype = DNA  length = 303
FEATURE                 Location/Qualifiers
misc_feature            1..303
                        note = Synthetic biopolymer
source                  1..303
                        mol_type = other DNA
```

```
                         organism = synthetic construct
SEQUENCE: 675
atggctgtca agcaccttat catcatcaaa ttcgtcgacg gaattacaga agcccagaaa  60
gaagaatttt tcaagaccta tgtaaacctg gtgaatatca tccctgcgat gaaagatgtt  120
tattggggca aagacgtcac ccaacgtaac aaagaagaag gttacactca catcgtcgaa  180
gtcactttcg agtcagtatc aacgatccaa gattacataa tacacccggc ccatgtggga  240
ttcggagacg tttaccgtag cttctgggaa aaacttttga ttttcgacta taccccgaga  300
aaa                                                                303

SEQ ID NO: 676           moltype = AA  length = 101
FEATURE                  Location/Qualifiers
REGION                   1..101
                         note = Synthetic biopolymer
source                   1..101
                         mol_type = protein
                         organism = synthetic construct
SEQUENCE: 676
MAVKHLIIIK FVDGITEAQK EEFFKTYVNL VNIIPAMKDV YWGKDVTQRN KEEGYTHIVE  60
VTFESVSTIQ DYIIHPAHVG FGDVYRSFWE KLLIFDYTPR K                      101

SEQ ID NO: 677           moltype = DNA  length = 303
FEATURE                  Location/Qualifiers
misc_feature             1..303
                         note = Synthetic biopolymer
source                   1..303
                         mol_type = other DNA
                         organism = synthetic construct
SEQUENCE: 677
atggctgtca agcaccttat catcatcaaa ttcaaggacg aaattacaga agcccagaaa  60
gaagaatttt tcaacaccta tgtaaacctg gtgaatatca tccctgcgat gaaagatgtt  120
tattggggca aagacgtcac ccaacgtaac aaagaagaag gttacactca cgtcgtcgaa  180
gtcactttcg agtcagtaga gtcaatccaa gattacataa tacacccggc ccatgtggga  240
ttcggagacg tttaccgtag cttctgggaa aaacttttga ttttcgacta taccccgaga  300
aaa                                                                303

SEQ ID NO: 678           moltype = AA  length = 101
FEATURE                  Location/Qualifiers
REGION                   1..101
                         note = Synthetic biopolymer
source                   1..101
                         mol_type = protein
                         organism = synthetic construct
SEQUENCE: 678
MAVKHLIIIK FKDEITEAQK EEFFNTYVNL VNIIPAMKDV YWGKDVTQRN KEEGYTHVVE  60
VTFESVESIQ DYIIHPAHVG FGDVYRSFWE KLLIFDYTPR K                      101

SEQ ID NO: 679           moltype = DNA  length = 303
FEATURE                  Location/Qualifiers
misc_feature             1..303
                         note = Synthetic biopolymer
source                   1..303
                         mol_type = other DNA
                         organism = synthetic construct
SEQUENCE: 679
atggctgtca agcaccttat catcatcaaa ttcaaggacg aaattacaga agcccagaaa  60
gaagaatttt tcaagaccta tgtaaacctg gtgaatatca tccctgcgat gaaagatgtt  120
tattggggca aagacgtcac ccaacgtaac aaagaagaag gttactcaca catcgtcgaa  180
gtcactttcg agtcaatcga gatgatccaa gattacataa tacacccggc ccatgtggga  240
ttcggagacg tttaccgtag cttctgggaa aaacttttga ttttcgacta taccccgaga  300
aaa                                                                303

SEQ ID NO: 680           moltype = AA  length = 101
FEATURE                  Location/Qualifiers
REGION                   1..101
                         note = Synthetic biopolymer
source                   1..101
                         mol_type = protein
                         organism = synthetic construct
SEQUENCE: 680
MAVKHLIIIK FKDEITEAQK EEFFKTYVNL VNIIPAMKDV YWGKDVTQRN KEEGYSHIVE  60
VTFESIEMIQ DYIIHPAHVG FGDVYRSFWE KLLIFDYTPR K                      101

SEQ ID NO: 681           moltype = DNA  length = 303
FEATURE                  Location/Qualifiers
misc_feature             1..303
                         note = Synthetic biopolymer
source                   1..303
                         mol_type = other DNA
                         organism = synthetic construct
```

```
SEQUENCE: 681
atggctgtca agcaccttat catcatcaaa ttcgtcgacg gaattacaga agcccagaaa  60
gaagaatttt tcaagaccta tgtaaacctg gtgaatatca tccctgcgat gaaagatgtt  120
tattggggca aagacgtcac ccaacgtaac aaagaagaag gttacactca catcgtcgaa  180
gtcactttcg agtcagtatc aacgatccaa gattacataa tacacccggc ccatgtggga  240
ttcggagacg tttaccgtag cttctgggaa aaacttttga ttttcgacta taccccgaga  300
aaa                                                                303

SEQ ID NO: 682         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 682
MAVKHLIIIK FVDGITEAQK EEFFKTYVNL VNIIPAMKDV YWGKDVTQRN KEEGYTHIVE  60
VTFESVSTIQ DYIIHPAHVG FGDVYRSFWE KLLIFDYTPR K                     101

SEQ ID NO: 683         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 683
atggctgtca agcaccttat catcatcaaa ttcaaggacg aaattacaga agcccagaaa  60
gaagaatttt tcaacaccta tgtaaacctg gtgaatatca tccctccgat gaaagatgtt  120
tattggggca aagacgtcac ccaaaaaaac aaagaagaag gttacactca catcgtcgaa  180
gtcactttcg agtcagtaga gggaatccaa gattacataa tgcacccggc ccatgtggga  240
ttcggagacg tttaccgtag cttctgggaa aaacttttga ttttcgacta taccccgaga  300
aaa                                                                303

SEQ ID NO: 684         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 684
MAVKHLIIIK FKDEITEAQK EEFFNTYVNL VNIIPPMKDV YWGKDVTQKN KEEGYTHIVE  60
VTFESVEGIQ DYIMHPAHVG FGDVYRSFWE KLLIFDYTPR K                     101

SEQ ID NO: 685         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 685
atggctgtca agcaccttat cgtaatcaaa ttcaaggacg aaattacaga agcccagaaa  60
gaagaatttt tcaagaccta tgtaaacctg gtgaatatca tccctgcgat gaaagatgtt  120
gaatggggca aagacgtcac ccaacgtaac aaagaagaag gttacactca cgtcgtcgaa  180
gtcactttcg agtcaatcga ggaaatccaa gattacataa tacacccggc ccatgtggga  240
ttcggagacg tttaccgtag cttctgggaa aaacttttga ttttcgacta taccccgaga  300
aaa                                                                303

SEQ ID NO: 686         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 686
MAVKHLIVIK FKDEITEAQK EEFFKTYVNL VNIIPAMKDV EWGKDVTQRN KEEGYTHVVE  60
VTFESIEEIQ DYIIHPAHVG FGDVYRSFWE KLLIFDYTPR K                     101

SEQ ID NO: 687         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 687
```

```
atggctgtaa agcaccttat catcatcaaa ttcaaggacg aaattacaga agcccagaaa  60
gaagaatttt tcaagaccta tgtaaacctg gtgaatatca tccctgcgat gaaagatgtt  120
tattggggca aagacgtcac ccaacgtaac aaagaagaag gttacactca catcgtcgaa  180
gtcactttcg actcagtaga gacgatccaa gattacataa tacacccggc ccatgtggga  240
ttcggagacg tttaccgtag cttctgggaa aaacttttga ttttcgactt caccccggga  300
aaa                                                                303

SEQ ID NO: 688          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 688
MAVKHLIIIK FKDEITEAQK EEFFKTYVNL VNIIPAMKDV YWGKDVTQRN KEEGYTHIVE  60
VTFDSVETIQ DYIIHPAHVG FGDVYRSFWE KLLIFDFTPG K                      101

SEQ ID NO: 689          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 689
atggctgtca agcaccttat catcatcaaa ttcgtcgacg gaattacaga agcccagaaa  60
gaagaatttt tcaagaccta tgtaaacctg gtgaatatca tccctgcgat gaaagatgtt  120
tattggggca aagacgtcac ccaacgtaac aaagaagaag gttacactca catcgtcgaa  180
gtcactttcg agtcagtatc aacgatccaa gattacataa tacacccggc ccatgtggga  240
ttcggagacg tttaccgtag cttctgggaa aaacttttga ttttcgacta taccccgaga  300
aaa                                                                303

SEQ ID NO: 690          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 690
MAVKHLIIIK FVDGITEAQK EEFFKTYVNL VNIIPAMKDV YWGKDVTQRN KEEGYTHIVE  60
VTFESVSTIQ DYIIHPAHVG FGDVYRSFWE KLLIFDYTPR K                      101

SEQ ID NO: 691          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 691
atggctgtca agcaccttat catcatcaaa ttcaaggacg aaattacaga agcccagaaa  60
gaagaatttt tcaagaccta tgtaaacctg gtgaatgtca tccctgcgat gaaagatgtt  120
tattggggca aagacgtcac ccaaaaaaac aaagaagaag gttacactca cgtcgtcgaa  180
gtcactttcg actcagtaga gacgatccaa gattacataa tacacccggc ccatgtggga  240
ttcggagacg tttaccgtag cttctgggaa aaacttttga ttttcgacta taccccggga  300
aaa                                                                303

SEQ ID NO: 692          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 692
MAVKHLIIIK FKDEITEAQK EEFFKTYVNL VNVIPAMKDV YWGKDVTQKN KEEGYTHVVE  60
VTFDSVETIQ DYIIHPAHVG FGDVYRSFWE KLLIFDYTPG K                      101

SEQ ID NO: 693          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 693
atggctgtca agcaccttat cgtaatcaaa ttcaaggacg aaattacaga agcccagaaa  60
```

```
gaagaatttt tcaagaccta tgtaaacctg gtgaatatca tcccttcaat gaaagatgtt  120
tattggggca aagacgtcac ccaacgtaac aaagaagaag gttacactca catcgtcgaa  180
gtcactttcg actcagtaga gatgatccaa gattacataa tgcacccggc ccatgtggga  240
ttcggagacg tttaccgtag cttctgggaa aaacttttga ttttcgacta taccccgaga  300
aaa                                                                303

SEQ ID NO: 694         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 694
MAVKHLIVIK FKDEITEAQK EEFFKTYVNL VNIIPSMKDV YWGKDVTQRN KEEGYTHIVE  60
VTFDSVEMIQ DYIMHPAHVG FGDVYRSFWE KLLIFDYTPR K                      101

SEQ ID NO: 695         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 695
atggctgtca agcaccttat catcatcaaa ttcaaggacg aaattacaga agcccagaaa  60
gaagaatttt tcaagaccta tgtaaacctg gtgaatatca tccctgcgat gaaagatgtt  120
tattggggca aagacgtcac ccaacgtaac aaagaagaag gttacactca catcgtcgaa  180
gtcactttcg actcagtaga gacgatccaa gattacataa tacacccggc ccatgtggga  240
ttcggagacg tttaccgtag cttctgggaa aaacttttga ttttcgactt caccccggga  300
aaa                                                                303

SEQ ID NO: 696         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 696
MAVKHLIIIK FKDEITEAQK EEFFKTYVNL VNIIPAMKDV YWGKDVTQRN KEEGYTHIVE  60
VTFDSVETIQ DYIIHPAHVG FGDVYRSFWE KLLIFDFTPG K                      101

SEQ ID NO: 697         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 697
atggctgtca agcaccttat catcatcaaa ttcaaggacg aaattacaga agcccagaaa  60
gaagaatttt tcaagaccta tgtaaacctg gtgaatatca tccctgcgat gaaagatgtt  120
gaatggggca aagacgtcac ccaaaaaaac aaagaagaag gttacactca cgtcgtcgaa  180
gtcactttcg actcagtaga ggccatccaa gattacataa tacacccggc ccatgtggga  240
ttcggagacg tttaccgtag cttctgggaa aaacttttga ttttcgacta taccccgaga  300
aaa                                                                303

SEQ ID NO: 698         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 698
MAVKHLIIIK FKDEITEAQK EEFFKTYVNL VNIIPAMKDV EWGKDVTQKN KEEGYTHVVE  60
VTFDSVEAIQ DYIIHPAHVG FGDVYRSFWE KLLIFDYTPR K                      101

SEQ ID NO: 699         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 699
atggctgtca agcaccttat catcctgaaa ttccaagacg aaattacaga agcccagaaa  60
gaagaatttt tcaagaccta tgtaaacctg atgaatatca tccctgcgat gaaagatgtt  120
```

```
tattggggca aagacgtcac ccaaaaaaac aaagaagaag gttacactca catcgtcgaa  180
gtcactttcg agtcaatcga gtcaatccaa gattacataa tgcacccggc ccatgtggga  240
ttcggagacg tttaccgtag cttctgggaa aaacttttga ttttcgacta taccccgaga  300
aaa                                                                303

SEQ ID NO: 700         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 700
MAVKHLIILK FQDEITEAQK EEFFKTYVNL MNIIPAMKDV YWGKDVTQKN KEEGYTHIVE  60
VTFESIESIQ DYIMHPAHVG FGDVYRSFWE KLLIFDYTPR K                      101

SEQ ID NO: 701         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 701
atggctgtca agcaccttat catcatcaaa ttcaaggacg aaattacaga agcccagaaa  60
gaagaatttt tcaagaccta tgtaaacctg gtgaatatca tccctgcgat gaaagatgtt  120
gaatggggca aagacgtcac ccaaaaaaac aaagaagaag gttacactca cgtcgtcgaa  180
gtcactttcg actcagtaga ggccatccaa gattacataa tacacccggc ccatgtggga  240
ttcggagacg tttaccgtag cttctgggaa aaacttttga ttttcgacta taccccgaga  300
aaa                                                                303

SEQ ID NO: 702         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 702
MAVKHLIIIK FKDEITEAQK EEFFKTYVNL VNIIPAMKDV EWGKDVTQKN KEEGYTHVVE  60
VTFDSVEAIQ DYIIHPAHVG FGDVYRSFWE KLLIFDYTPR K                      101

SEQ ID NO: 703         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 703
atggctgtaa agcaccttat cgtaatcaaa ttcaaggacg gaattacaga agcccagaaa  60
gaagaatttt tcaagaccta tgtaaacctg gtgaatatca tccctgcgat gaaagatgtt  120
tattggggca aagacgtcac ccaaaaaaac aaagaagaag gttacactca cgtcgtcgaa  180
gtctgtttcg actcaatcga gacgatccaa gattacataa tacacccggc ccatgtggga  240
ttcggagacg tttaccgtag cttctgggaa aaacttttga ttttcgacta taccccgaga  300
aaa                                                                303

SEQ ID NO: 704         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 704
MAVKHLIVIK FKDGITEAQK EEFFKTYVNL VNIIPAMKDV YWGKDVTQKN KEEGYTHVVE  60
VCFDSIETIQ DYIIHPAHVG FGDVYRSFWE KLLIFDYTPR K                      101

SEQ ID NO: 705         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 705
atggctgtca agcaccttat catcatcaaa ttcaaggacg aaattacaga agcccagaaa  60
gaagaatttt tcaagaccta tgtaaacctg gtgaatatca tccctgcgat gaaagatgtt  120
tattggggca aagacgtcac ccaacgtaac aaagaagaag gttactcaca catcgtcgaa  180
```

```
gtcactttcg agtcaatcga gatgatccaa gattacataa tacacccggc ccatgtggga  240
ttcggagacg tttaccgtag cttctgggaa aaacttttga ttttcgacta taccccgaga  300
aaa                                                                303

SEQ ID NO: 706         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 706
MAVKHLIIIK FKDEITEAQK EEFFKTYVNL VNIIPAMKDV YWGKDVTQRN KEEGYSHIVE  60
VTFESIEMIQ DYIIHPAHVG FGDVYRSFWE KLLIFDYTPR K                      101

SEQ ID NO: 707         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 707
atggctgtca agcaccttat catcatcaaa ttcaaggacg aaattacaga agcccagaaa  60
gaagaatttt tcaacaccta tgtaaacctg gtgaatatca tccctccgat gaaagatgtt  120
tattggggca aagacgtcac ccaaaaaaac aaagaagaag gttacactca catcgtcgaa  180
gtcactttcg agtcagtaga gggaatccaa gattacataa tgcacccggc ccatgtggga  240
ttcggagacg tttaccgtag cttctgggaa aaacttttga ttttcgacta taccccgaga  300
aaa                                                                303

SEQ ID NO: 708         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 708
MAVKHLIIIK FKDEITEAQK EEFFNTYVNL VNIIPPMKDV YWGKDVTQKN KEEGYTHIVE  60
VTFESVEGIQ DYIMHPAHVG FGDVYRSFWE KLLIFDYTPR K                      101

SEQ ID NO: 709         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 709
atggctgtca agcaccttat catcatcaaa ttcaaggacg aaattacaga agcccagaaa  60
gaagaatttt tcaacaccta tgtaaacctg gtgaatatca tccctgcgat gaaagatgtt  120
tattggggca aagacgtcac ccaacgtaac aaagaagaag gttacactca cgtcgtcgaa  180
gtcactttcg agtcagtaga gtcaatccaa gattacataa tacacccggc ccatgtggga  240
ttcggagacg tttaccgtag cttctgggaa aaacttttga ttttcgacta taccccgaga  300
aaa                                                                303

SEQ ID NO: 710         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 710
MAVKHLIIIK FKDEITEAQK EEFFNTYVNL VNIIPAMKDV YWGKDVTQRN KEEGYTHVVE  60
VTFESVESIQ DYIIHPAHVG FGDVYRSFWE KLLIFDYTPR K                      101

SEQ ID NO: 711         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 711
atggctgtaa agcaccttat cgtaatcaaa ttcaaggacg aaattcaaga agcccagaaa  60
gaagaatttt tcaagaccta tgtaaacctg gtgaatatca tccctgcgat gaaagatgtt  120
tattggggca aagacgtcac ccaacgtaac aaagaagaag gttacactca cgtcgtcgaa  180
gtcactttcg actcagtaga gacgatccaa gattacataa tacacccggc ccatgtggga  240
```

-continued

```
ttcggagacg tttaccgtag cttctgggaa aaacttttga ttttcgacta taccccggga  300
aaa                                                                303

SEQ ID NO: 712          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 712
MAVKHLIVIK FKDEIQEAQK EEFFKTYVNL VNIIPAMKDV YWGKDVTQRN KEEGYTHVVE  60
VTFDSVETIQ DYIIHPAHVG FGDVYRSFWE KLLIFDYTPG K                      101

SEQ ID NO: 713          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 713
atggctgtca agcaccttat catcctgaaa ttccaagacg aaattacaga agcccagaaa  60
gaagaatttt tcaagaccta tgtaaacctg atgaatatca tccctgcgat gaaagatgtt  120
tattggggca aagacgtcac ccaaaaaaac aaagaagaag gttacactca catcgtcgaa  180
gtcactttcg agtcaatcga gtcaatccaa gattacataa tgcacccggc ccatgtggga  240
ttcggagacg tttaccgtag cttctgggaa aaacttttga ttttcgacta taccccgaga  300
aaa                                                                303

SEQ ID NO: 714          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 714
MAVKHLIILK FQDEITEAQK EEFFKTYVNL MNIIPAMKDV YWGKDVTQKN KEEGYTHIVE  60
VTFESIESIQ DYIMHPAHVG FGDVYRSFWE KLLIFDYTPR K                      101

SEQ ID NO: 715          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 715
atggctgtca agcaccttat catcctgaaa ttccaagacg aaattacaga agcccagaaa  60
gaagaatttt tcaagaccta tgtaaacctg gtgaatgtca tccctgcgat gaaagatgtt  120
tattggggca aagacgtcac ccaacgtaac aaagaagaag gttacactca cgtcgtcgaa  180
gtcactttcg agtcagtaga gacgatccaa gattacataa tgcacccggc ccatgtggga  240
ttcggagacg tttaccgtag cttctgggaa aaacttttga ttttcgacta taccccgaga  300
aaa                                                                303

SEQ ID NO: 716          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 716
MAVKHLIILK FQDEITEAQK EEFFKTYVNL VNVIPAMKDV YWGKDVTQRN KEEGYTHVVE  60
VTFESVETIQ DYIMHPAHVG FGDVYRSFWE KLLIFDYTPR K                      101

SEQ ID NO: 717          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 717
atggctgtca agcaccttat catcatcaaa ttcaaggacg aaattacaga agcccagaaa  60
gaagaatttt tcaagaccta tgtaaacctg gtgaatatca tccctgcgat gaaagatgtt  120
tattggggca aagacgtcac ccaacgtaac aaagaagaag gttacactca catcgtcgaa  180
gtcactttcg actcagtaga gacgatccaa gattacataa tacacccggc ccatgtggga  240
ttcggagacg tttaccgtag cttctgggaa aaacttttga ttttcgactt caccccggga  300
```

```
aaa                                                                303

SEQ ID NO: 718         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 718
MAVKHLIIIK FKDEITEAQK EEFFKTYVNL VNIIPAMKDV YWGKDVTQRN KEEGYTHIVE  60
VTFDSVETIQ DYIIHPAHVG FGDVYRSFWE KLLIFDFTPG K                      101

SEQ ID NO: 719         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 719
atggctgtaa agcaccttat cgtaatcaaa ttcaaggacg aaattcaaga agcccagaaa  60
gaagaatttt tcaagaccta tgtaaacctg gtgaatatca tccctgcgat gaaagatgtt  120
tattggggca aagacgtcac ccaacgtaac aaagaagaag gttacactca cgtcgtcgaa  180
gtcactttcg actcagtaga gacgatccaa gattacataa tacacccggc ccatgtggga  240
ttcggagacg tttaccgtag cttctgggaa aaacttttga ttttcgacta taccccggga  300
aaa                                                                303

SEQ ID NO: 720         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 720
MAVKHLIVIK FKDEIQEAQK EEFFKTYVNL VNIIPAMKDV YWGKDVTQRN KEEGYTHVVE  60
VTFDSVETIQ DYIIHPAHVG FGDVYRSFWE KLLIFDYTPG K                      101

SEQ ID NO: 721         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 721
atggctgtca agcaccttat cgtaatcaaa ttcaaggacg gaattacaga agcccagaaa  60
gaagaatttt tcaagaccta tgtaaacctg gtgaatatca tccctgcgat gaaagatgtt  120
tattggggca aagacgtcac ccaaaaaaac aaagaagaag gttacactca cgtcgtcgaa  180
gtctgtttcg actcaatcga gacgatccaa gattacataa tacacccggc ccatgtggga  240
ttcggagacg tttaccgtag cttctgggaa aaacttttga ttttcgacta taccccgaga  300
aaa                                                                303

SEQ ID NO: 722         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 722
MAVKHLIVIK FKDGITEAQK EEFFKTYVNL VNIIPAMKDV YWGKDVTQKN KEEGYTHVVE  60
VCFDSIETIQ DYIIHPAHVG FGDVYRSFWE KLLIFDYTPR K                      101

SEQ ID NO: 723         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 723
atggctgtaa agcaccttat catcatcaaa ttcaaggacg aaattacaga agcccagaaa  60
gaagaatttt tcaagaccta tgtaaacctg gtgaatatca tccctgcgat gaaagatgtt  120
tattggggca aagacgtcac ccaacgtaac aaagaagaag gttacactca catcgtcgaa  180
gtcactttcg actcagtaga gacgatccaa gattacataa tacacccggc ccatgtggga  240
ttcggagacg tttaccgtag cttctgggaa aaacttttga ttttcgactt caccccggga  300
aag                                                                303
```

```
SEQ ID NO: 724          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 724
MAVKHLIIIK FKDEITEAQK EEFFKTYVNL VNIIPAMKDV YWGKDVTQRN KEEGYTHIVE  60
VTFDSVETIQ DYIIHPAHVG FGDVYRSFWE KLLIFDFTPG K                     101

SEQ ID NO: 725          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 725
atggctgtca agcaccttat catcctgaaa ttcaacgacg aaattacaga agcccagaaa  60
gaagaatttt tcaagaccta tgtaaacctg gtgaatgtca tccctgcgat gaaagatgtt  120
tattggggca aagacgtcac ccaaaaaaac aaagaagaag gttacactca cgtcgtcgaa  180
gtcactttcg actcaatcga gacgatccaa gattacataa tacacccggc ccatgtggga  240
ttcggagacg tttaccgtag cttctgggaa aaacttttga ttttcgacta taccccgaga  300
aaa                                                               303

SEQ ID NO: 726          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 726
MAVKHLIILK FNDEITEAQK EEFFKTYVNL VNVIPAMKDV YWGKDVTQKN KEEGYTHVVE  60
VTFDSIETIQ DYIIHPAHVG FGDVYRSFWE KLLIFDYTPR K                     101

SEQ ID NO: 727          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 727
atgccggtca agcaccttat cgtaatcaaa ttcaaggacg aaattacaga agcccagaaa  60
gaagaatttt tcaacaccta tgtaaacctg atgaatatca tccctgcgat gaaagatgtt  120
tattggggca aagacgtcac ccaacgtaac aaagaagaag gttggactca catcgtcgaa  180
gtcactttcg agtcagtaga gacgatccaa gattacataa tacacccggc ccatgtggga  240
ttcggagacg tttaccgtag cttctgggaa aaacttttga ttttcgacta taccccgaga  300
aaa                                                               303

SEQ ID NO: 728          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 728
MPVKHLIVIK FKDEITEAQK EEFFNTYVNL MNIIPAMKDV YWGKDVTQRN KEEGWTHIVE  60
VTFESVETIQ DYIIHPAHVG FGDVYRSFWE KLLIFDYTPR K                     101

SEQ ID NO: 729          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 729
atggctgtaa agcaccttat catcatcaaa ttcaacgacg aaattcaaga agcccagaaa  60
gaagaatttt tcaagaccta tgtaaacctg gtgaatatca tccctgcgat gaaagatgtt  120
tattggggca aagacgtcac ccaacgtaac aaagaagaag gttacactca cgtcgtcgaa  180
gtcactttcg agtcagtaga gacgatccaa gattacataa tacacccggc ccatgtggga  240
ttcggagacg tttaccgtag cttctgggaa aaacttttga ttttcgacta taccccgaga  300
aaa                                                               303
```

```
SEQ ID NO: 730          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 730
MAVKHLIIIK FNDEIQEAQK EEFFKTYVNL VNIIPAMKDV YWGKDVTQRN KEEGYTHVVE  60
VTFESVETIQ DYIIHPAHVG FGDVYRSFWE KLLIFDYTPR K                     101

SEQ ID NO: 731          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 731
atggctgtca agcaccttat cgtaatcaaa ttcaaggacg aaattacaga agcccagaaa  60
gaagaatttt tcaagaccta tgtaaacctg gtgaatatca tcccttcaat gaaagatgtt  120
tattggggca aagacgtcac ccaacgtaac aaagaagaag gttacactca catcgtcgaa  180
gtcactttcg actcagtaga gatgatccaa gattacataa tgcacccggc ccatgtggga  240
ttcggagacg tttaccgtag cttctgggaa aaacttttga ttttcgacta taccccgaga  300
aaa                                                               303

SEQ ID NO: 732          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 732
MAVKHLIVIK FKDEITEAQK EEFFKTYVNL VNIIPSMKDV YWGKDVTQRN KEEGYTHIVE  60
VTFDSVEMIQ DYIMHPAHVG FGDVYRSFWE KLLIFDYTPR K                     101

SEQ ID NO: 733          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 733
atggctgtca agcaccttat cgtaatcaaa ttcaaggacg aaattacaga agcccagaaa  60
gaagaatttt tcaagaccta tgtaaacctg gtgaatatca tccctgcgat gaaagatgtt  120
tattggggca aagacgtcac ccaacgtaac aaagaagaag gttacactca cgtcgtcgaa  180
gtcactttcg agtcagtaga ggccatccaa acctacataa tacacccggc ccatgtggga  240
ttcggagacg tttaccgtag cttctgggaa aaacttttga aattcgacta taccccgaga  300
aaa                                                               303

SEQ ID NO: 734          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 734
MAVKHLIVIK FKDEITEAQK EEFFKTYVNL VNIIPAMKDV YWGKDVTQRN KEEGYTHVVE  60
VTFESVEAIQ TYIIHPAHVG FGDVYRSFWE KLLKFDYTPR K                     101

SEQ ID NO: 735          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 735
atggctgtca agcaccttat cgtaatcaaa ttcaaggacg gaattacaga agcccagaaa  60
gaagaatttt tcaagaccta tgtaaacctg gtgaatatca tccctgcgat gaaagatgtt  120
tattggggca aagacgtcac ccaaaaaaac aaagaagaag gttacactca cgtcgtcgaa  180
gtctgtttcg actcaatcga gacgatccaa gattacataa tacacccggc ccatgtggga  240
ttcggagacg tttaccgtag cttctgggaa aaacttttga ttttcgacta taccccgaga  300
aaa                                                               303

SEQ ID NO: 736          moltype = AA  length = 101
```

```
FEATURE                 Location/Qualifiers
REGION                  1..101
                        note = Synthetic biopolymer
source                  1..101
                        mol_type = protein
                        organism = synthetic construct
SEQUENCE: 736
MAVKHLIVIK FKDGITEAQK EEFFKTYVNL VNIIPAMKDV YWGKDVTQKN KEEGYTHVVE  60
VCFDSIETIQ DYIIHPAHVG FGDVYRSFWE KLLIFDYTPR K                     101

SEQ ID NO: 737          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 737
atggctgtca agcaccttat catcctgaaa ttcaaggacg gaattacaga agcccagaaa  60
gaagaatttt tcaagaccta tgtaaacctg gtgaatatca tccctgcgat gaaagatgtt  120
tattggggca aagacgtcac ccaacgtaac aaagaagaag gttacactca cgtcgtcgaa  180
gtcactttcg actcagtaga gacgatccaa gattacataa tacacccggc ccatgtggga  240
ttcggagacg tttaccgtag cttctgggaa aaacttttga ttttcgacta taccccggcc  300
aaa                                                               303

SEQ ID NO: 738          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 738
MAVKHLIILK FKDGITEAQK EEFFKTYVNL VNIIPAMKDV YWGKDVTQRN KEEGYTHVVE  60
VTFDSVETIQ DYIIHPAHVG FGDVYRSFWE KLLIFDYTPA K                     101

SEQ ID NO: 739          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 739
atggccgtca agcatttaat cgtcgtcaaa tttaaggacg gtatcacaga agctcaaaag  60
gaggaattct tcaaaaccta tgtaaactta gtgaacataa ttcctgctat gaaagacgtt  120
tattggggta aggatgttac gcaaagaaat aaggaatcgg gatacaccca cattgtagaa  180
gtcacttttg aatcagtgga aaccatacaa ggttatatca tacaccctgc acatgttggg  240
ttcggtgatg tctacagatc attttgggaa gaattattga tctttgatta cactccaagg  300
aag                                                               303

SEQ ID NO: 740          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 740
MAVKHLIVVK FKDGITEAQK EEFFKTYVNL VNIIPAMKDV YWGKDVTQRN KESGYTHIVE  60
VTFESVETIQ GYIIHPAHVG FGDVYRSFWE ELLIFDYTPR K                     101

SEQ ID NO: 741          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 741
atgtcagtca agcaccttat catcctgaaa ttcaaggacg aaattacaga agcccagaaa  60
gaagaatttt tcaagaccta tgtaaacctg gtgaatatca tccctgcgat gaaagatgtt  120
tattggggca aagacgtcac ccaacgtaac aaagaagtcg gttactcaca catcgtcgaa  180
gtcactttcg agtcagtaga gtcaatccaa gattacataa tacacccggc ccatgtggga  240
ttcggagacg tttaccgtag cttctgggaa aaacttttga ttttcgacta taccccgaga  300
aaa                                                               303

SEQ ID NO: 742          moltype = AA  length = 101
FEATURE                 Location/Qualifiers
```

```
REGION                  1..101
                        note = Synthetic biopolymer
source                  1..101
                        mol_type = protein
                        organism = synthetic construct
SEQUENCE: 742
MSVKHLIILK FKDEITEAQK EEFFKTYVNL VNIIPAMKDV YWGKDVTQRN KEVGYSHIVE  60
VTFESVESIQ DYIIHPAHVG FGDVYRSFWE KLLIFDYTPR K                     101

SEQ ID NO: 743          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 743
atggctgtca agcaccttat catcctgaaa ttccaagacg aaattacaga agcccagaaa  60
gaagaatttt tcaagaccta tgtaaacctg atgaatatca tccctgcgat gaaagatgtt  120
tattggggca aagacgtcac ccaaaaaaac aaagaagaag gttacactca catcgtcgaa  180
gtcactttcg agtcaatcga gtcaatccaa gattacataa tgcacccggc ccatgtggga  240
ttcggagacg tttaccgtag cttctgggaa aaacttttga ttttcgacta taccccgaga  300
aaa                                                               303

SEQ ID NO: 744          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 744
MAVKHLIILK FQDEITEAQK EEFFKTYVNL MNIIPAMKDV YWGKDVTQKN KEEGYTHIVE  60
VTFESIESIQ DYIMHPAHVG FGDVYRSFWE KLLIFDYTPR K                     101

SEQ ID NO: 745          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 745
atggctgtaa agcaccttat catcctgaaa ttccaagacg aaattacaga agcccagaaa  60
gaagaatttt tcaagaccta tgtaaacctg atgaatatca tccctgcgat gaaagatgtt  120
tattggggca aagacgtcac ccaaaaaaac aaagaagaag gttacactca catcgtcgaa  180
gtcactttcg agtcaatcga gtcaatccaa gattacataa tgcacccggc ccatgtggga  240
ttcggagacg tttaccgtag cttctgggaa aaacttttga ttttcgacta taccccgaga  300
aaa                                                               303

SEQ ID NO: 746          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 746
MAVKHLIILK FQDEITEAQK EEFFKTYVNL MNIIPAMKDV YWGKDVTQKN KEEGYTHIVE  60
VTFESIESIQ DYIMHPAHVG FGDVYRSFWE KLLIFDYTPR K                     101

SEQ ID NO: 747          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 747
atgccggtca agcaccttat catcctgaaa ttcaaggacg aaattacaga agcccagaaa  60
gaagaatttt tcaagaccta tgtaaacctg gtgaatatca tccctgcgat gaaagatgtt  120
tattggggca aagacgtcac ccaacgtaac aaagaagaag gttacactca catcgtcgaa  180
gtctgtttcg agtcagtaga ggaaatccaa gattacataa tgcacccggc ccatgtggga  240
ttcggagacg tttaccgtag cttctgggaa aaacttttga ttttcgacta taccccgaga  300
aaa                                                               303

SEQ ID NO: 748          moltype = AA  length = 101
FEATURE                 Location/Qualifiers
REGION                  1..101
```

```
                        note = Synthetic biopolymer
source                  1..101
                        mol_type = protein
                        organism = synthetic construct
SEQUENCE: 748
MPVKHLIILK FKDEITEAQK EEFFKTYVNL VNIIPAMKDV YWGKDVTQRN KEEGYTHIVE  60
VCFESVEEIQ DYIMHPAHVG FGDVYRSFWE KLLIFDYTPR K                      101

SEQ ID NO: 749          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 749
atggctgtaa agcaccttat catcatcaaa ttcaacgacg aaattcaaga agcccagaaa  60
gaagaatttt tcaagaccta tgtaaacctg gtgaatatca tccctgcgat gaaagatgtt  120
tattggggca aagacgtcac ccaacgtaac aaagaagaag gttacactca cgtcgtcgaa  180
gtcactttcg agtcagtaga gacgatccaa gattacataa tacacccggc ccatgtggga  240
ttcggagacg tttaccgtag cttctgggaa aaacttttga ttttcgacta taccccgaga  300
aaa                                                                303

SEQ ID NO: 750          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 750
MAVKHLIIIK FNDEIQEAQK EEFFKTYVNL VNIIPAMKDV YWGKDVTQRN KEEGYTHVVE  60
VTFESVETIQ DYIIHPAHVG FGDVYRSFWE KLLIFDYTPR K                      101

SEQ ID NO: 751          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 751
atggctgtca agcaccttat catcatcaaa ttcaaggacg aaattacaga agcccagaaa  60
gaagaatttt tcaagaccta tgtaaacctg gtgaatgtca tccctgcgat gaaagatgtt  120
tattggggca aagacgtcac ccaacgtaac aaagaagaag gttacactca catcgtcgaa  180
gtctgtttcg actcagtaga gacgatccaa gattacataa tacacccggc ccatgtggga  240
ttcggagacg tttaccgtag cttctgggaa aaacttttga ttttcgacta taccccgaga  300
aaa                                                                303

SEQ ID NO: 752          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 752
MAVKHLIIIK FKDEITEAQK EEFFKTYVNL VNVIPAMKDV YWGKDVTQRN KEEGYTHIVE  60
VCFDSVETIQ DYIIHPAHVG FGDVYRSFWE KLLIFDYTPR K                      101

SEQ ID NO: 753          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 753
atggctgtca agcaccttat catcctgaaa ttccaagacg aaattacaga agcccagaaa  60
gaagaatttt tcaagaccta tgtaaacctg atgaatatca tccctgcgat gaaagatgtt  120
tattggggca aagacgtcac ccaaaaaaac aaagaagaag gttacactca catcgtcgaa  180
gtcactttcg agtcaatcga gtcaatccaa gattacataa tgcacccggc ccatgtggga  240
ttcggagacg tttaccgtag cttctgggaa aaacttttga ttttcgacta taccccgaga  300
aaa                                                                303

SEQ ID NO: 754          moltype = AA  length = 101
FEATURE                 Location/Qualifiers
REGION                  1..101
                        note = Synthetic biopolymer
```

```
source                  1..101
                        mol_type = protein
                        organism = synthetic construct
SEQUENCE: 754
MAVKHLIILK FQDEITEAQK EEFFKTYVNL MNIIPAMKDV YWGKDVTQKN KEEGYTHIVE  60
VTFESIESIQ DYIMHPAHVG FGDVYRSFWE KLLIFDYTPR K                      101

SEQ ID NO: 755          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 755
atggctgtca agcaccttat cgtaatcaaa ttcaaggacg aaattacaga agcccagaaa  60
gaagaatttt tcaagaccta tgtaaacctg gtgaatatca tccctgcgat gaaagatgtt  120
tattggggca aagacgtcac ccaaaaaaac aaagaagtcg gttacactca cgtcgtcgaa  180
gtcactttcg actcagtaga gtcaatccaa gattacataa tgcacccggc ccatgtggga  240
ttcggagacg tttaccgtag cttctgggaa aaacttttga ttttcgacta taccccgaga  300
aaa                                                                303

SEQ ID NO: 756          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 756
MAVKHLIVIK FKDEITEAQK EEFFKTYVNL VNIIPAMKDV YWGKDVTQKN KEVGYTHVVE  60
VTFDSVESIQ DYIMHPAHVG FGDVYRSFWE KLLIFDYTPR K                      101

SEQ ID NO: 757          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 757
atggctgtca agcaccttat catcctgaaa ttcaaggacg aaattacaga agcccagaaa  60
gaagaatttt tcaagaccta ttgtaacctg gtgaatatca tcccttcaat gaaagatgtt  120
tattggggca aagacgtcac ccaacgtaac aaagaagaag gttactcaca catcgtcgaa  180
gtcactttcg agtcaatcga gacgatccaa gattacataa tacacccggc ccatgtggga  240
ttcggagacg tttaccgtag cttctgggaa aaacttttga ttttcgacta taccccgaga  300
aaa                                                                303

SEQ ID NO: 758          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 758
MAVKHLIILK FKDEITEAQK EEFFKTYCNL VNIIPSMKDV YWGKDVTQRN KEEGYSHIVE  60
VTFESIETIQ DYIIHPAHVG FGDVYRSFWE KLLIFDYTPR K                      101

SEQ ID NO: 759          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 759
atggctgtca agcaccttat catcctgaaa ttccaagacg aaattacaga agcccagaaa  60
gaagaatttt tcaagaccta tgtaaacctg atgaatatca tccctgcgat gaaagatgtt  120
tattggggca aagacgtcac ccaaaaaaac aaagaagaag gttacactca catcgtcgaa  180
gtcactttcg agtcaatcga gtcaatccaa gattacataa tgcacccggc ccatgtggga  240
ttcggagacg tttaccgtag cttctgggaa aaacttttga ttttcgacta taccccgaga  300
aaa                                                                303

SEQ ID NO: 760          moltype = AA  length = 101
FEATURE                 Location/Qualifiers
REGION                  1..101
                        note = Synthetic biopolymer
source                  1..101
```

```
                        mol_type = protein
                        organism = synthetic construct
SEQUENCE: 760
MAVKHLIILK FQDEITEAQK EEFFKTYVNL MNIIPAMKDV YWGKDVTQKN KEEGYTHIVE  60
VTFESIESIQ DYIMHPAHVG FGDVYRSFWE KLLIFDYTPR K                      101

SEQ ID NO: 761          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 761
atggctgtca agcaccttat catcatcaaa ttcaaggacg aaattacaga agcccagaaa  60
gaagaatttt tcaagaccta tgtaaacctg gtgaatatca tccctgcgat gaaagatgtt  120
tattggggca aagacgtcac ccaacgtaac aaagaagaag gttacactca catcgtcgaa  180
gtcactttcg actcagtaga gacgatccaa gattacataa tacacccggc ccatgtggga  240
ttcggagacg tttaccgtag cttctgggaa aaacttttga ttttcgactt caccccggga  300
aaa                                                                303

SEQ ID NO: 762          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 762
MAVKHLIIIK FKDEITEAQK EEFFKTYVNL VNIIPAMKDV YWGKDVTQRN KEEGYTHIVE  60
VTFDSVETIQ DYIIHPAHVG FGDVYRSFWE KLLIFDFTPG K                      101

SEQ ID NO: 763          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 763
atggctgtaa agcaccttat catcatcaaa ttcaaggacg aaattacaga agcccagaaa  60
gaagaatttt tcaagaccta tgtaaacctg gtgaatgtca tccctgcgat gaaagatgtt  120
tattggggca aagacgtcac ccaaaaaaac aaagaagaag gttacactca cgtcgtcgaa  180
gtcactttcg actcagtaga gacgatccaa gattacataa tacacccggc ccatgtggga  240
ttcggagacg tttaccgtag cttctgggaa aaacttttga ttttcgacta taccccggga  300
aaa                                                                303

SEQ ID NO: 764          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 764
MAVKHLIIIK FKDEITEAQK EEFFKTYVNL VNVIPAMKDV YWGKDVTQKN KEEGYTHVVE  60
VTFDSVETIQ DYIIHPAHVG FGDVYRSFWE KLLIFDYTPG K                      101

SEQ ID NO: 765          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 765
atggctgtaa agcaccttat catcctgaaa ttcaaggacg gaattacaga agcccagaaa  60
gaagaatttt tcaagaccta tgtaaacctg gtgaatatca tccctgcgat gaaagatgtt  120
tattggggca aagacgtcac ccaacgtaac aaagaagaag gttacactca cgtcgtcgaa  180
gtcactttcg actcagtaga gacgatccaa gattacataa tacacccggc ccatgtggga  240
ttcggagacg tttaccgtag cttctgggaa aaacttttga ttttcgacta taccccggcc  300
aaa                                                                303

SEQ ID NO: 766          moltype = AA  length = 101
FEATURE                 Location/Qualifiers
REGION                  1..101
                        note = Synthetic biopolymer
source                  1..101
                        mol_type = protein
```

```
                         organism = synthetic construct
SEQUENCE: 766
MAVKHLIILK FKDGITEAQK EEFFKTYVNL VNIIPAMKDV YWGKDVTQRN KEEGYTHVVE  60
VTFDSVETIQ DYIIHPAHVG FGDVYRSFWE KLLIFDYTPA K                      101

SEQ ID NO: 767           moltype = DNA  length = 303
FEATURE                  Location/Qualifiers
misc_feature             1..303
                         note = Synthetic biopolymer
source                   1..303
                         mol_type = other DNA
                         organism = synthetic construct
SEQUENCE: 767
atggctgtaa agcaccttat catcatcaaa ttcaaggacg aaattacaga agcccagaaa  60
gaagaatttt tcaacaccta tgtaaacctg gtgaatatca tccctccgat gaaagatgtt  120
tattggggca aagacgtcac ccaaaaaaac aaagaagaag gttacactca catcgtcgaa  180
gtcactttcg agtcagtaga gggaatccaa gattacataa tgcacccggc ccatgtggga  240
ttcggagacg tttaccgtag cttctgggaa aaacttttga ttttcgacta taccccgaga  300
aaa                                                                303

SEQ ID NO: 768           moltype = AA  length = 101
FEATURE                  Location/Qualifiers
REGION                   1..101
                         note = Synthetic biopolymer
source                   1..101
                         mol_type = protein
                         organism = synthetic construct
SEQUENCE: 768
MAVKHLIIIK FKDEITEAQK EEFFNTYVNL VNIIPPMKDV YWGKDVTQKN KEEGYTHIVE  60
VTFESVEGIQ DYIMHPAHVG FGDVYRSFWE KLLIFDYTPR K                      101

SEQ ID NO: 769           moltype = DNA  length = 303
FEATURE                  Location/Qualifiers
misc_feature             1..303
                         note = Synthetic biopolymer
source                   1..303
                         mol_type = other DNA
                         organism = synthetic construct
SEQUENCE: 769
atggctgtaa agcaccttat catcctgaaa ttcaaggacg aaattacaga agcccagaaa  60
gaagaatttt tcaagaccta tgtaaacctg atgaatatca tccctgcgat gaaagatgtt  120
tattggggca aagacgtcac ccaaaaaaac aaagaagaag gttacactca catcgtcgaa  180
gtcactttcg actcagtaga gcaaatcaaa acctacataa tacacccggc ccatgtggga  240
ttcggagacg tttaccgtag cttctgggaa aaacttttga ttttcgacta taccccgaga  300
aaa                                                                303

SEQ ID NO: 770           moltype = AA  length = 101
FEATURE                  Location/Qualifiers
REGION                   1..101
                         note = Synthetic biopolymer
source                   1..101
                         mol_type = protein
                         organism = synthetic construct
SEQUENCE: 770
MAVKHLIILK FKDEITEAQK EEFFKTYVNL MNIIPAMKDV YWGKDVTQKN KEEGYTHIVE  60
VTFDSVEQIK TYIIHPAHVG FGDVYRSFWE KLLIFDYTPR K                      101

SEQ ID NO: 771           moltype = DNA  length = 303
FEATURE                  Location/Qualifiers
misc_feature             1..303
                         note = Synthetic biopolymer
source                   1..303
                         mol_type = other DNA
                         organism = synthetic construct
SEQUENCE: 771
atggctgtca agcaccttat cgtaatcaaa ttcaaggacg aaattacaga agcccagaaa  60
gaagaatttt tcaacaccta tgtaaacctg gtgaatatca tccctcaaat gaaagatgtt  120
tattggggca aagacgtcac ccaacgtaac aaagaagaag gttacactca catcgtcgaa  180
gtcactttcg agtcaatcga gcaaatccaa gattacataa tacacccggc ccatgtggga  240
ttcggagacg tttaccgtag cttctgggaa aaacttttga ttttcgacta taccccgaga  300
aaa                                                                303

SEQ ID NO: 772           moltype = AA  length = 101
FEATURE                  Location/Qualifiers
REGION                   1..101
                         note = Synthetic biopolymer
source                   1..101
                         mol_type = protein
                         organism = synthetic construct
```

```
SEQUENCE: 772
MAVKHLIVIK FKDEITEAQK EEFFNTYVNL VNIIPQMKDV YWGKDVTQRN KEEGYTHIVE  60
VTFESIEQIQ DYIIHPAHVG FGDVYRSFWE KLLIFDYTPR K                      101

SEQ ID NO: 773         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 773
atggctgtaa agcaccttat cgtaatcaaa ttcaaggacg aaattacaga agcccagaaa  60
gaagaatttt tcaacaccta tgtaaacctg gtgaatatca tccctcaaat gaaagatgtt  120
tattggggca aagacgtcac ccaacgtaac aaagaagaag gttacactca catcgtcgaa  180
gtcactttcg agtcaatcga gcaaatccaa gattacataa tacacccggc ccatgtggga  240
ttcggagacg tttaccgtag cttctgggaa aaactttga ttttcgacta taccccgaga  300
aaa                                                                303

SEQ ID NO: 774         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 774
MAVKHLIVIK FKDEITEAQK EEFFNTYVNL VNIIPQMKDV YWGKDVTQRN KEEGYTHIVE  60
VTFESIEQIQ DYIIHPAHVG FGDVYRSFWE KLLIFDYTPR K                      101

SEQ ID NO: 775         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 775
atggctgtca agcaccttat catcctgaaa ttcaaggacg aaattacaga agcccagaaa  60
gaagaatttt tcaagaccta tgtaaacctg gtgaatatca tccctgcgat gaaagatgtt  120
tattggggca aagacgtcac ccaacgtaac aaagaagaag gttacactca catcgtcgaa  180
gtcactttcg actcagtaga gtcaatccaa gattacataa tacacccggc ccatgtggga  240
ttcggagacg tttaccgtag cttctgggac aaacttttga aattcgacta taccccgaga  300
aaa                                                                303

SEQ ID NO: 776         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 776
MAVKHLIILK FKDEITEAQK EEFFKTYVNL VNIIPAMKDV YWGKDVTQRN KEEGYTHIVE  60
VTFDSVESIQ DYIIHPAHVG FGDVYRSFWD KLLKFDYTPR K                      101

SEQ ID NO: 777         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 777
atggctgtca agcaccttat catcctgaaa ttcaaggacg aaattacaga agcccagaaa  60
gaagaatttt tcaagaccta tgtaaacctg gtgaatatca tcccttcaat gaaagatgtt  120
tattggggca aagacgtcac ccaaaaaaac aaagaagaag gttactcaca catcgtcgaa  180
gtcactttcg agtcagtaga gtcaatccaa gattacataa tacacccggc ccatgtggga  240
ttcggagacg tttaccgtag cttctgggac aaacttttga aattcgacta taccccgaga  300
aaa                                                                303

SEQ ID NO: 778         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 778
```

```
MAVKHLIILK FKDEITEAQK EEFFKTYVNL VNIIPSMKDV YWGKDVTQKN KEEGYSHIVE  60
VTFESVESIQ DYIIHPAHVG FGDVYRSFWD KLLKFDYTPR K                      101

SEQ ID NO: 779         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 779
atggctgtca agcaccttat cgtaatcaaa ttcaaggacg aaattacaga agcccagaaa  60
gaagaatttt tcaagaccta tgtaaacctg gtgaatatca tccctgcgat gaaagatgtt  120
tattggggca aagacgtcac ccaacgtaac aaagaagaag gttacactca catcgtcgaa  180
gtctgtttcg actcagtaga gggaatccaa gattacataa tgcacccggc ccatgtggga  240
ttcggagacg tttaccgtag cttctgggaa aaacttttga ttttcgacta taccccgaga  300
aaa                                                                303

SEQ ID NO: 780         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 780
MAVKHLIVIK FKDEITEAQK EEFFKTYVNL VNIIPAMKDV YWGKDVTQRN KEEGYTHIVE  60
VCFDSVEGIQ DYIMHPAHVG FGDVYRSFWE KLLIFDYTPR K                      101

SEQ ID NO: 781         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 781
atggctgtca agcaccttat cgtactgaaa ttcaacgacg aaattacaga agcccagaaa  60
gaagaatttt tcaagaccta tgtaaacctg gtgaatatca tccctgcgat gaaagatgtt  120
tattggggca aagacgtcac ccaaaaaaac aaagaagaag gttactcaca cgtcgtcgaa  180
gtcactttcg agtcaatcga ggccatccaa acctacataa tacacccggc ccatgtggga  240
ttcggagacg tttaccgtag cttctgggaa aaacttttga ttttcgacta taccccgaga  300
aaa                                                                303

SEQ ID NO: 782         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 782
MAVKHLIVLK FNDEITEAQK EEFFKTYVNL VNIIPAMKDV YWGKDVTQKN KEEGYSHVVE  60
VTFESIEAIQ TYIIHPAHVG FGDVYRSFWE KLLIFDYTPR K                      101

SEQ ID NO: 783         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 783
atggctgtca agcaccttat cgtaatcaaa ttcaaggacg aaattacaga agcccagaaa  60
gaagaatttt tcaagaccta tgtaaacctg gtgaatgtca tccctgcgat gaaagatgtt  120
tattggggca aagacgtcac catgaaaaac aaagaagaag gttacactca cgtcgtcgaa  180
gtcactttcg actcagtaga gacgatccaa gattacataa tgcacccggc ccatgtggga  240
ttcggagacg tttaccgtag cttctgggaa aaacttttga ttttcgacta taccccgaga  300
aaa                                                                303

SEQ ID NO: 784         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 784
MAVKHLIVIK FKDEITEAQK EEFFKTYVNL VNVIPAMKDV YWGKDVTMKN KEEGYTHVVE  60
```

```
VTFDSVETIQ DYIMHPAHVG FGDVYRSFWE KLLIFDYTPR K                    101

SEQ ID NO: 785         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 785
atggctgtca agcaccttat cgtaatcaaa ttcaaggacg aaattacaga agcccagaaa  60
gaagaatttt tcaagaccta tgtaaacctg atgaatatca tccctgcgat gaaagatgtt  120
tattggggca aagacgtcac ccaacgttat aaagaagaag gttacactca catcgtcgaa  180
gtcactttcg agtcagtaga gtcaatccaa gattacataa tgcacccggc ccatgtggga  240
ttcggagacg tttaccgtag cttctgggaa aaacttttga ttttcgacta taccccgaga  300
aaa                                                                303

SEQ ID NO: 786         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 786
MAVKHLIVIK FKDEITEAQK EEFFKTYVNL MNIIPAMKDV YWGKDVTQRY KEEGYTHIVE  60
VTFESVESIQ DYIMHPAHVG FGDVYRSFWE KLLIFDYTPR K                    101

SEQ ID NO: 787         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 787
atggctgtaa agcaccttat catcctgaaa ttcaaggacg aaattacaga agcccagaaa  60
gaagaatttt tcaacaccta tgtaaacctg gtgaatgtca tccctgcgat gaaagatgtt  120
tattggggca aagacgtcac ccaacgtaac aaagaagaag gttacactca catcgtcgaa  180
gtcactttcg actcagtaga gacgatccaa gattacataa tgcacccggc ccatgtggga  240
ttcggagacg tttaccgtag cttctgggaa aaacttttga ttttcgacta taccccgaga  300
aaa                                                                303

SEQ ID NO: 788         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 788
MAVKHLIILK FKDEITEAQK EEFFNTYVNL VNVIPAMKDV YWGKDVTQRN KEEGYTHIVE  60
VTFDSVETIQ DYIMHPAHVG FGDVYRSFWE KLLIFDYTPR K                    101

SEQ ID NO: 789         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 789
atggctgtca agcaccttat cgtaatcaaa ttcaaggacg aaattacaga atcacagaaa  60
gaagaatttt tcaacaccta tgtaaacctg gtgaatatca tccctgcgat gaaagatgtt  120
tattggggca aagacgtcac ccaacgtaac aaagaagaag gttacactca cgtcgtcgaa  180
gtcactttcg agtcagtaga gacgatccaa gattacataa tacacccggc ccatgtggga  240
ttcggagacg tttaccgtcc gttctgggaa aaacttttga ttttcgacta taccccgaga  300
aaa                                                                303

SEQ ID NO: 790         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 790
MAVKHLIVIK FKDEITESQK EEFFNTYVNL VNIIPAMKDV YWGKDVTQRN KEEGYTHVVE  60
VTFESVETIQ DYIIHPAHVG FGDVYRPFWE KLLIFDYTPR K                    101
```

```
SEQ ID NO: 791          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 791
atggctgtca agcaccttat cgtaatcaaa ttcaaggacg aaattacaga agcccagaaa  60
gaactttttt tcaagaccta tgtaaacctg gtgaatatca tccctgcgat gaaagatgtt  120
tattggggca aagacgtcac ccaacgtaac aaagaagaag gttacactca catcgtcgaa  180
gtcactttcg actcagtaga gacgatccaa gattacataa tgcacccggc ccatgtggga  240
ttcggagacg tttaccgtag cttctgggaa aaacttttga ttttcgactt caccccgaga  300
aaa                                                                303

SEQ ID NO: 792          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 792
MAVKHLIVIK FKDEITEAQK ELFFKTYVNL VNIIPAMKDV YWGKDVTQRN KEEGYTHIVE  60
VTFDSVETIQ DYIMHPAHVG FGDVYRSFWE KLLIFDFTPR K                      101

SEQ ID NO: 793          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 793
atggctgtaa agcaccttat catcctgaaa ttcaaggacg aaattacaga agcccagaaa  60
gaagaatttt tcaagaccta tgtaaacctg gtgaatatca tccctgcgat gaaagatgtt  120
tattggggca aagacgtcac ccaacgtaac aaagaagaag gttacactca catcgtcgaa  180
gtcactttcg actcagtaga gtcaatccaa gattacataa tacacccggc ccatgtggga  240
ttcggagacg tttaccgtag cttctgggac aaacttttga aattcgacta taccccgaga  300
aaa                                                                303

SEQ ID NO: 794          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 794
MAVKHLIILK FKDEITEAQK EEFFKTYVNL VNIIPAMKDV YWGKDVTQRN KEEGYTHIVE  60
VTFDSVESIQ DYIIHPAHVG FGDVYRSFWD KLLKFDYTPR K                      101

SEQ ID NO: 795          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 795
atggctgtaa agcaccttat cgtaatcaaa ttcaaggacg aaattacaga agcccagaaa  60
gaactttttt tcaagaccta tgtaaacctg gtgaatatca tccctgcgat gaaagatgtt  120
tattggggca aagacatcac ccaaaaaaac aaagaagaag gttacactca catcgtcgaa  180
gtcactttcg actcagtaga gacgatccaa gattacataa tgcacccggc ccatgtggga  240
ttcggagacg tttaccgtag cttctgggaa aaacttttga ttttcgactt caccccaaga  300
aaa                                                                303

SEQ ID NO: 796          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 796
MAVKHLIVIK FKDEITEAQK ELFFKTYVNL VNIIPAMKDV YWGKDITQKN KEEGYTHIVE  60
VTFDSVETIQ DYIMHPAHVG FGDVYRSFWE KLLIFDFTPR K                      101
```

```
SEQ ID NO: 797          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 797
atggctgtaa agcaccttat catcctgaaa ttcaaggacg aaattacaga atcacagaaa  60
gaagaatttt tcaagaccta tgtaaacctg gtgaatatca tccctgcgat gaaagatgtt  120
tattggggca aagacgtcac ccaacgtaac aaagaagaag gttacactca catcgtcgaa  180
gtcactttcg actcaatcga gacgatccaa gattacataa tacacccggc ccatgtggga  240
ttcggagacg tttaccgtag cttctgggaa aaacttttga aattcgacta taccccgaga  300
aaa                                                                303

SEQ ID NO: 798          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 798
MAVKHLIILK FKDEITESQK EEFFKTYVNL VNIIPAMKDV YWGKDVTQRN KEEGYTHIVE  60
VTFDSIETIQ DYIIHPAHVG FGDVYRSFWE KLLKFDYTPR K                    101

SEQ ID NO: 799          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 799
atggctgtca agcaccttat cgtaatcaaa ttcaaggacg aaattacaga agcccagaaa  60
gaacttttt tcaagaccta tgtaaacctg gtgaatatca tccctgcgat gaaagatgtt  120
tattggggca aagacgtcac ccaacgtaac aaagaagaag gttacactca catcgtcgaa  180
gtcactttcg actcagtaga gacgatccaa gattacataa tgcacccggc ccatgtggga  240
ttcggagacg tttaccgtag cttctgggaa aaacttttga ttttcgactt caccccgaga  300
aaa                                                                303

SEQ ID NO: 800          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 800
MAVKHLIVIK FKDEITEAQK ELFFKTYVNL VNIIPAMKDV YWGKDVTQRN KEEGYTHIVE  60
VTFDSVETIQ DYIMHPAHVG FGDVYRSFWE KLLIFDFTPR K                    101

SEQ ID NO: 801          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 801
atgtcagtca agcaccttat catcctgaaa ttcaaggacg aaattacaga agcccagaaa  60
gaagaatttt tcaagaccta tgtaaacctg gtgaatatca tccctgcgat gaaagatgtt  120
tattggggca aagacgtcac ccaaaaaaac aaagaagaag gttactcaca catcgtcgaa  180
gtctgtttcg agtcagtaga gtcaatccaa gattacataa tgcacccggc ccatgtggga  240
ttcggagacg tttaccgtag cttctgggaa aaacttttga ttttcgacta taccccgaga  300
aaa                                                                303

SEQ ID NO: 802          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 802
MSVKHLIILK FKDEITEAQK EEFFKTYVNL VNIIPAMKDV YWGKDVTQKN KEEGYSHIVE  60
VCFESVESIQ DYIMHPAHVG FGDVYRSFWE KLLIFDYTPR K                    101

SEQ ID NO: 803          moltype = DNA  length = 303
```

```
FEATURE                Location/Qualifiers
misc_feature           1..303
                       note = Synthetic biopolymer
source                 1..303
                       mol_type = other DNA
                       organism = synthetic construct
SEQUENCE: 803
atggctgtca agcaccttat cgtactgaaa ttcaaggacg aaattacaga agcccagaaa  60
gaagaatttt tcaagaccta tgtaaacctg gtgaatatca tccctgcgat gaaagatgtt  120
gaatggggca aagacgtcac ccaacgtaac aaagaagaag gttactcaca cgtcgtcgaa  180
gtcactttcg agtcaatcga ggccatccaa gattacataa tacacccggc ccatgtggga  240
ttcggagacg tttaccgtag cttctgggaa aaacttttga ttttcgacta taccccgaga  300
aaa                                                                 303

SEQ ID NO: 804         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 804
MAVKHLIVLK FKDEITEAQK EEFFKTYVNL VNIIPAMKDV EWGKDVTQRN KEEGYSHVVE  60
VTFESIEAIQ DYIIHPAHVG FGDVYRSFWE KLLIFDYTPR K                       101

SEQ ID NO: 805         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 805
atggctgtca agcaccttat cgtactggcc ttcaaggacg aaattacaga agcccagaaa  60
gaagaatttt tcaagaccta tgtaaacctg gtgaatatca tccctgcgat gaaagatgtt  120
tattggggca aagacgtcac ccaacgtaac aaagaagaag gttacactca cgtcgtcgaa  180
gtcactttcg actcaatcga ggaaatccaa gattacataa tacacccggc ccatgtggga  240
ttcggagacg tttaccgtag cttctgggaa aaacttttga ttttcgacta taccccgaga  300
aaa                                                                 303

SEQ ID NO: 806         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 806
MAVKHLIVLA FKDEITEAQK EEFFKTYVNL VNIIPAMKDV YWGKDVTQRN KEEGYTHVVE  60
VTFDSIEEIQ DYIIHPAHVG FGDVYRSFWE KLLIFDYTPR K                       101

SEQ ID NO: 807         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 807
atggctgtca agcaccttat cgtactgaaa ttcaacgacg aaattacaga atcacagaaa  60
gaagaatttt tcaagaccta tgtaaacctg gtgaatatca tccctgcgat gaaagatgtt  120
tattggggca aagacgtcac ccaacgtaac aaagaagaag gttacactca cgtcgtcgaa  180
gtcactttcg agtcaatcga gacgatccaa gattacataa tgcacccggc ccatgtggga  240
ttcggagacg tttaccgtag cttctgggaa aaacttttga ttttcgacta taccccgaga  300
aaa                                                                 303

SEQ ID NO: 808         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 808
MAVKHLIVLK FNDEITESQK EEFFKTYVNL VNIIPAMKDV YWGKDVTQRN KEEGYTHVVE  60
VTFESIETIQ DYIMHPAHVG FGDVYRSFWE KLLIFDYTPR K                       101

SEQ ID NO: 809         moltype = DNA  length = 303
FEATURE                Location/Qualifiers
```

```
misc_feature          1..303
                      note = Synthetic biopolymer
source                1..303
                      mol_type = other DNA
                      organism = synthetic construct
SEQUENCE: 809
atggctgtaa agcaccttat cgtactgaaa ttcaaggacg aaattacaga agcccagaaa  60
gaagaatttt tcaagaccta tgtaaacctg gtgaatatca tccctgcgat gaaagatgtt  120
tattggggca aagacgtcac ccaacgtaac aaagaagaag gttacactca cgtcgtcgaa  180
gtctgtttcg agtcagtaga ggaaatccaa acctacataa tgcacccggc ccatgtggga  240
ttcggagacg tttaccgtag cttctgggaa aaacttttga ttttcgacta taccccgaga  300
aaa                                                                303

SEQ ID NO: 810        moltype = AA  length = 101
FEATURE               Location/Qualifiers
REGION                1..101
                      note = Synthetic biopolymer
source                1..101
                      mol_type = protein
                      organism = synthetic construct
SEQUENCE: 810
MAVKHLIVLK FKDEITEAQK EEFFKTYVNL VNIIPAMKDV YWGKDVTQRN KEEGYTHVVE  60
VCFESVEEIQ TYIMHPAHVG FGDVYRSFWE KLLIFDYTPR K                      101

SEQ ID NO: 811        moltype = DNA  length = 303
FEATURE               Location/Qualifiers
misc_feature          1..303
                      note = Synthetic biopolymer
source                1..303
                      mol_type = other DNA
                      organism = synthetic construct
SEQUENCE: 811
atggctgtaa agcaccttat cgtactgaaa ttcaaggacg aaattacaga agcccagaaa  60
gaagaatttt tcaagaccta tgtaaacctg gtgaatgtca tccctgcgat gaaagatgtt  120
tattggggca aagacgtcac ccaacgtaac aaagaagaag gttacactca catcgtcgaa  180
gtctgtttcg actcaatcga gacgatccaa gattacataa tgcacccggc ccatgtggga  240
ttcggagacg tttaccgtag cttctgggaa aaacttttga ttttcgacta taccccgaga  300
aaa                                                                303

SEQ ID NO: 812        moltype = AA  length = 101
FEATURE               Location/Qualifiers
REGION                1..101
                      note = Synthetic biopolymer
source                1..101
                      mol_type = protein
                      organism = synthetic construct
SEQUENCE: 812
MAVKHLIVLK FKDEITEAQK EEFFKTYVNL VNVIPAMKDV YWGKDVTQRN KEEGYTHIVE  60
VCFDSIETIQ DYIMHPAHVG FGDVYRSFWE KLLIFDYTPR K                      101

SEQ ID NO: 813        moltype = DNA  length = 303
FEATURE               Location/Qualifiers
misc_feature          1..303
                      note = Synthetic biopolymer
source                1..303
                      mol_type = other DNA
                      organism = synthetic construct
SEQUENCE: 813
atggctgtca agcaccttat cgtactgaaa ttcaaggacg aaattcaaga agcccagaaa  60
gaagaatttt tcaacaccta tgtaaacctg gtgaatatca tccctcaaat gaaagatgtt  120
tattggggca aagacgtcac ccaacgtaac aaagaagaag gttacactca catcgtcgaa  180
gtcactttcg agtcaatcga gacgatccaa gattacataa tgcacccggc ccatgtggga  240
ttcggagacg tttaccgtag cttctgggaa aaacttttga ttttcgacta taccccgaga  300
aaa                                                                303

SEQ ID NO: 814        moltype = AA  length = 101
FEATURE               Location/Qualifiers
REGION                1..101
                      note = Synthetic biopolymer
source                1..101
                      mol_type = protein
                      organism = synthetic construct
SEQUENCE: 814
MAVKHLIVLK FKDEIQEAQK EEFFNTYVNL VNIIPQMKDV YWGKDVTQRN KEEGYTHIVE  60
VTFESIETIQ DYIMHPAHVG FGDVYRSFWE KLLIFDYTPR K                      101

SEQ ID NO: 815        moltype = DNA  length = 303
FEATURE               Location/Qualifiers
misc_feature          1..303
```

```
                         note = Synthetic biopolymer
source                   1..303
                         mol_type = other DNA
                         organism = synthetic construct
SEQUENCE: 815
atgccggtca agcaccttat cgtactgaaa ttcaaggacg aaattacaga agcccagaaa  60
gaagaatttt tcaagaccta tgtaaacctg gtgaatatca tccctgcgat gaaagatgtt  120
tattggggca aagacgtcac ccaaaaaaac aaagaagaag gttacactca cgtcgtcgaa  180
gtcactttcg actcagtatc acaaatccaa gattacataa tacacccggc ccatgtggga  240
ttcggagacg tttaccgtag cttctgggaa aaacttttga ttttcgacta taccccggga  300
aaa                                                               303

SEQ ID NO: 816         moltype = AA  length = 101
FEATURE                  Location/Qualifiers
REGION                   1..101
                         note = Synthetic biopolymer
source                   1..101
                         mol_type = protein
                         organism = synthetic construct
SEQUENCE: 816
MPVKHLIVLK FKDEITEAQK EEFFKTYVNL VNIIPAMKDV YWGKDVTQKN KEEGYTHVVE  60
VTFDSVSQIQ DYIIHPAHVG FGDVYRSFWE KLLIFDYTPG K                     101

SEQ ID NO: 817         moltype = DNA  length = 303
FEATURE                  Location/Qualifiers
misc_feature             1..303
                         note = Synthetic biopolymer
source                   1..303
                         mol_type = other DNA
                         organism = synthetic construct
SEQUENCE: 817
atggctgtca agcaccttat cgtactgaaa ttcaaggacg aaattacaga agcccagaaa  60
gaagaatttt tcaagaccta tgtaaacctg gtgaatgtca tccctgcgat gaaagatgtt  120
tattggggca aagacgtcac ccaacgtaac aaagaagaag gttacactca catcgtcgaa  180
gtctgtttcg actcaatcga gacgatccaa gattacataa tgcacccggc ccatgtggga  240
ttcggagacg tttaccgtag cttctgggaa aaacttttga ttttcgacta taccccgaga  300
aaa                                                               303

SEQ ID NO: 818         moltype = AA  length = 101
FEATURE                  Location/Qualifiers
REGION                   1..101
                         note = Synthetic biopolymer
source                   1..101
                         mol_type = protein
                         organism = synthetic construct
SEQUENCE: 818
MAVKHLIVLK FKDEITEAQK EEFFKTYVNL VNVIPAMKDV YWGKDVTQRN KEEGYTHIVE  60
VCFDSIETIQ DYIMHPAHVG FGDVYRSFWE KLLIFDYTPR K                     101

SEQ ID NO: 819         moltype = DNA  length = 303
FEATURE                  Location/Qualifiers
misc_feature             1..303
                         note = Synthetic biopolymer
source                   1..303
                         mol_type = other DNA
                         organism = synthetic construct
SEQUENCE: 819
atggctgtaa agcaccttat cgtactgaaa ttcaaggacg aaattacaga agcccagaaa  60
gaagaatttt tcaagaccta tgtaaacctg gtgaatatca tccctgcgat gaaagatgtt  120
tattggggca aagacgtcac ccaacgtaac aaagaagaag gttacactca cgtcgtcgaa  180
gtcactttcg agtcagtaga ggccatccaa acctacataa tgcacccggc ccatgtggga  240
ttcggagacg tttaccgtag cttctgggaa aaacttttga ttttcgacta taccccggga  300
aaa                                                               303

SEQ ID NO: 820         moltype = AA  length = 101
FEATURE                  Location/Qualifiers
REGION                   1..101
                         note = Synthetic biopolymer
source                   1..101
                         mol_type = protein
                         organism = synthetic construct
SEQUENCE: 820
MAVKHLIVLK FKDEITEAQK EEFFKTYVNL VNIIPAMKDV YWGKDVTQRN KEEGYTHVVE  60
VTFESVEAIQ TYIMHPAHVG FGDVYRSFWE KLLIFDYTPG K                     101

SEQ ID NO: 821         moltype = DNA  length = 303
FEATURE                  Location/Qualifiers
misc_feature             1..303
                         note = Synthetic biopolymer
```

```
source                  1..303
                        mol_type = other DNA
                        organism = synthetic construct
SEQUENCE: 821
atggctgtca agcaccttat cgtactgaaa ttcaaggacg aaattacaga agcccagaaa  60
gaagaatttt tcaacaccta tgtaaacctg gtgaatatca tccctgcgat gaaagatgtt  120
tattggggca aagacgtcac ccaacgtaac aaagaagaag gttacactca cgtcgtcgaa  180
gtcactttcg actcaatcga gtcaatccaa gattacataa tacacccggc ccatgtggga  240
ttcggagacg tttaccgtag cttctgggaa aaacttttga ttttcgacta taccccgaga  300
aaa                                                                 303

SEQ ID NO: 822          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 822
MAVKHLIVLK FKDEITEAQK EEFFNTYVNL VNIIPAMKDV YWGKDVTQRN KEEGYTHVVE  60
VTFDSIESIQ DYIIHPAHVG FGDVYRSFWE KLLIFDYTPR K                     101

SEQ ID NO: 823          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 823
atggctgtca agcaccttat cgtactgaaa ttcaaggacg aaattacaga agcccagaaa  60
gaagaatttt tcaagaccta tgtaaacctg gtgaatatca tccctcaaat gaaagatgtt  120
tattggggca aagacgtcac ccaacgtaac aaagaagaag gttacactca cgtcgtcgaa  180
gtcactttcg actcaatcga gacgatccaa gattacataa tacacccggc ccatgtggga  240
ttcggagacg tttaccgtag cttctgggaa gaacttttga ttttcgacta taccccgaga  300
aaa                                                                 303

SEQ ID NO: 824          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 824
MAVKHLIVLK FKDEITEAQK EEFFKTYVNL VNIIPQMKDV YWGKDVTQRN KEEGYTHVVE  60
VTFDSIETIQ DYIIHPAHVG FGDVYRSFWE ELLIFDYTPR K                     101

SEQ ID NO: 825          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 825
atggctgtaa agcaccttat cgtactgaaa ttcaacgacg aaattacaga atcacagaaa  60
gaagaatttt tcaagaccta tgtaaacctg gtgaatatca tccctgcgat gaaagatgtt  120
tattggggca aagacgtcac ccaacgtaac aaagaagaag gttacactca cgtcgtcgaa  180
gtcactttcg agtcaatcga gacgatccaa gattacataa tgcacccggc ccatgtggga  240
ttcggagacg tttaccgtag cttctgggaa aaacttttga ttttcgacta taccccgaga  300
aaa                                                                 303

SEQ ID NO: 826          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 826
MAVKHLIVLK FNDEITESQK EEFFKTYVNL VNIIPAMKDV YWGKDVTQRN KEEGYTHVVE  60
VTFESIETIQ DYIMHPAHVG FGDVYRSFWE KLLIFDYTPR K                     101

SEQ ID NO: 827          moltype = DNA  length = 303
FEATURE                 Location/Qualifiers
misc_feature            1..303
                        note = Synthetic biopolymer
source                  1..303
```

```
                        mol_type = other DNA
                        organism = synthetic construct
SEQUENCE: 827
atggctgtca agcaccttat cgtactgaaa ttcaaggacg aaattacaga agcccagaaa  60
gtcgaatttt tcaagaccta tgtaaacctg gtgaatatca tccctcaaat gaaagatgtt  120
tattggggca aagacgtcac ccaaaaaaac aaagaagaag gttacactca cgtcgtcgaa  180
gtcactttcg agtcaatctc aacgatccaa gattacataa tgcacccggc ccatgtggga  240
ttcggagacg tttaccgtag cttctgggaa aaacttttga ttttcgacta taccccgaga  300
aaa                                                                 303

SEQ ID NO: 828          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 828
MAVKHLIVLK FKDEITEAQK VEFFKTYVNL VNIIPQMKDV YWGKDVTQKN KEEGYTHVVE  60
VTFESISTIQ DYIMHPAHVG FGDVYRSFWE KLLIFDYTPR K                       101

SEQ ID NO: 829          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 829
atgccggtca agcaccttat cgtactgaaa ttcaaggacg gaattacaga agcccagaaa  60
gaagaatttt tcaagaccta tgtaaacctg gtgaatatca tccctgcgat gaaagatgtt  120
tattggggca aagacgtcac ctgtaaaaac aaagaagaag gttacactca cgtcgtcgaa  180
gtcactttcg actcaatcga gacgatccaa gattacataa tacacccggc ccatgtggga  240
ttcggagacg tttaccgtag cttctgggaa aaacttttga ttttcgacta taccccgaga  300
aaa                                                                 303

SEQ ID NO: 830          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 830
MPVKHLIVLK FKDGITEAQK EEFFKTYVNL VNIIPAMKDV YWGKDVTCKN KEEGYTHVVE  60
VTFDSIETIQ DYIIHPAHVG FGDVYRSFWE KLLIFDYTPR K                       101

SEQ ID NO: 831          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 831
atgccggtca agcaccttat cgtactgaaa ttcgtcgacg aaattcaaga agcccagaaa  60
gaagaatttt tcaagaccta tgtaaacctg gtgaatatca tccctgcgat gaaagatgtt  120
tattggggca aagacgtcac ccaacgtaac aaagaagaag gttacactca cgtcgtcgaa  180
gtcactttcg agtcaatcga gacgatccaa gattacataa tacacccggc ccatgtggga  240
ttcggagacg tttaccgtag cttctgggaa aaacttttga ttttcgacta taccccgaga  300
aaa                                                                 303

SEQ ID NO: 832          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 832
MPVKHLIVLK FVDEIQEAQK EEFFKTYVNL VNIIPAMKDV YWGKDVTQRN KEEGYTHVVE  60
VTFESIETIQ DYIIHPAHVG FGDVYRSFWE KLLIFDYTPR K                       101

SEQ ID NO: 833          moltype = DNA  length = 303
FEATURE                 Location/Qualifiers
misc_feature            1..303
                        note = Synthetic biopolymer
source                  1..303
                        mol_type = other DNA
```

```
                         organism = synthetic construct
SEQUENCE: 833
atgccggtca agcaccttat cgtactgaaa ttcgtcgacg aaattcaaga agcccagaaa  60
gaagaatttt tcaagaccta tgtaaacctg gtgaatatca tccctgcgat gaaagatgtt  120
tattggggca aagacgtcac ccaacgtaac aaagaagaag gttacactca cgtcgtcgaa  180
gtcactttcg agtcaatcga gacgatccaa gattacataa tacacccggc ccatgtggga  240
ttcggagacg tttaccgtag cttctgggaa aaacttttga ttttcgacta taccccgaga  300
aaa                                                                303

SEQ ID NO: 834           moltype = AA  length = 101
FEATURE                  Location/Qualifiers
REGION                   1..101
                         note = Synthetic biopolymer
source                   1..101
                         mol_type = protein
                         organism = synthetic construct
SEQUENCE: 834
MPVKHLIVLK FVDEIQEAQK EEFFKTYVNL VNIIPAMKDV YWGKDVTQRN KEEGYTHVVE  60
VTFESIETIQ DYIIHPAHVG FGDVYRSFWE KLLIFDYTPR K                      101

SEQ ID NO: 835           moltype = DNA  length = 303
FEATURE                  Location/Qualifiers
misc_feature             1..303
                         note = Synthetic biopolymer
source                   1..303
                         mol_type = other DNA
                         organism = synthetic construct
SEQUENCE: 835
atggctgtca agcaccttat cgtactgaaa ttcaaggacg aaattacaga agcccagaaa  60
gaagaatttt tcaagaccta tgtaaacctg gtgaatgtca tccctgcgat gaaagatgtt  120
tattggggca aagacgtcac ccaacgtaac aaagaagaag gttacactca catcgtcgaa  180
gtctgtttcg actcaatcga gacgatccaa gattacataa tgcacccggc ccatgtggga  240
ttcggagacg tttaccgtag cttctgggaa aaacttttga ttttcgacta taccccgaga  300
aaa                                                                303

SEQ ID NO: 836           moltype = AA  length = 101
FEATURE                  Location/Qualifiers
REGION                   1..101
                         note = Synthetic biopolymer
source                   1..101
                         mol_type = protein
                         organism = synthetic construct
SEQUENCE: 836
MAVKHLIVLK FKDEITEAQK EEFFKTYVNL VNVIPAMKDV YWGKDVTQRN KEEGYTHIVE  60
VCFDSIETIQ DYIMHPAHVG FGDVYRSFWE KLLIFDYTPR K                      101

SEQ ID NO: 837           moltype = DNA  length = 303
FEATURE                  Location/Qualifiers
misc_feature             1..303
                         note = Synthetic biopolymer
source                   1..303
                         mol_type = other DNA
                         organism = synthetic construct
SEQUENCE: 837
atgccggtca agcaccttat cgtactgaaa ttcaaggacg aaattacaga agcccagaaa  60
gaagaatttt tcaagaccta tgtaaacctg atgaatatca tccctgcgat gaaagatgtt  120
tattggggca aagacgtcac ccaaaaaaac aaagaagaag gttacactca cgtcgtcgaa  180
gtctgtttcg actcagtaga gtcaatccaa gattacataa tacacccggc ccatgtggga  240
ttcggagacg tttaccgtag cttctgggaa aaacttttga ttttcgacta taccccgaga  300
aaa                                                                303

SEQ ID NO: 838           moltype = AA  length = 101
FEATURE                  Location/Qualifiers
REGION                   1..101
                         note = Synthetic biopolymer
source                   1..101
                         mol_type = protein
                         organism = synthetic construct
SEQUENCE: 838
MPVKHLIVLK FKDEITEAQK EEFFKTYVNL MNIIPAMKDV YWGKDVTQKN KEEGYTHVVE  60
VCFDSVESIQ DYIIHPAHVG FGDVYRSFWE KLLIFDYTPR K                      101

SEQ ID NO: 839           moltype = DNA  length = 303
FEATURE                  Location/Qualifiers
misc_feature             1..303
                         note = Synthetic biopolymer
source                   1..303
                         mol_type = other DNA
                         organism = synthetic construct
```

```
SEQUENCE: 839
atggctgtaa agcaccttat cgtactgaaa ttcaaggacg aaattacaga agcccagaaa  60
gaagaatttt tcaagaccta tgtaaacctg gtgaatatca tccctccgat gaaagatgtt  120
tattggggca aagacgtcac ccaaaaaaac aaagaagaag gttacactca cgtcgtcgaa  180
gtcactttcg agtcagtatc atcaatccaa gattacataa tgcacccggc ccatgtggga  240
ttcggagacg tttaccgtag cttctgggaa aaacttttga ttttcgacta taccccggga  300
aaa                                                               303

SEQ ID NO: 840         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 840
MAVKHLIVLK FKDEITEAQK EEFFKTYVNL VNIIPPMKDV YWGKDVTQKN KEEGYTHVVE  60
VTFESVSSIQ DYIMHPAHVG FGDVYRSFWE KLLIFDYTPG K                     101

SEQ ID NO: 841         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 841
atggctgtca agcaccttat cgtactgaaa ttcaaggacg aaattacaga agcccagaaa  60
gaagaaatct tcaagaccta tgtaaacctg gtgaatatca tccctgcgat gaaagatgtt  120
tattggggca aagacgtcac ccaacgtaac aaagaagaag gttacactca catcgtcgaa  180
gtcactttcg agtcaatcga gcaaatcgcc gattacataa tgcacccggc ccatgtggga  240
ttcggagacg tttaccgtag cttctgggaa aaacttttga ttttcgacta taccccgaga  300
aaa                                                               303

SEQ ID NO: 842         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 842
MAVKHLIVLK FKDEITEAQK EEIFKTYVNL VNIIPAMKDV YWGKDVTQRN KEEGYTHIVE  60
VTFESIEQIA DYIMHPAHVG FGDVYRSFWE KLLIFDYTPR K                     101

SEQ ID NO: 843         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 843
atggctgtca agcaccttat cgtactgaaa ttcaaggacg aaattacaga agcccagaaa  60
gaacttttt tcaagaccta tgtaaacctg atgaatatca tcccttcaat gaaagatgtt  120
tattggggca aagacgtcac ccaaaaaaac aaagaagaag gttacactca catcgtcgaa  180
gtcactttcg agtcaatcga gtcaatccaa gattacataa tgcacccggc ccatgtggga  240
ttcggagacg tttaccgtag cttctgggaa aaacttttga ttttcgacta taccccgaga  300
aaa                                                               303

SEQ ID NO: 844         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 844
MAVKHLIVLK FKDEITEAQK ELFFKTYVNL MNIIPSMKDV YWGKDVTQKN KEEGYTHIVE  60
VTFESIESIQ DYIMHPAHVG FGDVYRSFWE KLLIFDYTPR K                     101

SEQ ID NO: 845         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 845
```

```
atggctgtca agcaccttat cgtactgaaa ttcaaggacg aaattacaga agcccagaaa  60
gaagaatttt tcaagaccta tgtaaacctg gtgaatatca tcccttcaat gaaagatgtt  120
tattggggca aagacgtcac ccaacgtaac aaagaagaag gttacactca ctgtgtcgaa  180
gtcactttcg actcaatcga gtcaatccaa gattacataa tacacccggc ccatgtggga  240
ttcggagacg tttaccgtag cttctgggaa aaacttttga ttttcgacta taccccgaga  300
aaa                                                                303

SEQ ID NO: 846         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 846
MAVKHLIVLK FKDEITEAQK EEFFKTYVNL VNIIPSMKDV YWGKDVTQRN KEEGYTHCVE  60
VTFDSIESIQ DYIIHPAHVG FGDVYRSFWE KLLIFDYTPR K                     101

SEQ ID NO: 847         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 847
atggctgtca agcaccttat cgtactgaaa ttcaaggacg aaattcaaga agcccagaaa  60
gaagaatttt tcaagaccta tgtaaacctg gtgaatatca tccctcaaat gaaagatgtt  120
tattggggca aagacgtcac ccacaaaaac aaagaagaag gttacactca cgtcgtcgaa  180
gtcactttcg actcagtaga gacgatccaa gattacataa tgcacccggc ccatgtggga  240
ttcggagacg tttaccgtag cttctgggaa aaacttttaa tttttgatta cactccaagg  300
aag                                                                303

SEQ ID NO: 848         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 848
MAVKHLIVLK FKDEIQEAQK EEFFKTYVNL VNIIPQMKDV YWGKDVTHKN KEEGYTHVVE  60
VTFDSVETIQ DYIMHPAHVG FGDVYRSFWE KLLIFDYTPR K                     101

SEQ ID NO: 849         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 849
atggctgtaa agcaccttat cgtactgaaa ttcaaggacg aaattacaga agcccagaaa  60
gaagaatttt tcaacaccta tgtaaacctg gtgaatatca tccctgcgat gaaagatgtt  120
tattggggca aagacgtcac ccaacgtaac aaagaagaag gttggactca cgtcgtcgaa  180
gtcactttcg actcagtaga gacgatccaa gattacataa tgcacccggc ccatgtggga  240
ttcggagacg tttaccgtag cttctgggaa aaacttttga ttttcgacta taccccgaga  300
aaa                                                                303

SEQ ID NO: 850         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 850
MAVKHLIVLK FKDEITEAQK EEFFNTYVNL VNIIPAMKDV YWGKDVTQRN KEEGWTHVVE  60
VTFDSVETIQ DYIMHPAHVG FGDVYRSFWE KLLIFDYTPR K                     101

SEQ ID NO: 851         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 851
atggctgtca agcaccttat cgtactgaaa ttcaaggacg aaattacaga agcccagaaa  60
```

```
gaagaatttt tcaagaccta tgtaaacctg gtgaatatca tcccttcaat gaaagatgtt  120
tattggggca aagacgtcac ctgtaaaaac aaagaagaag gttacactca catcgtcgaa  180
gtcactttcg actcagtaga ggaaatccaa gattacataa tgcacccggc ccatgtggga  240
ttcggagacg tttaccgtcc gttctgggaa aaacttttga ttttcgacta taccccgaga  300
aaa                                                                303

SEQ ID NO: 852         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 852
MAVKHLIVLK FKDEITEAQK EEFFKTYVNL VNIIPSMKDV YWGKDVTCKN KEEGYTHIVE  60
VTFDSVEEIQ DYIMHPAHVG FGDVYRPFWE KLLIFDYTPR K                      101

SEQ ID NO: 853         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 853
atggctgtaa agcaccttat cgtactgaaa ttcaaggacg aaattacaga agcccagaaa  60
gaagaatttt tcaagaccta tgtaaacctg gtgaatatca tccctgcgat gaaagatgtt  120
tattggggca aagacgtcac ccaacgtaac aaagaagaag gttacactca catcgtcgaa  180
gtcactttcg agtcaatcga gcaaatccaa acctacataa tgcacccggc ccatgtggga  240
ttcggagacg tttaccgtag cttctgggaa aaacttttga aattcgacta taccccgaga  300
aaa                                                                303

SEQ ID NO: 854         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 854
MAVKHLIVLK FKDEITEAQK EEFFKTYVNL VNIIPAMKDV YWGKDVTQRN KEEGYTHIVE  60
VTFESIEQIQ TYIMHPAHVG FGDVYRSFWE KLLKFDYTPR K                      101

SEQ ID NO: 855         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 855
atgccggtca agcaccttat catcgttaaa ttcaaggacg aaattacaga agcccagaaa  60
gaagaatttt tcaagaccta tgtaaacctg gtgaatatca tccctgcgat gaaagatgtt  120
tattggggca aagacgtcac ccaaaaaaac aaagaagaag gttacactca catcgtcgaa  180
gtcactttcg actcagtaga gtcaatccaa gattacataa tacacccggc ccatgtcgga  240
ttcggagacg tttaccgtag cttctgggaa aaacttttga ttttcgacta taccccggga  300
aaa                                                                303

SEQ ID NO: 856         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 856
MPVKHLIIVK FKDEITEAQK EEFFKTYVNL VNIIPAMKDV YWGKDVTQKN KEEGYTHIVE  60
VTFDSVESIQ DYIIHPAHVG FGDVYRSFWE KLLIFDYTPG K                      101

SEQ ID NO: 857         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 857
atgccggtca agcaccttat catcactaaa ttcaaggacg aaattacaga agcccagaaa  60
gaagaatttt tcaagaccta tgtaaacctg gtgaatatca tccctgcgat gaaagatgtt  120
```

```
tattggggca aagacgtcac ccaaaaaaac aaagaagaag gttacactca catcgtcgaa  180
gtcactttcg actcagtaga gtcaatccaa gattacataa tacacccggc ccatgtggga  240
ttcggagacg tttaccgtag cttctgggaa aaacttttga ttttcgacta taccccggga  300
aaa                                                                303

SEQ ID NO: 858         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 858
MPVKHLIITK FKDEITEAQK EEFFKTYVNL VNIIPAMKDV YWGKDVTQKN KEEGYTHIVE  60
VTFDSVESIQ DYIIHPAHVG FGDVYRSFWE KLLIFDYTPG K                      101

SEQ ID NO: 859         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 859
atgccggtca agcaccttat catctgtaaa ttcaaggacg aaattacaga agcccagaaa  60
gaagaatttt tcaagaccta tgtaaacctg gtgaatatca tccctgcgat gaaagatgtt  120
tattggggca aagacgtcac ccaaaaaaac aaagaagaag gttacactca catcgtcgaa  180
gtcactttcg actcagtaga gtcaatccaa gattacataa tacacccggc ccatgtggga  240
ttcggagacg tttaccgtag cttctgggaa aaacttttga ttttcgacta taccccggga  300
aaa                                                                303

SEQ ID NO: 860         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 860
MPVKHLIICK FKDEITEAQK EEFFKTYVNL VNIIPAMKDV YWGKDVTQKN KEEGYTHIVE  60
VTFDSVESIQ DYIIHPAHVG FGDVYRSFWE KLLIFDYTPG K                      101

SEQ ID NO: 861         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 861
atgccggtca agcaccttat catcgggaaa ttcaaggacg aaattacaga agcccagaaa  60
gaagaatttt tcaagaccta tgtaaacctg gtgaatatca tccctgcgat gaaagatgtt  120
tattggggca aagacgtcac ccaaaaaaac aaagaagaag gttacactca catcgtcgaa  180
gtcactttcg actcagtaga gtcaatccaa gattacataa tacacccggc ccatgtggga  240
ttcggagacg tttaccgtag cttctgggaa aaacttttga ttttcgacta taccccggga  300
aaa                                                                303

SEQ ID NO: 862         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 862
MPVKHLIIGK FKDEITEAQK EEFFKTYVNL VNIIPAMKDV YWGKDVTQKN KEEGYTHIVE  60
VTFDSVESIQ DYIIHPAHVG FGDVYRSFWE KLLIFDYTPG K                      101

SEQ ID NO: 863         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 863
atgccggtca agcaccttat catcgcgaaa ttcaaggacg aaattacaga agcccagaaa  60
gaagaatttt tcaagaccta tgtaaacctg gtgaatatca tccctgcgat gaaagatgtt  120
tattggggca aagacgtcac ccaaaaaaac aaagaagaag gttacactca catcgtcgaa  180
```

```
gtcactttcg actcagtaga gtcaatccaa gattacataa tacacccggc ccatgtggga  240
ttcggagacg tttaccgtag cttctgggaa aaacttttga ttttcgacta taccccggga  300
aaa                                                                 303

SEQ ID NO: 864         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 864
MPVKHLIIAK FKDEITEAQK EEFFKTYVNL VNIIPAMKDV YWGKDVTQKN KEEGYTHIVE  60
VTFDSVESIQ DYIIHPAHVG FGDVYRSFWE KLLIFDYTPG K                      101

SEQ ID NO: 865         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 865
atgccggtca agcaccttat catcatgaaa ttcaaggacg aaattacaga agcccagaaa  60
gaagaatttt tcaagaccta tgtaaacctg gtgaatatca tccctgcgat gaaagatgtt  120
tattggggca aagacgtcac ccaaaaaaac aaagaagaag gttacactca catcgtcgaa  180
gtcactttcg actcagtaga gtcaatccaa gattacataa tacacccggc ccatgtggga  240
ttcggagacg tttaccgtag cttctgggaa aaacttttga ttttcgacta taccccggga  300
aaa                                                                 303

SEQ ID NO: 866         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 866
MPVKHLIIMK FKDEITEAQK EEFFKTYVNL VNIIPAMKDV YWGKDVTQKN KEEGYTHIVE  60
VTFDSVESIQ DYIIHPAHVG FGDVYRSFWE KLLIFDYTPG K                      101

SEQ ID NO: 867         moltype = DNA  length = 305
FEATURE                Location/Qualifiers
misc_feature           1..305
                       note = Synthetic biopolymer
source                 1..305
                       mol_type = other DNA
                       organism = synthetic construct
SEQUENCE: 867
atgccggtca agcaccttat catctttaaa ttcaaggacg aaattacaga agcccagaaa  60
gaagaatttt tcaagaccta tgtaaacctg gtgaatatca tccctgcgat gaaagatgtt  120
tattggggca aagacgtcac ccaaaaaaac aaagaagaag gttacactca catcgtcgaa  180
gtcactttcg actcagtaga gtcaatccaa gattacataa tacacccggc ccatgtggga  240
ttcggagacg tttaccgtag cttctgggaa aaacttttga ttttcgatat accccgggaa  300
aataa                                                               305

SEQ ID NO: 868         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 868
MPVKHLIIFK FKDEITEAQK EEFFKTYVNL VNIIPAMKDV YWGKDVTQKN KEEGYTHIVE  60
VTFDSVESIQ DYIIHPAHVG FGDVYRSFWE KLLIFDYTPG K                      101

SEQ ID NO: 869         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 869
atgccggtca agcaccttat catctcgaaa ttcaaggacg aaattacaga agcccagaaa  60
gaagaatttt tcaagaccta tgtaaacctg gtgaatatca tccctgcgat gaaagatgtt  120
tattggggca aagacgtcac ccaaaaaaac aaagaagaag gttacactca catcgtcgaa  180
gtcactttcg actcagtaga gtcaatccaa gattacataa tacacccggc ccatgtggga  240
```

```
ttcggagacg tttaccgtag cttctgggaa aaacttttga ttttcgacta taccccggga  300
aaa                                                                303

SEQ ID NO: 870         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 870
MPVKHLIISK FKDEITEAQK EEFFKTYVNL VNIIPAMKDV YWGKDVTQKN KEEGYTHIVE  60
VTFDSVESIQ DYIIHPAHVG FGDVYRSFWE KLLIFDYTPG K                      101

SEQ ID NO: 871         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 871
atggctgtca agcaccttat catcctgaaa ttcaaggacg aaattacaga agcccagaaa  60
gaagaatttt tcaagaccta tgtaaacctg gtgaatatca tccctgcgat gaaagatgtt  120
tattggggca aagacgtcac ccaaggtaac aaagaagaag gttacactca cgtcgtcgaa  180
gtcactttcg actcagtaga gatgatccaa gattacataa tgcacccggc ccatgtggga  240
ttcggagacg tttaccgtag cttctgggaa aaacttttga ttttcgacta taccccgaga  300
aaa                                                                303

SEQ ID NO: 872         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 872
MAVKHLIILK FKDEITEAQK EEFFKTYVNL VNIIPAMKDV YWGKDVTQGN KEEGYTHVVE  60
VTFDSVEMIQ DYIMHPAHVG FGDVYRSFWE KLLIFDYTPR K                      101

SEQ ID NO: 873         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 873
atggctgtca agcaccttat catcctgaaa ttcaaggacg aaattacaga agcccagaaa  60
gaagaatttt tcaagaccta tgtaaacctg gtgaatatca tccctgcgat gaaagatgtt  120
tattggggca aagacgtcac ccaagcgaac aaagaagaag gttacactca cgtcgtcgaa  180
gtcactttcg actcagtaga gatgatccaa gattacataa tgcacccggc ccatgtggga  240
ttcggagacg tttaccgtag cttctgggaa aaacttttga ttttcgacta taccccgaga  300
aaa                                                                303

SEQ ID NO: 874         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 874
MAVKHLIILK FKDEITEAQK EEFFKTYVNL VNIIPAMKDV YWGKDVTQAN KEEGYTHVVE  60
VTFDSVEMIQ DYIMHPAHVG FGDVYRSFWE KLLIFDYTPR K                      101

SEQ ID NO: 875         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 875
atggctgtca agcaccttat catcctgaaa ttcaaggacg aaattacaga agcccagaaa  60
gaagaatttt tcaagaccta tgtaaacctg gtgaatatca tccctgcgat gaaagatgtt  120
tattggggca aagacgtcac ccaacataac aaagaagaag gttacactca cgtcgtcgaa  180
gtcactttcg actcagtaga gatgatccaa gattacataa tgcacccggc ccatgtggga  240
ttcggagacg tttaccgtag cttctgggaa aaacttttga ttttcgacta taccccgaga  300
```

```
aaa                                                                 303

SEQ ID NO: 876         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 876
MAVKHLIILK FKDEITEAQK EEFFKTYVNL VNIIPAMKDV YWGKDVTQHN KEEGYTHVVE  60
VTFDSVEMIQ DYIMHPAHVG FGDVYRSFWE KLLIFDYTPR K                      101

SEQ ID NO: 877         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 877
atggctgtca agcaccttat catcctgaaa ttcaaggacg aaattacaga agcccagaaa  60
gaagaatttt tcaagaccta tgtaaacctg gtgaatatca tccctgcgat gaaagatgtt  120
tattggggca aagacgtcac ccaatgtaac aaagaagaag gttacactca cgtcgtcgaa  180
gtcactttcg actcagtaga gatgatccaa gattacataa tgcacccggc ccatgtggga  240
ttcggagacg tttaccgtag cttctgggaa aaacttttga ttttcgacta taccccgaga  300
aaa                                                                 303

SEQ ID NO: 878         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 878
MAVKHLIILK FKDEITEAQK EEFFKTYVNL VNIIPAMKDV YWGKDVTQCN KEEGYTHVVE  60
VTFDSVEMIQ DYIMHPAHVG FGDVYRSFWE KLLIFDYTPR K                      101

SEQ ID NO: 879         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 879
atggctgtca agcaccttat catcctgaaa ttcaaggacg aaattacaga agcccagaaa  60
gaagaatttt tcaagaccta tgtaaacctg gtgaatatca tccctgcgat gaaagatgtt  120
tattggggca aagacgtcac ccaaactaac aaagaagaag gttacactca cgtcgtcgaa  180
gtcactttcg actcagtaga gatgatccaa gattacataa tgcacccggc ccatgtggga  240
ttcggagacg tttaccgtag cttctgggaa aaacttttga ttttcgacta taccccgaga  300
aaa                                                                 303

SEQ ID NO: 880         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 880
MAVKHLIILK FKDEITEAQK EEFFKTYVNL VNIIPAMKDV YWGKDVTQTN KEEGYTHVVE  60
VTFDSVEMIQ DYIMHPAHVG FGDVYRSFWE KLLIFDYTPR K                      101

SEQ ID NO: 881         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 881
atggctgtca agcaccttat catcctgaaa ttcaaggacg aaattacaga agcccagaaa  60
gaagaatttt tcaagaccta tgtaaacctg gtgaatatca tccctgcgat gaaagatgtt  120
tattggggca aagacgtcac ccaagtgaac aaagaagaag gttacactca cgtcgtcgaa  180
gtcactttcg actcagtaga gatgatccaa gattacataa tgcacccggc ccatgtggga  240
ttcggagacg tttaccgtag cttctgggaa aaacttttga ttttcgacta taccccgaga  300
aaa                                                                 303
```

```
SEQ ID NO: 882         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 882
MAVKHLIILK FKDEITEAQK EEFFKTYVNL VNIIPAMKDV YWGKDVTQVN KEEGYTHVVE  60
VTFDSVEMIQ DYIMHPAHVG FGDVYRSFWE KLLIFDYTPR K                      101

SEQ ID NO: 883         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 883
atggctgtca agcaccttat catcctgaaa ttcaaggacg aaattacaga agcccagaaa  60
gaagaatttt tcaagaccta tgtaaacctg gtgaatatca tccctgcgat gaaagatgtt  120
tattggggca aagacgtcac ccaatcgaac aaagaagaag gttacactca cgtcgtcgaa  180
gtcactttcg actcagtaga gatgatccaa gattacataa tgcacccggc ccatgtggga  240
ttcggagacg tttaccgtag cttctgggaa aaacttttga ttttcgacta taccccgaga  300
aaa                                                                303

SEQ ID NO: 884         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 884
MAVKHLIILK FKDEITEAQK EEFFKTYVNL VNIIPAMKDV YWGKDVTQSN KEEGYTHVVE  60
VTFDSVEMIQ DYIMHPAHVG FGDVYRSFWE KLLIFDYTPR K                      101

SEQ ID NO: 885         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 885
atggctgtca agcaccttat catcctgaaa ttcaaggacg aaattacaga agcccagaaa  60
gaagaatttt tcaagaccta tgtaaacctg gtgaatatca tccctgcgat gaaagatgtt  120
tattggggca aagacgtcac ccaaaataac aaagaagaag gttacactca cgtcgtcgaa  180
gtcactttcg actcagtaga gatgatccaa gattacataa tgcacccggc ccatgtggga  240
ttcggagacg tttaccgtag cttctgggaa aaacttttga ttttcgacta taccccgaga  300
aaa                                                                303

SEQ ID NO: 886         moltype = AA  length = 101
FEATURE                Location/Qualifiers
REGION                 1..101
                       note = Synthetic biopolymer
source                 1..101
                       mol_type = protein
                       organism = synthetic construct
SEQUENCE: 886
MAVKHLIILK FKDEITEAQK EEFFKTYVNL VNIIPAMKDV YWGKDVTQNN KEEGYTHVVE  60
VTFDSVEMIQ DYIMHPAHVG FGDVYRSFWE KLLIFDYTPR K                      101

SEQ ID NO: 887         moltype = DNA  length = 303
FEATURE                Location/Qualifiers
misc_feature           1..303
                       note = Synthetic biopolymer
source                 1..303
                       mol_type = other DNA
                       organism = synthetic construct
SEQUENCE: 887
atggctgtca agcaccttat catcctgaaa ttcaaggacg aaattacaga agcccagaaa  60
gaagaatttt tcaagaccta tgtaaacctg gtgaatatca tccctgcgat gaaagatgtt  120
tattggggca aagacgtcac ccaaccgaac aaagaagaag gttacactca cgtcgtcgaa  180
gtcactttcg actcagtaga gatgatccaa gattacataa tgcacccggc ccatgtggga  240
ttcggagacg tttaccgtag cttctgggaa aaacttttga ttttcgacta taccccgaga  300
aaa                                                                303
```

-continued

```
SEQ ID NO: 888          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 888
MAVKHLIILK FKDEITEAQK EEFFKTYVNL VNIIPAMKDV YWGKDVTQPN KEEGYTHVVE  60
VTFDSVEMIQ DYIMHPAHVG FGDVYRSFWE KLLIFDYTPR K                     101

SEQ ID NO: 889          moltype = DNA  length = 303
FEATURE                 Location/Qualifiers
misc_feature            1..303
                        note = Synthetic biopolymer
source                  1..303
                        mol_type = other DNA
                        organism = synthetic construct
SEQUENCE: 889
atggctgtca agcaccttat catcctgaaa ttcaaggacg aaattacaga agcccagaaa  60
gaagaatttt tcaagaccta tgtaaacctg gtgaatatca tccctgcgat gaaagatgtt  120
tattggggca aagacgtcac ccaactgaac aaagaagaag gttacactca cgtcgtcgaa  180
gtcactttcg actcagtaga gatgatccaa gattacataa tgcacccggc ccatgtggga  240
ttcggagacg tttaccgtag cttctgggaa aaacttttga ttttcgacta taccccgaga  300
aaa                                                               303

SEQ ID NO: 890          moltype = AA  length = 101
FEATURE                 Location/Qualifiers
REGION                  1..101
                        note = Synthetic biopolymer
source                  1..101
                        mol_type = protein
                        organism = synthetic construct
SEQUENCE: 890
MAVKHLIILK FKDEITEAQK EEFFKTYVNL VNIIPAMKDV YWGKDVTQLN KEEGYTHVVE  60
VTFDSVEMIQ DYIMHPAHVG FGDVYRSFWE KLLIFDYTPR K                     101
```